US007834154B2

(12) United States Patent
Koch et al.

(10) Patent No.: US 7,834,154 B2
(45) Date of Patent: Nov. 16, 2010

(54) ANTI-ROBO4 ANTIBODIES AND USES THEREFOR

(75) Inventors: Alexander W. Koch, Millbrae, CA (US); Scott Stawicki, San Francisco, CA (US); Yan Wu, Foster City, CA (US); Richard Carano, San Ramon, CA (US); Franklin V. Peale, Jr., San Carlos, CA (US); Ryan J. Watts, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 12/028,124

(22) Filed: Feb. 8, 2008

(65) Prior Publication Data

US 2008/0247951 A1 Oct. 9, 2008

Related U.S. Application Data

(60) Provisional application No. 60/891,475, filed on Feb. 23, 2007, provisional application No. 60/889,214, filed on Feb. 9, 2007.

(51) Int. Cl.
| | |
|---|---|
| C07K 16/00 | (2006.01) |
| C07K 17/00 | (2006.01) |
| C07K 17/14 | (2006.01) |
| C12P 21/08 | (2006.01) |
| A61K 39/395 | (2006.01) |
| A61K 39/00 | (2006.01) |

(52) U.S. Cl. .............. 530/387.1; 530/387.3; 530/391.1; 530/391.3; 530/391.5; 424/130.1; 424/133.1; 424/134.1; 424/178.1

(58) Field of Classification Search ........................ None
See application file for complete search history.

(56) References Cited

U.S. PATENT DOCUMENTS

| | | | |
|---|---|---|---|
| 6,069,007 | A | 5/2000 | Rossi et al. |
| 6,225,118 | B1 | 5/2001 | Grant et al. |
| 7,112,317 | B2 | 9/2006 | Thorpe et al. |
| 7,163,797 | B2 | 1/2007 | Ruben et al. |
| 7,459,931 | B1 | 12/2008 | Tang et al. |
| 2003/0027993 | A1 | 2/2003 | Eaton et al. |
| 2003/0072736 | A1 | 4/2003 | Baker et al. |
| 2003/0236210 | A1* | 12/2003 | Geng ........................... 514/44 |
| 2004/0071711 | A1 | 4/2004 | Bicknell et al. |
| 2006/0099143 | A1 | 5/2006 | Bicknell et al. |
| 2006/0160729 | A1 | 7/2006 | Li et al. |
| 2006/0205034 | A1 | 9/2006 | Fraser et al. |
| 2007/0025913 | A1 | 2/2007 | Bicknell et al. |

FOREIGN PATENT DOCUMENTS

| | | |
|---|---|---|
| EP | 0682113 A2 | 11/1995 |
| EP | 1074617 A2 | 2/2001 |
| WO | 99/06423 | 2/1999 |
| WO | 99/11293 | 3/1999 |
| WO | 99/46281 | 9/1999 |
| WO | 99/53051 | 10/1999 |
| WO | 00/53756 | 9/2000 |
| WO | 01/23523 A2 | 4/2001 |
| WO | 02/22660 A2 | 3/2002 |
| WO | 02/36771 A2 | 5/2002 |
| WO | 2004/046191 A2 | 6/2004 |
| WO | 2005/014051 A1 | 2/2005 |
| WO | 2005/044853 | 5/2005 |
| WO | 2006/042173 | 4/2006 |

OTHER PUBLICATIONS

Skolnick and Fetrow. From genes to protein structure and function: novel applications of computational approaches in the genomic era. Trends in Biotechnology, 2000. vol. 18, pp. 34-39.*

Burgess, Shaheen, Ravera, Jaye, Donohue, and Winkles. Possible dissociation of the heparin-binding and mitogenic activities of heparin-binding (acidic fibroblast) growth factor-1 from its receptor binding activities by site directed mutagenesis of a single lysine residue. Journal of Cell Biology, 1990. vol. 111, pp. 2129-2138.*

Lazar, Watanabe, Dalton, and Sporn. Transforming growth factor a: mutation of aspartic acid 47 and leucine 48 results in different biological activities. Molecular and Cellular Biology, 1988. vol. 8, pp. 1247-1252.*

Holm, Jafari, and Sundstrom. Functional mapping and single chain construction of the anti-cytokeratin 8 monoclonal antibody TS1. Molecular Immunology, 2007. vol. 44, pp. 1075-1084.*

Chen, Wiesmann, Fuh, Li, Christinger, Mc Kay, De Vos, and Lowman. Selection and analysis of an optimized anti-VEGF antibody: crystal structure of an affinity matured Fab in complex with antigen. Journal of Molecular Biology, 1999. vol. 293, pp. 865-881.*

Rudikoff, Giusti, Cook, and Scharff. Single amino acid substitution altering antigen-binding specificity. Proceedings of the National Academy of Sciences, 1982. vol. 79, pp. 1979-1983.*

Mac Callum, Martin, and Thornton. Antibody-antigen interactions: contact analysis and binding site topography. Journal of Molecular Biology, 1996. vol. 262, pp. 732-745.*

De Pascalis, Iwahasi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanized monoclonal antibody. Journal of Immunology, 2002. vol. 169, pp. 3076-3084.*

Casset, Roux, Mouchet, Bes, Chardes, Granier, Mani, Pugniere, Laune, Pau, Kaczorek, Lahana, and Rees. Biochemical and Biophysical Research Communications, 2003. vol. 307, pp. 198-205.*

Vajdos, Adams, Breece, Presta, De Vos, and Sidhu. Comprehensive functional maps of the antigen binding site of an anti-ErbB2 antibody obtained by shotgun scanning mutagenesis. Journal of Molecular Biology, 2002. vol. 320, pp. 415-428.*

(Continued)

*Primary Examiner*—Anne M. Gusow
(74) *Attorney, Agent, or Firm*—Carol Fang

(57) ABSTRACT

The invention provides anti-Robo4 antibodies, and compositions comprising the antibodies and methods of using these antibodies, including diagnostic and therapeutic methods.

12 Claims, 27 Drawing Sheets

OTHER PUBLICATIONS

Wu, Nie, Huse, and Watkins. Humanization of a murine monoclonal antibody by simultaneous optimization of framework and CDR residues. Journal of Molecular Biology, 1999. vol. 294, pp. 151-162.*

Fujiwara, M. et al., "Potential role of the Slit/Robo signal pathway in angiogensis" *Vascular Medicine* 11(2):115-121 (May 1, 2006).

Hoogenboom, "Selecting and screening recombinant antibody libraries" *Nature Biotechnology* 23(9):1105-1116 (Sep. 1, 2005).

Aaronson et al., "Toward the Development of a Gene Index to the Human Genome: an Assessment of the Nature of High-Throughput EST Sequence Data" *Genome Research* 6:829-845 (1996).

Abbas et al., "Chapter Three Antibodies and Antigens" *Cellular and Molecular Immunology*, 2nd edition pp. 41-43 (1994).

Adams et al., "Initial assessment of human gene diversity and expression patterns based upon 83 million nucleotides of cDNA sequence" *Nature* 377(SUPPL):3-174 (Sep. 28, 1995).

Adams, R.H., et al., "Roles of ephrinB ligands and EphB receptors in cardiovascular development: demarcation of arterial/venous domains, vascular morphogenesis, and sprouting angiogenesis" *Genes and Development* 13:295-306 (1999).

Aiello et al., "Suppression of retinal neovascularization in vivo by inhibition of vascular endothelial growth factor (VEGF) using soluble VEGF- receptor chimeric proteins" *Proc. Natl. Acad. Sci. USA* 92:10457-10461 (Nov. 1995).

Amalfitano et al., "Separating fact from fiction: assessing the potential of modified adenovirus vectors for use in human gene therapy" *Current Gene Therapy* 2(2):111-133 (2002).

AngioKit Protocol, Catalogue No. ZHA-1000, by TCS CellWorks Ltd, Buckingham MK18 2LR, UK (pp. 1-16), 2008.

Asano et al., "Inhibition of tumor growth and metastasis by an immunoneutralizing monoclonal antibody to human vascular endothelial growth factor/vascular permeability factor$_{121}$" *Cancer Research* 55:5296-5301 (Nov. 15, 1995).

Banerji et al., "LYVE-1, a new homologue of the CD44 glycoprotein, is a lymph-specific receptor for hyaluronan" *Journal of Cell Biology* 144(4):789-801 (Feb 1999).

Bashaw et al., "Chimeric Axon Guidance Receptors: The Cytoplasmic Domains of Slit and Netrin Receptors Specify Attraction Versus Repulsion" *Cell* 97:917-926 (Jun. 25, 1999).

Bashaw et al., "Repulsive Axon Guidance: Abelson and Enabled Play Opposing Roles Downstream of the Roundabout Receptor" *Cell* 101:703-715 (Jun. 23, 2000).

Bates et al., "Identification and analysis of a novel member of the ubiquitin family expressed in dendritic cells and mature B cells" *European Journal of Immunology* 27:2471-2477 (1997).

BD BioCoat™ Angiogenesis System—Endothelial Cell Migration; available as Catalog No. 354143 from BD Biosciences, Bedford, MA (2002) (6 pages).

Bechard et al., "Characterization of the Secreted Form of Endothelial-Cell Specific Molecule 1 by Specific Monoclonal Antibodies" *J Vasc Res*. 37:417-425 (2000).

Bedell et al., "roundabout4 is essential for angiogenesis in vivo" *Proc. Natl. Acad. Sci. USA* 102(18):6373-8 (May 3, 2005).

Bernstein et al., "Characterization of a Human Fovea cDNA Library and Regional Differential Gene Expression in the Human Retina" *Genomics* 32:301-308 (1996).

Bortoluzzi et al., "The Human Adult Skeletal Muscle Transcriptional Profile Reconstructed by a Novel Computational Approach" *Genome Research* 10:344-349 (2000).

Boyle et al., "DNA immunization: induction of higher avidity antibody and effect of route on T cell cytotoxicity" *Proc. Nat'l Acad. Sci. USA* 94:14626-14631 (Dec. 1997).

Brose et al., "Slit Proteins Bind Robo Receptors and Have an Evolutionarily Conserved Role in Repulsive Axon Guidance" *Cell* 96:795-806 (Mar. 19, 1999).

Casset, F. et al., "A peptide mimetic of an anti-CD4 monoclonal antibody by rational design" *Biochem. &Biophys. Res. Comm.* 307:198-205 (2003).

Chatterjee et al., "Idiotypic antibody immunotherapy of cancer" *Cancer Immunol Immunother*. 38:75-82 (1994).

Chen et al., "Characterization of Gene Expression in Resting and Activated Mast Cells" *Journal of Experimental Medicine* 188(9):1657-1668 (Nov. 2, 1998).

Clark et al., "Localization of VEGF and expression of its receptors fit and KDR in human placenta throughout pregnancy" *Human Reproduction* 11(5):1090-1098 (1996).

Cole et al., "The Genetics of Cancer—a 3D Model" *Nature Genetics Supp.* 21:38-41 (Jan. 1999).

Compton et al., "Nucleic Acid Sequence-Based Amplification" *Nature* 350:91-92 (Mar. 7, 1991).

Cross et al., "FGF and VEGF function in angiogenesis: signalling pathways, biological responses and therapeutic inhibition" *Trends Pharmacol. Sci.* 22(4):201-207 (Apr. 2001).

Cserzo et al., "Prediction of Transmembrane α-helics in Prokaryotic Membrane Alpha Helices in Prokaryotic Membrane Proteins: the Dense Alignment Surface Method" *Protein Eng.* 10(6):673-676 (1997).

Cwirla et al., "Peptides on phage: a vast library of peptides for identifying ligands" *Proc. Natl. Acad. Sci. USA* 87:6378-6382 (Aug. 1990).

Dermer, G., "Another anniversary for the war on cancer" *Biotechnology* 12:320 (1994).

Dillon et al., "Functional Gene Expression Domains: Defining the Functional Unit of Eukaryotic Gene Regulation" *BioEssays* 22.7:657-665 (2000).

Dobrzanski et al., "Antiangiogenic and Antitumor Efficacy of EphA2 Receptor Antagonist" *Cancer Research* 64:910-919 (Feb. 1, 2004).

Dorai et al., "Development of a hammerhead ribozyme against BCL-2. II. Ribozyme treatment sensitizes hormone-resistant prostate cancer cells to apoptotic agents" *Anticancer Res.* 17:3307-3312 (1997).

Felbor et al., "Genomic Organization and Chromosomal Localization of the Interphotoreceptor Matrix Proteoglycan-1 (IMPG1) Gene: a Candidate for 6q-linked Retinopathies" *Cytogenet Cell Genet*. 81:12-17 (1998).

Fong et al., "Role of the Flt-1 receptor tyrosine kinase in regulating the assembly of vascular endothelium" *Nature* 376:66-70 (Jul. 6, 1995).

GenBank Accession No. AAH39602; Strausberg; Jul. 15, 2006.
GenBank Accession No. AAL31867 (2001).
GenBank Accession No. AC011562; Birren et al.; Oct. 1999.
GenBank Accession No. AF361473 (2001).
GenBank Accession No. AK000805; Sugano et al.; Feb. 2000.
GenBank Accession No. AK025195; Sugano et al.; Aug. 2000.
GenBank Accession No. BB536291; Arakawa et al.; Jun. 2000.

Gerhold et al., "It's the Genes. EST Access to Human Genome Content" *BioEssays* 18(12):973-981 (1996).

Ginsburg et al., "Human von Willebrand Factor (vWF); Isolation of Complementary DNA (cDNA) Clones and Chromosomal Localization" *Science* 228:1401-1406 (Jun. 21, 1985).

Goetze et al., "Leptin induces endothelial cell migration through Akt, which is inhibited by PPARγ-ligands" *Hypertension* 40:748-754 (2002).

Gorn et al., "Serum levels of Magic Roundabout protein in patients with advanced non-small cell lung cancer (NSCLC)" *Lung Cancer* 49:71-6 (2005).

Grone et al., "Robo1/Robo4: differential expression of angiogenic markers in colorectal cancer" *Oncol Rep.* 15:1437-43 (2006).

Gura, T., "Systems for identifying new drugs are often faulty" *Science* 278:1041-1042 (Nov. 7, 1997).

Hagedorn et al., "A Short Peptide Domain of Platelet Factor 4 Blocks Angiogenic Key Events Induced by FGF-2" *FASEB* 15:550-552 (Mar. 2001).

Hayward et al., "An autosomal dominant, qualitative platelet disorder associated with multimerin deficiency, abnormalities in platelet factor V, thrombospondin, von Willebrand factor, and fibrinogen and an epinephrine aggregation defect" *Blood* 87(12):4967-4978 (Jun. 15, 1996).

Hayward et al., "Multimerin is Found in the α-Granules of Resting Platelets and is Synthesized by a Megakaryocytic Cell Line" *J. Clin. Invest.* 91:2630-2639 (Jun. 1993).

Hayward et al., "Studies of Multimerin in Human Endothelial Cells" *Blood* 91(4):1304-1317 (Feb. 15, 1998).

Hockel et al., "Tumor Hypoxia: Definitions and Current Clinical, Biologic, and Molecular Aspects" *J. of Nat'l Cancer Inst.* 93(4):266-276 (Feb. 21, 2001).

Holm, P. et al., "Functional mapping and single chain construction of the anti-cytokeratin 8 monoclonal antibody TS1" *Molecular Immunology* 44:1075-1084 (2007).

Hori et al., "Differential effects of angiostatic steroids and dexamethasone on angiogenesis and cytokine levels in rat sponge implants" *Br. J. Pharmacol.* 118:1584-1591 (1996).

Huminiecki et al., "In Silico Cloning of Novel Endothelial Specific Genes: Their Role in Angiogenesis" *Angiogenesis* 7:220-221 (Sep. 2001).

Huminiecki et al., "In Silico Cloning of Novel Endothelial-Specific Genes" *Genome Research* 10:1796-1806 (2000).

Huminiecki et al., "Magic roundabout is a new member of the roundabout receptor family that is endothelial specific and expressed at sites of active angiogenesis" *Genomics* 79(4):547-552 (Apr. 2002).

Itoh et al., "Expression Profile of Active Genes in Granulocytes" *Blood* 92(4):1432-1441 (Aug. 15, 1998).

Jain et al., "Tumor Angiogenesis and Accessibility: Role of Vascular Endothelial Growth Factor" *Seminars in Oncology* (Suppl. 16) 29(6):3-9 (Dec. 2002).

Jain, R., "Barriers to drug delivery in solid tumors" *Scientific American* pp. 58-65 (Jul. 1994).

Jones et al., "Robo4 stabilizes the vascular network by inhibiting pathologic angiogenesis and endothelial hyperpermeability" *Nat Med.* (Epub Mar. 16, 2008) 14(4):448-53 (Apr. 2008).

Kaur et al., "Robo4 signaling in endothelial cells implies attraction guidance mechanisms" *J Biol Chem.* 281(16):11347-56 (Apr. 21, 2006).

Kettleborough et al., "Humanization of a Mouse Monoclonal Antibody by CDR-grafting: the Importance of Framework Residues on Loop Conformation" *Protein Engineering* 4(7):773-783 (1991).

Kidd et al., "Roundabout Controls Axon Crossing of the CNS Midline and Defines a Novel Subfamily of Evolutionary Conserved Guidance Receptors" *Cell* 92(2):205-215 (Jan. 23, 1998).

Landis et al., "The measurement of observer agreement for categorical data" *Biometrics* 33:159-174 (Mar. 1977).

Lassalle et al., "ESM-1 is a novel human endothelial cell-specific molecule expressed in lung and regulated by cytokines" *Journal of Biological Chemistry* 271(34):20458-20464 (1996).

Legg et al., "Slits and Roundabouts in cancer, tumour angiogenesis and endothelial cell migration" *Angiogenesis* 11:13-21 (2008).

Li et al., "Vertebrate Slit, a Secreted Ligand for the Transmembrane Protein Roundabout, is a Repellant for Olfactory Bulb Axons" *Cell* 96:807-818 (Mar. 19, 1999).

Maier et al., "In vitro inhibition of endothelial cell growth by the antiangiogenic drug AGM-1470 (TNP-470) and the anti-endoglin antibody TEC-11" *Anti-Cancer Drugs* 8:238-244 (1997).

Matthews et al., "A Receptor Tyrosine Kinase cDNA Isolated from a Population of Enriched Primitive Hematopoietic Cells and Exhibiting Close Genetic Linkage to c-kit" *Proc. Natl. Acad. Sci. USA* 88:9026-30 (Oct. 1991).

Maxwell et al., "The Tumour Suppressor Protein VHL Targets Hypoxia-Inducible Factors for Oxygen Dependent Proteolysis" *Nature* 399:271-275 (May 20, 1999).

Miller et al., "Synthesis and Antitumor Activity of Boronated Dipeptides Containing Aromatic Amino Acids" *Anticancer Res.* 17(5A):3299-3306 (1997).

Miller et al., "Synthesis and antitumor activity of boronated dipeptides containing aromatic amino acids" *Anticancer Res.* 17:3299-3306 (1997).

Min et al., "Capsaicin Inhibits in Vitro and In Vivo Angiogenesis" *Cancer Research* 64:644-651 (Jan. 15, 2004).

Nichols et al., "Identification of Human Megakaryocyte Coagulation Factor V" *Blood* 65(6):1396-1406 (Jun. 1985).

Nielsen et al., "Identification of Prokaryotic and Eukaryotic Signal Peptides and Prediction of Their Cleavage Sites" *Protein Engineering* 10(1):1-6 (1997).

Obermair et al., "Vascular Endothelial Growth Factor and its Receptors in Male Fertility" *Fertility and Sterility* 72(2):269-275 (Aug. 1999).

Park et al., "Robo4 is a vascular-specific receptor that inhibits endothelial migration" *Dev Biol.* 261:251-267 (2003).

Partanen et al., "A Novel Endothelial Cell Surface Receptor Tyrosine Kinase with Extracellular Epidermal Growth Factor Homology Domains" *Molecular & Cellular Biology* 12(4):1698-1707 (Apr. 1992).

Petrenko et al., "The Molecular Characterization of the Fetal Stem Cell Marker AA4" *Immunity* 10:691-700 (Jun. 1999).

Rudikoff et al., "Single amino acid substitution altering antigen-binding specificity" *Proc. Natl. Acad. Sci. USA* 79:1979-1983 (Mar. 1982).

Ruggeri et al., "CEP-7055: a novel, orally active pan inhibitor of vascular endothelial growth factor receptor tyrosine kinases with potent antiangiogenic activity and antitumor efficacy in preclinical models" *Cancer Research* 63:5978-5991 (Sep. 15, 2003).

Rupnick et al., "Adipose tissue mass can be regulated through the vasculature" *Proc. Natl. Acad. Sci. USA* 99(16):10730-10735 (Aug. 6, 2002).

Sato et al., "Distinct roles of the receptor tyrosine kinases Tie-1 and Tie-2 in blood vessel formation" *Nature* 376:70-74 (Jul. 6, 1995).

Sato et al., "ie-1 and tie-2 define another class of putative receptor tyrosine kinase genes expressed in early embryonic vascular system" *Proc. Nat'l Acad. Sci. USA* 90:9355-9358 (Oct. 1993).

Schuler et al., "Pieces of the Puzzle: Expressed Sequence Tags and the Catalog of Human Genes" *J. Mol. Med.* 75:694-698 (1997).

Seaver, "Monoclonal Antibodies in Industry: More Difficult Than Originally Thought" *Genetic Engineering News* pp. 10 and 21 (Aug. 1994).

Seth et al., "Magic roundabout, a tumor endothelial marker: expression and signaling" *Biochem Biophys Res Commun.* 332:533-41 (2005).

Shalaby et al., "Failure of blood-island formation and vasculogenesis in Flk-1-deficient mice" *Nature* 376:62-66 (Jul. 6, 1995).

Shibuya et al., "Nucleotide Sequence and Expression of a Novel Human Receptor-Type Tyrosine Kinase Gene (flt) Closely Related to the fms Family" *Oncogene* 5:519-524 (1990).

Sierra-Honigmann et al., "Biological action of leptin as an angiogenic factor" *Science* 281:1683-1686 (Sep. 11, 1998).

Skolnick et al., "From Genes to protein structure and function: novel applications of computational approaches in the genomic era" *TIBTECH* 18:34-39 (Jan. 2000).

Soker et al., "Neuropilin-1 is Expressed by Endothelial and Tumor Cells as an Isoform-Specific Receptor for Vascular Endothelial Growth Factor" *Cell* 92:735-745 (Mar. 20, 1998).

Sporn et al., "Biosynthesis of von Willebrand Protein by Human Megakaryocytes" *J. Clin. Invest.* 76(3):1102-1106 (Sep. 1985).

Stein and Cheng, "Antisense oligonucleotides as therapeutic agents—is the bullet really magical?" *Science* 261:1004-1012 (Aug. 20, 1993).

Strausberg et al., "New Opportunities for Uncovering the Molecular Basis of Cancer" *Nat. Genet.* special issue:415-416 (Apr. 1997).

Suchting et al., "Soluble Robo4 receptor inhibits in vivo angiogenesis and endothelial cell migration" *FASEB J.* 19:121-3 (Jan. 2005).

Suda et al., "Hematopoiesis and Angiogenesis" *Int'l J. of Hematol.* 71:99-107 (2000).

Sun et al., "Blocking Angiogenesis and Tumorigenesis with GFA-116, a Synthetic Molecule Cancer Research that Inhibits Binding of Vascular Endothelial Growth Factor to its Receptor" *Cancer Research* 64:3586-3592 (May 15, 2004).

Tamura et al., "cDNA cloning and gene expression of human type Ialpha cGMP-dependent protein kinase" *Hypertension* 27(Pt 2):552-557 (1996).

Trachsel et al., "Antibodies for angiogenesis inhibition, vascular targeting and endothelial cell transcytosis" *Advanced Drug Delivery Reviews* 58:735-754 (2006).

Vajdos et al., "Comprehensive functional maps of the antigen-binding site of an anti-ErbB2 antibody obtained with shotgun scanning mutagenesis" *J Mol Biol.* 320:415-428 (2002).

Van der Schaft et al., "The Designer Antiangiogenic Peptide Anginex Targets Tumor Endothelial Cells and Inhibits Tumor Growth in Animal Models" *The FASEB Journal* 16:1991-3 (Dec. 2002).

Vasmatzis et al., "Discovery of three genes specifically expressed in human prostate by expressed sequence tag database analysis" *Proc. Nat'l Acad. Sci. USA* 95:300-304 (Jan. 1998).

Velculescu et al., "Serial analysis of gene expression" *Science* 270:484-487 (Oct. 20, 1995).

Verhoeyen et al., "Reshaping Human Antibodies: Grafting an Antilysozyme Activity" *Science* 239:1534-1536 (Mar. 1988).

Verma et al., "Gene therapy—promises, problems and prospects" *Nature* 389:239-242 (Sep. 18, 1997).

Vikkula et al., "Vascular dysmorphogenesis caused by an activating mutation in the receptor tyrosine kinase TIE2" *Cell* 87:1181-1190 (Dec. 27, 1996).

von Heijne, G., "Membrane protein structure prediction. Hydrophobicity analysis and the positive-inside rule" *J. Mol. Biol.* 225:487-494 (1992).

Welle et al., "Inventory of High-Abundance mRNAs in Skeletal Muscle of Normal Men" *Genome Research* 9(5):506-513 (1999).

Ziegler et al., "KDR Receptor: A Key Marker Defining Hematopoietic Stem Cells" *Science* 285:1553-1558 (Sep. 3, 1999).

"NCI Nanotechnology in Cancer" *National Cancer Institute* (Monthly Feature) pp. 1-3 (Jul. 2005).

"The Unexpected Brains Behind Blood Vessel Growth" *Development Biology* 307:665-667 (Feb. 4, 2005).

Carmeliet et al., "Common mechanisms of nerve and blood vessel wiring" *Nature* 436:193-199 (Jul. 14, 2005).

Cognet et al., "Single metallic nanoparticle imaging for protein detection in cells" *Proc. Natl. Acad. Sci. USA* 100(20):11350-11355 (Sep. 30, 2003).

Jones et al., "Common Cues Regulate Neural and Vascular Patterning" *Curr Opin Genet Dev.* 17(4):332-336 (Aug. 2007).

Klagsbrun et al., "A role for axon guidance receptors and ligands in blood vessel development and tumor angiogenesis" *Cytokine & Growth Factor Reviews* 16:535-548 (2005).

Lanza et al., "Targeted Antiproliferative Drug Delivery to Vascular Smooth Muscle Cells With a Magnetic Resonance Imaging Nanoparticle Contrast Agent" *Circulation* pp. 2842-2847 (Nov. 26, 2002).

Tartis et al., "Therapeutic Effects of Paclitaxel-Containing Ultrasound Contrast Agents" *Ultrasound in Medicine and Biology* 32(11):1771-1780 (2006).

* cited by examiner

Anti-Robo4 Antibody Variable Light Chain Alignment

|  |  | LC-FR1 |  |  |  |  |  |  |  |  |  |  |  |  |  |  |  |  |  |  |  |  | HVR-L1 |  |  |  |  |  |  |  |  |  |  |  | LC-FR2 |  |  |  |  |
|---|---|---|---|---|---|---|---|---|---|---|---|---|---|---|---|---|---|---|---|---|---|---|---|---|---|---|---|---|---|---|---|---|---|---|---|---|---|---|---|
| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 |
|  |  |  |  |  |  |  |  |  |  |  |  |  |  |  |  |  |  |  |  |  |  |  |  | Kabat - CDR L1 |  |  |  |  |  |  |  |  |  |  |  |  |  |  |  |  |
|  |  |  |  |  |  |  |  |  |  |  |  |  |  |  |  |  |  |  |  |  |  |  |  | Chothia - CDR L1 |  |  |  |  |  |  |  |  |  |  |  |  |  |  |  |  |
|  |  |  |  |  |  |  |  |  |  |  |  |  |  |  |  |  |  |  |  |  |  |  |  |  |  |  | Contact - CDR L1 |  |  |  |  |  |  |  |  |  |  |  |  |
| YW71.6VL | D | I | Q | M | T | Q | S | P | S | S | L | S | A | S | V | G | D | R | V | T | I | T | C | R | A | S | Q | D | V | S | T | A | V | A | W | Y | Q | Q | K | P |
| YW71.1VL | D | I | Q | M | T | Q | S | P | S | S | L | S | A | S | V | G | D | R | V | T | I | T | C | R | A | S | Q | D | V | S | T | A | V | A | W | Y | Q | Q | K | P |
| YW71.22VL | D | I | Q | M | T | Q | S | P | S | S | L | S | A | S | V | G | D | R | V | T | I | T | C | R | A | S | Q | D | V | S | T | A | V | A | W | Y | Q | Q | K | P |
| YW71.89VL | D | I | Q | M | T | Q | S | P | S | S | L | S | A | S | V | G | D | R | V | T | I | T | C | R | A | S | Q | D | V | S | T | A | V | A | W | Y | Q | Q | K | P |
| YW79.1VL | D | I | Q | M | T | Q | S | P | S | S | L | S | A | S | V | G | D | R | V | T | I | T | C | R | A | S | Q | S | I | S | S | Y | L | A | W | Y | Q | Q | K | P |
| YW79.8VL | D | I | Q | M | T | Q | S | P | S | S | L | S | A | S | V | G | D | R | V | T | I | T | C | R | A | S | Q | S | I | S | S | Y | L | A | W | Y | Q | Q | K | P |
| YW79.11VL | D | I | Q | M | T | Q | S | P | S | S | L | S | A | S | V | G | D | R | V | T | I | T | C | R | A | S | Q | S | I | S | S | Y | L | A | W | Y | Q | Q | K | P |

FIG. 1A-2

| Kabat# | 41 42 43 44 45 46 47 48 49 | HVR-L2<br>50 51 52 53 54 55 56 | 57 58 59 60 61 62 63 64 65 66 67 68 69 70 71 72 73 74 75 76 77 78 79 80 |
|---|---|---|---|
| | | Kabat - CDR L2<br>Chothia - CDR L2<br>Contact - CDR L2 | LC-FR3 |
| YW71.6VL  | G K A P K L L I Y | S A S F L Y S | G V P S R F S G S G S G T D F T L T I S S L Q P |
| YW71.1VL  | G K A P K L L I Y | S A S F L Y S | G V P S R F S G S G S G T D F T L T I S S L Q P |
| YW71.22VL | G K A P K L L I Y | S A S F L Y S | G V P S R F S G S G S G T D F T L T I S S L Q P |
| YW71.89VL | G K A P K L L I Y | S A S F L Y S | G V P S R F S G S G S G T D F T L T I S S L Q P |
| YW79.1VL  | G K A P K L L I Y | G A S S R A S | G V P S R F S G S G S G T D F T L T I S S L Q P |
| YW79.8VL  | G K A P K L L I Y | G A S S R A S | G V P S R F S G S G S G T D F T L T I S S L Q P |
| YW79.11VL | G K A P K L L I Y | G A S S R A S | G V P S R F S G S G S G T D F T L T I S S L Q P |

| Kabat# | 81 82 83 84 85 86 87 88 | HVR-L3<br>89 90 91 92 93 94 95 96 97 | 98 99 100 101 102 103 104 105 106 107 108 | SEQ ID NO: |
|---|---|---|---|---|
| | | Kabat - CDR L3<br>Chothia - CDR L3<br>Contact - CDR L3 | LC-FR4 | |
| YW71.6VL  | E D F A T Y Y C | Q Q S Y T T P P T | F G Q G T K V E I K R | 72 |
| YW71.1VL  | E D F A T Y Y C | Q Q S Y T T P P T | F G Q G T K V E I K R | 73 |
| YW71.22VL | E D F A T Y Y C | Q Q S Y T T P P T | F G Q G T K V E I K R | 74 |
| YW71.89VL | E D F A T Y Y C | Q Q S Y T T P P T | F G Q G T K V E I K R | 75 |
| YW79.1VL  | E D F A T Y Y C | Q Q S W S Y P L T | F G Q G T K V E I K R | 76 |
| YW79.8VL  | E D F A T Y Y C | Q Q S Y N T P F T | F G Q G T K V E I K R | 77 |
| YW79.11VL | E D F A T Y Y C | Q Q Y Y S S P L T | F G Q G T K V E I K R | 78 |

FIG. 1B

| FIG. 1B-1 |
|-----------|
| FIG. 1B-2 |

*FIG. 1B-1*

Anti-Robo4 Antibody Variable Heavy Chain Alignment

HC-FR1                                          HVR-H1                 HC-FR2

Chothia - CDR H1 | Kabat - CDR H1
Contact - CDRH1

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| YW71.6VH | E | V | Q | L | V | E | S | G | G | G | L | V | Q | P | G | G | S | L | R | L | S | C | A | A | S | G | F | T | I | S | G | S | W | I | H | W | V | R | Q | A | P | G |
| YW71.1VH | E | V | Q | L | V | E | S | G | G | G | L | V | Q | P | G | G | S | L | R | L | S | C | A | A | S | G | F | T | I | T | N | Y | W | I | H | W | V | R | Q | A | P | G |
| YW71.22VH | E | V | Q | L | V | E | S | G | G | G | L | V | Q | P | G | G | S | L | R | L | S | C | A | A | S | G | F | T | I | N | G | Y | Y | I | H | W | V | R | Q | A | P | G |
| YW71.89VH | E | V | Q | L | V | E | S | G | G | G | L | V | Q | P | G | G | S | L | R | L | S | C | A | A | S | G | F | T | I | N | N | Y | Y | I | H | W | V | R | Q | A | P | G |
| YW79.1VH | E | V | Q | L | V | E | S | G | G | G | L | V | Q | P | G | G | S | L | R | L | S | C | A | A | S | G | Y | T | F | S | S | Y | W | I | S | W | V | R | Q | A | P | G |
| YW79.8VH | E | V | Q | L | V | E | S | G | G | G | L | V | Q | P | G | G | S | L | R | L | S | C | A | A | S | G | F | T | F | S | S | R | Y | M | S | W | V | R | Q | A | P | G |
| YW79.11VH | E | V | Q | L | V | E | S | G | G | G | L | V | Q | P | G | G | S | L | R | L | S | C | A | A | S | G | F | T | F | S | S | Y | A | M | S | W | V | R | Q | A | P | G |

HVR-H2

| Kabat# | 43 | 44 | 45 | 46 | 47 | 48 | 49 | 50 | 51 | 52 | a | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | a |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
|  |  |  |  |  |  |  |  |  |  |  |  |  |  |  |  |  |  |  |  |  |  |  |  |  |  |  |  |  | Kabat - CDR H2 | | | | | | | | | | | | HC-FR3 | | |
|  |  |  |  |  |  |  |  |  |  |  |  |  |  |  | Chothia - CDR H2 | | | | | | | | | | | | | | | | | | | | | | | | | | | |
|  |  |  |  |  |  |  |  |  |  |  |  |  | Contact - CDR H2 | | | | | | | | | | | | | | | | | | | | | | | | | | | | |
| YW71.6VH | K | G | L | E | W | V | A | V | I | T | P | A | G | Y | T | Y | A | D | S | V | K | G | R | F | T | I | S | A | D | T | S | K | N | T | A | Y | L | Q | M | N |
| YW71.1VH | K | G | L | E | W | V | G | I | H | Y | P | A | D | Y | Y | Y | A | D | S | V | K | G | R | F | T | I | S | A | D | T | S | K | N | T | A | Y | L | Q | M | N |
| YW71.22VH | K | G | L | E | W | V | G | F | H | Y | P | A | G | G | D | Y | A | D | S | V | K | G | R | F | T | I | S | A | D | T | S | K | N | T | A | Y | L | Q | M | N |
| YW71.89VH | K | G | L | E | W | V | A | I | S | P | T | G | G | T | G | Y | A | D | S | V | K | G | R | F | T | I | S | A | D | T | S | K | N | T | A | Y | L | Q | M | N |
| YW79.1VH | K | G | L | E | W | V | S | T | H | Y | G | Y | D | G | S | T | Y | A | D | S | V | K | G | R | F | T | I | S | A | D | T | S | K | N | T | A | Y | L | Q | M | N |
| YW79.8VH | K | G | L | E | W | V | S | G | H | H | G | Y | M | G | G | T | Y | Y | A | D | S | V | K | G | R | F | T | I | S | A | D | T | S | K | N | T | A | Y | L | Q | M | N |
| YW79.11VH | K | G | L | E | W | V | S | G | H | S | P | Y | G | Y | P | Y | A | D | S | V | K | G | R | F | T | I | S | A | D | T | S | K | N | T | A | Y | L | Q | M | N |

HVR-H3

| Kabat# | b | c | 83 | 84 | 85 | 86 | 87 | 88 | 89 | 90 | 91 | 92 | 93 | 94 | 95 | 96 | 97 | 98 | 99 | 100 | a | b | c | d | e | f | g | h | 101 | 102 | 103 | 104 | 105 | 106 | 107 | 108 | 109 | 110 | 111 | 112 | 113 | SEQ ID NO: |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
|  |  |  |  |  |  |  |  |  |  |  |  |  |  | Kabat - CDR H3 | | | | | | | | | | | | | | | | | | | | | | HC-FR4 | | | | | |
|  |  |  |  |  |  |  |  |  |  |  |  |  | Chothia - CDR H3 | | | | | | | | | | | | | | | | | | | | | | | | | | | | |
|  |  |  |  |  |  |  |  |  |  |  |  | Contact - CDR H3 | | | | | | | | | | | | | | | | | | | | | | | | | | | | | |
| YW71.6VH | S | L | R | A | E | D | T | A | V | Y | Y | C | A | R | S | N | R | Y | S | G | Q | F | V | P | A | Y | A | M | D | Y | W | G | Q | G | T | L | V | T | V | S | S | 140 |
| YW71.1VH | S | L | R | A | E | D | T | A | V | Y | Y | C | A | S | S | G | G | Y | S | S | – | – | – | – | – | L | A | Y | W | G | Q | G | T | L | V | T | V | S | S | 141 |
| YW71.22VH | S | L | R | A | E | D | T | A | V | Y | Y | C | A | R | L | I | G | N | K | F | G | W | S | S | Y | G | – | M | D | Y | W | G | Q | G | T | L | V | T | V | S | S | 142 |
| YW71.89VH | S | L | R | A | E | D | T | A | V | Y | Y | C | A | R | D | V | N | V | Y | S | A | R | W | D | Y | – | V | M | D | V | W | G | Q | G | T | L | V | T | V | S | S | 143 |
| YW79.1VH | S | L | R | A | E | D | T | A | V | Y | Y | C | A | R | M | S | Y | N | W | S | S | P | G | H | G | – | – | M | D | Y | W | G | Q | G | T | L | V | T | V | S | S | 144 |
| YW79.8VH | S | L | R | A | E | D | T | A | V | Y | Y | C | A | R | G | N | Y | Y | S | G | S | E | – | – | – | – | F | D | Y | W | G | Q | G | T | L | V | T | V | S | S | 145 |
| YW79.11VH | S | L | R | A | E | D | T | A | V | Y | Y | C | A | R | W | G | Y | Y | M | P | Y | G | H | P | V | – | – | M | D | V | W | G | Q | G | T | L | V | T | V | S | S | 146 |

| FIG. 2A-1 |
| FIG. 2A-2 |
| FIG. 2A-3 |

FIG. 2A-1

Anti-Robo4 Antibody - Affinity Matured Variants
Variable Light Chain Alignment

\* HVR-L1
\*\* HVR-L2
\*\*\* HVR-L3

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | LC-FR1 | | | | | | | | | | | | | | Kabat - CDR L1 | | | | | | | | | | | * | | | | LC-FR2 | |
| | | | | | | | | | | | | | | | | | | | | | | | | Chothia - CDR L1 | | | | | | | | | | | | | | | | |
| | | | | | | | | | | | | | | | | | | | | | | | | | | Contact - CDR L1 | | | | | | | | | | | | | |
| YW71.22 VL    | D | I | Q | M | T | Q | S | P | S | S | L | S | A | S | V | G | D | R | V | T | I | T | C | R | A | S | Q | D | V | S | T | A | V | A | W | Y | Q | Q | K | P |
| YW71.22.S1.2 VL  | D | I | Q | M | T | Q | S | P | S | S | L | S | A | S | V | G | D | R | V | T | I | T | C | R | A | S | Q | D | V | S | T | A | V | A | W | Y | Q | Q | K | P |
| YW71.22.S1.8 VL  | D | I | Q | M | T | Q | S | P | S | S | L | S | A | S | V | G | D | R | V | T | I | T | C | R | A | S | Q | D | V | S | I | A | V | A | W | Y | Q | Q | K | P |
| YW71.22.S1.16 VL | D | I | Q | M | T | Q | S | P | S | S | L | S | A | S | V | G | D | R | V | T | I | T | C | R | A | S | Q | D | V | S | T | A | V | A | W | Y | Q | Q | K | P |
| YW71.22.S1.23 VL | D | I | Q | M | T | Q | S | P | S | S | L | S | A | S | V | G | D | R | V | T | I | T | C | R | A | S | Q | D | V | S | T | A | V | A | W | Y | Q | Q | K | P |
| YW71.22.S1.24 VL | D | I | Q | M | T | Q | S | P | S | S | L | S | A | S | V | G | D | R | V | T | I | T | C | R | A | S | Q | D | V | S | T | A | V | A | W | Y | Q | Q | K | P |
| YW71.22.S1.27 VL | D | I | Q | M | T | Q | S | P | S | S | L | S | A | S | V | G | D | R | V | T | I | T | C | R | A | S | Q | D | V | S | T | A | V | A | W | Y | Q | Q | K | P |
| YW71.22.S1.31 VL | D | I | Q | M | T | Q | S | P | S | S | L | S | A | S | V | G | D | R | V | T | I | T | C | R | A | S | Q | D | V | S | T | A | V | A | W | Y | Q | Q | K | P |
| YW71.22.S1.38 VL | D | I | Q | M | T | Q | S | P | S | S | L | S | A | S | V | G | D | R | V | T | I | T | C | R | A | S | Q | D | V | S | T | A | V | A | W | Y | Q | Q | K | P |
| YW71.22.S1.77 VL | D | I | Q | M | T | Q | S | P | S | S | L | S | A | S | V | G | D | R | V | T | I | T | C | R | A | S | Q | D | V | S | T | A | V | A | W | Y | Q | Q | K | P |
| YW71.22.S2.21 VL | D | I | Q | M | T | Q | S | P | S | S | L | S | A | S | V | G | D | R | V | T | I | T | C | R | A | S | Q | D | V | S | T | A | V | A | W | Y | Q | Q | K | P |
| YW71.22.S2.29 VL | D | I | Q | M | T | Q | S | P | S | S | L | S | A | S | V | G | D | R | V | T | I | T | C | R | A | S | Q | D | V | S | T | A | V | A | W | Y | Q | Q | K | P |
| YW71.22.S2.39 VL | D | I | Q | M | T | Q | S | P | S | S | L | S | A | S | V | G | D | R | V | T | I | T | C | R | A | S | Q | D | V | S | T | A | V | A | W | Y | Q | Q | K | P |
| YW71.22.S2.79 VL | D | I | Q | M | T | Q | S | P | S | S | L | S | A | S | V | G | D | R | V | T | I | T | C | R | A | S | Q | D | V | S | T | A | V | A | W | Y | Q | Q | K | P |
| YW71.22.H1.2 VL  | D | I | Q | M | T | Q | S | P | S | S | L | S | A | S | V | G | D | R | V | T | I | T | C | R | A | S | Q | D | V | S | T | A | V | A | W | Y | Q | Q | K | P |
| YW71.22.H1.9 VL  | D | I | Q | M | T | Q | S | P | S | S | L | S | A | S | V | G | D | R | V | T | I | T | C | R | A | S | Q | D | V | S | T | A | V | A | W | Y | Q | Q | K | P |
| YW71.22.H1.46 VL | D | I | Q | M | T | Q | S | P | S | S | L | S | A | S | V | G | D | R | V | T | I | T | C | R | A | S | Q | D | V | S | T | A | V | A | W | Y | Q | Q | K | P |
| YW71.22.H1.77 VL | D | I | Q | M | T | Q | S | P | S | S | L | S | A | S | V | G | D | R | V | T | I | T | C | R | A | S | Q | D | G | S | R | S | L | A | W | Y | Q | Q | K | P |
| YW71.22.H1.91 VL | D | I | Q | M | T | Q | S | P | S | S | L | S | A | S | V | G | D | R | V | T | I | T | C | R | A | S | Q | D | G | A | I | Y | L | A | W | Y | Q | Q | K | P |
| YW71.22.H2.31 VL | D | I | Q | M | T | Q | S | P | S | S | L | S | A | S | V | G | D | R | V | T | I | T | C | R | A | S | Q | D | V | S | T | A | V | A | W | Y | Q | Q | K | P |

FIG. 2A-2

| Kabat# | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | Kabat - CDR L2 | | | | | | ** | | | | | | | | | | | | | LC-FR3 | | | | | | | | | | | |
| | | | | | | | | | | | Chothia - CDR L2 | | | | | | | | | | | | | | | | | | | | | | | | | | | | | |
| | | | | | | | | Contact - CDR L2 | | | | | | | | | | | | | | | | | | | | | | | | | | | | | | | |
| YW71.22 VL | G | K | A | P | K | L | L | I | Y | S | A | S | F | L | Y | S | G | V | P | S | R | F | S | G | S | G | S | G | T | D | F | T | L | T | I | S | S | L | Q | P |
| YW71.22.S1.2 VL | G | K | A | P | K | L | L | I | Y | S | A | S | F | L | Y | S | G | V | P | S | R | F | S | G | S | G | S | G | T | D | F | T | L | T | I | S | S | L | Q | P |
| YW71.22.S1.8 VL | G | K | A | P | K | L | L | I | Y | S | A | S | F | L | Y | S | G | V | P | S | R | F | S | G | S | G | S | G | T | D | F | T | L | T | I | S | S | L | Q | P |
| YW71.22.S1.16 VL | G | K | A | P | K | L | L | I | Y | S | A | S | F | L | Y | S | G | V | P | S | R | F | S | G | S | G | S | G | T | D | F | T | L | T | I | S | S | L | Q | P |
| YW71.22.S1.23 VL | G | K | A | P | K | L | L | I | Y | S | A | S | F | L | Y | S | G | V | P | S | R | F | S | G | S | G | S | G | T | D | F | T | L | T | I | S | S | L | Q | P |
| YW71.22.S1.24 VL | G | K | A | P | K | L | L | I | Y | S | A | S | F | L | Y | S | G | V | P | S | R | F | S | G | S | G | S | G | T | D | F | T | L | T | I | S | S | L | Q | P |
| YW71.22.S1.27 VL | G | K | A | P | K | L | L | I | Y | S | A | S | F | L | Y | S | G | V | P | S | R | F | S | G | S | G | S | G | T | D | F | T | L | T | I | S | S | L | Q | P |
| YW71.22.S1.31 VL | G | K | A | P | K | L | L | I | Y | S | A | S | F | L | Y | S | G | V | P | S | R | F | S | G | S | G | S | G | T | D | F | T | L | T | I | S | S | L | Q | P |
| YW71.22.S1.38 VL | G | K | A | P | K | L | L | I | Y | S | A | S | F | L | Y | S | G | V | P | S | R | F | S | G | S | G | S | G | T | D | F | T | L | T | I | S | S | L | Q | P |
| YW71.22.S1.77 VL | G | K | A | P | K | L | L | I | Y | S | A | S | F | L | Y | S | G | V | P | S | R | F | S | G | S | G | S | G | T | D | F | T | L | T | I | S | S | L | Q | P |
| YW71.22.S2.21 VL | G | K | A | P | K | L | L | I | Y | S | A | S | F | L | A | S | G | V | P | S | R | F | S | G | S | G | S | G | T | D | F | T | L | T | I | S | S | L | Q | P |
| YW71.22.S2.29 VL | G | K | A | P | K | L | L | I | Y | S | A | S | F | L | Y | Y | G | V | P | S | R | F | S | G | S | G | S | G | T | D | F | T | L | T | I | S | S | L | Q | P |
| YW71.22.S2.39 VL | G | K | A | P | K | L | L | I | Y | S | A | T | F | L | E | S | G | V | P | S | R | F | S | G | S | G | S | G | T | D | F | T | L | T | I | S | S | L | Q | P |
| YW71.22.S2.79 VL | G | K | A | P | K | L | L | I | Y | S | A | S | F | L | A | S | G | V | P | S | R | F | S | G | S | G | S | G | T | D | F | T | L | T | I | S | S | L | Q | P |
| YW71.22.H1.2 VL | G | K | A | P | K | L | L | I | Y | S | A | S | F | L | E | - | G | V | P | S | R | F | S | G | S | G | S | G | T | D | F | T | L | T | I | S | S | L | Q | P |
| YW71.22.H1.9 VL | G | K | A | P | K | L | L | I | Y | S | A | S | F | L | A | - | G | V | P | S | R | F | S | G | S | G | S | G | T | D | F | T | L | T | I | S | S | L | Q | P |
| YW71.22.H1.46 VL | G | K | A | P | K | L | L | I | Y | S | A | S | N | L | A | S | G | V | P | S | R | F | S | G | S | G | S | G | T | D | F | T | L | T | I | S | S | L | Q | P |
| YW71.22.H1.77 VL | G | K | A | P | K | L | L | I | Y | S | A | T | T | L | A | S | G | V | P | S | R | F | S | G | S | G | S | G | T | D | F | T | L | T | I | S | S | L | Q | P |
| YW71.22.H1.91 VL | G | K | A | P | K | L | L | I | Y | S | A | S | F | L | A | S | G | V | P | S | R | F | S | G | S | G | S | G | T | D | F | T | L | T | I | S | S | L | Q | P |
| YW71.22.H2.31 VL | G | K | A | P | K | L | L | I | Y | S | A | S | T | L | A | S | G | V | P | S | R | F | S | G | S | G | S | G | T | D | F | T | L | T | I | S | S | L | Q | P |

FIG. 2A-3

| Kabat# | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | SEQ ID NO: |
|---|---|---|---|---|---|---|---|---|---|---|---|---|---|---|---|---|---|---|---|---|---|---|---|---|---|---|---|---|---|
| | | | | | | | | | | Kabat - CDR L3 | | | | | | | | | | | | | LC-FR4 | | | | | | |
| | | | | | | | | | | | Chothia - CDR L3 | | | | | | | | | | | | | | | | | | |
| | | | | | | | | | | | | Contact - CDR L3 | | | | | | | | | | | | | | | | |
| YW71.22 VL | E | D | F | A | T | Y | C | Q | Q | S | Y | T | T | P | P | T | F | G | Q | G | T | K | V | E | I | K | R | | 74 |
| YW71.22.S1.2 VL | E | D | F | A | T | Y | C | Q | Q | S | F | A | A | T | P | A | T | F | G | Q | G | T | K | V | E | I | K | R | 79 |
| YW71.22.S1.8 VL | E | D | F | A | T | Y | C | Q | Q | S | R | A | S | A | L | P | T | F | G | Q | G | T | K | V | E | I | K | R | 80 |
| YW71.22.S1.16 VL | E | D | F | A | T | Y | C | Q | Q | S | R | S | D | T | H | P | T | F | G | Q | G | T | K | V | E | I | K | R | 81 |
| YW71.22.S1.23 VL | E | D | F | A | T | Y | C | Q | Q | S | R | T | N | P | T | P | T | F | G | Q | G | T | K | V | E | I | K | R | 82 |
| YW71.22.S1.24 VL | E | D | F | A | T | Y | C | Q | Q | P | F | D | L | P | P | M | T | F | G | Q | G | T | K | V | E | I | K | R | 83 |
| YW71.22.S1.27 VL | E | D | F | A | T | Y | C | Q | Q | P | N | S | T | P | H | F | T | F | G | Q | G | T | K | V | E | I | K | R | 84 |
| YW71.22.S1.31 VL | E | D | F | A | T | Y | C | Q | Q | S | R | F | D | I | T | S | T | F | G | Q | G | T | K | V | E | I | K | R | 85 |
| YW71.22.S1.38 VL | E | D | F | A | T | Y | C | Q | Q | S | Y | H | T | H | P | P | T | F | G | Q | G | T | K | V | E | I | K | R | 86 |
| YW71.22.S1.77 VL | E | D | F | A | T | Y | C | Q | Q | S | R | D | I | M | P | A | T | F | G | Q | G | T | K | V | E | I | K | R | 87 |
| YW71.22.S2.21 VL | E | D | F | A | T | Y | C | Q | Q | S | R | N | V | M | P | P | T | F | G | Q | G | T | K | V | E | I | K | R | 88 |
| YW71.22.S2.29 VL | E | D | F | A | T | Y | C | Q | Q | T | T | T | H | I | P | F | T | F | G | Q | G | T | K | V | E | I | K | R | 89 |
| YW71.22.S2.39 VL | E | D | F | A | T | Y | C | Q | Q | T | Y | A | Y | P | P | P | T | F | G | Q | G | T | K | V | E | I | K | R | 90 |
| YW71.22.S2.79 VL | E | D | F | A | T | Y | C | Q | Q | S | Y | D | L | G | G | P | T | F | G | Q | G | T | K | V | E | I | K | R | 91 |
| YW71.22.H1.2 VL | E | D | F | A | T | Y | C | Q | Q | S | Y | N | Y | P | P | F | T | F | G | Q | G | T | K | V | E | I | K | R | 92 |
| YW71.22.H1.9 VL | E | D | F | A | T | Y | C | Q | Q | F | Y | S | D | P | P | F | T | F | G | Q | G | T | K | V | E | I | K | R | 93 |
| YW71.22.H1.46 VL | E | D | F | A | T | Y | C | Q | Q | Q | G | Y | N | Y | P | F | T | F | G | Q | G | T | K | V | E | I | K | R | 94 |
| YW71.22.H1.77 VL | E | D | F | A | T | Y | C | Q | Q | S | Y | T | T | P | P | T | F | G | Q | G | T | K | V | E | I | K | R | 95 |
| YW71.22.H1.91 VL | E | D | F | A | T | Y | C | Q | Q | S | Y | T | T | P | P | T | F | G | Q | G | T | K | V | E | I | K | R | 96 |
| YW71.22.H2.31 VL | E | D | F | A | T | Y | C | Q | Q | S | Y | T | T | P | P | T | F | G | Q | G | T | K | V | E | I | K | R | 97 |

FIG. 2B

| FIG. 2B-1 |
| FIG. 2B-2 |
| FIG. 2B-3 |

FIG. 2B-1

Anti-Robo4 Antibody - Affinity Matured Variants
Variable Heavy Chain Alignment

\* HVR-H1  
\*\* HVR-H2  
\*\*\* HVR-H3

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | HC-FR1 | | | | | | | | | | | | | | | | | | | | | | | | | | | | HC-FR2 | | |
| YW71.22 VH              | E | V | Q | L | V | E | S | G | G | G | L | V | Q | P | G | G | S | L | R | L | S | C | A | A | S | G | F | T | I | N | G | Y | Y | I | H | W | V | R | Q | A | P | G |
| YW71.22.S1.2 VH         | E | V | Q | L | V | E | S | G | G | G | L | V | Q | P | G | G | S | L | R | L | S | C | A | A | S | G | F | S | I | Y | S | Y | Y | F | E | W | V | R | Q | A | P | G |
| YW71.22.S1.8 VH         | E | V | Q | L | V | E | S | G | G | G | L | V | Q | P | G | G | S | L | R | L | S | C | A | A | S | G | F | T | I | N | G | Y | Y | I | H | W | V | R | Q | A | P | G |
| YW71.22.S1.16 VH        | E | V | Q | L | V | E | S | G | G | G | L | V | Q | P | G | G | S | L | R | L | S | C | A | A | S | G | F | T | I | H | G | Y | Y | I | H | W | V | R | Q | A | P | G |
| YW71.22.S1.23 VH        | E | V | Q | L | V | E | S | G | G | G | L | V | Q | P | G | G | S | L | R | L | S | C | A | A | S | G | F | T | I | H | G | Y | Y | I | H | W | V | R | Q | A | P | G |
| YW71.22.S1.24 VH        | E | V | Q | L | V | E | S | G | G | G | L | V | Q | P | G | G | S | L | R | L | S | C | A | A | S | G | F | T | I | H | G | Y | Y | I | H | W | V | R | Q | A | P | G |
| YW71.22.S1.27 VH        | E | V | Q | L | V | E | S | G | G | G | L | V | Q | P | G | G | S | L | R | L | S | C | A | A | S | G | F | T | I | D | G | Y | Y | L | H | W | V | R | Q | A | P | G |
| YW71.22.S1.31 VH        | E | V | Q | L | V | E | S | G | G | G | L | V | Q | P | G | G | S | L | R | L | S | C | A | A | S | G | F | T | I | H | G | Y | Y | N | Q | W | V | R | Q | A | P | G |
| YW71.22.S1.38 VH        | E | V | Q | L | V | E | S | G | G | G | L | V | Q | P | G | G | S | L | R | L | S | C | A | A | S | G | F | S | I | K | G | Y | Y | I | Q | W | V | R | Q | A | P | G |
| YW71.22.S1.77 VH        | E | V | Q | L | V | E | S | G | G | G | L | V | Q | P | G | G | S | L | R | L | S | C | A | A | S | G | F | T | I | N | G | Y | Y | I | H | W | V | R | Q | A | P | G |
| YW71.22.S2.21 VH        | E | V | Q | L | V | E | S | G | G | G | L | V | Q | P | G | G | S | L | R | L | S | C | A | A | S | G | F | T | I | N | G | Y | Y | I | H | W | V | R | Q | A | P | G |
| YW71.22.S2.29 VH        | E | V | Q | L | V | E | S | G | G | G | L | V | Q | P | G | G | S | L | R | L | S | C | A | A | S | G | F | T | I | N | G | Y | Y | I | H | W | V | R | Q | A | P | G |
| YW71.22.S2.39 VH        | E | V | Q | L | V | E | S | G | G | G | L | V | Q | P | G | G | S | L | R | L | S | C | A | A | S | G | F | T | I | N | G | Y | Y | I | H | W | V | R | Q | A | P | G |
| YW71.22.S2.79 VH        | E | V | Q | L | V | E | S | G | G | G | L | V | Q | P | G | G | S | L | R | L | S | C | A | A | S | G | F | T | I | N | G | Y | Y | I | H | W | V | R | Q | A | P | G |
| YW71.22.H1.2 VH         | E | V | Q | L | V | E | S | G | G | G | L | V | Q | P | G | G | S | L | R | L | S | C | A | A | S | G | F | T | I | N | G | Y | Y | I | H | W | V | R | Q | A | P | G |
| YW71.22.H1.9 VH         | E | V | Q | L | V | E | S | G | G | G | L | V | Q | P | G | G | S | L | R | L | S | C | A | A | S | G | F | T | I | N | G | Y | Y | I | H | W | V | R | Q | A | P | G |
| YW71.22.H1.46 VH        | E | V | Q | L | V | E | S | G | G | G | L | V | Q | P | G | G | S | L | R | L | S | C | A | A | S | G | F | T | I | N | G | Y | Y | I | H | W | V | R | Q | A | P | G |
| YW71.22.H1.77 VH        | E | V | Q | L | V | E | S | G | G | G | L | V | Q | P | G | G | S | L | R | L | S | C | A | A | S | G | F | T | I | N | G | Y | Y | I | H | W | V | R | Q | A | P | G |
| YW71.22.H1.91 VH        | E | V | Q | L | V | E | S | G | G | G | L | V | Q | P | G | G | S | L | R | L | S | C | A | A | S | G | F | T | I | N | G | Y | Y | I | H | W | V | R | Q | A | P | G |
| YW71.22.H2.31 VH        | E | V | Q | L | V | E | S | G | G | G | L | V | Q | P | G | G | S | L | R | L | S | C | A | A | S | G | F | T | I | N | G | Y | Y | I | H | W | V | R | Q | A | P | G |

Chothia - CDR H1: positions 26–32  
Kabat - CDR H1: positions 31–35  
Contact - CDR H1: positions 30–35

| Kabat# | b | c | 83 | 84 | 85 | 86 | 87 | 88 | 89 | 90 | 91 | 92 | 93 | 94 | 95 | 96 | 97 | 98 | 99 | 100 | a | b | c | d | e | f | g | h | 101 | 102 | 103 | 104 | 105 | 106 | 107 | 108 | 109 | 110 | 111 | 112 | 113 | SEQ ID NO: |
|---|---|---|---|---|---|---|---|---|---|---|---|---|---|---|---|---|---|---|---|---|---|---|---|---|---|---|---|---|---|---|---|---|---|---|---|---|---|---|---|---|---|
| YW71.22 VH | S | L | R | A | E | D | T | A | V | Y | Y | C | A | R | L | I | G | N | K | F | G | W | S | S | Y | G | - | M | D | Y | W | G | Q | G | T | L | V | T | V | S | 142 |
| YW71.22.S1.2 VH | S | L | R | A | E | D | T | A | V | Y | Y | C | A | R | L | H | G | N | K | F | G | W | S | S | Y | G | - | M | D | Y | W | G | Q | G | T | L | V | T | V | S | 147 |
| YW71.22.S1.8 VH | S | L | R | A | E | D | T | A | V | Y | Y | C | A | R | L | H | G | N | K | F | G | W | S | S | Y | G | - | M | D | Y | W | G | Q | G | T | L | V | T | V | S | 148 |
| YW71.22.S1.16 VH | S | L | R | A | E | D | T | A | V | Y | Y | C | A | R | L | H | G | N | K | F | G | W | S | S | Y | G | - | M | D | Y | W | G | Q | G | T | L | V | T | V | S | 149 |
| YW71.22.S1.23 VH | S | L | R | A | E | D | T | A | V | Y | Y | C | A | R | L | H | G | N | K | F | G | W | S | S | Y | G | - | M | D | Y | W | G | Q | G | T | L | V | T | V | S | 150 |
| YW71.22.S1.24 VH | S | L | R | A | E | D | T | A | V | Y | Y | C | A | R | L | H | G | N | K | F | G | W | S | S | Y | G | - | M | D | Y | W | G | Q | G | T | L | V | T | V | S | 151 |
| YW71.22.S1.27 VH | S | L | R | A | E | D | T | A | V | Y | Y | C | A | R | L | H | G | N | K | F | G | W | S | S | Y | G | - | M | D | Y | W | G | Q | G | T | L | V | T | V | S | 152 |
| YW71.22.S1.31 VH | S | L | R | A | E | D | T | A | V | Y | Y | C | A | R | L | H | G | N | K | F | G | W | S | S | Y | G | - | M | D | Y | W | G | Q | G | T | L | V | T | V | S | 153 |
| YW71.22.S1.38 VH | S | L | R | A | E | D | T | A | V | Y | Y | C | A | R | L | H | G | N | K | F | G | W | S | S | Y | G | - | M | D | Y | W | G | Q | G | T | L | V | T | V | S | 154 |
| YW71.22.S1.77 VH | S | L | R | A | E | D | T | A | V | Y | Y | C | A | R | L | H | G | N | K | F | G | W | S | S | Y | G | - | M | D | Y | W | G | Q | G | T | L | V | T | V | S | 155 |
| YW71.22.S2.21 VH | S | L | R | A | E | D | T | A | V | Y | Y | C | A | R | L | H | G | N | K | F | G | W | S | S | Y | G | - | M | D | Y | W | G | Q | G | T | L | V | T | V | S | 156 |
| YW71.22.S2.29 VH | S | L | R | A | E | D | T | A | V | Y | Y | C | A | R | L | H | G | N | K | F | G | W | S | S | Y | G | - | M | D | Y | W | G | Q | G | T | L | V | T | V | S | 157 |
| YW71.22.S2.39 VH | S | L | R | A | E | D | T | A | V | Y | Y | C | A | R | L | H | G | N | K | F | G | W | S | S | Y | G | - | M | D | Y | W | G | Q | G | T | L | V | T | V | S | 158 |
| YW71.22.S2.79 VH | S | L | R | A | E | D | T | A | V | Y | Y | C | A | R | L | H | G | N | K | F | G | W | S | S | Y | G | - | M | D | Y | W | G | Q | G | T | L | V | T | V | S | 159 |
| YW71.22.H1.2 VH | S | L | R | A | E | D | T | A | V | Y | Y | C | A | R | L | H | G | N | K | F | G | W | S | S | Y | G | - | M | D | Y | W | G | Q | G | T | L | V | T | V | S | 160 |
| YW71.22.H1.9 VH | S | L | R | A | E | D | T | A | V | Y | Y | C | A | R | L | H | G | N | K | F | G | W | S | S | Y | G | - | M | D | Y | W | G | Q | G | T | L | V | T | V | S | 161 |
| YW71.22.H1.46 VH | S | L | R | A | E | D | T | A | V | Y | Y | C | A | R | L | H | G | N | K | F | G | W | S | S | Y | G | - | M | D | Y | W | G | Q | G | T | L | V | T | V | S | 162 |
| YW71.22.H1.77 VH | S | L | R | A | E | D | T | A | V | Y | Y | C | A | R | L | H | G | N | K | F | G | W | S | S | Y | G | - | M | D | Y | W | G | Q | G | T | L | V | T | V | S | 163 |
| YW71.22.H1.91 VH | S | L | R | A | E | D | T | A | V | Y | Y | C | A | R | L | H | G | N | K | F | G | W | S | S | Y | G | - | M | D | Y | W | G | Q | G | T | L | V | T | V | S | 164 |
| YW71.22.H2.31 VH | S | L | R | A | E | D | T | A | V | Y | Y | C | A | R | L | H | G | N | K | F | G | W | S | S | Y | G | - | M | D | Y | W | G | Q | G | T | L | V | T | V | S | 165 |

Kabat - CDR H3: positions 95–102
Chothia - CDR H3: positions 96–101
Contact - CDR H3: positions 94–101
HC-FR4: positions 103–113

| | |
|---|---|
| kv1  | DIQMTQSPSSLSASVGDRVTITC -L1- WYQQKPGKAPKLLIY -L2- GVPSRFSGSGSGTDFTLTISSLQ |
| kv1' | DIQMTQSPSSLSASVGDRVTITC -L1- WYQQKPGKAPKLLI  -L2- GVPSRFSGSGSGTDFTLTISSLQ |
| kv2  | DIVMTQSPLSLPVTPGEPASISC -L1- WYLQKPGQSPQLLIY -L2- GVPDRFSGSGSGTDFTLKISRVE |
| kv3  | EIVLTQSPGTLSLSPGERATLSC -L1- WYQQKPGQAPRLLIY -L2- GIPDRFSGSGSGTDFTLTISRLE |
| kv4  | DIVMTQSPDSLAVSLGERATINC -L1- WYQQKPGQPPKLLIY -L2- GVPDRFSGSGSGTDFTLTISSLQ |

FIG. 3A

| | | |
|---|---|---|
| kv1  | PEDFATYYC -L3- FGQGTKVEIK | SEQ ID NOs.: 9, 10, 99, 100 |
| kv1' | PEDFATYYC -L3- FGQGTKVEIK | SEQ ID NOs.: 9, 101, 99, 100 |
| kv2  | AEDVGVYYC -L3- FGQGTKVEIK | SEQ ID NOs.: 102, 103, 104, 100 |
| kv3  | PEDFAVYYC -L3- FGQGTKVEIK | SEQ ID NOs.: 105, 106, 107, 100 |
| kv4  | AEDVAVYYC -L3- FGQGTKVEIK | SEQ ID NOs.: 108, 109, 110, 100 |

FIG. 3B

|   |   |   |   |   |
|---|---|---|---|---|
| I |   |   |   |   |
| A | QVQLVQSGAEVKKPGASVKVSCKASGYTFT | -H1- | WVRQAPGQGLEWMG | -H2- | RVTIT |
| B | QVQLVQSGAEVKKPGASVKVSCKAS | -H1- | WVRQAPGQGLEWM | -H2- | RVTIT |
| C | QVQLVQSGAEVKKPGASVKVSCKAS | -H1- | WVRQAPGQGLEWM | -H2- | RVTIT |
| D | QVQLVQSGAEVKKPGASVKVSCKAS | -H1- | WVRQAPGQGLEWM | -H2- | RVTIT |
| II |   |   |   |   |
| A | QVQLQESGPGLVKPSQTLSLTCTVSGGSVS | -H1- | WIRQPPGKGLEWIG | -H2- | RVTIS |
| B | QVQLQESGPGLVKPSQTLSLTCTVS | -H1- | WIRQPPGKGLEWI | -H2- | RVTIS |
| C | QVQLQESGPGLVKPSQTLSLTCTVS | -H1- | WIRQPPGKGLEWI | -H2- | RVTIS |
| D | QVQLQESGPGLVKPSQTLSLTCTVS | -H1- | WIRQPPGKGLEWI | -H2- | RVTIS |
| III |   |   |   |   |
| A | EVQLVESGGGLVQPGGSLRLSCAASGFTFS | -H1- | WVRQAPGKGLEWVS | -H2- | RFTIS |
| B | EVQLVESGGGLVQPGGSLRLSCAAS | -H1- | WVRQAPGKGLEWV | -H2- | RFTIS |
| C | EVQLVESGGGLVQPGGSLRLSCAAS | -H1- | WVRQAPGKGLEWV | -H2- | RFTIS |
| D | EVQLVESGGGLVQPGGSLRLSCAAS | -H1- | WVRQAPGKGLEWV | -H2- | RFTIS |
| Acceptor-1 |   |   |   |   |
| A | EVQLVESGGGLVQPGGSLRLSCAASGFNIK | -H1- | WVRQAPGKGLEWVS | -H2- | RFTIS |
| B | EVQLVESGGGLVQPGGSLRLSCAAS | -H1- | WVRQAPGKGLEWV | -H2- | RFTIS |
| C | EVQLVESGGGLVQPGGSLRLSCAAS | -H1- | WVRQAPGKGLEWV | -H2- | RFTIS |
| D | EVQLVESGGGLVQPGGSLRLSCAAS | -H1- | WVRQAPGKGLEWV | -H2- | RFTIS |
| Acceptor-2 |   |   |   |   |
| A | EVQLVESGGGLVQPGGSLRLSCAASGFNIK | -H1- | WVRQAPGKGLEWVS | -H2- | RFTIS |
| B | EVQLVESGGGLVQPGGSLRLSCAAS | -H1- | WVRQAPGKGLEWV | -H2- | RFTIS |
| C | EVQLVESGGGLVQPGGSLRLSCAAS | -H1- | WVRQAPGKGLEWV | -H2- | RFTIS |
| D | EVQLVESGGGLVQPGGSLRLSCAAS | -H1- | WVRQAPGKGLEWV | -H2- | RFTIS |

*FIG. 4A*

I
A ADTSTSTAYMELSSLRSEDTAVYYCAR -H3- WGQGTLVTVSS  SEQ ID NOs.: 111, 112, 113, 16
B ADTSTSTAYMELSSLRSEDTAVYYCAR -H3- WGQGTLVTVSS  SEQ ID NOs.: 114, 115, 113, 16
C ADTSTSTAYMELSSLRSEDTAVYYCA  -H3- WGQGTLVTVSS  SEQ ID NOs.: 114, 115, 116, 16
D ADTSTSTAYMELSSLRSEDTAVYYC   -H3- WGQGTLVTVSS  SEQ ID NOs.: 114, 115, 117, 16

II
A VDTSKNQFSLKLSSVTAADTAVYYCAR -H3- WGQGTLVTVSS  SEQ ID NOs.: 118, 119, 120, 16
B VDTSKNQFSLKLSSVTAADTAVYYCAR -H3- WGQGTLVTVSS  SEQ ID NOs.: 121, 122, 120, 16
C VDTSKNQFSLKLSSVTAADTAVYYCA  -H3- WGQGTLVTVSS  SEQ ID NOs.: 121, 122, 123, 16
D VDTSKNQFSLKLSSVTAADTAVYYC   -H3- WGQGTLVTVSS  SEQ ID NOs.: 121, 122, 124, 16

III
A RDNSKNTLYLQMNSLRAEDTAVYYCAR -H3- WGQGTLVTVSS  SEQ ID NOs.: 125, 126, 127, 16
B RDNSKNTLYLQMNSLRAEDTAVYYCAR -H3- WGQGTLVTVSS  SEQ ID NOs.: 128, 129, 127, 16
C RDNSKNTLYLQMNSLRAEDTAVYYCA  -H3- WGQGTLVTVSS  SEQ ID NOs.: 128, 129, 130, 16
D RDNSKNTLYLQMNSLRAEDTAVYYC   -H3- WGQGTLVTVSS  SEQ ID NOs.: 128, 129, 131, 16

Acceptor-1
A ADTSKNTAYLQMNSLRAEDTAVYYCSR -H3- WGQGTLVTVSS  SEQ ID NOs.: 132, 126, 133, 16
B ADTSKNTAYLQMNSLRAEDTAVYYCSR -H3- WGQGTLVTVSS  SEQ ID NOs.: 128, 129, 133, 16
C ADTSKNTAYLQMNSLRAEDTAVYYCS  -H3- WGQGTLVTVSS  SEQ ID NOs.: 128, 129, 134, 16

Acceptor-2
A ADTSKNTAYLQMNSLRAEDTAVYYCAR -H3- WGQGTLVTVSS  SEQ ID NOs.: 132, 126, 135, 16
B ADTSKNTAYLQMNSLRAEDTAVYYCAR -H3- WGQGTLVTVSS  SEQ ID NOs.: 128, 129, 135, 16
C ADTSKNTAYLQMNSLRAEDTAVYYCA  -H3- WGQGTLVTVSS  SEQ ID NOs.: 128, 129, 136, 16
D ADTSKNTAYLQMNSLRAEDTAVYYC   -H3- WGQGTLVTVSS  SEQ ID NOs.: 128, 129, 137, 16

FIG. 4B

MGSGGDSLLGGRGSLPLLLLLIMGGMAQDSPPQILVHPQDQLFQGPGPARMSCRASGQPPPTIR
WLLNGQPLSMVPPDPHHLLPDGTLLLLQPPARGHAHDGQALSTDLGVYTCEASNRLGTAVSRGA
RLSVAVLREDFQIQPRDMVAVVGEQFTLECGPPWGHPEPTVSWWKDGKPLALQPGRHTVSGGSL
LMARAEKSDEGTYMCVATNSAGHRESRAARVSIQEPQDYTEPVELLAVRIQLENVTLLNPDPAE
GPKPRPAVWLSWKVSGPAAPAQSYTALFRTQTAPGGQGAPWAEELLAGWQSAELGGLHWGQDYE
FKVRPSSGRARGPDSNVLLLRLPEKVPSAPPQEVTLKPGNGTVFVSWVPPPAENHNGIIRGYQV
WSLGNTSLPPANWTVVGEQTQLEIATHMPGSYCVQVAAVTGAGAGEPSRPVCLLLEQAMERATQ
EPSEHGPWTLEQLRATLKRPEVIATCGVALWLLLLGTAVCIHRRRRARVHLGPGLYRYTSEDAI
LKHRMDHSDSQWLADTWRSTGSRDLSSSSSLSSRLGADARDPLDCRRSLLSWDSRSPGVPLLP
DTSTFYGSLIAELPSSTPARPSPQVPAVRRLPPQLAQLSSPCSSSDSLCSRRGLSSPRLSLAPA
EAWKAKKKQELQHANSSPLLRGSHSLELRACELGNRGSKNLSQSPGAVPQALVAWRALGPKLLS
SSNELVTRHLPPAPLFPHETPPTQSQQTQPPVAPQAPSSILLPAAPIPILSPCSPPSPQASSLS
GPSPASSRLSSSSLSSLGEDQDSVLTPEEVALCLELSEGEETPRNSVSPMPRAPSPPTTYGYIS
VPTASEFTDMGRTGGGVGPKGGVLLCPPRPCLTPTSEGSLANGWGSASEDNAASARASLVSSS
DGSFLADAHFARALAVAVDSFGFGLEPREADCVFIDASSPPSPRDEIFLTPNLSLPLWEWRPDW
LEDMEVSHTQRLGRGMPPWPPDSQISSQRSQLHCRMPKAGASPVDYS

FIG. 5A

QDSPPQILVHPQDQLFQGPGPARMSCQASGQPPPTIRWLLNGQPLSMVPPDPHHLLPDGTLLLL
QPPARGHAHDGQALSTDLGVYTCEASNRLGTAVSRGARLSVAVLREDFQIQPRDMVAVVGEQFT
LECGPPWGHPEPTVSWWKDGKPLALQPGRHTVSGGSLLMARAEKSDEGTYMCVATNSAGHRESR
AARVSIQEPQDYRAHHHHHHHH

FIG. 5B

EVQLVESGGGLVQPGGSLRLSCAASGFTINGYYIHWVRQAPGKGLEWVGFIYPAGGDTDYADSV
KGRFTISADTSKNTAYLQMNSLRAEDTAVYYCARLIGNKFGWSSYGMDYWGQGTLVTVSSASTK
GPSVFPLAPSSKSTSGGTAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAPELLGGPSVFLFPPKPKD
TLMISRTPEVTCVVVDVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQVSLTCLVKGFYPSDI
AVEWESNGQPENNYKTTPPVLDSDGSFFLYSKLTVDKSRWQQGNVFSCSVMHEALHNHYTQKSL
SLSPGK

FIG. 6A

DIQMTQSPSSLSASVGDRVTITCRASQDVSTAVAWYQQKPGKAPKLLIYSASFLYSGVPSRFSG
SGSGTDFTLTISSLQPEDFATTYCQQSYTTPPTFGQGTKVEIKRTVAAPSVFIFPPSDEQLKSG
TASVVCLLNNFYPREAKVQWKVDNALQSGNSQESVTEQDSKDSTYSLSSTLTLSKADYEKHKVY
ACEVTHQGLSSPVTKSFNRGEC

FIG. 6B

MGSGGTGLLGTEWPLPLLLLFIMGGEALDSPPQILVHPDQLLQGSGPAKMRCRSSGQPPPTIR
WLLNGQPLSMATPDLHYLLPDGTLLLHRPSVQGRPQDDQNILSAILGVYTCEASNRLGTAVSRG
ARLSVAVLQEDFQIQPRDTVAVVGESLVLECGPPWGYPKPSVSWWKDGKPLVLQPGRRTVSGDS
LMVSRAEKNDSGTYMCMATNNAGQRESRAARVSIQESQDHRRAHHHHHHHH

FIG. 7

HM-7 Colon Tumor

HM-7 Colon Tumor

MDA-MB175 Mammary Tumor

MDA-MB175 Mammary Tumor

Malignant Melanoma

Malignant Melanoma

Malignant Melanoma

Malignant Melanoma

Small Cell Lung Cancer

Small Cell Lung Cancer

Small Cell Lung Cancer

Small Cell Lung Cancer

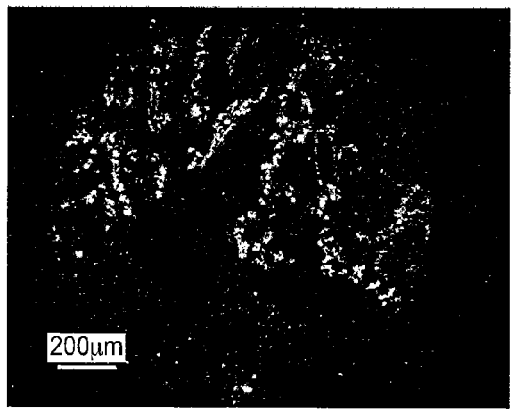
FIG. 14E
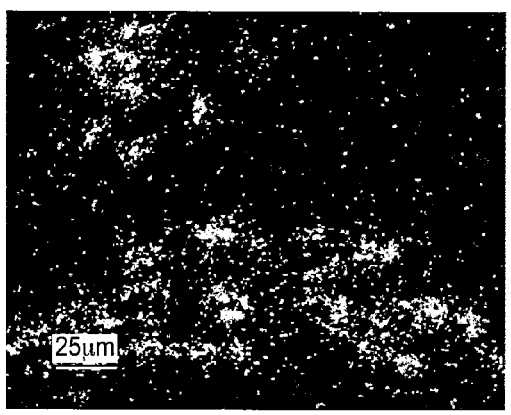
FIG. 14G
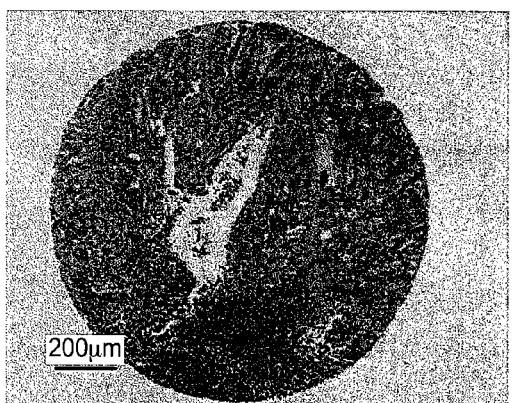
FIG. 14F
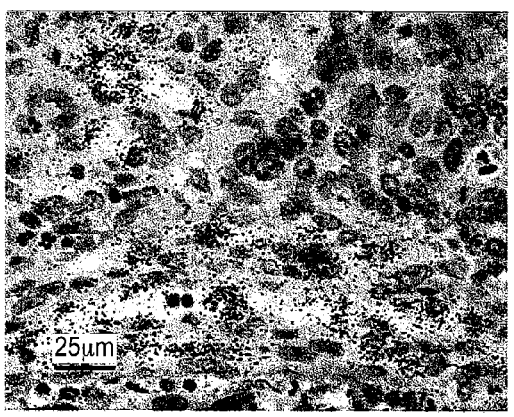
FIG. 14H
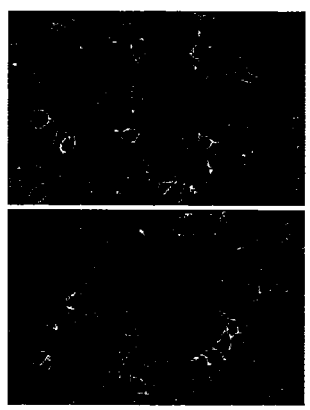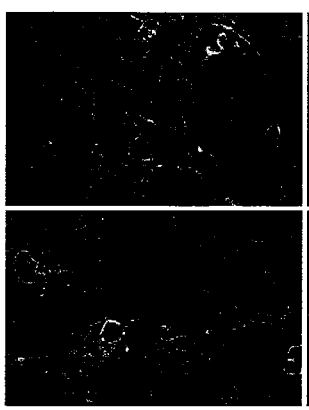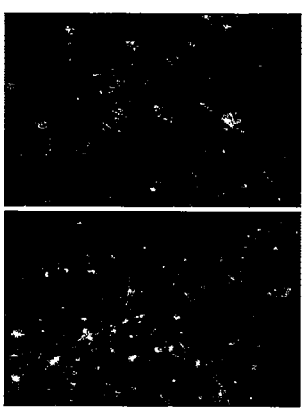
FIG. 15A

Time Course of anti-Robo4 YW71.22 Redistribution

Time Course of anti-Robo4 YW71.22.S1.16 Redistribution

SEQUENCE LISTING

```
<160> NUMBER OF SEQ ID NOS: 187

<210> SEQ ID NO 1
<211> LENGTH: 11
<212> TYPE: PRT
<213> ORGANISM: Artificial sequence
<220> FEATURE:
<223> OTHER INFORMATION: antibody hypervariable region

<400> SEQUENCE: 1

Arg Ala Ser Gln Asp Val Ser Thr Ala Val Ala
                  5                  10

<210> SEQ ID NO 2
<211> LENGTH: 7
<212> TYPE: PRT
<213> ORGANISM: Artificial sequence
<220> FEATURE:
<223> OTHER INFORMATION: antibody hypervariable region

<400> SEQUENCE: 2

Ser Ala Ser Phe Leu Tyr Ser
                  5

<210> SEQ ID NO 3
<211> LENGTH: 9
<212> TYPE: PRT
<213> ORGANISM: Artificial sequence
<220> FEATURE:
<223> OTHER INFORMATION: antibody hypervariable region
```

<400> SEQUENCE: 3

Gln Gln Ser Tyr Thr Thr Pro Pro Thr
                5

<210> SEQ ID NO 4
<211> LENGTH: 10
<212> TYPE: PRT
<213> ORGANISM: Artificial sequence
<220> FEATURE:
<223> OTHER INFORMATION: antibody hypervariable region

<400> SEQUENCE: 4

Gly Phe Thr Ile Ser Gly Ser Trp Ile His
                5                   10

<210> SEQ ID NO 5
<211> LENGTH: 18
<212> TYPE: PRT
<213> ORGANISM: Artificial sequence
<220> FEATURE:
<223> OTHER INFORMATION: antibody hypervariable region

<400> SEQUENCE: 5

Ala Val Ile Thr Pro Ala Gly Gly Tyr Thr Tyr Tyr Ala Asp Ser
  1               5                  10                  15

Val Lys Gly

<210> SEQ ID NO 6
<211> LENGTH: 18
<212> TYPE: PRT
<213> ORGANISM: Artificial sequence
<220> FEATURE:
<223> OTHER INFORMATION: antibody hypervariable region

<400> SEQUENCE: 6

Ala Arg Ser Asn Arg Tyr Ser Gly Gln Phe Val Pro Ala Tyr Ala
  1               5                  10                  15

Met Asp Tyr

<210> SEQ ID NO 7
<211> LENGTH: 11
<212> TYPE: PRT
<213> ORGANISM: Artificial sequence
<220> FEATURE:
<223> OTHER INFORMATION: antibody hypervariable region

<400> SEQUENCE: 7

Arg Ala Ser Gln Ser Ile Ser Ser Tyr Leu Ala
                5                   10

<210> SEQ ID NO 8
<211> LENGTH: 7
<212> TYPE: PRT
<213> ORGANISM: Artificial sequence
<220> FEATURE:
<223> OTHER INFORMATION: antibody hypervariable region

<400> SEQUENCE: 8

Gly Ala Ser Ser Arg Ala Ser
                5

<210> SEQ ID NO 9
<211> LENGTH: 23
<212> TYPE: PRT

<213> ORGANISM: Artificial sequence
<220> FEATURE:
<223> OTHER INFORMATION: antibody light chain framework region

<400> SEQUENCE: 9

Asp Ile Gln Met Thr Gln Ser Pro Ser Ser Leu Ser Ala Ser Val
1               5                   10                  15

Gly Asp Arg Val Thr Ile Thr Cys
            20

<210> SEQ ID NO 10
<211> LENGTH: 15
<212> TYPE: PRT
<213> ORGANISM: Artificial sequence
<220> FEATURE:
<223> OTHER INFORMATION: antibody light chain framework region

<400> SEQUENCE: 10

Trp Tyr Gln Gln Lys Pro Gly Lys Ala Pro Lys Leu Leu Ile Tyr
1               5                   10                  15

<210> SEQ ID NO 11
<211> LENGTH: 32
<212> TYPE: PRT
<213> ORGANISM: Artificial sequence
<220> FEATURE:
<223> OTHER INFORMATION: antibody light chain framework region

<400> SEQUENCE: 11

Gly Val Pro Ser Arg Phe Ser Gly Ser Gly Ser Gly Thr Asp Phe
1               5                   10                  15

Thr Leu Thr Ile Ser Ser Leu Gln Pro Glu Asp Phe Ala Thr Thr
                20                  25                  30

Tyr Cys

<210> SEQ ID NO 12
<211> LENGTH: 10
<212> TYPE: PRT
<213> ORGANISM: Artificial sequence
<220> FEATURE:
<223> OTHER INFORMATION: antibody light chain framework region

<400> SEQUENCE: 12

Phe Gly Gln Gly Thr Lys Val Glu Ile Lys
1               5                   10

<210> SEQ ID NO 13
<211> LENGTH: 25
<212> TYPE: PRT
<213> ORGANISM: Artificial sequence
<220> FEATURE:
<223> OTHER INFORMATION: antibody light chain framework region

<400> SEQUENCE: 13

Glu Val Gln Leu Val Glu Ser Gly Gly Gly Leu Val Gln Pro Gly
1               5                   10                  15

Gly Ser Leu Arg Leu Ser Cys Ala Ala Ser
                20                  25

<210> SEQ ID NO 14
<211> LENGTH: 13
<212> TYPE: PRT
<213> ORGANISM: Artificial sequence
<220> FEATURE:
<223> OTHER INFORMATION: antibody light chain framework region

```
<400> SEQUENCE: 14

Trp Val Arg Gln Ala Pro Gly Lys Gly Leu Glu Trp Val
                5                   10

<210> SEQ ID NO 15
<211> LENGTH: 30
<212> TYPE: PRT
<213> ORGANISM: Artificial sequence
<220> FEATURE:
<223> OTHER INFORMATION: antibody light chain framework region

<400> SEQUENCE: 15

Arg Phe Thr Ile Ser Ala Asp Thr Ser Lys Asn Thr Ala Tyr Leu
  1               5                  10                  15

Gln Met Asn Ser Leu Arg Ala Glu Asp Thr Ala Val Tyr Tyr Cys
                 20                  25                  30

<210> SEQ ID NO 16
<211> LENGTH: 11
<212> TYPE: PRT
<213> ORGANISM: Artificial sequence
<220> FEATURE:
<223> OTHER INFORMATION: antibody heavy chain framework region

<400> SEQUENCE: 16

Trp Gly Gln Gly Thr Leu Val Thr Val Ser Ser
                 5                  10

<210> SEQ ID NO 17
<211> LENGTH: 10
<212> TYPE: PRT
<213> ORGANISM: Artificial sequence
<220> FEATURE:
<223> OTHER INFORMATION: antibody hypervariable region

<400> SEQUENCE: 17

Gly Phe Thr Ile Asn Gly Tyr Tyr Ile His
                 5                  10

<210> SEQ ID NO 18
<211> LENGTH: 18
<212> TYPE: PRT
<213> ORGANISM: Artificial sequence
<220> FEATURE:
<223> OTHER INFORMATION: antibody hypervariable region

<400> SEQUENCE: 18

Gly Phe Ile Tyr Pro Ala Gly Gly Asp Thr Asp Tyr Ala Asp Ser
  1               5                  10                  15

Val Lys Gly

<210> SEQ ID NO 19
<211> LENGTH: 17
<212> TYPE: PRT
<213> ORGANISM: Artificial sequence
<220> FEATURE:
<223> OTHER INFORMATION: antibody hypervariable region

<400> SEQUENCE: 19

Ala Arg Leu Ile Gly Asn Lys Phe Gly Trp Ser Ser Tyr Gly Met
  1               5                  10                  15

Asp Tyr
```

```
<210> SEQ ID NO 20
<211> LENGTH: 9
<212> TYPE: PRT
<213> ORGANISM: Artificial sequence
<220> FEATURE:
<223> OTHER INFORMATION: antibody hypervariable region

<400> SEQUENCE: 20

Gln Gln Ser Arg Ser Asp His Pro Thr
                5

<210> SEQ ID NO 21
<211> LENGTH: 9
<212> TYPE: PRT
<213> ORGANISM: Artificial sequence
<220> FEATURE:
<223> OTHER INFORMATION: antibody hypervariable region

<400> SEQUENCE: 21

Gln Gln Ser Trp Ser Tyr Pro Leu Thr
                5

<210> SEQ ID NO 22
<211> LENGTH: 9
<212> TYPE: PRT
<213> ORGANISM: Artificial sequence
<220> FEATURE:
<223> OTHER INFORMATION: antibody hypervariable region

<400> SEQUENCE: 22

Gln Gln Ser Tyr Asn Thr Pro Phe Thr
                5

<210> SEQ ID NO 23
<211> LENGTH: 9
<212> TYPE: PRT
<213> ORGANISM: Artificial sequence
<220> FEATURE:
<223> OTHER INFORMATION: antibody hypervariable region

<400> SEQUENCE: 23

Gln Gln Tyr Tyr Ser Ser Pro Leu Thr
                5

<210> SEQ ID NO 24
<211> LENGTH: 10
<212> TYPE: PRT
<213> ORGANISM: Artificial sequence
<220> FEATURE:
<223> OTHER INFORMATION: antibody hypervariable region

<400> SEQUENCE: 24

Gly Phe Thr Ile Thr Asn Tyr Trp Ile His
                5                   10

<210> SEQ ID NO 25
<211> LENGTH: 10
<212> TYPE: PRT
<213> ORGANISM: Artificial sequence
<220> FEATURE:
<223> OTHER INFORMATION: antibody hypervariable region

<400> SEQUENCE: 25

Gly Phe Thr Ile Asn Asn Tyr Ile His
                5                   10

<210> SEQ ID NO 26
```

```
<211> LENGTH: 10
<212> TYPE: PRT
<213> ORGANISM: Artificial sequence
<220> FEATURE:
<223> OTHER INFORMATION: antibody hypervariable region

<400> SEQUENCE: 26

Gly Tyr Thr Phe Ser Ser Tyr Trp Ile Ser
                5                   10

<210> SEQ ID NO 27
<211> LENGTH: 10
<212> TYPE: PRT
<213> ORGANISM: Artificial sequence
<220> FEATURE:
<223> OTHER INFORMATION: antibody hypervariable region

<400> SEQUENCE: 27

Gly Phe Thr Phe Ser Ser Arg Tyr Met Ser
                5                   10

<210> SEQ ID NO 28
<211> LENGTH: 10
<212> TYPE: PRT
<213> ORGANISM: Artificial sequence
<220> FEATURE:
<223> OTHER INFORMATION: antibody hypervariable region

<400> SEQUENCE: 28

Gly Phe Thr Phe Ser Ser Tyr Ala Met Ser
                5                   10

<210> SEQ ID NO 29
<211> LENGTH: 18
<212> TYPE: PRT
<213> ORGANISM: Artificial sequence
<220> FEATURE:
<223> OTHER INFORMATION: antibody hypervariable region

<400> SEQUENCE: 29

Gly Gly Ile Tyr Pro Ala Asp Gly Tyr Thr Tyr Tyr Ala Asp Ser
 1               5                  10                  15

Val Lys Gly

<210> SEQ ID NO 30
<211> LENGTH: 18
<212> TYPE: PRT
<213> ORGANISM: Artificial sequence
<220> FEATURE:
<223> OTHER INFORMATION: antibody hypervariable region

<400> SEQUENCE: 30

Ala Ile Ile Ser Pro Thr Gly Gly Tyr Thr Asp Tyr Ala Asp Ser
 1               5                  10                  15

Val Lys Gly

<210> SEQ ID NO 31
<211> LENGTH: 18
<212> TYPE: PRT
<213> ORGANISM: Artificial sequence
<220> FEATURE:
<223> OTHER INFORMATION: antibody hypervariable region

<400> SEQUENCE: 31

Ser Thr Ile Tyr Gly Tyr Asp Gly Ser Thr Asn Tyr Ala Asp Ser
 1               5                  10                  15
```

Val Lys Gly

<210> SEQ ID NO 32
<211> LENGTH: 18
<212> TYPE: PRT
<213> ORGANISM: Artificial sequence
<220> FEATURE:
<223> OTHER INFORMATION: antibody hypervariable region

<400> SEQUENCE: 32

Ser Gly Ile Tyr Pro Met Gly Gly Thr Thr Tyr Tyr Ala Asp Ser
1               5                   10                  15
Val Lys Gly

<210> SEQ ID NO 33
<211> LENGTH: 18
<212> TYPE: PRT
<213> ORGANISM: Artificial sequence
<220> FEATURE:
<223> OTHER INFORMATION: antibody hypervariable region

<400> SEQUENCE: 33

Ser Gly Ile Ser Pro Tyr Gly Gly Tyr Thr Tyr Tyr Ala Asp Ser
1               5                   10                  15
Val Lys Gly

<210> SEQ ID NO 34
<211> LENGTH: 10
<212> TYPE: PRT
<213> ORGANISM: Artificial sequence
<220> FEATURE:
<223> OTHER INFORMATION: antibody hypervariable region

<400> SEQUENCE: 34

Ala Ser Gly Gly Tyr Ser Ser Leu Ala Tyr
                5                   10

<210> SEQ ID NO 35
<211> LENGTH: 18
<212> TYPE: PRT
<213> ORGANISM: Artificial sequence
<220> FEATURE:
<223> OTHER INFORMATION: antibody hypervariable region

<400> SEQUENCE: 35

Ala Arg Asp Val Asn Val Tyr Ser Ala Arg Trp Trp Asp Tyr Val
1               5                   10                  15
Met Asp Tyr

<210> SEQ ID NO 36
<211> LENGTH: 16
<212> TYPE: PRT
<213> ORGANISM: Artificial sequence
<220> FEATURE:
<223> OTHER INFORMATION: antibody hypervariable region

<400> SEQUENCE: 36

Ala Arg Met Ser Tyr Asn Trp Ser Ser Pro Gly His Gly Met Asp
1               5                   10                  15
Val

<210> SEQ ID NO 37
<211> LENGTH: 13

```
<212> TYPE: PRT
<213> ORGANISM: Artificial sequence
<220> FEATURE:
<223> OTHER INFORMATION: antibody hypervariable region

<400> SEQUENCE: 37

Ala Arg Gly Asn Tyr Tyr Ser Gly Ser Glu Phe Asp Tyr
                  5                  10

<210> SEQ ID NO 38
<211> LENGTH: 16
<212> TYPE: PRT
<213> ORGANISM: Artificial sequence
<220> FEATURE:
<223> OTHER INFORMATION: antibody hypervariable region

<400> SEQUENCE: 38

Ala Arg Trp Gly Tyr Tyr Met Pro Tyr Gly His Pro Val Met Asp
 1               5                  10                  15
Val

<210> SEQ ID NO 39
<211> LENGTH: 11
<212> TYPE: PRT
<213> ORGANISM: Artificial sequence
<220> FEATURE:
<223> OTHER INFORMATION: antibody hypervariable region

<400> SEQUENCE: 39

Arg Ala Ser Gln Asp Gly Ala Arg Ser Leu Ala
                  5                  10

<210> SEQ ID NO 40
<211> LENGTH: 11
<212> TYPE: PRT
<213> ORGANISM: Artificial sequence
<220> FEATURE:
<223> OTHER INFORMATION: antibody hypervariable region

<400> SEQUENCE: 40

Arg Ala Ser Gln Asp Gly Ala Ile Tyr Leu Ala
                  5                  10

<210> SEQ ID NO 41
<211> LENGTH: 7
<212> TYPE: PRT
<213> ORGANISM: Artificial sequence
<220> FEATURE:
<223> OTHER INFORMATION: antibody hypervariable region

<400> SEQUENCE: 41

Ser Ala Ser Phe Leu Ala Ser
                  5

<210> SEQ ID NO 42
<211> LENGTH: 6
<212> TYPE: PRT
<213> ORGANISM: Artificial sequence
<220> FEATURE:
<223> OTHER INFORMATION: antibody hypervariable region

<400> SEQUENCE: 42

Ser Ala Ser Leu Glu Ser
                  5

<210> SEQ ID NO 43
```

```
<211> LENGTH: 6
<212> TYPE: PRT
<213> ORGANISM: Artificial sequence
<220> FEATURE:
<223> OTHER INFORMATION: antibody hypervariable region

<400> SEQUENCE: 43

Ser Ala Thr Leu Ala Ser
                5

<210> SEQ ID NO 44
<211> LENGTH: 7
<212> TYPE: PRT
<213> ORGANISM: Artificial sequence
<220> FEATURE:
<223> OTHER INFORMATION: antibody hypervariable region

<400> SEQUENCE: 44

Ser Ala Ser Phe Leu Tyr Tyr
                5

<210> SEQ ID NO 45
<211> LENGTH: 7
<212> TYPE: PRT
<213> ORGANISM: Artificial sequence
<220> FEATURE:
<223> OTHER INFORMATION: antibody hypervariable region

<400> SEQUENCE: 45

Ser Ala Ser Asn Leu Ala Ser
                5

<210> SEQ ID NO 46
<211> LENGTH: 7
<212> TYPE: PRT
<213> ORGANISM: Artificial sequence
<220> FEATURE:
<223> OTHER INFORMATION: antibody hypervariable region

<400> SEQUENCE: 46

Ser Ala Ser Thr Leu Ala Ser
                5

<210> SEQ ID NO 47
<211> LENGTH: 9
<212> TYPE: PRT
<213> ORGANISM: Artificial sequence
<220> FEATURE:
<223> OTHER INFORMATION: antibody hypervariable region

<400> SEQUENCE: 47

Gln Gln Ser Phe Ala Thr Pro Ala Thr
                5

<210> SEQ ID NO 48
<211> LENGTH: 9
<212> TYPE: PRT
<213> ORGANISM: Artificial sequence
<220> FEATURE:
<223> OTHER INFORMATION: antibody hypervariable region

<400> SEQUENCE: 48

Gln Gln Ser Arg Ala Ala Leu Pro Thr
                5

<210> SEQ ID NO 49
<211> LENGTH: 9
```

```
<212> TYPE: PRT
<213> ORGANISM: Artificial sequence
<220> FEATURE:
<223> OTHER INFORMATION: antibody hypervariable region

<400> SEQUENCE: 49

Gln Gln Ser Arg Ala Asn Thr Pro Thr
                 5

<210> SEQ ID NO 50
<211> LENGTH: 9
<212> TYPE: PRT
<213> ORGANISM: Artificial sequence
<220> FEATURE:
<223> OTHER INFORMATION: antibody hypervariable region

<400> SEQUENCE: 50

Gln Gln Ser Arg Thr Thr Pro Pro Thr
                 5

<210> SEQ ID NO 51
<211> LENGTH: 9
<212> TYPE: PRT
<213> ORGANISM: Artificial sequence
<220> FEATURE:
<223> OTHER INFORMATION: antibody hypervariable region

<400> SEQUENCE: 51

Gln Gln Pro Phe Asp Leu Pro Met Thr
                 5

<210> SEQ ID NO 52
<211> LENGTH: 9
<212> TYPE: PRT
<213> ORGANISM: Artificial sequence
<220> FEATURE:
<223> OTHER INFORMATION: antibody hypervariable region

<400> SEQUENCE: 52

Gln Gln Pro Asn Ser Thr Pro Phe Thr
                 5

<210> SEQ ID NO 53
<211> LENGTH: 9
<212> TYPE: PRT
<213> ORGANISM: Artificial sequence
<220> FEATURE:
<223> OTHER INFORMATION: antibody hypervariable region

<400> SEQUENCE: 53

Gln Gln Ser Arg Phe Asp His Pro Thr
                 5

<210> SEQ ID NO 54
<211> LENGTH: 9
<212> TYPE: PRT
<213> ORGANISM: Artificial sequence
<220> FEATURE:
<223> OTHER INFORMATION: antibody hypervariable region

<400> SEQUENCE: 54

Gln Gln Ser Tyr His Thr His Ser Thr
                 5

<210> SEQ ID NO 55
<211> LENGTH: 9
<212> TYPE: PRT
```

```
<213> ORGANISM: Artificial sequence
<220> FEATURE:
<223> OTHER INFORMATION: antibody hypervariable region

<400> SEQUENCE: 55

Gln Gln Ser Arg Asp Ile Pro Pro Thr
                5

<210> SEQ ID NO 56
<211> LENGTH: 9
<212> TYPE: PRT
<213> ORGANISM: Artificial sequence
<220> FEATURE:
<223> OTHER INFORMATION: antibody hypervariable region

<400> SEQUENCE: 56

Gln Gln Ser Arg Asn Met Pro Ala Thr
                5

<210> SEQ ID NO 57
<211> LENGTH: 9
<212> TYPE: PRT
<213> ORGANISM: Artificial sequence
<220> FEATURE:
<223> OTHER INFORMATION: antibody hypervariable region

<400> SEQUENCE: 57

Gln Gln Thr Arg Val Met Pro Ala Thr
                5

<210> SEQ ID NO 58
<211> LENGTH: 9
<212> TYPE: PRT
<213> ORGANISM: Artificial sequence
<220> FEATURE:
<223> OTHER INFORMATION: antibody hypervariable region

<400> SEQUENCE: 58

Gln Gln Thr Tyr Thr Ile Pro Pro Thr
                5

<210> SEQ ID NO 59
<211> LENGTH: 9
<212> TYPE: PRT
<213> ORGANISM: Artificial sequence
<220> FEATURE:
<223> OTHER INFORMATION: antibody hypervariable region

<400> SEQUENCE: 59

Gln Gln Ser Tyr Ala Tyr Pro Phe Thr
                5

<210> SEQ ID NO 60
<211> LENGTH: 9
<212> TYPE: PRT
<213> ORGANISM: Artificial sequence
<220> FEATURE:
<223> OTHER INFORMATION: antibody hypervariable region

<400> SEQUENCE: 60

Gln Gln Ser Tyr Asp Leu Pro Phe Thr
                5

<210> SEQ ID NO 61
<211> LENGTH: 9
<212> TYPE: PRT
<213> ORGANISM: Artificial sequence
```

```
<220> FEATURE:
<223> OTHER INFORMATION: antibody hypervariable region

<400> SEQUENCE: 61

Gln Gln Ser Tyr Gly Gly Pro Phe Thr
                5

<210> SEQ ID NO 62
<211> LENGTH: 9
<212> TYPE: PRT
<213> ORGANISM: Artificial sequence
<220> FEATURE:
<223> OTHER INFORMATION: antibody hypervariable region

<400> SEQUENCE: 62

Gln Gln Ser Tyr Asn Tyr Pro Phe Thr
                5

<210> SEQ ID NO 63
<211> LENGTH: 9
<212> TYPE: PRT
<213> ORGANISM: Artificial sequence
<220> FEATURE:
<223> OTHER INFORMATION: antibody hypervariable region

<400> SEQUENCE: 63

Gln Gln Phe Tyr Ser Asp Pro Phe Thr
                5

<210> SEQ ID NO 64
<211> LENGTH: 9
<212> TYPE: PRT
<213> ORGANISM: Artificial sequence
<220> FEATURE:
<223> OTHER INFORMATION: antibody hypervariable region

<400> SEQUENCE: 64

Gln Gln Gly Tyr Asn Tyr Pro Phe Thr
                5

<210> SEQ ID NO 65
<211> LENGTH: 10
<212> TYPE: PRT
<213> ORGANISM: Artificial sequence
<220> FEATURE:
<223> OTHER INFORMATION: antibody hypervariable region

<400> SEQUENCE: 65

Gly Phe Ser Ile Tyr Ser Tyr Tyr Phe Glu
                5                   10

<210> SEQ ID NO 66
<211> LENGTH: 10
<212> TYPE: PRT
<213> ORGANISM: Artificial sequence
<220> FEATURE:
<223> OTHER INFORMATION: antibody hypervariable region

<400> SEQUENCE: 66

Gly Phe Thr Leu Asp Gly Tyr Tyr Leu Gln
                5                   10

<210> SEQ ID NO 67
<211> LENGTH: 10
<212> TYPE: PRT
<213> ORGANISM: Artificial sequence
<220> FEATURE:
```

```
<223> OTHER INFORMATION: antibody hypervariable region

<400> SEQUENCE: 67

Gly Phe Ser Ile Asn Gly Tyr Tyr Asn Gln
 1               5                  10

<210> SEQ ID NO 68
<211> LENGTH: 18
<212> TYPE: PRT
<213> ORGANISM: Artificial sequence
<220> FEATURE:
<223> OTHER INFORMATION: antibody hypervariable region

<400> SEQUENCE: 68

Gly Arg Ile Tyr Ser Ala Gly Gly His Thr Ala Tyr Ala Asp Ser
 1               5                  10                  15

Val Lys Gly

<210> SEQ ID NO 69
<211> LENGTH: 18
<212> TYPE: PRT
<213> ORGANISM: Artificial sequence
<220> FEATURE:
<223> OTHER INFORMATION: antibody hypervariable region

<400> SEQUENCE: 69

Gly Phe Ile Tyr Pro Ala Gly Gly Lys Thr Glu Tyr Ala Asp Ser
 1               5                  10                  15

Val Lys Gly

<210> SEQ ID NO 70
<211> LENGTH: 18
<212> TYPE: PRT
<213> ORGANISM: Artificial sequence
<220> FEATURE:
<223> OTHER INFORMATION: antibody hypervariable region

<400> SEQUENCE: 70

Gly Phe Ile Tyr Pro Ala Gly Gly Ala Thr Ile Tyr Ala Asp Ser
 1               5                  10                  15

Val Lys Gly

<210> SEQ ID NO 71
<211> LENGTH: 18
<212> TYPE: PRT
<213> ORGANISM: Artificial sequence
<220> FEATURE:
<223> OTHER INFORMATION: antibody hypervariable region

<400> SEQUENCE: 71

Gly Phe Ile Tyr Pro Ala Leu Ser Val Ile Glu Tyr Ala Asp Ser
 1               5                  10                  15

Val Lys Gly

<210> SEQ ID NO 72
<211> LENGTH: 108
<212> TYPE: PRT
<213> ORGANISM: Artificial sequence
<220> FEATURE:
<223> OTHER INFORMATION: antibody light chain

<400> SEQUENCE: 72

Asp Ile Gln Met Thr Gln Ser Pro Ser Ser Leu Ser Ala Ser Val
 1               5                  10                  15
```

Gly Asp Arg Val Thr Ile Thr Cys Arg Ala Ser Gln Asp Val Ser
            20                  25                  30

Thr Ala Val Ala Trp Tyr Gln Gln Lys Pro Gly Lys Ala Pro Lys
        35                  40                  45

Leu Leu Ile Tyr Ser Ala Ser Phe Leu Tyr Ser Gly Val Pro Ser
    50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
            80                  85                  90

Ser Tyr Thr Thr Pro Pro Thr Phe Gly Gln Gly Thr Lys Val Glu
        95                  100                 105

Ile Lys Arg

<210> SEQ ID NO 73
<211> LENGTH: 108
<212> TYPE: PRT
<213> ORGANISM: Artificial sequence
<220> FEATURE:
<223> OTHER INFORMATION: antibody light chain

<400> SEQUENCE: 73

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Ser
            20                  25                  30

Thr Ala Val Ala Trp Tyr Gln Gln Lys Pro Gly Lys Ala Pro Lys
        35                  40                  45

Leu Leu Ile Tyr Ser Ala Ser Phe Leu Tyr Ser Gly Val Pro Ser
    50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
            80                  85                  90

Ser Tyr Thr Thr Pro Pro Thr Phe Gly Gln Gly Thr Lys Val Glu
        95                  100                 105

Ile Lys Arg

<210> SEQ ID NO 74
<211> LENGTH: 108
<212> TYPE: PRT
<213> ORGANISM: Artificial sequence
<220> FEATURE:
<223> OTHER INFORMATION: antibody light chain

<400> SEQUENCE: 74

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Ser
            20                  25                  30

Thr Ala Val Ala Trp Tyr Gln Gln Lys Pro Gly Lys Ala Pro Lys
        35                  40                  45

Leu Leu Ile Tyr Ser Ala Ser Phe Leu Tyr Ser Gly Val Pro Ser
    50                  55                  60

Arg Phe Ser Gly Ser Gly Ser Gly Thr Asp Phe Thr Leu Thr Ile
65                  70                  75

```
Ser Ser Leu Gln Pro Glu Asp Phe Ala Thr Tyr Tyr Cys Gln Gln
                80                  85                  90

Ser Tyr Thr Thr Pro Pro Thr Phe Gly Gln Gly Thr Lys Val Glu
                95                 100                 105

Ile Lys Arg

<210> SEQ ID NO 75
<211> LENGTH: 108
<212> TYPE: PRT
<213> ORGANISM: Artificial sequence
<220> FEATURE:
<223> OTHER INFORMATION: antibody light chain

<400> SEQUENCE: 75

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Ser Tyr Thr Thr Pro Pro Thr Phe Gly Gln Gly Thr Lys Val Glu
                95                 100                 105

Ile Lys Arg

<210> SEQ ID NO 76
<211> LENGTH: 108
<212> TYPE: PRT
<213> ORGANISM: Artificial sequence
<220> FEATURE:
<223> OTHER INFORMATION: antibody light chain

<400> SEQUENCE: 76

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Ser Ile Ser
                20                  25                  30

Ser Tyr Leu Ala Trp Tyr Gln Gln Lys Pro Gly Lys Ala Pro Lys
                35                  40                  45

Leu Leu Ile Tyr Gly Ala Ser Ser Arg Ala Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Ser Trp Ser Tyr Pro Leu Thr Phe Gly Gln Gly Thr Lys Val Glu
                95                 100                 105

Ile Lys Arg

<210> SEQ ID NO 77
<211> LENGTH: 108
<212> TYPE: PRT
<213> ORGANISM: Artificial sequence
```

```
<220> FEATURE:
<223> OTHER INFORMATION: antibody light chain

<400> SEQUENCE: 77

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Ser Ile Ser
                20                  25                  30

Ser Tyr Leu Ala Trp Tyr Gln Gln Lys Pro Gly Lys Ala Pro Lys
                35                  40                  45

Leu Leu Ile Tyr Gly Ala Ser Ser Arg Ala Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Ser Tyr Asn Thr Pro Phe Thr Phe Gly Gln Gly Thr Lys Val Glu
                95                 100                 105

Ile Lys Arg

<210> SEQ ID NO 78
<211> LENGTH: 108
<212> TYPE: PRT
<213> ORGANISM: Artificial sequence
<220> FEATURE:
<223> OTHER INFORMATION: antibody light chain

<400> SEQUENCE: 78

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Ser Ile Ser
                20                  25                  30

Ser Tyr Leu Ala Trp Tyr Gln Gln Lys Pro Gly Lys Ala Pro Lys
                35                  40                  45

Leu Leu Ile Tyr Gly Ala Ser Ser Arg Ala Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Tyr Ser Ser Pro Leu Thr Phe Gly Gln Gly Thr Lys Val Glu
                95                 100                 105

Ile Lys Arg

<210> SEQ ID NO 79
<211> LENGTH: 108
<212> TYPE: PRT
<213> ORGANISM: Artificial sequence
<220> FEATURE:
<223> OTHER INFORMATION: antibody light chain

<400> SEQUENCE: 79

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
                35                  40                  45
```

```
Leu Leu Ile Tyr Ser Ala Ser Phe Leu Tyr Ser Gly Val Pro Ser
             50                  55                  60

Arg Phe Ser Gly Ser Gly Ser Gly Thr Asp Phe Thr Leu Thr Ile
             65                  70                  75

Ser Ser Leu Gln Pro Glu Asp Phe Ala Thr Tyr Tyr Cys Gln Gln
             80                  85                  90

Ser Phe Ala Thr Pro Ala Thr Phe Gly Gln Gly Thr Lys Val Glu
             95                 100                 105

Ile Lys Arg

<210> SEQ ID NO 80
<211> LENGTH: 108
<212> TYPE: PRT
<213> ORGANISM: Artificial sequence
<220> FEATURE:
<223> OTHER INFORMATION: antibody light chain

<400> SEQUENCE: 80

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
             20                  25                  30

Thr Ala Val Ala Trp Tyr Gln Gln Lys Pro Gly Lys Ala Pro Lys
             35                  40                  45

Leu Leu Ile Tyr Ser Ala Ser Phe Leu Tyr Ser Gly Val Pro Ser
             50                  55                  60

Arg Phe Ser Gly Ser Gly Ser Gly Thr Asp Phe Thr Leu Thr Ile
             65                  70                  75

Ser Ser Leu Gln Pro Glu Asp Phe Ala Thr Tyr Tyr Cys Gln Gln
             80                  85                  90

Ser Arg Ala Ala Leu Pro Thr Phe Gly Gln Gly Thr Lys Val Glu
             95                 100                 105

Ile Lys Arg

<210> SEQ ID NO 81
<211> LENGTH: 108
<212> TYPE: PRT
<213> ORGANISM: Artificial sequence
<220> FEATURE:
<223> OTHER INFORMATION: antibody light chain

<400> SEQUENCE: 81

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
             20                  25                  30

Thr Ala Val Ala Trp Tyr Gln Gln Lys Pro Gly Lys Ala Pro Lys
             35                  40                  45

Leu Leu Ile Tyr Ser Ala Ser Phe Leu Tyr Ser Gly Val Pro Ser
             50                  55                  60

Arg Phe Ser Gly Ser Gly Ser Gly Thr Asp Phe Thr Leu Thr Ile
             65                  70                  75

Ser Ser Leu Gln Pro Glu Asp Phe Ala Thr Tyr Tyr Cys Gln Gln
             80                  85                  90

Ser Arg Ser Asp His Pro Thr Phe Gly Gln Gly Thr Lys Val Glu
             95                 100                 105
```

```
Ile Lys Arg

<210> SEQ ID NO 82
<211> LENGTH: 108
<212> TYPE: PRT
<213> ORGANISM: Artificial sequence
<220> FEATURE:
<223> OTHER INFORMATION: antibody light chain

<400> SEQUENCE: 82

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Ser Arg Ala Asn Thr Pro Thr Phe Gly Gln Gly Thr Lys Val Glu
                95                  100                 105

Ile Lys Arg

<210> SEQ ID NO 83
<211> LENGTH: 108
<212> TYPE: PRT
<213> ORGANISM: Artificial sequence
<220> FEATURE:
<223> OTHER INFORMATION: antibody light chain

<400> SEQUENCE: 83

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Ser Arg Thr Thr Pro Pro Thr Phe Gly Gln Gly Thr Lys Val Glu
                95                  100                 105

Ile Lys Arg

<210> SEQ ID NO 84
<211> LENGTH: 108
<212> TYPE: PRT
<213> ORGANISM: Artificial sequence
<220> FEATURE:
<223> OTHER INFORMATION: antibody light chain

<400> SEQUENCE: 84

Asp Ile Gln Met Thr Gln Ser Pro Ser Ser Leu Ser Ala Ser Val
```

```
               1               5                  10                 15
Gly Asp Arg Val Thr Ile Thr Cys Arg Ala Ser Gln Asp Val Ser
                        20                  25                  30

Thr Ala Val Ala Trp Tyr Gln Gln Lys Pro Gly Lys Ala Pro Lys
                        35                  40                  45

Leu Leu Ile Tyr Ser Ala Ser Phe Leu Tyr Ser Gly Val Pro Ser
                        50                  55                  60

Arg Phe Ser Gly Ser Gly Ser Gly Thr Asp Phe Thr Leu Thr Ile
                        65                  70                  75

Ser Ser Leu Gln Pro Glu Asp Phe Ala Thr Tyr Tyr Cys Gln Gln
                        80                  85                  90

Pro Phe Asp Leu Pro Met Thr Phe Gly Gln Gly Thr Lys Val Glu
                        95                 100                 105

Ile Lys Arg

<210> SEQ ID NO 85
<211> LENGTH: 108
<212> TYPE: PRT
<213> ORGANISM: Artificial sequence
<220> FEATURE:
<223> OTHER INFORMATION: antibody light chain

<400> SEQUENCE: 85

Asp Ile Gln Met Thr Gln Ser Pro Ser Ser Leu Ser Ala Ser Val
 1               5                  10                 15

Gly Asp Arg Val Thr Ile Thr Cys Arg Ala Ser Gln Asp Val Ser
                        20                  25                  30

Thr Ala Val Ala Trp Tyr Gln Gln Lys Pro Gly Lys Ala Pro Lys
                        35                  40                  45

Leu Leu Ile Tyr Ser Ala Ser Phe Leu Tyr Ser Gly Val Pro Ser
                        50                  55                  60

Arg Phe Ser Gly Ser Gly Ser Gly Thr Asp Phe Thr Leu Thr Ile
                        65                  70                  75

Ser Ser Leu Gln Pro Glu Asp Phe Ala Thr Tyr Tyr Cys Gln Gln
                        80                  85                  90

Pro Asn Ser Thr Pro Phe Thr Phe Gly Gln Gly Thr Lys Val Glu
                        95                 100                 105

Ile Lys Arg

<210> SEQ ID NO 86
<211> LENGTH: 108
<212> TYPE: PRT
<213> ORGANISM: Artificial sequence
<220> FEATURE:
<223> OTHER INFORMATION: antibody light chain

<400> SEQUENCE: 86

Asp Ile Gln Met Thr Gln Ser Pro Ser Ser Leu Ser Ala Ser Val
 1               5                  10                 15

Gly Asp Arg Val Thr Ile Thr Cys Arg Ala Ser Gln Asp Val Ser
                        20                  25                  30

Thr Ala Val Ala Trp Tyr Gln Gln Lys Pro Gly Lys Ala Pro Lys
                        35                  40                  45

Leu Leu Ile Tyr Ser Ala Ser Phe Leu Tyr Ser Gly Val Pro Ser
                        50                  55                  60

Arg Phe Ser Gly Ser Gly Ser Gly Thr Asp Phe Thr Leu Thr Ile
                        65                  70                  75
```

```
Ser Ser Leu Gln Pro Glu Asp Phe Ala Thr Tyr Tyr Cys Gln Gln
                80                  85                  90

Ser Arg Phe Asp His Pro Thr Phe Gly Gln Gly Thr Lys Met Glu
                95                 100                 105

Ile Lys Arg

<210> SEQ ID NO 87
<211> LENGTH: 108
<212> TYPE: PRT
<213> ORGANISM: Artificial sequence
<220> FEATURE:
<223> OTHER INFORMATION: antibody light chain

<400> SEQUENCE: 87

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Tyr Tyr Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Ser Tyr His Thr His Ser Thr Phe Gly Gln Gly Thr Lys Val Glu
                95                 100                 105

Ile Lys Arg

<210> SEQ ID NO 88
<211> LENGTH: 108
<212> TYPE: PRT
<213> ORGANISM: Artificial sequence
<220> FEATURE:
<223> OTHER INFORMATION: antibody light chain

<400> SEQUENCE: 88

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Ser Arg Asp Ile Pro Pro Thr Phe Gly Gln Gly Thr Lys Val Glu
                95                 100                 105

Ile Lys Arg

<210> SEQ ID NO 89
<211> LENGTH: 108
<212> TYPE: PRT
```

```
<213> ORGANISM: Artificial sequence
<220> FEATURE:
<223> OTHER INFORMATION: antibody light chain

<400> SEQUENCE: 89

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
                50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
                80                  85                  90

Ser Arg Asn Met Pro Ala Thr Phe Gly Gln Gly Thr Lys Val Glu
                95                 100                 105

Ile Lys Arg

<210> SEQ ID NO 90
<211> LENGTH: 108
<212> TYPE: PRT
<213> ORGANISM: Artificial sequence
<220> FEATURE:
<223> OTHER INFORMATION: antibody light chain

<400> SEQUENCE: 90

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
                50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
                80                  85                  90

Thr Arg Val Met Pro Ala Thr Phe Gly Gln Gly Thr Lys Val Glu
                95                 100                 105

Ile Lys Arg

<210> SEQ ID NO 91
<211> LENGTH: 108
<212> TYPE: PRT
<213> ORGANISM: Artificial sequence
<220> FEATURE:
<223> OTHER INFORMATION: antibody light chain

<400> SEQUENCE: 91

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
```

```
                        35                  40                  45

Leu Leu Ile Tyr Ser Ala Ser Phe Leu Tyr Tyr Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Thr Tyr Thr Ile Pro Pro Thr Phe Gly Gln Gly Thr Lys Val Glu
                95                 100                 105

Ile Lys Arg

<210> SEQ ID NO 92
<211> LENGTH: 108
<212> TYPE: PRT
<213> ORGANISM: Artificial sequence
<220> FEATURE:
<223> OTHER INFORMATION: antibody light chain

<400> SEQUENCE: 92

Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Ala Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Ser Tyr Ala Tyr Pro Phe Thr Phe Gly Gln Gly Thr Lys Val Glu
                95                 100                 105

Ile Lys Arg

<210> SEQ ID NO 93
<211> LENGTH: 107
<212> TYPE: PRT
<213> ORGANISM: Artificial sequence
<220> FEATURE:
<223> OTHER INFORMATION: antibody light chain

<400> SEQUENCE: 93

Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
                35                  40                  45

Leu Leu Ile Tyr Ser Ala Ser Leu Glu Ser Gly Val Pro Ser Arg
                50                  55                  60

Phe Ser Gly Ser Gly Ser Gly Thr Asp Phe Thr Leu Thr Ile Ser
                65                  70                  75

Ser Leu Gln Pro Glu Asp Phe Ala Thr Tyr Tyr Cys Gln Gln Ser
                80                  85                  90

Tyr Asp Leu Pro Phe Thr Phe Gly Gln Gly Thr Lys Val Glu Ile
                95                 100                 105
```

<210> SEQ ID NO 94
<211> LENGTH: 107
<212> TYPE: PRT
<213> ORGANISM: Artificial sequence
<220> FEATURE:
<223> OTHER INFORMATION: antibody light chain

<400> SEQUENCE: 94

```
Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
                35                  40                  45

Leu Leu Ile Tyr Ser Ala Thr Leu Ala Ser Gly Val Pro Ser Arg
                50                  55                  60

Phe Ser Gly Ser Gly Ser Gly Thr Asp Phe Thr Leu Thr Ile Ser
                65                  70                  75

Ser Leu Gln Pro Glu Asp Phe Ala Thr Tyr Tyr Cys Gln Gln Ser
                80                  85                  90

Tyr Gly Gly Pro Phe Thr Phe Gly Gln Gly Thr Lys Val Glu Ile
                95                 100                 105

Lys Arg
```

<210> SEQ ID NO 95
<211> LENGTH: 108
<212> TYPE: PRT
<213> ORGANISM: Artificial sequence
<220> FEATURE:
<223> OTHER INFORMATION: antibody light chain

<400> SEQUENCE: 95

```
Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Ala Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Ser Tyr Asn Tyr Pro Phe Thr Phe Gly Gln Gly Thr Lys Val Glu
                95                 100                 105

Ile Lys Arg
```

<210> SEQ ID NO 96
<211> LENGTH: 108
<212> TYPE: PRT
<213> ORGANISM: Artificial sequence
<220> FEATURE:
<223> OTHER INFORMATION: antibody light chain

<400> SEQUENCE: 96

```
Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Asp Gly Ala
             20                  25                  30

Arg Ser Leu Ala Trp Tyr Gln Gln Lys Pro Gly Lys Ala Pro Lys
         35                  40                  45

Leu Leu Ile Tyr Ser Ala Ser Asn Leu Ala Ser Gly Val Pro Ser
     50                  55                  60

Arg Phe Ser Gly Ser Gly Ser Gly Thr Asp Phe Thr Leu Thr Ile
 65                  70                  75

Ser Ser Leu Gln Pro Glu Asp Phe Ala Thr Tyr Tyr Cys Gln Gln
             80                  85                  90

Phe Tyr Ser Asp Pro Phe Thr Phe Gly Gln Gly Thr Lys Val Glu
         95                 100                 105

Ile Lys Arg

<210> SEQ ID NO 97
<211> LENGTH: 108
<212> TYPE: PRT
<213> ORGANISM: Artificial sequence
<220> FEATURE:
<223> OTHER INFORMATION: antibody light chain

<400> SEQUENCE: 97

Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Asp Gly Ala
             20                  25                  30

Ile Tyr Leu Ala Trp Tyr Gln Gln Lys Pro Gly Lys Ala Pro Lys
         35                  40                  45

Leu Leu Ile Tyr Ser Ala Ser Thr Leu Ala Ser Gly Val Pro Ser
     50                  55                  60

Arg Phe Ser Gly Ser Gly Ser Gly Thr Asp Phe Thr Leu Thr Ile
 65                  70                  75

Ser Ser Leu Gln Pro Glu Asp Phe Ala Thr Tyr Tyr Cys Gln Gln
             80                  85                  90

Gly Tyr Asn Tyr Pro Phe Thr Phe Gly Gln Gly Thr Lys Val Glu
         95                 100                 105

Ile Lys Arg

<210> SEQ ID NO 98
<211> LENGTH: 107
<212> TYPE: PRT
<213> ORGANISM: Artificial sequence
<220> FEATURE:
<223> OTHER INFORMATION: antibody light chain

<400> SEQUENCE: 98

Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Asp Val Asn
             20                  25                  30

Thr Ala Val Ala Trp Tyr Gln Gln Lys Pro Gly Lys Ala Pro Lys
         35                  40                  45

Leu Leu Ile Tyr Ser Ala Ser Phe Leu Tyr Ser Gly Val Pro Ser
     50                  55                  60

Arg Phe Ser Gly Ser Arg Ser Gly Thr Asp Phe Thr Leu Thr Ile
```

```
                    65                  70                  75
Ser Ser Leu Gln Pro Glu Asp Phe Ala Thr Tyr Tyr Cys Gln Gln
                80                  85                  90

His Tyr Thr Thr Pro Pro Thr Phe Gly Gln Gly Thr Lys Val Glu
                95                 100                 105

Ile Lys

<210> SEQ ID NO 99
<211> LENGTH: 32
<212> TYPE: PRT
<213> ORGANISM: Artificial sequence
<220> FEATURE:
<223> OTHER INFORMATION: antibody light chain framework region

<400> SEQUENCE: 99

Gly Val Pro Ser Arg Phe Ser Gly Ser Gly Ser Gly Thr Asp Phe
  1               5                  10                  15

Thr Leu Thr Ile Ser Ser Leu Gln Pro Glu Asp Phe Ala Thr Tyr
                 20                  25                  30

Tyr Cys

<210> SEQ ID NO 100
<211> LENGTH: 10
<212> TYPE: PRT
<213> ORGANISM: Artificial sequence
<220> FEATURE:
<223> OTHER INFORMATION: antibody light chain framework region

<400> SEQUENCE: 100

Phe Gly Gln Gly Thr Lys Val Glu Ile Lys
  1               5                  10

<210> SEQ ID NO 101
<211> LENGTH: 14
<212> TYPE: PRT
<213> ORGANISM: Artificial sequence
<220> FEATURE:
<223> OTHER INFORMATION: antibody light chain framework region

<400> SEQUENCE: 101

Trp Tyr Gln Gln Lys Pro Gly Lys Ala Pro Lys Leu Leu Ile
  1               5                  10

<210> SEQ ID NO 102
<211> LENGTH: 23
<212> TYPE: PRT
<213> ORGANISM: Artificial sequence
<220> FEATURE:
<223> OTHER INFORMATION: antibody light chain framework region

<400> SEQUENCE: 102

Asp Ile Val Met Thr Gln Ser Pro Leu Ser Leu Pro Val Thr Pro
  1               5                  10                  15

Gly Glu Pro Ala Ser Ile Ser Cys
                 20

<210> SEQ ID NO 103
<211> LENGTH: 15
<212> TYPE: PRT
<213> ORGANISM: Artificial sequence
<220> FEATURE:
<223> OTHER INFORMATION: antibody light chain framework region

<400> SEQUENCE: 103
```

Trp Tyr Leu Gln Lys Pro Gly Gln Ser Pro Gln Leu Leu Ile Tyr
1               5                   10                  15

<210> SEQ ID NO 104
<211> LENGTH: 32
<212> TYPE: PRT
<213> ORGANISM: Artificial sequence
<220> FEATURE:
<223> OTHER INFORMATION: antibody light chain framework region

<400> SEQUENCE: 104

Gly Val Pro Asp Arg Phe Ser Gly Ser Gly Ser Gly Thr Asp Phe
1               5                   10                  15

Thr Leu Lys Ile Ser Arg Val Glu Ala Glu Asp Val Gly Val Tyr
                20                  25                  30

Tyr Cys

<210> SEQ ID NO 105
<211> LENGTH: 23
<212> TYPE: PRT
<213> ORGANISM: Artificial sequence
<220> FEATURE:
<223> OTHER INFORMATION: antibody light chain framework region

<400> SEQUENCE: 105

Glu Ile Val Leu Thr Gln Ser Pro Gly Thr Leu Ser Leu Ser Pro
1               5                   10                  15

Gly Glu Arg Ala Thr Leu Ser Cys
                20

<210> SEQ ID NO 106
<211> LENGTH: 15
<212> TYPE: PRT
<213> ORGANISM: Artificial sequence
<220> FEATURE:
<223> OTHER INFORMATION: antibody light chain framework region

<400> SEQUENCE: 106

Trp Tyr Gln Gln Lys Pro Gly Gln Ala Pro Arg Leu Leu Ile Tyr
1               5                   10                  15

<210> SEQ ID NO 107
<211> LENGTH: 32
<212> TYPE: PRT
<213> ORGANISM: Artificial sequence
<220> FEATURE:
<223> OTHER INFORMATION: antibody light chain framework region

<400> SEQUENCE: 107

Gly Ile Pro Asp Arg Phe Ser Gly Ser Gly Ser Gly Thr Asp Phe
1               5                   10                  15

Thr Leu Thr Ile Ser Arg Leu Glu Pro Glu Asp Phe Ala Val Tyr
                20                  25                  30

Tyr Cys

<210> SEQ ID NO 108
<211> LENGTH: 23
<212> TYPE: PRT
<213> ORGANISM: Artificial sequence
<220> FEATURE:
<223> OTHER INFORMATION: antibody light chain framework region

<400> SEQUENCE: 108

```
Asp Ile Val Met Thr Gln Ser Pro Asp Ser Leu Ala Val Ser Leu
 1               5                  10                  15

Gly Glu Arg Ala Thr Ile Asn Cys
                 20
```

```
<210> SEQ ID NO 109
<211> LENGTH: 15
<212> TYPE: PRT
<213> ORGANISM: Artificial sequence
<220> FEATURE:
<223> OTHER INFORMATION: antibody light chain framework region

<400> SEQUENCE: 109
```

```
Trp Tyr Gln Gln Lys Pro Gly Gln Pro Pro Lys Leu Leu Ile Tyr
 1               5                  10                  15
```

```
<210> SEQ ID NO 110
<211> LENGTH: 32
<212> TYPE: PRT
<213> ORGANISM: Artificial sequence
<220> FEATURE:
<223> OTHER INFORMATION: antibody light chain framework region

<400> SEQUENCE: 110
```

```
Gly Val Pro Asp Arg Phe Ser Gly Ser Gly Ser Gly Thr Asp Phe
 1               5                  10                  15

Thr Leu Thr Ile Ser Ser Leu Gln Ala Glu Asp Val Ala Val Tyr
                 20                  25                  30

Tyr Cys
```

```
<210> SEQ ID NO 111
<211> LENGTH: 30
<212> TYPE: PRT
<213> ORGANISM: Artificial sequence
<220> FEATURE:
<223> OTHER INFORMATION: antibody heavy chain framework region

<400> SEQUENCE: 111
```

```
Gln Val Gln Leu Val Gln Ser Gly Ala Glu Val Lys Lys Pro Gly
 1               5                  10                  15

Ala Ser Val Lys Val Ser Cys Lys Ala Ser Gly Tyr Thr Phe Thr
                 20                  25                  30
```

```
<210> SEQ ID NO 112
<211> LENGTH: 14
<212> TYPE: PRT
<213> ORGANISM: Artificial sequence
<220> FEATURE:
<223> OTHER INFORMATION: antibody heavy chain framework region

<400> SEQUENCE: 112
```

```
Trp Val Arg Gln Ala Pro Gly Gln Gly Leu Glu Trp Met Gly
                 5                  10
```

```
<210> SEQ ID NO 113
<211> LENGTH: 32
<212> TYPE: PRT
<213> ORGANISM: Artificial sequence
<220> FEATURE:
<223> OTHER INFORMATION: antibody heavy chain framework region

<400> SEQUENCE: 113
```

```
Arg Val Thr Ile Thr Ala Asp Thr Ser Thr Ser Thr Ala Tyr Met
 1               5                  10                  15
```

```
Glu Leu Ser Ser Leu Arg Ser Glu Asp Thr Ala Val Tyr Tyr Cys
            20                  25                  30

Ala Arg

<210> SEQ ID NO 114
<211> LENGTH: 25
<212> TYPE: PRT
<213> ORGANISM: Artificial sequence
<220> FEATURE:
<223> OTHER INFORMATION: antibody heavy chain framework region

<400> SEQUENCE: 114

Gln Val Gln Leu Val Gln Ser Gly Ala Glu Val Lys Lys Pro Gly
 1               5                  10                  15

Ala Ser Val Lys Val Ser Cys Lys Ala Ser
            20                  25

<210> SEQ ID NO 115
<211> LENGTH: 13
<212> TYPE: PRT
<213> ORGANISM: Artificial sequence
<220> FEATURE:
<223> OTHER INFORMATION: antibody heavy chain framework region

<400> SEQUENCE: 115

Trp Val Arg Gln Ala Pro Gly Gln Gly Leu Glu Trp Met
 1               5                  10

<210> SEQ ID NO 116
<211> LENGTH: 31
<212> TYPE: PRT
<213> ORGANISM: Artificial sequence
<220> FEATURE:
<223> OTHER INFORMATION: antibody heavy chain framework region

<400> SEQUENCE: 116

Arg Val Thr Ile Thr Ala Asp Thr Ser Thr Ser Thr Ala Tyr Met
 1               5                  10                  15

Glu Leu Ser Ser Leu Arg Ser Glu Asp Thr Ala Val Tyr Tyr Cys
            20                  25                  30

Ala

<210> SEQ ID NO 117
<211> LENGTH: 30
<212> TYPE: PRT
<213> ORGANISM: Artificial sequence
<220> FEATURE:
<223> OTHER INFORMATION: antibody heavy chain framework region

<400> SEQUENCE: 117

Arg Val Thr Ile Thr Ala Asp Thr Ser Thr Ser Thr Ala Tyr Met
 1               5                  10                  15

Glu Leu Ser Ser Leu Arg Ser Glu Asp Thr Ala Val Tyr Tyr Cys
            20                  25                  30

<210> SEQ ID NO 118
<211> LENGTH: 30
<212> TYPE: PRT
<213> ORGANISM: Artificial sequence
<220> FEATURE:
<223> OTHER INFORMATION: antibody heavy chain framework region

<400> SEQUENCE: 118

Gln Val Gln Leu Gln Glu Ser Gly Pro Gly Leu Val Lys Pro Ser
```

```
                1               5                  10                 15
Gln Thr Leu Ser Leu Thr Cys Thr Val Ser Gly Gly Ser Val Ser
                20                 25                 30

<210> SEQ ID NO 119
<211> LENGTH: 14
<212> TYPE: PRT
<213> ORGANISM: Artificial sequence
<220> FEATURE:
<223> OTHER INFORMATION: antibody heavy chain framework region

<400> SEQUENCE: 119

Trp Ile Arg Gln Pro Pro Gly Lys Gly Leu Glu Trp Ile Gly
                5                   10

<210> SEQ ID NO 120
<211> LENGTH: 32
<212> TYPE: PRT
<213> ORGANISM: Artificial sequence
<220> FEATURE:
<223> OTHER INFORMATION: antibody heavy chain framework region

<400> SEQUENCE: 120

Arg Val Thr Ile Ser Val Asp Thr Ser Lys Asn Gln Phe Ser Leu
 1               5                  10                  15
Lys Leu Ser Ser Val Thr Ala Ala Asp Thr Ala Val Tyr Tyr Cys
                20                 25                  30
Ala Arg

<210> SEQ ID NO 121
<211> LENGTH: 25
<212> TYPE: PRT
<213> ORGANISM: Artificial sequence
<220> FEATURE:
<223> OTHER INFORMATION: antibody heavy chain framework region

<400> SEQUENCE: 121

Gln Val Gln Leu Gln Glu Ser Gly Pro Gly Leu Val Lys Pro Ser
 1               5                  10                  15
Gln Thr Leu Ser Leu Thr Cys Thr Val Ser
                20                 25

<210> SEQ ID NO 122
<211> LENGTH: 13
<212> TYPE: PRT
<213> ORGANISM: Artificial sequence
<220> FEATURE:
<223> OTHER INFORMATION: antibody heavy chain framework region

<400> SEQUENCE: 122

Trp Ile Arg Gln Pro Pro Gly Lys Gly Leu Glu Trp Ile
                5                   10

<210> SEQ ID NO 123
<211> LENGTH: 31
<212> TYPE: PRT
<213> ORGANISM: Artificial sequence
<220> FEATURE:
<223> OTHER INFORMATION: antibody heavy chain framework region

<400> SEQUENCE: 123

Arg Val Thr Ile Ser Val Asp Thr Ser Lys Asn Gln Phe Ser Leu
 1               5                  10                  15
Lys Leu Ser Ser Val Thr Ala Ala Asp Thr Ala Val Tyr Tyr Cys
```

Ala

<210> SEQ ID NO 124
<211> LENGTH: 30
<212> TYPE: PRT
<213> ORGANISM: Artificial sequence
<220> FEATURE:
<223> OTHER INFORMATION: antibody heavy chain framework region

<400> SEQUENCE: 124

Arg Val Thr Ile Ser Val Asp Thr Ser Lys Asn Gln Phe Ser Leu
 1               5                  10                  15

Lys Leu Ser Ser Val Thr Ala Ala Asp Thr Ala Val Tyr Tyr Cys
                20                  25                  30

<210> SEQ ID NO 125
<211> LENGTH: 30
<212> TYPE: PRT
<213> ORGANISM: Artificial sequence
<220> FEATURE:
<223> OTHER INFORMATION: antibody heavy chain framework region

<400> SEQUENCE: 125

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
                20                  25                  30

<210> SEQ ID NO 126
<211> LENGTH: 14
<212> TYPE: PRT
<213> ORGANISM: Artificial sequence
<220> FEATURE:
<223> OTHER INFORMATION: antibody heavy chain framework region

<400> SEQUENCE: 126

Trp Val Arg Gln Ala Pro Gly Lys Gly Leu Glu Trp Val Ser
                 5                  10

<210> SEQ ID NO 127
<211> LENGTH: 32
<212> TYPE: PRT
<213> ORGANISM: Artificial sequence
<220> FEATURE:
<223> OTHER INFORMATION: antibody heavy chain framework region

<400> SEQUENCE: 127

Arg Phe Thr Ile Ser Arg Asp Asn Ser Lys Asn Thr Leu Tyr Leu
 1               5                  10                  15

Gln Met Asn Ser Leu Arg Ala Glu Asp Thr Ala Val Tyr Tyr Cys
                20                  25                  30

Ala Arg

<210> SEQ ID NO 128
<211> LENGTH: 25
<212> TYPE: PRT
<213> ORGANISM: Artificial sequence
<220> FEATURE:
<223> OTHER INFORMATION: antibody heavy chain framework region

<400> SEQUENCE: 128

Glu Val Gln Leu Val Glu Ser Gly Gly Gly Leu Val Gln Pro Gly
 1               5                  10                  15

```
Gly Ser Leu Arg Leu Ser Cys Ala Ala Ser
            20                  25

<210> SEQ ID NO 129
<211> LENGTH: 13
<212> TYPE: PRT
<213> ORGANISM: Artificial sequence
<220> FEATURE:
<223> OTHER INFORMATION: antibody heavy chain framework region

<400> SEQUENCE: 129

Trp Val Arg Gln Ala Pro Gly Lys Gly Leu Glu Trp Val
 1               5                  10

<210> SEQ ID NO 130
<211> LENGTH: 31
<212> TYPE: PRT
<213> ORGANISM: Artificial sequence
<220> FEATURE:
<223> OTHER INFORMATION: antibody heavy chain framework region

<400> SEQUENCE: 130

Arg Phe Thr Ile Ser Arg Asp Asn Ser Lys Asn Thr Leu Tyr Leu
 1               5                  10                  15

Gln Met Asn Ser Leu Arg Ala Glu Asp Thr Ala Val Tyr Tyr Cys
            20                  25                  30

Ala

<210> SEQ ID NO 131
<211> LENGTH: 30
<212> TYPE: PRT
<213> ORGANISM: Artificial sequence
<220> FEATURE:
<223> OTHER INFORMATION: antibody heavy chain framework region

<400> SEQUENCE: 131

Arg Phe Thr Ile Ser Arg Asp Asn Ser Lys Asn Thr Leu Tyr Leu
 1               5                  10                  15

Gln Met Asn Ser Leu Arg Ala Glu Asp Thr Ala Val Tyr Tyr Cys
            20                  25                  30

<210> SEQ ID NO 132
<211> LENGTH: 30
<212> TYPE: PRT
<213> ORGANISM: Artificial sequence
<220> FEATURE:
<223> OTHER INFORMATION: antibody heavy chain framework region

<400> SEQUENCE: 132

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Asn Ile Lys
            20                  25                  30

<210> SEQ ID NO 133
<211> LENGTH: 32
<212> TYPE: PRT
<213> ORGANISM: Artificial sequence
<220> FEATURE:
<223> OTHER INFORMATION: antibody heavy chain framework region

<400> SEQUENCE: 133

Arg Phe Thr Ile Ser Ala Asp Thr Ser Lys Asn Thr Ala Tyr Leu
 1               5                  10                  15
```

Gln Met Asn Ser Leu Arg Ala Glu Asp Thr Ala Val Tyr Tyr Cys
            20                  25                  30

Ser Arg

<210> SEQ ID NO 134
<211> LENGTH: 31
<212> TYPE: PRT
<213> ORGANISM: Artificial sequence
<220> FEATURE:
<223> OTHER INFORMATION: antibody heavy chain framework region

<400> SEQUENCE: 134

Arg Phe Thr Ile Ser Ala Asp Thr Ser Lys Asn Thr Ala Tyr Leu
 1               5                  10                  15

Gln Met Asn Ser Leu Arg Ala Glu Asp Thr Ala Val Tyr Tyr Cys
            20                  25                  30

Ser

<210> SEQ ID NO 135
<211> LENGTH: 32
<212> TYPE: PRT
<213> ORGANISM: Artificial sequence
<220> FEATURE:
<223> OTHER INFORMATION: antibody heavy chain framework region

<400> SEQUENCE: 135

Arg Phe Thr Ile Ser Ala Asp Thr Ser Lys Asn Thr Ala Tyr Leu
 1               5                  10                  15

Gln Met Asn Ser Leu Arg Ala Glu Asp Thr Ala Val Tyr Tyr Cys
            20                  25                  30

Ala Arg

<210> SEQ ID NO 136
<211> LENGTH: 31
<212> TYPE: PRT
<213> ORGANISM: Artificial sequence
<220> FEATURE:
<223> OTHER INFORMATION: antibody heavy chain framework region

<400> SEQUENCE: 136

Arg Phe Thr Ile Ser Ala Asp Thr Ser Lys Asn Thr Ala Tyr Leu
 1               5                  10                  15

Gln Met Asn Ser Leu Arg Ala Glu Asp Thr Ala Val Tyr Tyr Cys
            20                  25                  30

Ala

<210> SEQ ID NO 137
<211> LENGTH: 30
<212> TYPE: PRT
<213> ORGANISM: Artificial sequence
<220> FEATURE:
<223> OTHER INFORMATION: antibody heavy chain framework region

<400> SEQUENCE: 137

Arg Phe Thr Ile Ser Ala Asp Thr Ser Lys Asn Thr Ala Tyr Leu
 1               5                  10                  15

Gln Met Asn Ser Leu Arg Ala Glu Asp Thr Ala Val Tyr Tyr Cys
            20                  25                  30

<210> SEQ ID NO 138
<211> LENGTH: 1007

<212> TYPE: PRT
<213> ORGANISM: Homo sapiens

<400> SEQUENCE: 138

Met Gly Ser Gly Gly Asp Ser Leu Leu Gly Arg Gly Ser Leu
1               5                   10                  15
Pro Leu Leu Leu Leu Ile Met Gly Gly Met Ala Gln Asp Ser
            20                  25                  30
Pro Pro Gln Ile Leu Val His Pro Gln Asp Gln Leu Phe Gln Gly
            35                  40                  45
Pro Gly Pro Ala Arg Met Ser Cys Arg Ala Ser Gly Gln Pro Pro
            50                  55                  60
Pro Thr Ile Arg Trp Leu Leu Asn Gly Gln Pro Leu Ser Met Val
            65                  70                  75
Pro Pro Asp Pro His His Leu Leu Pro Asp Gly Thr Leu Leu Leu
            80                  85                  90
Leu Gln Pro Pro Ala Arg Gly His Ala His Asp Gly Gln Ala Leu
            95                  100                 105
Ser Thr Asp Leu Gly Val Tyr Thr Cys Glu Ala Ser Asn Arg Leu
            110                 115                 120
Gly Thr Ala Val Ser Arg Gly Ala Arg Leu Ser Val Ala Val Leu
            125                 130                 135
Arg Glu Asp Phe Gln Ile Gln Pro Arg Asp Met Val Ala Val Val
            140                 145                 150
Gly Glu Gln Phe Thr Leu Glu Cys Gly Pro Pro Trp Gly His Pro
            155                 160                 165
Glu Pro Thr Val Ser Trp Trp Lys Asp Gly Lys Pro Leu Ala Leu
            170                 175                 180
Gln Pro Gly Arg His Thr Val Ser Gly Gly Ser Leu Leu Met Ala
            185                 190                 195
Arg Ala Glu Lys Ser Asp Glu Gly Thr Tyr Met Cys Val Ala Thr
            200                 205                 210
Asn Ser Ala Gly His Arg Glu Ser Arg Ala Ala Arg Val Ser Ile
            215                 220                 225
Gln Glu Pro Gln Asp Tyr Thr Glu Pro Val Glu Leu Leu Ala Val
            230                 235                 240
Arg Ile Gln Leu Glu Asn Val Thr Leu Leu Asn Pro Asp Pro Ala
            245                 250                 255
Glu Gly Pro Lys Pro Arg Pro Ala Val Trp Leu Ser Trp Lys Val
            260                 265                 270
Ser Gly Pro Ala Ala Pro Ala Gln Ser Tyr Thr Ala Leu Phe Arg
            275                 280                 285
Thr Gln Thr Ala Pro Gly Gly Gln Gly Ala Pro Trp Ala Glu Glu
            290                 295                 300
Leu Leu Ala Gly Trp Gln Ser Ala Glu Leu Gly Gly Leu His Trp
            305                 310                 315
Gly Gln Asp Tyr Glu Phe Lys Val Arg Pro Ser Ser Gly Arg Ala
            320                 325                 330
Arg Gly Pro Asp Ser Asn Val Leu Leu Leu Arg Leu Pro Glu Lys
            335                 340                 345
Val Pro Ser Ala Pro Pro Gln Glu Val Thr Leu Lys Pro Gly Asn
            350                 355                 360
Gly Thr Val Phe Val Ser Trp Val Pro Pro Ala Glu Asn His
            365                 370                 375

```
Asn Gly Ile Ile Arg Gly Tyr Gln Val Trp Ser Leu Gly Asn Thr
                380                 385                 390

Ser Leu Pro Pro Ala Asn Trp Thr Val Gly Glu Gln Thr Gln
            395                 400                 405

Leu Glu Ile Ala Thr His Met Pro Gly Ser Tyr Cys Val Gln Val
                410                 415                 420

Ala Ala Val Thr Gly Ala Gly Ala Gly Glu Pro Ser Arg Pro Val
                425                 430                 435

Cys Leu Leu Leu Glu Gln Ala Met Glu Arg Ala Thr Gln Glu Pro
                440                 445                 450

Ser Glu His Gly Pro Trp Thr Leu Glu Gln Leu Arg Ala Thr Leu
                455                 460                 465

Lys Arg Pro Glu Val Ile Ala Thr Cys Gly Val Ala Leu Trp Leu
                470                 475                 480

Leu Leu Leu Gly Thr Ala Val Cys Ile His Arg Arg Arg Arg Ala
                485                 490                 495

Arg Val His Leu Gly Pro Gly Leu Tyr Arg Tyr Thr Ser Glu Asp
                500                 505                 510

Ala Ile Leu Lys His Arg Met Asp His Ser Asp Ser Gln Trp Leu
                515                 520                 525

Ala Asp Thr Trp Arg Ser Thr Ser Gly Ser Arg Asp Leu Ser Ser
                530                 535                 540

Ser Ser Ser Leu Ser Ser Arg Leu Gly Ala Asp Ala Arg Asp Pro
                545                 550                 555

Leu Asp Cys Arg Arg Ser Leu Leu Ser Trp Asp Ser Arg Ser Pro
                560                 565                 570

Gly Val Pro Leu Leu Pro Asp Thr Ser Thr Phe Tyr Gly Ser Leu
                575                 580                 585

Ile Ala Glu Leu Pro Ser Ser Thr Pro Ala Arg Pro Ser Pro Gln
                590                 595                 600

Val Pro Ala Val Arg Arg Leu Pro Pro Gln Leu Ala Gln Leu Ser
                605                 610                 615

Ser Pro Cys Ser Ser Asp Ser Leu Cys Ser Arg Arg Gly Leu
                620                 625                 630

Ser Ser Pro Arg Leu Ser Leu Ala Pro Ala Glu Ala Trp Lys Ala
                635                 640                 645

Lys Lys Lys Gln Glu Leu Gln His Ala Asn Ser Ser Pro Leu Leu
                650                 655                 660

Arg Gly Ser His Ser Leu Glu Leu Arg Ala Cys Glu Leu Gly Asn
                665                 670                 675

Arg Gly Ser Lys Asn Leu Ser Gln Ser Pro Gly Ala Val Pro Gln
                680                 685                 690

Ala Leu Val Ala Trp Arg Ala Leu Gly Pro Lys Leu Leu Ser Ser
                695                 700                 705

Ser Asn Glu Leu Val Thr Arg His Leu Pro Ala Pro Leu Phe
                710                 715                 720

Pro His Glu Thr Pro Thr Gln Ser Gln Thr Gln Pro Pro
                725                 730                 735

Val Ala Pro Gln Ala Pro Ser Ser Ile Leu Leu Pro Ala Ala Pro
                740                 745                 750

Ile Pro Ile Leu Ser Pro Cys Ser Pro Pro Ser Pro Gln Ala Ser
                755                 760                 765
```

-continued

```
Ser Leu Ser Gly Pro Ser Pro Ala Ser Arg Leu Ser Ser
            770                 775                 780

Ser Leu Ser Ser Leu Gly Glu Asp Gln Asp Ser Val Leu Thr Pro
            785                 790                 795

Glu Glu Val Ala Leu Cys Leu Glu Leu Ser Gly Gly Glu Glu Thr
            800                 805                 810

Pro Arg Asn Ser Val Ser Pro Met Pro Arg Ala Pro Ser Pro Pro
            815                 820                 825

Thr Thr Tyr Gly Tyr Ile Ser Val Pro Thr Ala Ser Glu Phe Thr
            830                 835                 840

Asp Met Gly Arg Thr Gly Gly Val Gly Pro Lys Gly Gly Val
            845                 850                 855

Leu Leu Cys Pro Pro Arg Pro Cys Leu Thr Pro Thr Pro Ser Glu
            860                 865                 870

Gly Ser Leu Ala Asn Gly Trp Gly Ser Ala Ser Glu Asp Asn Ala
            875                 880                 885

Ala Ser Ala Arg Ala Ser Leu Val Ser Ser Ser Asp Gly Ser Phe
            890                 895                 900

Leu Ala Asp Ala His Phe Ala Arg Ala Leu Ala Val Ala Val Asp
            905                 910                 915

Ser Phe Gly Phe Gly Leu Glu Pro Arg Glu Ala Asp Cys Val Phe
            920                 925                 930

Ile Asp Ala Ser Ser Pro Ser Pro Arg Asp Glu Ile Phe Leu
            935                 940                 945

Thr Pro Asn Leu Ser Leu Pro Leu Trp Glu Trp Arg Pro Asp Trp
            950                 955                 960

Leu Glu Asp Met Glu Val Ser His Thr Gln Arg Leu Gly Arg Gly
            965                 970                 975

Met Pro Pro Trp Pro Pro Asp Ser Gln Ile Ser Ser Gln Arg Ser
            980                 985                 990

Gln Leu His Cys Arg Met Pro Lys Ala Gly Ala Ser Pro Val Asp
            995                 1000                1005

Tyr Ser

<210> SEQ ID NO 139
<211> LENGTH: 11
<212> TYPE: PRT
<213> ORGANISM: Artificial sequence
<220> FEATURE:
<223> OTHER INFORMATION: antibody light chain framework region

<400> SEQUENCE: 139

Phe Gly Gln Gly Thr Lys Met Glu Ile Lys Arg
                5                   10

<210> SEQ ID NO 140
<211> LENGTH: 125
<212> TYPE: PRT
<213> ORGANISM: Artificial sequence
<220> FEATURE:
<223> OTHER INFORMATION: antibody light chain

<400> SEQUENCE: 140

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Ile Ser
            20                  25                  30
```

-continued

```
Gly Ser Trp Ile His Trp Val Arg Gln Ala Pro Gly Lys Gly Leu
             35                  40                  45

Glu Trp Val Ala Val Ile Thr Pro Ala Gly Gly Tyr Thr Tyr Tyr
         50                  55                  60

Ala Asp Ser Val Lys Gly Arg Phe Thr Ile Ser Ala Asp Thr Ser
     65                  70                  75

Lys Asn Thr Ala Tyr Leu Gln Met Asn Ser Leu Arg Ala Glu Asp
 80                  85                  90

Thr Ala Val Tyr Tyr Cys Ala Arg Ser Asn Arg Tyr Ser Gly Gln
             95                 100                 105

Phe Val Pro Ala Tyr Ala Met Asp Tyr Trp Gly Gln Gly Thr Leu
        110                 115                 120

Val Thr Val Ser Ser
            125

<210> SEQ ID NO 141
<211> LENGTH: 117
<212> TYPE: PRT
<213> ORGANISM: Artificial sequence
<220> FEATURE:
<223> OTHER INFORMATION: antibody heavy chain variable region

<400> SEQUENCE: 141

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Thr Ile Thr
             20                  25                  30

Asn Tyr Trp Ile His Trp Val Arg Gln Ala Pro Gly Lys Gly Leu
             35                  40                  45

Glu Trp Val Gly Gly Ile Tyr Pro Ala Asp Gly Tyr Thr Tyr Tyr
         50                  55                  60

Ala Asp Ser Val Lys Gly Arg Phe Thr Ile Ser Ala Asp Thr Ser
     65                  70                  75

Lys Asn Thr Ala Tyr Leu Gln Met Asn Ser Leu Arg Ala Glu Asp
 80                  85                  90

Thr Ala Val Tyr Tyr Cys Ala Ser Gly Gly Tyr Ser Ser Leu Ala
             95                 100                 105

Tyr Trp Gly Gln Gly Thr Leu Val Thr Val Ser Ser
        110                 115

<210> SEQ ID NO 142
<211> LENGTH: 124
<212> TYPE: PRT
<213> ORGANISM: Artificial sequence
<220> FEATURE:
<223> OTHER INFORMATION: antibody heavy chain variable region

<400> SEQUENCE: 142

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Thr Ile Asn
             20                  25                  30

Gly Tyr Tyr Ile His Trp Val Arg Gln Ala Pro Gly Lys Gly Leu
             35                  40                  45

Glu Trp Val Gly Phe Ile Tyr Pro Ala Gly Gly Asp Thr Asp Tyr
         50                  55                  60

Ala Asp Ser Val Lys Gly Arg Phe Thr Ile Ser Ala Asp Thr Ser
     65                  70                  75
```

Lys Asn Thr Ala Tyr Leu Gln Met Asn Ser Leu Arg Ala Glu Asp
                80                  85                  90

Thr Ala Val Tyr Tyr Cys Ala Arg Leu Ile Gly Asn Lys Phe Gly
                95                  100                 105

Trp Ser Ser Tyr Gly Met Asp Tyr Trp Gly Gln Gly Thr Leu Val
                110                 115                 120

Thr Val Ser Ser

<210> SEQ ID NO 143
<211> LENGTH: 125
<212> TYPE: PRT
<213> ORGANISM: Artificial sequence
<220> FEATURE:
<223> OTHER INFORMATION: antibody heavy chain variable region

<400> SEQUENCE: 143

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Ile Asn
                20                  25                  30

Asn Asn Tyr Ile His Trp Val Arg Gln Ala Pro Gly Lys Gly Leu
                35                  40                  45

Glu Trp Val Ala Ile Ile Ser Pro Thr Gly Gly Tyr Thr Asp Tyr
                50                  55                  60

Ala Asp Ser Val Lys Gly Arg Phe Thr Ile Ser Ala Asp Thr Ser
                65                  70                  75

Lys Asn Thr Ala Tyr Leu Gln Met Asn Ser Leu Arg Ala Glu Asp
                80                  85                  90

Thr Ala Val Tyr Tyr Cys Ala Arg Asp Val Asn Val Tyr Ser Ala
                95                  100                 105

Arg Trp Trp Asp Tyr Val Met Asp Tyr Trp Gly Gln Gly Thr Leu
                110                 115                 120

Val Thr Val Ser Ser
                125

<210> SEQ ID NO 144
<211> LENGTH: 123
<212> TYPE: PRT
<213> ORGANISM: Artificial sequence
<220> FEATURE:
<223> OTHER INFORMATION: antibody heavy chain variable region

<400> SEQUENCE: 144

Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Ser
                20                  25                  30

Ser Tyr Trp Ile Ser Trp Val Arg Gln Ala Pro Gly Lys Gly Leu
                35                  40                  45

Glu Trp Val Ser Thr Ile Tyr Gly Tyr Asp Gly Ser Thr Asn Tyr
                50                  55                  60

Ala Asp Ser Val Lys Gly Arg Phe Thr Ile Ser Ala Asp Thr Ser
                65                  70                  75

Lys Asn Thr Ala Tyr Leu Gln Met Asn Ser Leu Arg Ala Glu Asp
                80                  85                  90

Thr Ala Val Tyr Tyr Cys Ala Arg Met Ser Tyr Asn Trp Ser Ser
                95                  100                 105

```
Pro Gly His Gly Met Asp Val Trp Gly Gln Gly Thr Leu Val Thr
            110                 115                 120

Val Ser Ser

<210> SEQ ID NO 145
<211> LENGTH: 120
<212> TYPE: PRT
<213> ORGANISM: Artificial sequence
<220> FEATURE:
<223> OTHER INFORMATION: antibody heavy chain variable region

<400> SEQUENCE: 145

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
            20                  25                  30

Ser Arg Tyr Met Ser Trp Val Arg Gln Ala Pro Gly Lys Gly Leu
            35                  40                  45

Glu Trp Val Ser Gly Ile Tyr Pro Met Gly Gly Thr Thr Tyr Tyr
            50                  55                  60

Ala Asp Ser Val Lys Gly Arg Phe Thr Ile Ser Ala Asp Thr Ser
            65                  70                  75

Lys Asn Thr Ala Tyr Leu Gln Met Asn Ser Leu Arg Ala Glu Asp
            80                  85                  90

Thr Ala Val Tyr Tyr Cys Ala Arg Gly Asn Tyr Tyr Ser Gly Ser
            95                 100                 105

Glu Phe Asp Tyr Trp Gly Gln Gly Thr Leu Val Thr Val Ser Ser
            110                 115                 120

<210> SEQ ID NO 146
<211> LENGTH: 123
<212> TYPE: PRT
<213> ORGANISM: Artificial sequence
<220> FEATURE:
<223> OTHER INFORMATION: antibody heavy chain variable region

<400> SEQUENCE: 146

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu
            35                  40                  45

Glu Trp Val Ser Gly Ile Ser Pro Tyr Gly Gly Tyr Thr Tyr Tyr
            50                  55                  60

Ala Asp Ser Val Lys Gly Arg Phe Thr Ile Ser Ala Asp Thr Ser
            65                  70                  75

Lys Asn Thr Ala Tyr Leu Gln Met Asn Ser Leu Arg Ala Glu Asp
            80                  85                  90

Thr Ala Val Tyr Tyr Cys Ala Arg Trp Gly Tyr Tyr Met Pro Tyr
            95                 100                 105

Gly His Pro Val Met Asp Val Trp Gly Gln Gly Thr Leu Val Thr
            110                 115                 120

Val Ser Ser

<210> SEQ ID NO 147
<211> LENGTH: 124
```

```
<212> TYPE: PRT
<213> ORGANISM: Artificial sequence
<220> FEATURE:
<223> OTHER INFORMATION: antibody heavy chain variable region

<400> SEQUENCE: 147

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Ser Ile Tyr
                20                  25                  30

Ser Tyr Tyr Phe Glu Trp Val Arg Gln Ala Pro Gly Lys Gly Leu
                35                  40                  45

Glu Trp Val Gly Arg Ile Tyr Ser Ala Gly Gly His Thr Ala Tyr
            50                  55                  60

Ala Asp Ser Val Lys Gly Arg Phe Thr Ile Ser Ala Asp Thr Ser
65                  70                  75

Lys Asn Thr Ala Tyr Leu Gln Met Asn Ser Leu Arg Ala Glu Asp
                80                  85                  90

Thr Ala Val Tyr Tyr Cys Ala Arg Leu Ile Gly Asn Lys Phe Gly
                95                 100                 105

Trp Ser Ser Tyr Gly Met Asp Tyr Trp Gly Gln Gly Thr Leu Val
               110                 115                 120

Thr Val Ser Ser

<210> SEQ ID NO 148
<211> LENGTH: 124
<212> TYPE: PRT
<213> ORGANISM: Artificial sequence
<220> FEATURE:
<223> OTHER INFORMATION: antibody heavy chain variable region

<400> SEQUENCE: 148

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Ile Asn
                20                  25                  30

Gly Tyr Tyr Ile His Trp Val Arg Gln Ala Pro Gly Lys Gly Leu
                35                  40                  45

Glu Trp Val Gly Phe Ile Tyr Pro Ala Gly Gly Asp Thr Asp Tyr
            50                  55                  60

Ala Asp Ser Val Lys Gly Arg Phe Thr Ile Ser Ala Asp Thr Ser
65                  70                  75

Lys Asn Thr Ala Tyr Leu Gln Met Asn Ser Leu Arg Ala Glu Asp
                80                  85                  90

Thr Ala Val Tyr Tyr Cys Ala Arg Leu Ile Gly Asn Lys Phe Gly
                95                 100                 105

Trp Ser Ser Tyr Gly Met Asp Tyr Trp Gly Gln Gly Thr Leu Val
               110                 115                 120

Thr Val Ser Ser

<210> SEQ ID NO 149
<211> LENGTH: 124
<212> TYPE: PRT
<213> ORGANISM: Artificial sequence
<220> FEATURE:
<223> OTHER INFORMATION: antibody heavy chain variable region

<400> SEQUENCE: 149
```

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Ile Asn
                20                  25                  30

Gly Tyr Tyr Ile His Trp Val Arg Gln Ala Pro Gly Lys Gly Leu
            35                  40                  45

Glu Trp Val Gly Phe Ile Tyr Pro Ala Gly Gly Asp Thr Asp Tyr
        50                  55                  60

Ala Asp Ser Val Lys Gly Arg Phe Thr Ile Ser Ala Asp Thr Ser
    65                  70                  75

Lys Asn Thr Ala Tyr Leu Gln Met Asn Ser Leu Arg Ala Glu Asp
                80                  85                  90

Thr Ala Val Tyr Tyr Cys Ala Arg Leu Ile Gly Asn Lys Phe Gly
            95                  100                 105

Trp Ser Ser Tyr Gly Met Asp Tyr Trp Gly Gln Gly Thr Leu Val
        110                 115                 120

Thr Val Ser Ser

<210> SEQ ID NO 150
<211> LENGTH: 124
<212> TYPE: PRT
<213> ORGANISM: Artificial sequence
<220> FEATURE:
<223> OTHER INFORMATION: antibody heavy chain variable region

<400> SEQUENCE: 150

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Ile Asn
                20                  25                  30

Gly Tyr Tyr Ile His Trp Val Arg Gln Ala Pro Gly Lys Gly Leu
            35                  40                  45

Glu Trp Val Gly Phe Ile Tyr Pro Ala Gly Gly Asp Thr Asp Tyr
        50                  55                  60

Ala Asp Ser Val Lys Gly Arg Phe Thr Ile Ser Ala Asp Thr Ser
    65                  70                  75

Lys Asn Thr Ala Tyr Leu Gln Met Asn Ser Leu Arg Ala Glu Asp
                80                  85                  90

Thr Ala Val Tyr Tyr Cys Ala Arg Leu Ile Gly Asn Lys Phe Gly
            95                  100                 105

Trp Ser Ser Tyr Gly Met Asp Tyr Trp Gly Gln Gly Thr Leu Val
        110                 115                 120

Thr Val Ser Ser

<210> SEQ ID NO 151
<211> LENGTH: 124
<212> TYPE: PRT
<213> ORGANISM: Artificial sequence
<220> FEATURE:
<223> OTHER INFORMATION: antibody heavy chain variable region

<400> SEQUENCE: 151

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Ile Asn
                20                  25                  30

Gly Tyr Tyr Ile His Trp Val Arg Gln Ala Pro Gly Lys Gly Leu

```
                    35                  40                  45

Glu Trp Val Gly Phe Ile Tyr Pro Ala Gly Gly Asp Thr Asp Tyr
             50                  55                  60

Ala Asp Ser Val Lys Gly Arg Phe Thr Ile Ser Ala Asp Thr Ser
         65                  70                  75

Lys Asn Thr Ala Tyr Leu Gln Met Asn Ser Leu Arg Ala Glu Asp
                 80                  85                  90

Thr Ala Val Tyr Tyr Cys Ala Arg Leu Ile Gly Asn Lys Phe Gly
             95                 100                 105

Trp Ser Ser Tyr Gly Met Asp Tyr Trp Gly Gln Gly Thr Leu Val
                110                 115                 120

Thr Val Ser Ser

<210> SEQ ID NO 152
<211> LENGTH: 124
<212> TYPE: PRT
<213> ORGANISM: Artificial sequence
<220> FEATURE:
<223> OTHER INFORMATION: antibody heavy chain variable region

<400> SEQUENCE: 152

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Thr Leu Asp
                 20                  25                  30

Gly Tyr Tyr Leu Gln Trp Val Arg Gln Ala Pro Gly Lys Gly Leu
             35                  40                  45

Glu Trp Val Gly Phe Ile Tyr Pro Ala Gly Gly Lys Thr Glu Tyr
             50                  55                  60

Ala Asp Ser Val Lys Gly Arg Phe Thr Ile Ser Ala Asp Thr Ser
         65                  70                  75

Lys Asn Thr Ala Tyr Leu Gln Met Asn Ser Leu Arg Ala Glu Asp
                 80                  85                  90

Thr Ala Val Tyr Tyr Cys Ala Arg Leu Ile Gly Asn Lys Phe Gly
             95                 100                 105

Trp Ser Ser Tyr Gly Met Asp Tyr Trp Gly Gln Gly Thr Leu Val
                110                 115                 120

Thr Val Ser Ser

<210> SEQ ID NO 153
<211> LENGTH: 124
<212> TYPE: PRT
<213> ORGANISM: Artificial sequence
<220> FEATURE:
<223> OTHER INFORMATION: antibody heavy chain variable region

<400> SEQUENCE: 153

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Ser Ile Asn
                 20                  25                  30

Gly Tyr Tyr Asn Gln Trp Val Arg Gln Ala Pro Gly Lys Gly Leu
             35                  40                  45

Glu Trp Val Gly Phe Ile Tyr Pro Ala Gly Gly Ala Thr Ile Tyr
             50                  55                  60

Ala Asp Ser Val Lys Gly Arg Phe Thr Ile Ser Ala Asp Thr Ser
         65                  70                  75
```

```
Lys Asn Thr Ala Tyr Leu Gln Met Asn Ser Leu Arg Ala Glu Asp
                80                  85                  90

Thr Ala Val Tyr Tyr Cys Ala Arg Leu Ile Gly Asn Lys Phe Gly
                95                 100                 105

Trp Ser Ser Tyr Gly Met Asp Tyr Trp Gly Gln Gly Thr Leu Val
               110                 115                 120

Thr Val Ser Ser

<210> SEQ ID NO 154
<211> LENGTH: 124
<212> TYPE: PRT
<213> ORGANISM: Artificial sequence
<220> FEATURE:
<223> OTHER INFORMATION: antibody heavy chain variable region

<400> SEQUENCE: 154

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Thr Ile Asn
                 20                  25                  30

Gly Tyr Tyr Ile His Trp Val Arg Gln Ala Pro Gly Lys Gly Leu
                 35                  40                  45

Glu Trp Val Gly Phe Ile Tyr Pro Ala Gly Gly Asp Thr Asp Tyr
                 50                  55                  60

Ala Asp Ser Val Lys Gly Arg Phe Thr Ile Ser Ala Asp Thr Ser
                 65                  70                  75

Lys Asn Thr Ala Tyr Leu Gln Met Asn Ser Leu Arg Ala Glu Asp
                 80                  85                  90

Thr Ala Val Tyr Tyr Cys Ala Arg Leu Ile Gly Asn Lys Phe Gly
                 95                 100                 105

Trp Ser Ser Tyr Gly Met Asp Tyr Trp Gly Gln Gly Thr Leu Val
                110                 115                 120

Thr Val Ser Ser

<210> SEQ ID NO 155
<211> LENGTH: 124
<212> TYPE: PRT
<213> ORGANISM: Artificial sequence
<220> FEATURE:
<223> OTHER INFORMATION: antibody heavy chain variable region

<400> SEQUENCE: 155

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Thr Ile Asn
                 20                  25                  30

Gly Tyr Tyr Ile His Trp Val Arg Gln Ala Pro Gly Lys Gly Leu
                 35                  40                  45

Glu Trp Val Gly Phe Ile Tyr Pro Ala Leu Ser Val Ile Glu Tyr
                 50                  55                  60

Ala Asp Ser Val Lys Gly Arg Phe Thr Ile Ser Ala Asp Thr Ser
                 65                  70                  75

Lys Asn Thr Ala Tyr Leu Gln Met Asn Ser Leu Arg Ala Glu Asp
                 80                  85                  90

Thr Ala Val Tyr Tyr Cys Ala Arg Leu Ile Gly Asn Lys Phe Gly
                 95                 100                 105
```

Trp Ser Ser Tyr Gly Met Asp Tyr Trp Gly Gln Gly Thr Leu Val
                110                 115                 120

Thr Val Ser Ser

<210> SEQ ID NO 156
<211> LENGTH: 124
<212> TYPE: PRT
<213> ORGANISM: Artificial sequence
<220> FEATURE:
<223> OTHER INFORMATION: antibody heavy chain variable region

<400> SEQUENCE: 156

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Thr Ile Asn
                 20                  25                  30

Gly Tyr Tyr Ile His Trp Val Arg Gln Ala Pro Gly Lys Gly Leu
                 35                  40                  45

Glu Trp Val Gly Phe Ile Tyr Pro Ala Gly Gly Asp Thr Asp Tyr
                 50                  55                  60

Ala Asp Ser Val Lys Gly Arg Phe Thr Ile Ser Ala Asp Thr Ser
 65                  70                  75

Lys Asn Thr Ala Tyr Leu Gln Met Asn Ser Leu Arg Ala Glu Asp
                 80                  85                  90

Thr Ala Val Tyr Tyr Cys Ala Arg Leu Ile Gly Asn Lys Phe Gly
                 95                 100                 105

Trp Ser Ser Tyr Gly Met Asp Tyr Trp Gly Gln Gly Thr Leu Val
                110                 115                 120

Thr Val Ser Ser

<210> SEQ ID NO 157
<211> LENGTH: 124
<212> TYPE: PRT
<213> ORGANISM: Artificial sequence
<220> FEATURE:
<223> OTHER INFORMATION: antibody heavy chain variable region

<400> SEQUENCE: 157

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Thr Ile Asn
                 20                  25                  30

Gly Tyr Tyr Ile His Trp Val Arg Gln Ala Pro Gly Lys Gly Leu
                 35                  40                  45

Glu Trp Val Gly Phe Ile Tyr Pro Ala Gly Gly Asp Thr Asp Tyr
                 50                  55                  60

Ala Asp Ser Val Lys Gly Arg Phe Thr Ile Ser Ala Asp Thr Ser
 65                  70                  75

Lys Asn Thr Ala Tyr Leu Gln Met Asn Ser Leu Arg Ala Glu Asp
                 80                  85                  90

Thr Ala Val Tyr Tyr Cys Ala Arg Leu Ile Gly Asn Lys Phe Gly
                 95                 100                 105

Trp Ser Ser Tyr Gly Met Asp Tyr Trp Gly Gln Gly Thr Leu Val
                110                 115                 120

Thr Val Ser Ser

<210> SEQ ID NO 158

-continued

```
<211> LENGTH: 124
<212> TYPE: PRT
<213> ORGANISM: Artificial sequence
<220> FEATURE:
<223> OTHER INFORMATION: antibody heavy chain variable region

<400> SEQUENCE: 158

Glu Val Gln Leu Val Glu Ser Gly Gly Gly Leu Val Gln Pro Gly
 1               5                   10                  15

Gly Ser Leu Arg Leu Ser Cys Ala Ala Ser Gly Phe Thr Ile Asn
                20                  25                  30

Gly Tyr Tyr Ile His Trp Val Arg Gln Ala Pro Gly Lys Gly Leu
            35                  40                  45

Glu Trp Val Gly Phe Ile Tyr Pro Ala Gly Gly Asp Thr Asp Tyr
        50                  55                  60

Ala Asp Ser Val Lys Gly Arg Phe Thr Ile Ser Ala Asp Thr Ser
    65                  70                  75

Lys Asn Thr Ala Tyr Leu Gln Met Asn Ser Leu Arg Ala Glu Asp
                80                  85                  90

Thr Ala Val Tyr Tyr Cys Ala Arg Leu Ile Gly Asn Lys Phe Gly
                95                 100                 105

Trp Ser Ser Tyr Gly Met Asp Tyr Trp Gly Gln Gly Thr Leu Val
            110                 115                 120

Thr Val Ser Ser

<210> SEQ ID NO 159
<211> LENGTH: 124
<212> TYPE: PRT
<213> ORGANISM: Artificial sequence
<220> FEATURE:
<223> OTHER INFORMATION: antibody heavy chain variable region

<400> SEQUENCE: 159

Glu Val Gln Leu Val Glu Ser Gly Gly Gly Leu Val Gln Pro Gly
 1               5                   10                  15

Gly Ser Leu Arg Leu Ser Cys Ala Ala Ser Gly Phe Thr Ile Asn
                20                  25                  30

Gly Tyr Tyr Ile His Trp Val Arg Gln Ala Pro Gly Lys Gly Leu
            35                  40                  45

Glu Trp Val Gly Phe Ile Tyr Pro Ala Gly Gly Asp Thr Asp Tyr
        50                  55                  60

Ala Asp Ser Val Lys Gly Arg Phe Thr Ile Ser Ala Asp Thr Ser
    65                  70                  75

Lys Asn Thr Ala Tyr Leu Gln Met Asn Ser Leu Arg Ala Glu Asp
                80                  85                  90

Thr Ala Val Tyr Tyr Cys Ala Arg Leu Ile Gly Asn Lys Phe Gly
                95                 100                 105

Trp Ser Ser Tyr Gly Met Asp Tyr Trp Gly Gln Gly Thr Leu Val
            110                 115                 120

Thr Val Ser Ser

<210> SEQ ID NO 160
<211> LENGTH: 124
<212> TYPE: PRT
<213> ORGANISM: Artificial sequence
<220> FEATURE:
<223> OTHER INFORMATION: antibody heavy chain variable region

<400> SEQUENCE: 160
```

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Ile Asn
            20                  25                  30

Gly Tyr Tyr Ile His Trp Val Arg Gln Ala Pro Gly Lys Gly Leu
            35                  40                  45

Glu Trp Val Gly Phe Ile Tyr Pro Ala Gly Gly Asp Thr Asp Tyr
            50                  55                  60

Ala Asp Ser Val Lys Gly Arg Phe Thr Ile Ser Ala Asp Thr Ser
            65                  70                  75

Lys Asn Thr Ala Tyr Leu Gln Met Asn Ser Leu Arg Ala Glu Asp
            80                  85                  90

Thr Ala Val Tyr Tyr Cys Ala Arg Leu Ile Gly Asn Lys Phe Gly
            95                  100                 105

Trp Ser Ser Tyr Gly Met Asp Tyr Trp Gly Gln Gly Thr Leu Val
            110                 115                 120

Thr Val Ser Ser

<210> SEQ ID NO 161
<211> LENGTH: 124
<212> TYPE: PRT
<213> ORGANISM: Artificial sequence
<220> FEATURE:
<223> OTHER INFORMATION: antibody heavy chain variable region

<400> SEQUENCE: 161

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Ile Asn
            20                  25                  30

Gly Tyr Tyr Ile His Trp Val Arg Gln Ala Pro Gly Lys Gly Leu
            35                  40                  45

Glu Trp Val Gly Phe Ile Tyr Pro Ala Gly Gly Asp Thr Asp Tyr
            50                  55                  60

Ala Asp Ser Val Lys Gly Arg Phe Thr Ile Ser Ala Asp Thr Ser
            65                  70                  75

Lys Asn Thr Ala Tyr Leu Gln Met Asn Ser Leu Arg Ala Glu Asp
            80                  85                  90

Thr Ala Val Tyr Tyr Cys Ala Arg Leu Ile Gly Asn Lys Phe Gly
            95                  100                 105

Trp Ser Ser Tyr Gly Met Asp Tyr Trp Gly Gln Gly Thr Leu Val
            110                 115                 120

Thr Val Ser Ser

<210> SEQ ID NO 162
<211> LENGTH: 124
<212> TYPE: PRT
<213> ORGANISM: Artificial sequence
<220> FEATURE:
<223> OTHER INFORMATION: antibody heavy chain variable region

<400> SEQUENCE: 162

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Ile Asn
            20                  25                  30

```
Gly Tyr Tyr Ile His Trp Val Arg Gln Ala Pro Gly Lys Gly Leu
            35                  40                  45

Glu Trp Val Gly Phe Ile Tyr Pro Ala Gly Gly Asp Thr Asp Tyr
        50                  55                  60

Ala Asp Ser Val Lys Gly Arg Phe Thr Ile Ser Ala Asp Thr Ser
    65                  70                  75

Lys Asn Thr Ala Tyr Leu Gln Met Asn Ser Leu Arg Ala Glu Asp
                80                  85                  90

Thr Ala Val Tyr Tyr Cys Ala Arg Leu Ile Gly Asn Lys Phe Gly
                95                 100                 105

Trp Ser Ser Tyr Gly Met Asp Tyr Trp Gly Gln Gly Thr Leu Val
               110                 115                 120

Thr Val Ser Ser

<210> SEQ ID NO 163
<211> LENGTH: 124
<212> TYPE: PRT
<213> ORGANISM: Artificial sequence
<220> FEATURE:
<223> OTHER INFORMATION: antibody heavy chain variable region

<400> SEQUENCE: 163

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Ile Asn
                20                  25                  30

Gly Tyr Tyr Ile His Trp Val Arg Gln Ala Pro Gly Lys Gly Leu
            35                  40                  45

Glu Trp Val Gly Phe Ile Tyr Pro Ala Gly Gly Asp Thr Asp Tyr
        50                  55                  60

Ala Asp Ser Val Lys Gly Arg Phe Thr Ile Ser Ala Asp Thr Ser
    65                  70                  75

Lys Asn Thr Ala Tyr Leu Gln Met Asn Ser Leu Arg Ala Glu Asp
                80                  85                  90

Thr Ala Val Tyr Tyr Cys Ala Arg Leu Ile Gly Asn Lys Phe Gly
                95                 100                 105

Trp Ser Ser Tyr Gly Met Asp Tyr Trp Gly Gln Gly Thr Leu Val
               110                 115                 120

Thr Val Ser Ser

<210> SEQ ID NO 164
<211> LENGTH: 124
<212> TYPE: PRT
<213> ORGANISM: Artificial sequence
<220> FEATURE:
<223> OTHER INFORMATION: antibody heavy chain variable region

<400> SEQUENCE: 164

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Ile Asn
                20                  25                  30

Gly Tyr Tyr Ile His Trp Val Arg Gln Ala Pro Gly Lys Gly Leu
            35                  40                  45

Glu Trp Val Gly Phe Ile Tyr Pro Ala Gly Gly Asp Thr Asp Tyr
        50                  55                  60

Ala Asp Ser Val Lys Gly Arg Phe Thr Ile Ser Ala Asp Thr Ser
```

```
                65                  70                  75
Lys Asn Thr Ala Tyr Leu Gln Met Asn Ser Leu Arg Ala Glu Asp
                80                  85                  90

Thr Ala Val Tyr Tyr Cys Ala Arg Leu Ile Gly Asn Lys Phe Gly
                95                 100                 105

Trp Ser Ser Tyr Gly Met Asp Tyr Trp Gly Gln Gly Thr Leu Val
               110                 115                 120

Thr Val Ser Ser

<210> SEQ ID NO 165
<211> LENGTH: 124
<212> TYPE: PRT
<213> ORGANISM: Artificial sequence
<220> FEATURE:
<223> OTHER INFORMATION: antibody heavy chain variable region

<400> SEQUENCE: 165

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Thr Ile Asn
                 20                  25                  30

Gly Tyr Tyr Ile His Trp Val Arg Gln Ala Pro Gly Lys Gly Leu
                 35                  40                  45

Glu Trp Val Gly Phe Ile Tyr Pro Ala Gly Gly Asp Thr Asp Tyr
                 50                  55                  60

Ala Asp Ser Val Lys Gly Arg Phe Thr Ile Ser Ala Asp Thr Ser
                 65                  70                  75

Lys Asn Thr Ala Tyr Leu Gln Met Asn Ser Leu Arg Ala Glu Asp
                 80                  85                  90

Thr Ala Val Tyr Tyr Cys Ala Arg Leu Ile Gly Asn Lys Phe Gly
                 95                 100                 105

Trp Ser Ser Tyr Gly Met Asp Tyr Trp Gly Gln Gly Thr Leu Val
                110                 115                 120

Thr Val Ser Ser

<210> SEQ ID NO 166
<211> LENGTH: 10
<212> TYPE: PRT
<213> ORGANISM: Artificial sequence
<220> FEATURE:
<223> OTHER INFORMATION: antibody light chain framework region

<400> SEQUENCE: 166

Phe Gly Gln Gly Thr Lys Met Glu Ile Lys
                  5                  10

<210> SEQ ID NO 167
<211> LENGTH: 107
<212> TYPE: PRT
<213> ORGANISM: Artificial sequence
<220> FEATURE:
<223> OTHER INFORMATION: antibody light chain

<400> SEQUENCE: 167

Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Asp Val Ser
                 20                  25                  30

Thr Ala Val Ala Trp Tyr Gln Gln Lys Pro Gly Lys Ala Pro Lys
```

```
                    35                  40                  45
Leu Leu Ile Tyr Ser Ala Ser Phe Leu Tyr Ser Gly Val Pro Ser
                50                  55                  60
Arg Phe Ser Gly Ser Gly Ser Gly Thr Asp Phe Thr Leu Thr Ile
            65                  70                  75
Ser Ser Leu Gln Pro Glu Asp Phe Ala Thr Tyr Tyr Cys Gln Gln
        80                  85                  90
Ser Tyr Thr Thr Pro Pro Thr Phe Gly Gln Gly Thr Lys Val Glu
    95                 100                 105
Ile Lys

<210> SEQ ID NO 168
<211> LENGTH: 32
<212> TYPE: PRT
<213> ORGANISM: Artificial sequence
<220> FEATURE:
<223> OTHER INFORMATION: antibody light chain framework region

<400> SEQUENCE: 168

Gly Val Pro Ser Arg Phe Ser Gly Ser Arg Ser Gly Thr Asp Phe
  1               5                  10                  15
Thr Leu Thr Ile Ser Ser Leu Gln Pro Glu Asp Phe Ala Thr Tyr
                20                  25                  30
Tyr Cys

<210> SEQ ID NO 169
<211> LENGTH: 454
<212> TYPE: PRT
<213> ORGANISM: Artificial sequence
<220> FEATURE:
<223> OTHER INFORMATION: antibody heavy chain

<400> SEQUENCE: 169

Glu Val Gln Leu Val Glu Ser Gly Gly Gly Leu Val Gln Pro Gly
  1               5                  10                  15
Gly Ser Leu Arg Leu Ser Cys Ala Ala Ser Gly Phe Thr Ile Asn
                20                  25                  30
Gly Tyr Tyr Ile His Trp Val Arg Gln Ala Pro Gly Lys Gly Leu
                35                  40                  45
Glu Trp Val Gly Phe Ile Tyr Pro Ala Gly Gly Asp Thr Asp Tyr
                50                  55                  60
Ala Asp Ser Val Lys Gly Arg Phe Thr Ile Ser Ala Asp Thr Ser
            65                  70                  75
Lys Asn Thr Ala Tyr Leu Gln Met Asn Ser Leu Arg Ala Glu Asp
        80                  85                  90
Thr Ala Val Tyr Tyr Cys Ala Arg Leu Ile Gly Asn Lys Phe Gly
    95                 100                 105
Trp Ser Ser Tyr Gly Met Asp Tyr Trp Gly Gln Gly Thr Leu Val
               110                 115                 120
Thr Val Ser Ser Ala Ser Thr Lys Gly Pro Ser Val Phe Pro Leu
               125                 130                 135
Ala Pro Ser Ser Lys Ser Thr Ser Gly Gly Thr Ala Ala Leu Gly
               140                 145                 150
Cys Leu Val Lys Asp Tyr Phe Pro Glu Pro Val Thr Val Ser Trp
               155                 160                 165
Asn Ser Gly Ala Leu Thr Ser Gly Val His Thr Phe Pro Ala Val
               170                 175                 180
```

```
Leu Gln Ser Ser Gly Leu Tyr Ser Leu Ser Ser Val Val Thr Val
            185                 190                 195

Pro Ser Ser Ser Leu Gly Thr Gln Thr Tyr Ile Cys Asn Val Asn
            200                 205                 210

His Lys Pro Ser Asn Thr Lys Val Asp Lys Lys Val Glu Pro Lys
            215                 220                 225

Ser Cys Asp Lys Thr His Thr Cys Pro Pro Cys Pro Ala Pro Glu
            230                 235                 240

Leu Leu Gly Gly Pro Ser Val Phe Leu Phe Pro Pro Lys Pro Lys
            245                 250                 255

Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr
            275                 280                 285

Val Asp Gly Val Glu Val His Asn Ala Lys Thr Lys Pro Arg Glu
            290                 295                 300

Glu Gln Tyr Asn Ser Thr Tyr Arg Val Val Ser Val Leu Thr Val
            305                 310                 315

Leu His Gln Asp Trp Leu Asn Gly Lys Glu Tyr Lys Cys Lys Val
            320                 325                 330

Ser Asn Lys Ala Leu Pro Ala Pro Ile Glu Lys Thr Ile Ser Lys
            335                 340                 345

Ala Lys Gly Gln Pro Arg Glu Pro Gln Val Tyr Thr Leu Pro Pro
            350                 355                 360

Ser Arg Glu Glu Met Thr Lys Asn Gln Val Ser Leu Thr Cys Leu
            365                 370                 375

Val Lys Gly Phe Tyr Pro Ser Asp Ile Ala Val Glu Trp Glu Ser
            380                 385                 390

Asn Gly Gln Pro Glu Asn Asn Tyr Lys Thr Thr Pro Pro Val Leu
            395                 400                 405

Asp Ser Asp Gly Ser Phe Phe Leu Tyr Ser Lys Leu Thr Val Asp
            410                 415                 420

Lys Ser Arg Trp Gln Gln Gly Asn Val Phe Ser Cys Ser Val Met
            425                 430                 435

His Glu Ala Leu His Asn His Tyr Thr Gln Lys Ser Leu Ser Leu
            440                 445                 450

Ser Pro Gly Lys

<210> SEQ ID NO 170
<211> LENGTH: 214
<212> TYPE: PRT
<213> ORGANISM: Artificial sequence
<220> FEATURE:
<223> OTHER INFORMATION: antibody light chain

<400> SEQUENCE: 170

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
                50                  55                  60
```

```
Arg Phe Ser Gly Ser Gly Ser Gly Thr Asp Phe Thr Leu Thr Ile
            65                  70                  75

Ser Ser Leu Gln Pro Glu Asp Phe Ala Thr Thr Tyr Cys Gln Gln
            80                  85                  90

Ser Tyr Thr Thr Pro Pro Thr Phe Gly Gln Gly Thr Lys Val Glu
            95                 100                 105

Ile Lys Arg Thr Val Ala Ala Pro Ser Val Phe Ile Phe Pro Pro
           110                 115                 120

Ser Asp Glu Gln Leu Lys Ser Gly Thr Ala Ser Val Val Cys Leu
           125                 130                 135

Leu Asn Asn Phe Tyr Pro Arg Glu Ala Lys Val Gln Trp Lys Val
           140                 145                 150

Asp Asn Ala Leu Gln Ser Gly Asn Ser Gln Glu Ser Val Thr Glu
           155                 160                 165

Gln Asp Ser Lys Asp Ser Thr Tyr Ser Leu Ser Ser Thr Leu Thr
           170                 175                 180

Leu Ser Lys Ala Asp Tyr Glu Lys His Lys Val Tyr Ala Cys Glu
           185                 190                 195

Val Thr His Gln Gly Leu Ser Ser Pro Val Thr Lys Ser Phe Asn
           200                 205                 210

Arg Gly Glu Cys

<210> SEQ ID NO 171
<211> LENGTH: 214
<212> TYPE: PRT
<213> ORGANISM: Artificial sequence
<220> FEATURE:
<223> OTHER INFORMATION: His-tagged Robo4

<400> SEQUENCE: 171

Gln Asp Ser Pro Pro Gln Ile Leu Val His Pro Gln Asp Gln Leu
  1               5                  10                  15

Phe Gln Gly Pro Gly Pro Ala Arg Met Ser Cys Gln Ala Ser Gly
             20                  25                  30

Gln Pro Pro Pro Thr Ile Arg Trp Leu Leu Asn Gly Gln Pro Leu
             35                  40                  45

Ser Met Val Pro Asp Pro His His Leu Leu Pro Asp Gly Thr
             50                  55                  60

Leu Leu Leu Leu Gln Pro Pro Ala Arg Gly His Ala His Asp Gly
             65                  70                  75

Gln Ala Leu Ser Thr Asp Leu Gly Val Tyr Thr Cys Glu Ala Ser
             80                  85                  90

Asn Arg Leu Gly Thr Ala Val Ser Arg Gly Ala Arg Leu Ser Val
             95                 100                 105

Ala Val Leu Arg Glu Asp Phe Gln Ile Gln Pro Arg Asp Met Val
            110                 115                 120

Ala Val Val Gly Glu Gln Phe Thr Leu Glu Cys Gly Pro Pro Trp
            125                 130                 135

Gly His Pro Glu Pro Thr Val Ser Trp Trp Lys Asp Gly Lys Pro
            140                 145                 150

Leu Ala Leu Gln Pro Gly Arg His Thr Val Ser Gly Gly Ser Leu
            155                 160                 165

Leu Met Ala Arg Ala Glu Lys Ser Asp Glu Gly Thr Tyr Met Cys
            170                 175                 180

Val Ala Thr Asn Ser Ala Gly His Arg Glu Ser Arg Ala Ala Arg
```

-continued

```
                185                 190                 195
Val Ser Ile Gln Glu Pro Gln Asp Tyr Arg Ala His His His
                200                 205                 210

His His His His

<210> SEQ ID NO 172
<211> LENGTH: 243
<212> TYPE: PRT
<213> ORGANISM: Artificial sequence
<220> FEATURE:
<223> OTHER INFORMATION: His-tagged Robo4

<400> SEQUENCE: 172

Met Gly Ser Gly Gly Thr Gly Leu Leu Gly Thr Glu Trp Pro Leu
  1               5                  10                  15

Pro Leu Leu Leu Leu Phe Ile Met Gly Gly Glu Ala Leu Asp Ser
                 20                  25                  30

Pro Pro Gln Ile Leu Val His Pro Gln Asp Gln Leu Leu Gln Gly
                 35                  40                  45

Ser Gly Pro Ala Lys Met Arg Cys Arg Ser Ser Gly Gln Pro Pro
                 50                  55                  60

Pro Thr Ile Arg Trp Leu Leu Asn Gly Gln Pro Leu Ser Met Ala
                 65                  70                  75

Thr Pro Asp Leu His Tyr Leu Leu Pro Asp Gly Thr Leu Leu Leu
                 80                  85                  90

His Arg Pro Ser Val Gln Gly Arg Pro Gln Asp Asp Gln Asn Ile
                 95                 100                 105

Leu Ser Ala Ile Leu Gly Val Tyr Thr Cys Glu Ala Ser Asn Arg
                110                 115                 120

Leu Gly Thr Ala Val Ser Arg Gly Ala Arg Leu Ser Val Ala Val
                125                 130                 135

Leu Gln Glu Asp Phe Gln Ile Gln Pro Arg Asp Thr Val Ala Val
                140                 145                 150

Val Gly Glu Ser Leu Val Leu Glu Cys Gly Pro Pro Trp Gly Tyr
                155                 160                 165

Pro Lys Pro Ser Val Ser Trp Trp Lys Asp Gly Lys Pro Leu Val
                170                 175                 180

Leu Gln Pro Gly Arg Arg Thr Val Ser Gly Asp Ser Leu Met Val
                185                 190                 195

Ser Arg Ala Glu Lys Asn Asp Ser Gly Thr Tyr Met Cys Met Ala
                200                 205                 210

Thr Asn Asn Ala Gly Gln Arg Glu Ser Arg Ala Ala Arg Val Ser
                215                 220                 225

Ile Gln Glu Ser Gln Asp His Arg Ala His His His His
                230                 235                 240

His His His

<210> SEQ ID NO 173
<211> LENGTH: 11
<212> TYPE: PRT
<213> ORGANISM: Artificial sequence
<220> FEATURE:
<223> OTHER INFORMATION: antibody light chain framework region

<400> SEQUENCE: 173

Phe Gly Gln Gly Thr Lys Val Glu Ile Lys Arg
                  5                  10
```

```
<210> SEQ ID NO 174
<211> LENGTH: 11
<212> TYPE: PRT
<213> ORGANISM: Artificial sequence
<220> FEATURE:
<223> OTHER INFORMATION: antibody hypervariable region
<220> FEATURE:
<221> NAME/KEY: Xaa
<222> LOCATION: 5
<223> OTHER INFORMATION: X1 is D or S
<220> FEATURE:
<221> NAME/KEY: Xaa
<222> LOCATION: 6
<223> OTHER INFORMATION: X2 is V, I or G
<220> FEATURE:
<221> NAME/KEY: Xaa
<222> LOCATION: 7
<223> OTHER INFORMATION: X3 is S or A
<220> FEATURE:
<221> NAME/KEY: Xaa
<222> LOCATION: 8
<223> OTHER INFORMATION: X4 is T, S, R, or I
<220> FEATURE:
<221> NAME/KEY: Xaa
<222> LOCATION: 9
<223> OTHER INFORMATION: X5 is A, Y or S
<220> FEATURE:
<221> NAME/KEY: Xaa
<222> LOCATION: 10
<223> OTHER INFORMATION: X6 is V or L

<400> SEQUENCE: 174

Arg Ala Ser Gln Xaa Xaa Xaa Xaa Xaa Xaa Ala
                 5                  10

<210> SEQ ID NO 175
<211> LENGTH: 7
<212> TYPE: PRT
<213> ORGANISM: Artificial sequence
<220> FEATURE:
<223> OTHER INFORMATION: antibody hypervariable region
<220> FEATURE:
<221> NAME/KEY: Xaa
<222> LOCATION: 1
<223> OTHER INFORMATION: X1 is S or G
<220> FEATURE:
<221> NAME/KEY: Xaa
<222> LOCATION: 3
<223> OTHER INFORMATION: X2 is T or S
<220> FEATURE:
<221> NAME/KEY: Xaa
<222> LOCATION: 4
<223> OTHER INFORMATION: X3 is F, S, L, N, or T
<220> FEATURE:
<221> NAME/KEY: Xaa
<222> LOCATION: 5
<223> OTHER INFORMATION: X4 is L, R, E, or A
<220> FEATURE:
<221> NAME/KEY: Xaa
<222> LOCATION: 6
<223> OTHER INFORMATION: X5 is Y, A, or S
<220> FEATURE:
<221> NAME/KEY: Xaa
<222> LOCATION: 7
<223> OTHER INFORMATION: X6 is S or Y

<400> SEQUENCE: 175

Xaa Ala Xaa Xaa Xaa Xaa Xaa
             5

<210> SEQ ID NO 176
<211> LENGTH: 9
<212> TYPE: PRT
```

```
<213> ORGANISM: Artificial sequence
<220> FEATURE:
<223> OTHER INFORMATION: antibody hypervariable region
<220> FEATURE:
<221> NAME/KEY: Xaa
<222> LOCATION: 3
<223> OTHER INFORMATION: X1 is S, Y, P, T, F or G
<220> FEATURE:
<221> NAME/KEY: Xaa
<222> LOCATION: 4
<223> OTHER INFORMATION: X2 is Y, W, F, R or N
<220> FEATURE:
<221> NAME/KEY: Xaa
<222> LOCATION: 5
<223> OTHER INFORMATION: X3 is T, S, N, A, D, F,  H, V or G
<220> FEATURE:
<221> NAME/KEY: Xaa
<222> LOCATION: 6
<223> OTHER INFORMATION: X4 is T, Y, S, A, D, N, L, I, M, Y or G
<220> FEATURE:
<221> NAME/KEY: Xaa
<222> LOCATION: 7
<223> OTHER INFORMATION: X5 is P, L, H, or T
<220> FEATURE:
<221> NAME/KEY: Xaa
<222> LOCATION: 8
<223> OTHER INFORMATION: X6 is P, L, F, A, M or S

<400> SEQUENCE: 176

Gln Gln Xaa Xaa Xaa Xaa Xaa Xaa Thr
                5

<210> SEQ ID NO 177
<211> LENGTH: 10
<212> TYPE: PRT
<213> ORGANISM: Artificial sequence
<220> FEATURE:
<223> OTHER INFORMATION: antibody hypervariable region
<220> FEATURE:
<221> NAME/KEY: Xaa
<222> LOCATION: 2
<223> OTHER INFORMATION: X1 is F or Y
<220> FEATURE:
<221> NAME/KEY: Xaa
<222> LOCATION: 3
<223> OTHER INFORMATION: X2 is T or S
<220> FEATURE:
<221> NAME/KEY: Xaa
<222> LOCATION: 4
<223> OTHER INFORMATION: X3 is I, F, or L
<220> FEATURE:
<221> NAME/KEY: Xaa
<222> LOCATION: 5
<223> OTHER INFORMATION: X4 is S, N, T, Y, D, or K
<220> FEATURE:
<221> NAME/KEY: Xaa
<222> LOCATION: 6
<223> OTHER INFORMATION: X5 is G, N, or S
<220> FEATURE:
<221> NAME/KEY: Xaa
<222> LOCATION: 7
<223> OTHER INFORMATION: X6 is S, Y, N or R
<220> FEATURE:
<221> NAME/KEY: Xaa
<222> LOCATION: 8
<223> OTHER INFORMATION: X7 is W, Y or A
<220> FEATURE:
<221> NAME/KEY: Xaa
<222> LOCATION: 9
<223> OTHER INFORMATION: X8 is I, M, F, L or N
<220> FEATURE:
<221> NAME/KEY: Xaa
<222> LOCATION: 10
<223> OTHER INFORMATION: X9 is H, S, E or Q

<400> SEQUENCE: 177
```

```
Gly Xaa Xaa Xaa Xaa Xaa Xaa Xaa Xaa Xaa
            5                  10
```

<210> SEQ ID NO 178
<211> LENGTH: 18
<212> TYPE: PRT
<213> ORGANISM: Artificial sequence
<220> FEATURE:
<223> OTHER INFORMATION: antibody hypervariable region
<220> FEATURE:
<221> NAME/KEY: Xaa
<222> LOCATION: 1
<223> OTHER INFORMATION: X1 is A, G or S
<220> FEATURE:
<221> NAME/KEY: Xaa
<222> LOCATION: 2
<223> OTHER INFORMATION: X2 is V, F, G, I, T or R
<220> FEATURE:
<221> NAME/KEY: Xaa
<222> LOCATION: 4
<223> OTHER INFORMATION: X3 is T, Y or S
<220> FEATURE:
<221> NAME/KEY: Xaa
<222> LOCATION: 5
<223> OTHER INFORMATION: X4 is P, G or S
<220> FEATURE:
<221> NAME/KEY: Xaa
<222> LOCATION: 6
<223> OTHER INFORMATION: X5 is A, T, Y, or M
<220> FEATURE:
<221> NAME/KEY: Xaa
<222> LOCATION: 7
<223> OTHER INFORMATION: X6 is G, D, or L
<220> FEATURE:
<221> NAME/KEY: Xaa
<222> LOCATION: 8
<223> OTHER INFORMATION: X7 is G or S
<220> FEATURE:
<221> NAME/KEY: Xaa
<222> LOCATION: 9
<223> OTHER INFORMATION: X8 is Y, D, S, T, H, K, A or V
<220> FEATURE:
<221> NAME/KEY: Xaa
<222> LOCATION: 10
<223> OTHER INFORMATION: X9 is T or I
<220> FEATURE:
<221> NAME/KEY: Xaa
<222> LOCATION: 11
<223> OTHER INFORMATION: X10 is Y, D, N, A, E, or I

<400> SEQUENCE: 178

```
Xaa Xaa Ile Xaa Xaa Xaa Xaa Xaa Xaa Xaa Xaa Tyr Ala Asp Ser
 1               5                  10                  15

Val Lys Gly
```

<210> SEQ ID NO 179
<211> LENGTH: 18
<212> TYPE: PRT
<213> ORGANISM: Artificial sequence
<220> FEATURE:
<223> OTHER INFORMATION: antibody hypervariable region
<220> FEATURE:
<221> NAME/KEY: Xaa
<222> LOCATION: 2
<223> OTHER INFORMATION: X1 is R or S
<220> FEATURE:
<221> NAME/KEY: Xaa
<222> LOCATION: 3
<223> OTHER INFORMATION: X2 is S, L, G, D, M or W
<220> FEATURE:
<221> NAME/KEY: Xaa
<222> LOCATION: 4
<223> OTHER INFORMATION: X3 is N, I, G, V, or S
<220> FEATURE:
<221> NAME/KEY: Xaa

```
<222> LOCATION: 5
<223> OTHER INFORMATION: X4 is R, G, Y or N
<220> FEATURE:
<221> NAME/KEY: Xaa
<222> LOCATION: 6
<223> OTHER INFORMATION: X5 is Y, N, S, or V
<220> FEATURE:
<221> NAME/KEY: Xaa
<222> LOCATION: 7
<223> OTHER INFORMATION: X6 is S, K, Y, W, or M
<220> FEATURE:
<221> NAME/KEY: Xaa
<222> LOCATION: 8
<223> OTHER INFORMATION: X7 is G, F, S, P or a deletion
<220> FEATURE:
<221> NAME/KEY: Xaa
<222> LOCATION: 9
<223> OTHER INFORMATION: X8 is Q, G, A, S, Y or a deletion
<220> FEATURE:
<221> NAME/KEY: Xaa
<222> LOCATION: 10
<223> OTHER INFORMATION: X9 is F, W, R, P, E, G or a deletion
<220> FEATURE:
<221> NAME/KEY: Xaa
<222> LOCATION: 11
<223> OTHER INFORMATION: X10 is V, S, W, G, H, or a deletion
<220> FEATURE:
<221> NAME/KEY: Xaa
<222> LOCATION: 12
<223> OTHER INFORMATION: X11 is P, S, W, H, or a deletion
<220> FEATURE:
<221> NAME/KEY: Xaa
<222> LOCATION: 13
<223> OTHER INFORMATION: X12 is A, Y, D, G, V, or a deletion
<220> FEATURE:
<221> NAME/KEY: Xaa
<222> LOCATION: 14
<223> OTHER INFORMATION: X13 is Y, G or a deletion
<220> FEATURE:
<221> NAME/KEY: Xaa
<222> LOCATION: 15
<223> OTHER INFORMATION: X14 is A, V or a deletion
<220> FEATURE:
<221> NAME/KEY: Xaa
<222> LOCATION: 16
<223> OTHER INFORMATION: X15 is M, L, or F
<220> FEATURE:
<221> NAME/KEY: Xaa
<222> LOCATION: 17
<223> OTHER INFORMATION: X16 is D or A
<220> FEATURE:
<221> NAME/KEY: Xaa
<222> LOCATION: 18
<223> OTHER INFORMATION: X17 is Y or V

<400> SEQUENCE: 179

Ala Xaa Xaa Xaa Xaa Xaa Xaa Xaa Xaa Xaa Xaa Xaa Xaa Xaa Xaa
  1               5                  10                  15

Xaa Xaa Xaa

<210> SEQ ID NO 180
<211> LENGTH: 10
<212> TYPE: PRT
<213> ORGANISM: Artificial sequence
<220> FEATURE:
<223> OTHER INFORMATION: antibody hypervariable region
<220> FEATURE:
<221> NAME/KEY: Xaa
<222> LOCATION: 2
<223> OTHER INFORMATION: X1 is F or Y
<220> FEATURE:
<221> NAME/KEY: Xaa
<222> LOCATION: 3
<223> OTHER INFORMATION: X2 is T or S
<220> FEATURE:
<221> NAME/KEY: Xaa
```

```
<222> LOCATION: 4
<223> OTHER INFORMATION: X3 is I, F, or L
<220> FEATURE:
<221> NAME/KEY: Xaa
<222> LOCATION: 5
<223> OTHER INFORMATION: X4 is S, T, Y, D, or K
<220> FEATURE:
<221> NAME/KEY: Xaa
<222> LOCATION: 6
<223> OTHER INFORMATION: X5 is G, N, or S
<220> FEATURE:
<221> NAME/KEY: Xaa
<222> LOCATION: 7
<223> OTHER INFORMATION: X6 is S, N or R
<220> FEATURE:
<221> NAME/KEY: Xaa
<222> LOCATION: 8
<223> OTHER INFORMATION: X7 is W or A
<220> FEATURE:
<221> NAME/KEY: Xaa
<222> LOCATION: 9
<223> OTHER INFORMATION: X8 is I, M, F, L or N
<220> FEATURE:
<221> NAME/KEY: Xaa
<222> LOCATION: 10
<223> OTHER INFORMATION: X9 is H, S, E or Q

<400> SEQUENCE: 180

Gly Xaa Xaa Xaa Xaa Xaa Xaa Xaa Xaa
                5                   10

<210> SEQ ID NO 181
<211> LENGTH: 18
<212> TYPE: PRT
<213> ORGANISM: Artificial sequence
<220> FEATURE:
<223> OTHER INFORMATION: antibody hypervariable region
<220> FEATURE:
<221> NAME/KEY: Xaa
<222> LOCATION: 1
<223> OTHER INFORMATION: X1 is A or S
<220> FEATURE:
<221> NAME/KEY: Xaa
<222> LOCATION: 2
<223> OTHER INFORMATION: X2 is V, G, I, T, or R
<220> FEATURE:
<221> NAME/KEY: Xaa
<222> LOCATION: 4
<223> OTHER INFORMATION: X3 is T or S
<220> FEATURE:
<221> NAME/KEY: Xaa
<222> LOCATION: 5
<223> OTHER INFORMATION: X4 is P, G, or S
<220> FEATURE:
<221> NAME/KEY: Xaa
<222> LOCATION: 6
<223> OTHER INFORMATION: X5 is A, T, Y, or M
<220> FEATURE:
<221> NAME/KEY: Xaa
<222> LOCATION: 7
<223> OTHER INFORMATION: X6 is G, D, or L
<220> FEATURE:
<221> NAME/KEY: Xaa
<222> LOCATION: 8
<223> OTHER INFORMATION: X7 is G or S
<220> FEATURE:
<221> NAME/KEY: Xaa
<222> LOCATION: 9
<223> OTHER INFORMATION: X8 is Y, S, T, H, K, A or V
<220> FEATURE:
<221> NAME/KEY: Xaa
<222> LOCATION: 10
<223> OTHER INFORMATION: X9 is T or I
<220> FEATURE:
<221> NAME/KEY: Xaa
<222> LOCATION: 11
<223> OTHER INFORMATION: X10 is Y, N, A, E, or I
```

<400> SEQUENCE: 181

Xaa Xaa Ile Xaa Xaa Xaa Xaa Xaa Xaa Xaa Xaa Tyr Ala Asp Ser
 1               5                  10                  15

Val Lys Gly

<210> SEQ ID NO 182
<211> LENGTH: 16
<212> TYPE: PRT
<213> ORGANISM: Artificial sequence
<220> FEATURE:
<223> OTHER INFORMATION: antibody hypervariable region
<220> FEATURE:
<221> NAME/KEY: Xaa
<222> LOCATION: 1
<223> OTHER INFORMATION: X1 is S, G, D, M or W
<220> FEATURE:
<221> NAME/KEY: Xaa
<222> LOCATION: 2
<223> OTHER INFORMATION: X2 is N, G, V, or S
<220> FEATURE:
<221> NAME/KEY: Xaa
<222> LOCATION: 3
<223> OTHER INFORMATION: X3 is R, Y, or N
<220> FEATURE:
<221> NAME/KEY: Xaa
<222> LOCATION: 4
<223> OTHER INFORMATION: X4 is Y, S, or V
<220> FEATURE:
<221> NAME/KEY: Xaa
<222> LOCATION: 5
<223> OTHER INFORMATION: X5 is S, Y, W, or M
<220> FEATURE:
<221> NAME/KEY: Xaa
<222> LOCATION: 6
<223> OTHER INFORMATION: X6 is G, S, P, or a deletion
<220> FEATURE:
<221> NAME/KEY: Xaa
<222> LOCATION: 7
<223> OTHER INFORMATION: X7 is Q, A, S, Y, or a deletion
<220> FEATURE:
<221> NAME/KEY: Xaa
<222> LOCATION: 8
<223> OTHER INFORMATION: X8 is F, R, P, E, G, or a deletion
<220> FEATURE:
<221> NAME/KEY: Xaa
<222> LOCATION: 9
<223> OTHER INFORMATION: X9 is V, W, G, H, or a deletion
<220> FEATURE:
<221> NAME/KEY: Xaa
<222> LOCATION: 10
<223> OTHER INFORMATION: X10 is P, W, G, H, or a deletion
<220> FEATURE:
<221> NAME/KEY: Xaa
<222> LOCATION: 11
<223> OTHER INFORMATION: X11 is A, D, G, V, or a deletion
<220> FEATURE:
<221> NAME/KEY: Xaa
<222> LOCATION: 12
<223> OTHER INFORMATION: X12 is Y or a deletion
<220> FEATURE:
<221> NAME/KEY: Xaa
<222> LOCATION: 13
<223> OTHER INFORMATION: X13 is A or V
<220> FEATURE:
<221> NAME/KEY: Xaa
<222> LOCATION: 14
<223> OTHER INFORMATION: X14 is M, L, or F
<220> FEATURE:
<221> NAME/KEY: Xaa
<222> LOCATION: 16
<223> OTHER INFORMATION: X15 is Y or V

<400> SEQUENCE: 182

Xaa Xaa Xaa Xaa Xaa Xaa Xaa Xaa Xaa Xaa Xaa Xaa Xaa Xaa Asp

```
              1               5                  10                  15
Xaa

<210> SEQ ID NO 183
<211> LENGTH: 11
<212> TYPE: PRT
<213> ORGANISM: Artificial sequence
<220> FEATURE:
<223> OTHER INFORMATION: antibody hypervariable region
<220> FEATURE:
<221> NAME/KEY: Xaa
<222> LOCATION: 6
<223> OTHER INFORMATION: X1 is V or G
<220> FEATURE:
<221> NAME/KEY: Xaa
<222> LOCATION: 7
<223> OTHER INFORMATION: X2 is S or A
<220> FEATURE:
<221> NAME/KEY: Xaa
<222> LOCATION: 8
<223> OTHER INFORMATION: X3 is T, R, or I
<220> FEATURE:
<221> NAME/KEY: Xaa
<222> LOCATION: 9
<223> OTHER INFORMATION: X4 is A, S, or Y
<220> FEATURE:
<221> NAME/KEY: Xaa
<222> LOCATION: 10
<223> OTHER INFORMATION: X5 is V or L

<400> SEQUENCE: 183

Arg Ala Ser Gln Asp Xaa Xaa Xaa Xaa Xaa Ala
                  5                  10

<210> SEQ ID NO 184
<211> LENGTH: 7
<212> TYPE: PRT
<213> ORGANISM: Artificial sequence
<220> FEATURE:
<223> OTHER INFORMATION: antibody hypervariable region
<220> FEATURE:
<221> NAME/KEY: Xaa
<222> LOCATION: 3
<223> OTHER INFORMATION: X1 is S or T
<220> FEATURE:
<221> NAME/KEY: Xaa
<222> LOCATION: 4
<223> OTHER INFORMATION: X2 is F, L, N or T
<220> FEATURE:
<221> NAME/KEY: Xaa
<222> LOCATION: 5
<223> OTHER INFORMATION: X3 is L, E, or A
<220> FEATURE:
<221> NAME/KEY: Xaa
<222> LOCATION: 6
<223> OTHER INFORMATION: X4 is Y, A, or S
<220> FEATURE:
<221> NAME/KEY: Xaa
<222> LOCATION: 7
<223> OTHER INFORMATION: X5 is S, Y or a deletion

<400> SEQUENCE: 184

Ser Ala Xaa Xaa Xaa Xaa Xaa
                  5

<210> SEQ ID NO 185
<211> LENGTH: 9
<212> TYPE: PRT
<213> ORGANISM: Artificial sequence
<220> FEATURE:
<223> OTHER INFORMATION: antibody hypervariable region
<220> FEATURE:
<221> NAME/KEY: Xaa
```

```
<222> LOCATION: 3
<223> OTHER INFORMATION: X1 is S, P, T, F, or G
<220> FEATURE:
<221> NAME/KEY: Xaa
<222> LOCATION: 4
<223> OTHER INFORMATION: X2 is Y, F, R, or N
<220> FEATURE:
<221> NAME/KEY: Xaa
<222> LOCATION: 5
<223> OTHER INFORMATION: X3 is T, A, S, D, F, H, N, V, or G
<220> FEATURE:
<221> NAME/KEY: Xaa
<222> LOCATION: 6
<223> OTHER INFORMATION: X4 is T, A, D, N, L, I, M, Y, or G
<220> FEATURE:
<221> NAME/KEY: Xaa
<222> LOCATION: 7
<223> OTHER INFORMATION: X5 is P, L, H, or T
<220> FEATURE:
<221> NAME/KEY: Xaa
<222> LOCATION: 8
<223> OTHER INFORMATION: X6 is P, A, M, F, or S

<400> SEQUENCE: 185

Gln Gln Xaa Xaa Xaa Xaa Xaa Xaa Thr
                5

<210> SEQ ID NO 186
<211> LENGTH: 10
<212> TYPE: PRT
<213> ORGANISM: Artificial sequence
<220> FEATURE:
<223> OTHER INFORMATION: antibody hypervariable region
<220> FEATURE:
<221> NAME/KEY: Xaa
<222> LOCATION: 3
<223> OTHER INFORMATION: X1 is T or S
<220> FEATURE:
<221> NAME/KEY: Xaa
<222> LOCATION: 4
<223> OTHER INFORMATION: X2 is I or L
<220> FEATURE:
<221> NAME/KEY: Xaa
<222> LOCATION: 5
<223> OTHER INFORMATION: X3 is N, Y, D, or K
<220> FEATURE:
<221> NAME/KEY: Xaa
<222> LOCATION: 9
<223> OTHER INFORMATION: X4 is I, F, L or N
<220> FEATURE:
<221> NAME/KEY: Xaa
<222> LOCATION: 10
<223> OTHER INFORMATION: X5 is H, E, or Q

<400> SEQUENCE: 186

Gly Phe Xaa Xaa Xaa Gly Tyr Tyr Xaa Xaa
                5                   10

<210> SEQ ID NO 187
<211> LENGTH: 18
<212> TYPE: PRT
<213> ORGANISM: Artificial sequence
<220> FEATURE:
<223> OTHER INFORMATION: antibody hypervariable region
<220> FEATURE:
<221> NAME/KEY: Xaa
<222> LOCATION: 2
<223> OTHER INFORMATION: X1 is F or R
<220> FEATURE:
<221> NAME/KEY: Xaa
<222> LOCATION: 5
<223> OTHER INFORMATION: X2 is P or S
<220> FEATURE:
<221> NAME/KEY: Xaa
<222> LOCATION: 7
```

```
-continued
<223> OTHER INFORMATION: X3 is G or L
<220> FEATURE:
<221> NAME/KEY: Xaa
<222> LOCATION: 9
<223> OTHER INFORMATION: X4 is D, H, K, A, or V
<220> FEATURE:
<221> NAME/KEY: Xaa
<222> LOCATION: 11
<223> OTHER INFORMATION: X5 is D, A, E or I

<400> SEQUENCE: 187

Gly Xaa Ile Tyr Xaa Ala Xaa Gly Xaa Thr Xaa Tyr Ala Asp Ser
  1               5                  10                  15

Val Lys Gly
```

ANTI-ROBO4 ANTIBODIES AND USES THEREFOR

RELATED APPLICATIONS

This application claims the benefit of U.S. Provisional Patent Applications Nos. 60/889,214, filed Feb. 9, 2007 and 60/891,475, filed Feb. 23, 2007, the disclosures of which are hereby incorporated by reference in their entirety for all purposes.

FIELD OF THE INVENTION

The present invention relates generally to the fields of angiogenesis, and endothelial cell proliferation and migration. More specifically, the invention concerns modulators of Robo4, and uses of such modulators.

BACKGROUND OF THE INVENTION

The Roundabout family of receptors are molecular guidance molecules which regulate axon guidance, neuronal migration and leukocyte chemotaxis in response to interaction with Slit proteins (Suchting et al., *FASEB J.* 19:121-123 (2005)). Roundabout receptor molecules contain five immunoglobulin and three fibronectin domains in their extracellular region. Magic Roundabout (i.e., Robo4 or endothelial cell-specific molecule 4 (ESCSM4)) is structurally distinct from other roundabout family members. Human Magic Roundabout (Robo4) comprises two immunoglobulin and major histocompatibility complex domains (amino acids 46-116 and 151-209), two fibronectin type III domains (amino acids 252-335 and 347-432), a transmembrane region (468-490), and a proline rich region (amino acids 715-772) (see Huminiecki et al., *Genomics* 79(4):547-552 (2002), and FIG. 1 therein). Mouse and human Robo4 show 75% nucleotide sequence identity (Huminiecki et al., supra (2002)).

Robo4 expression analysis indicated that Robo4 expression is highly restricted, with strong expression in placenta and tumors including brain, bladder, and colonic metastasis to the liver, where tumor expression is restricted to tumor vasculature (Huminiecki et al., supra (2002)). In addition, Robo4 expression is associated with sites of active angiogenesis, but is not detected in neuronal tissue (Huminiecki, L. et al., supra (2002)).

As a membrane associated receptor with extracellular domains, Robo4 is a useful target for delivering cytotoxic therapeutics for inhibition of vascular endothelial cell proliferation during angiogenesis. Robo4 is also a useful target to delivery of detectable markers to proliferating vascular endothelial cells. Antibody conjugates targeted to Robo4 (also referred to as ECSM4) have also been reported as potential therapeutic compounds where the conjugate comprises a cytotoxin and as potential diagnostic markers where the conjugate comprises a detectable label (see, for example, WO 2002036771).

The use of antibody-drug conjugates for the local delivery of cytotoxic or cytostatic agents, i.e. drugs to kill or inhibit tumor cells in the treatment of cancer (Syrigos and Epenetos, *Anticancer Res.* 19:605-614 (1999); Niculescu-Duvaz and Springer, *Adv. Drg Del. Rev.* 26:151-172 (1997); U.S. Pat. No. 4,975,278) allows targeted delivery of the drug moiety to tumors, and intracellular accumulation of the drugs.

A number of antibody-drug conjugates that target other molecules have been or are being developed. For example, ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al., *Eur. Jour. Nucl. Med.* 27(7): 766-77 (2000); Wiseman et al. *Blood* 99(12):4336-42 (2002); Witzig et al., *J. Clin. Oncol.* 20(10):2453-63 (2002); Witzig et al., *J. Clin. Oncol.* 20(15):3262-69 (2002)). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), composed of a huCD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), composed of a huC242 antibody linked via the disulfide linker SPP to the maytansinoid drug moiety, DM1, is being developed for the treatment of cancers that express CanAg antigen, such as colon, pancreatic, gastric, and others. MLN-2704 (Millennium Pharm., BZL Biologics, Immunogen Inc.), composed of an anti-prostate specific membrane antigen (PSMA) monoclonal antibody linked to the maytansinoid drug moiety, DM1, is being developed for the potential treatment of prostate tumors. The same maytansinoid drug moiety, DM1, was linked through a non-disulfide noncleavable linker, SMCC, to a mouse murine monoclonal antibody, TA.1 (Chari et al., *Cancer Res.* 52:127-131 (1992)). This conjugate was reported to be 200-fold less potent than the corresponding disulfide linker conjugate.

The auristatin peptides, auristain E (AE) and monomethylauristatin (MMAE), synthetic analogs of dolastatin, have been conjugated to: (i) cBR96, a chimeric monoclonal antibody specific for Lewis Y on carcinomas; (ii) cAC10 which is specific to CD30 on hematological malignancies (Klussman et al., *Bioconjugate Chemistry* 15(4):765-773 (2004); Doronina et al. *Nature Biotech.* 21(7):778-784 (2003); Francisco et al. *Blood* 102(4):1458-1465 (2003); U.S. Patent Publication No. 2004/0018194; (iii) anti-CD20 antibodies such as Rituxan® (rituximab) (WO 04/032828) for the treatment of CD20-expressing cancers and immune disorders; (iv) anti-EphB2 antibodies 2H9 and anti-IL-8 for treatment of colorectal cancer (Mao et al. *Cancer Res.* 64(3):781-788 (2004)); (v) E-selectin antibody (Bhaskar et al. *Cancer Res.* 63:6387-6394 (2003)); and (vi) other anti-CD30 antibodies (WO 03/043583). Monomethylauristatin (MMAE) has also been conjugated to 2H9, an antibody against EphB2R which is a type 1 TM tyrosine kinase receptor with close homology between mouse and human, and is over-expressed in colorectal cancer cells (Mao et al., *Cancer Res.* 64:781-788 (2004)).

Monomethylauristatin MMAF, a variant of auristatin E (MMAE) with a phenylalanine at the C-terminus (U.S. Pat. Nos. 5,767,237 and 6,124,431), has been reported to be less potent than MMAE, but more potent when conjugated to monoclonal antibodies (Senter et al, Proceedings of the American Association for Cancer Research, Volume 45, Abstract Number 623, presented Mar. 28, 2004). Auristatin F phenylene diamine (AFP); a phenylalanine variant of MMAE was linked to an anti-CD70 mAb, 1F6, through the C-terminus of 1F6 via a phenylene diamine spacer (Law et al, Proceedings of the American Association for Cancer Research, Volume 45, Abstract Number 625, presented Mar. 28, 2004).

There exists a need in the art for additional drugs to treat diseases and disorders associated angiogenesis including, e.g., aberrant angiogenesis associated with cancers dependent on the growth and proliferation of vasculature of endothelial origin. There also exists a need in the art for additional endothelial cell-targeted anti-Robo4 antibody-drug conjugates for the detection and visualization of blood vessel growth and proliferation in, for example, cancers or ocular disorders supported or caused by excess proliferation of blood vessels, as well as in disorders or other physiological states in which monitoring blood vessel growth is useful in understanding or treating the physiological state. The present invention meets these and other needs.

SUMMARY OF THE INVENTION

The invention provides antibodies that specifically bind to Robo4 (including, e.g., primate and/or rodent Robo4, such as human and/or mouse Robo4) and diagnostic and therapeutic methods using such antibodies. In some embodiments, the antibodies are humanized or human. In some embodiments, the antibody is selected from the group consisting of: an intact antibody, an antibody variant, and antibody derivative, a Fab, a Fab', a (Fab')$_2$, and an Fv. In one embodiment, the invention provides an anti-Robo4 antibody having affinity and specificity for human Robo4 and, optionally, murine Robo4, the antibody comprising, consisting of or consisting essentially of hypervariable regions (HVRs) of a light chain and heavy chain variable domain sequence as depicted in FIGS. 1A, 1B, 2A, and 2B (SEQ ID NOS:1-8, 17-71). In another embodiment, the invention provides an anti-Robo4 antibody having affinity and specificity for human Robo4 and, optionally, murine Robo4, the antibody comprising, consisting of or consisting essentially of framework regions (FRs) of a light chain and heavy chain variable domain sequence as depicted in FIGS. 1A, 1B, 2A, 2B, 3A, 3B, 4A, and 4B (SEQ ID NOS:9-16, SEQ ID NO:12, where V is replaced by M, and SEQ ID NOS:99-139). In another embodiment, the invention provides an anti-Robo4 antibody having affinity and specificity for human Robo4 and, optionally, murine Robo4, the antibody comprising, consisting of or consisting essentially of the light chain and heavy chain variable domain sequences as depicted in FIGS. 1A and 1B (SEQ ID NOS:72-97) and FIGS. 2A and 2B (SEQ ID NOS: 140-165).

In one embodiment the invention provides an anti-Robo4 antibody comprising: at least one, two, three, four, five, or six hypervariable region (HVR) sequence(s) selected from the group consisting of:

(i) HVR-L1 comprising sequence A1-A11, wherein A1-A11 is RASQDVSTAVA (SEQ ID NO:1)

(ii) HVR-L2 comprising sequence B1-B7, wherein B1-B7 is SASFLYS (SEQ ID NO:2)

(iii) HVR-L3 comprising sequence C1-C9, wherein C1-C9 is QQSYTTPPT (SEQ ID NO:3)

(iv) HVR-H1 comprising sequence D1-D10, wherein D1-D10 is GFTINGYYIH (SEQ ID NO:17)

(v) HVR-H2 comprising sequence E1-E18, wherein E1-E18 is GFIYPAGGDTDYADSVKG (SEQ ID NO:18);

(vi) HVR-H3 comprising sequence F1-F17 wherein F1-F17 is ARLIGNKFGWSSYGMDY (SEQ ID NO:19); and (vii) at least one variant HVR, wherein the variant HVR comprises an insertion, deletion, or substitution of at least one amino acid residue of the sequence depicted in SEQ ID NO: 1, 2, 3, 17, 18, or 19.

In another embodiment, the invention provides an anti-Robo4 antibody comprising:

at least one, two, three, four, five or six hypervariable region (HVR) sequences selected from the group consisting of:

(i) HVR-L1 comprising sequence A1-A11, wherein A1-A11 is RASQDVSTAVA (SEQ ID NO:1)

(ii) HVR-L2 comprising sequence B1-B7, wherein B1-B7 is SASFLYS (SEQ ID NO:2)

(iii) HVR-L3 comprising sequence C1-C9, wherein C1-C9 is QQSYTTPPT (SEQ ID NO:3)

(iv) HVR-H1 comprising sequence D1-D10, wherein D1-D11 is GFTISGSWIH (SEQ ID NO:4)

(v) HVR-H2 comprising sequence E1-E18, wherein E1-E18 is AVITPAGGYTYYADSVKG (SEQ ID NO:5) and (vi) HVR-H3 comprising sequence F1-F16, wherein F1-F16 is SNRYSGQFVPAYAMDY (SEQ ID NO:6).

In one embodiment, HVR-L1 of an antibody of the invention comprises the sequence of SEQ ID NO:1. In one embodiment, HVR-L2 of an antibody of the invention comprises the sequence of SEQ ID NO:2. In one embodiment, HVR-L3 of an antibody of the invention comprises the sequence of SEQ ID NO:3. In one embodiment, HVR-H1 of an antibody of the invention comprises the sequence of SEQ ID NO:4. In one embodiment, HVR-H2 of an antibody of the invention comprises the sequence of SEQ ID NO:5. In one embodiment, HVR-H3 of an antibody of the invention comprises the sequence of SEQ ID NO:6. In one embodiment, HVR-L1 comprises RASQSISSYLA (SEQ ID NO:7) or RASQDGARSLA (SEQ ID NO:39) or RASQDGAIYLA (SEQ ID NO:40). In one embodiment, HVR-L2 comprises GASSRAS (SEQ ID NO:8) or SASFLAS (SEQ ID NO:41) or SASLES (SEQ ID NO:42) or SATLAS (SEQ ID NO:43) or SASFLAS (SEQ ID NO:44) or SASNLAS (SEQ ID NO:45) or SASTLAS (SEQ ID NO:46). In one embodiment, an antibody of the invention comprising these sequences (in combination as described herein) is humanized or human.

In one aspect, the invention provides an antibody comprising one, two, three, four, five or six HVRs, wherein each HVR comprises, consists or consists essentially of a sequence selected from the group consisting of SEQ ID NOS: 1, 2, 3, 4, 5, 6, 7, and 8, and wherein SEQ ID NO: 1 or 7 corresponds to an HVR-L1, SEQ ID NO:2 or 8 corresponds to an HVR-L2, SEQ ID NO:3 corresponds to an HVR-L3, SEQ ID NO:4 corresponds to an HVR-H1, SEQ ID NO:5 corresponds to an HVR-H2, and SEQ ID NO:6 corresponds to an HVR-H3. In one embodiment, an antibody of the invention comprises an HVR-L1 comprising SEQ ID NO:7, an HVR-L2 comprising SEQ ID NO:2, an HVR-L3 comprising SEQ ID NO:3, an HVR-H1 comprising SEQ ID NO:4, an HVR-H2 comprising SEQ ID NO:5, and an HVR-H3 comprising SEQ ID NO:6. In another embodiment, an antibody of the invention comprises an HVR-L1 comprising SEQ ID NO:1, an HVR-L2 comprising SEQ ID NO:8, an HVR-L3 comprising SEQ ID NO:3, an HVR-H1 comprising SEQ ID NO:4, an HVR-H2 comprising SEQ ID NO:5, and an HVR-H3 comprising SEQ ID NO:6. In one embodiment, an antibody of the invention comprises an HVR-L1 comprising SEQ ID NO:1, an HVR-L2 comprising SEQ ID NO:2, an HVR-L3 comprising SEQ ID NO:3, an HVR-H1 comprising SEQ ID NO:4, an HVR-H2 comprising SEQ ID NO:5, and an HVR-H3 comprising SEQ ID NO:6. In another embodiment, an antibody of the invention comprises an HVR-L1 comprising SEQ ID NO:1, an HVR-L2 comprising SEQ ID NO:2, an HVR-L3 comprising SEQ ID NO:20, an HVR-H1 comprising SEQ ID NO:17, an HVR-H2 comprising SEQ ID NO:18, and an HVR-H3 comprising SEQ ID NO:19.

Variant HVRs in an antibody of the invention can have modifications of one or more residues within the HVR. In one embodiment, a HVR-L1 variant comprises SEQ ID NO:1 wherein A1-11 comprises 1-6 (1, 2, 3, 4, 5, or 6) substitutions in any combination of the following positions: A5 (S), A6 (I or G), A7 (A), A8 (S, R, or I), A9 (Y or S), and A10 (L). In one embodiment, a HVR-L2 variant comprises SEQ ID NO:2 wherein B1-7 comprises 1-4 (1, 2, 3, 4, 5, or 6) substitutions in any combination of the following positions: B1 (G), B3 (T), B4 (S, L, N, or T), B5 (R, E, or A), B6 (A or S) and B7 (Y). In one embodiment, a HVR-L3 variant comprises SEQ ID NO:3 wherein C1-9 comprises 1-6 (1, 2, 3, 4, 5, or 6) substitutions in any combination of the following positions: C3 (Y, P, T, F or G), C4 (W, F, R or N), C5 (S, N, A, D, F, H, V or G), C6 (Y, S, A, D, N, L, I, M, Y or G), C7 (L, H, or T) and C8 (L, F, A, M or S). In one embodiment, a HVR-H1 variant comprises SEQ ID NO:4 wherein D1-10 comprises 1-9 (1, 2, 3, 4, 5, 6, 7, 8 or 9) substitutions in any combination of the following positions: D2 (Y), D3 (S), D4 (F or L), D5 (N, T, Y, D, or K), D6 (N or S), D7 (Y, N or R), D8 (Y or A), D9 (M, F, L or N) and D10 (S, E or Q). In one embodiment, a HVR-H2 variant comprises SEQ ID NO:5 wherein E1-18 comprises 1-10 (1, 2, 3, 4, 5, 6, 7, 8, 9, or 10) substitutions in any combination of the following positions: E1 (G or S), E2 (F, G, I, T, or R), E4 (Y or S), E5 (G or S), E6 (T, Y, or M), E7 (D or L), E8 (S), E9 (D, S, T, H, K, A or V), E10 (I), and E11 (D, N, A, E, or 1). In one embodiment, a HVR-H3 variant comprises SEQ ID NO:6 wherein F1-18 comprises 1-17 (1, 2, 3, 4, 5, 6, 7, 8, 9, 10, 11, 12, 13, 14, 15, 16 or 17) substitutions in any combination of the following positions: F2 (S), F3 (L, G, D, M or W), F4 (I, G, V, or S), F5 (G, Y, or N), F6 (N, S, or V), F7 (K, Y, W, or M), F8 (F, S, P, or a deletion), F9 (G, A, S, Y, or a deletion), F10 (W, R, P, E, G, or a deletion), F11 (S, W, G, H, or a deletion), F12 (S, W, H, or a deletion), F13 (Y, D, G, V, or a deletion), F14 (G or a deletion), F15 (V or a deletion), F16 (L or F), F17 (a), and F18 (V). Letter(s) in parenthesis following each position indicates an illustrative substitution (i.e., replacement) amino acid or, where indicated, an amino acid deletion. In one embodiment, a HVR-L1 comprises the sequence of SEQ ID NO:1; a HVR-L2 comprises SEQ ID NO:2; a HVR-L3 variant comprises SEQ ID NO:3 wherein C4, C5, C6, and C6 are R, S, D, and H, respectively; a HVR-H1 comprises SEQ ID NO:17; a HVR-H2 comprises SEQ ID NO:18; and a HVR-H3 comprises SEQ ID NO:19 or a HVR-H3 variant comprising SEQ ID NO:19. In one embodiment of these antibodies, these antibodies further comprise a human κlight chain framework consensus sequence. In one embodiment, position 104 in framework region 4 of the light chain (LC-FR4) (Kabat numbering) is V. In one embodiment, position 104 of LC-FR4 is M.

In one embodiment, an antibody of the invention comprises a variant HVR-H1 SEQ ID NO:4 numbered D1-D10, wherein from 1 to 6 substitutions are selected from the following: D2 (Y), D3 (S), D4 (F or L), D5 (S, T, Y, D, or K), D6 (N or S), D7 (S, N, or R), D8 (W or A), D9 (M, F, L or N), and D10 (S, E, or Q). In one embodiment, an antibody of the invention comprises a variant HVR-H1 comprising SEQ ID NO:24, 25, 26, 27 or 28. In one embodiment, an antibody of the invention comprises a variant HVR-H2 SEQ ID NO:5 numbered E1-E18, wherein from 1 to 7 substitutions are selected from the following: E1 (A or S), E2 (V, G, I, T or R), E4 (T or S), E5 (G or S), E6 (T, Y, or M), E7 (D or L), E8 (S), E9 (Y, S, T, H, K, A or V), E10 (I) and E11 (Y, N, A, E, or 1). In one embodiment, an antibody of the invention comprises a variant HVR-H2 comprising SEQ ID NO:29, 30, 31, 32, or 33. In one embodiment, an antibody of the invention comprises a variant HVR-H3 comprising SEQ ID NO:6 numbered F1-F16, wherein from 1-15 substitutions are selected from the following: F1 (S, G, D, M, or W), F2 (N, G, V, or S), F3 (R, Y or N), F4 (Y, S, or V), F5 (S, Y, W or M), F6 (G, S, P or a deletion), F7 (Q, A, S, Y, or a deletion), F8 (F, R, P, E, G, or a deletion), F9 (V, W, G, H, or a deletion), F10 (P, W, H, or a deletion), F11 (A, D, G, V, or a deletion), F12 (Y or a deletion), F13 (A or V), F14 (L or F), and F15 (V). According to the invention, an amino acid substitution may encompass an amino acid deletion in a given sequence. In one embodiment of the invention, an antibody of the invention comprises a variant HVR-H3 comprising SEQ ID NO:34, 35, 36, 37, or 38. In one embodiment of these antibodies, the framework consensus sequence comprises substitution at position 71, 73 and/or 78. In some embodiments of these antibodies, position 71 is A, 73 is T and/or 78 is A. In one embodiment of these antibodies, these antibodies further comprise a human subgroup III heavy chain framework consensus sequence.

In one aspect, the invention provides an anti-Robo4 antibody comprising one, two, three, four, five six, or more of the HVR sequences depicted in FIG. 1, 2, 3, and (SEQ ID NOS: 1-8, 17-71).

In one embodiment, the invention provides a humanized anti-Robo4 antibody. A humanized anti-Robo4 antibody of the invention may comprise one or more human and/or human consensus non-hypervariable region (e.g., framework) sequences in its heavy and/or light chain variable domain. In some embodiments, one or more additional modifications are present within the human and/or human consensus non-hypervariable region sequences. In one embodiment, the heavy chain variable domain of an antibody of the invention comprises a human consensus framework sequence, which in one embodiment is the subgroup III consensus framework sequence. In one embodiment, an antibody of the invention comprises a variant subgroup III consensus framework sequence modified at least one amino acid position. For example, in one embodiment, a variant subgroup III consensus framework sequence may comprise a substitution at one or more of positions 71, 73 and/or 78. In one embodiment, said substitution is R71A, N73T and/or N78A and/or L/78A, in any combination thereof. In one embodiment, the light chain variable domain of an antibody of the invention comprises a human consensus framework sequence, which in one embodiment is the subgroup κI consensus framework sequence. In one embodiment, the light chain consensus framework sequence is modified at one or more positions. In one embodiment, the light chain consensus sequence has at position 104 the amino acid V. In one embodiment, the light chain consensus sequence is modified at position 104 according to the Kabat numbering system, wherein position 104 is M.

In one aspect, the invention provides an antibody comprising 1 to 4 or all of the light chain FR sequences LC-FR1 (SEQ ID NO:9), LC-FR2 (SEQ ID NO: 10, LC-FR3 (SEQ ID NO:11), and LC-FR4 (SEQ ID NO:12). In one embodiment, LC-FR4 (SEQ ID NO:12) is a variant wherein position 104 is M.

In one aspect, the invention provides an antibody comprising 1 to 4 or all of the heavy chain FR sequences HC-FR1 (SEQ ID NO:13), HC-FR2 (SEQ ID NO:14), HC-FR3 (SEQ ID NO:15), and HC-FR4 (SEQ ID NO:16).

In one embodiment, the invention provides a therapeutic agent for use in a host subject that elicits little to no immunogenic response against the agent in said subject. For example, in one embodiment, the invention provides a humanized antibody that elicits and/or is expected to elicit a human anti-mouse antibody response (HAMA) at a substantially reduced level in a host subject compared to a murine antibody raised against human Robo4. In another example, the invention provides a humanized antibody that elicits and/ or is expected to elicit minimal or no human anti-mouse antibody response (HAMA). In one example, an antibody of the invention elicits an anti-mouse antibody response that is at or below a clinically-acceptable level.

The invention also provides antibodies comprising modifications in hybrid hypervariable positions as described herein below. In one embodiment, an antibody of the invention comprises a variant human subgroup consensus framework sequence modified at one or more hybrid hypervariable positions. In one embodiment, an antibody of the invention comprises a heavy chain variable domain comprising a variant human subgroup III consensus framework sequence modified at one or more of positions 26-35, 49-65, 95-102, and 94. In one embodiment, an antibody of the invention comprises a light chain variable domain comprising a variant human kappa subgroup I consensus framework sequence modified at one or more of positions 24-34, 50-56, and 39-97.

In one embodiment, an antibody of the invention comprises at least a portion (or all) of the framework sequence of human κ light chain. In one embodiment, an antibody of the invention comprises at least a portion (or all) of human κ subgroup I framework consensus sequence. In one embodiment, an antibody of the invention comprises the framework sequences shown in FIGS. 3A and 3B.

An antibody of the invention can comprise any suitable human or human consensus heavy chain framework sequences, provided the antibody exhibits the desired biological characteristics (e.g., a desired binding affinity). In one embodiment, an antibody of the invention comprises at least a portion (or all) of the framework sequence of human subgroup III heavy chain. In one embodiment, an antibody of the invention comprises the framework sequences shown in FIGS. 4A and 4B.

In one embodiment, an antibody of the invention comprises a heavy and/or light chain variable domain comprising framework sequence depicted in SEQ ID NOS:72-137 (FIGS. 1A, 1B, 2A, 2B, 3A, 3B, 4A and 4B).

In one aspect, an antibody of the invention is a humanized anti-Robo4 antibody that binds human Robo4 vascular endothelial cell marker. For example, in one embodiment, an antibody of the invention binds human Robo4 with an IC50 value that is, less than 1000 nM, less than 500 nM, less than 200 nM, less than 100 nM, less than 50 nM, less than 30 nM, less than 20 nM less than 10 nM, less than 5 nM, less than 3 nM, less than 1 nM, less than 0.1 nM, or less than 0.01 nM. Comparison of abilities to inhibit ligand binding to its receptor can be performed according to various methods known in the art, including as described in the Examples below.

In one aspect, an antibody of the invention is an anti-Robo4 antibody conjugated to a cytotoxic moiety (an anti-Robo4 antibody drug conjugate, also referred to as an anti-Robo4 ADC), wherein the anti-Robo4 ADC inhibits Robo4-dependent cell proliferation in a cell expressing Robo4. Robo4 expressing cells include, but are not limited to, endothelial cells such as vascular endothelial cells. Exemplary anti-Robo4 ADCs are disclosed herein. In one embodiment, the anti-Robo4 antibody is humanized. In one embodiment, the anti-Robo4 antibody is a human antibody. In one embodiment, the anti-Robo4 antibody is derived from phage display mutagenesis and selection.

In one aspect, an antibody of the invention is an anti-Robo4 antibody ADC that inhibits Robo4-dependent cell proliferation better than a reference anti-Robo4 antibody that is not conjugated to a cytotoxic agent. For example, in one embodiment, an anti-Robo4 ADC antibody of the invention inhibits cell proliferation with an IC50 value that is less than about half that of the reference anti-Robo4 antibody that is not conjugated to a cytotoxic agent. In one embodiment, the IC50 value of an ADC antibody of the invention is about 0.001, 0.01 0.1, 0.2, 0.3 or 0.4 that of the non-ADC reference antibody. Comparison of abilities to inhibit cell proliferation can be performed according to various methods known in the art, including as described in the Examples below. In one embodiment, IC50 values are determined across an antibody concentration range from about 0.01 nM to about 100 nM.

In one embodiment, both the humanized antibody and chimeric antibody are monovalent. In one embodiment, both the humanized antibody and chimeric antibody comprise a single Fab region linked to an Fc region. In one embodiment, the reference chimeric antibody comprises variable domain sequences depicted in FIG. 7 (SEQ ID NO: 9 and 10) linked to a human Fc region. In one embodiment, the human Fc region is that of an IgG (e.g., IgG1, 2, 3 or 4).

In one aspect, the antibody of the invention comprises an Fc region. In an embodiment, the Fc region is an IgG1, 2, 3 or 4. In one embodiment the IgG is a native IgG. In one embodiment, the Fc region exhibits enhance antibody dependent cellular cytotoxicity (ADCC) relative to wild type ADCC activity of the native IgG1, 2, 3, or 4. In one embodiment, the IgG is an Fc region altered from the native IgG such that the altered Fc region exhibits enhanced ADCC activity relative to the native Fc region.

In one aspect, an antibody of the invention is an anti-Robo4 antibody conjugated to a detectable moiety, such as an imaging agent. In one aspect, antibodies of the invention may be conjugated with any label moiety which can be covalently attached to the antibody through a reactive moiety, an activated moiety, or a reactive cysteine thiol group (Singh et al., *Anal. Biochem.* 304:147-15 (2002); Harlow E. and Lane, D. (1999) Using Antibodies: A Laboratory Manual, Cold Springs Harbor Laboratory Press, Cold Spring Harbor, N.Y.; Lundblad R. L. (1991) Chemical Reagents for Protein Modification, 2nd ed. CRC Press, Boca Raton, Fla.). The attached label may function to: (i) provide a detectable signal; (ii) interact with a second label to modify the detectable signal provided by the first or second label, e.g. to give FRET (fluorescence resonance energy transfer); (iii) stabilize interactions or increase affinity of binding, with antigen or ligand; (iv) affect mobility, e.g. electrophoretic mobility or cell-permeability, by charge, hydrophobicity, shape, or other physical parameters, or (v) provide a capture moiety, to modulate ligand affinity, antibody/antigen binding, or ionic complexation. Labeled antibodies of the invention are further disclosed herein.

In an embodiment, the detectable label is an aqueous insoluble particle that is detectable in vitro or in vivo. In an embodiment, the particle is a magnetic or metallic particle. Metallic particles are detectable by such methods as magnetic resonance imaging (MRI), single-particle or single-molecule tracking, immunocytochemistry, plasmon frequency with dark-field illumination, differential interference contrast and video enhancement, total internal reflection, and photothermal interference contrast (PIC) technique (see, for example *PNAS USA* 100(20): 11350-11355 (2003); Sheetz et al., *Nature* 340:284-288 (1989); Baschong et al., *Histochemistry* 83:409-411 (1985); Slot and Geuze, *Eur. J. Cell Biol.* 38:87-93 (1935); Frey and Frey, *J. Struct. Biol.* 127:94-100 (1999); Hainfeld and Powell, *J. Histochem. Cytochem.* 48:471-480 (2000); Schultz et al., *PNAS USA* 97:996-1001 (2000); Gelles et al., *Nature* 331:450-453 (1988); Sonnichsen et al., *Appl. Phys. Lett.* 77:2949-2951 (2000); Boyer et al., *Science* 297: 1160-1163 (2002)). Nanoparticulate agents of the invention may also include, but are not limited to, microbubbles (see Ellegala et al., *Circulation* 108:336-341 (2003)), also referred to as acoustically active liospheres (AALs) (see Tartis et al., *Ultrasound Med. Biol.* 32(11): 1771-80 (2006)), superparamagnetic agents, liposomes, perfluorocarbon nanoparticle emulsions (WO 2005104051), and dendrimers (see Caruthers et al., *Methods in Molecular Medicine*, 124:387-400 (2006) and references cited therein, all of which references are hereby incorporated by reference in their entirety).

In one aspect, the invention provides an antibody comprising a heavy chain variable domain comprising the HVR-H1, HVR-H2 and/or HVR-H3 sequence depicted in FIGS. 1B and 2B. In one embodiment, the variable domain comprises HC-FR1, HC-FR2, HC-FR3 and/or HC-FR4 sequence depicted in FIGS. 1B, 2B, 4A and 4B. In one embodiment, the antibody comprises a CH1 and/or Fc sequence. In one embodiment, an antibody of the invention comprises a heavy chain variable domain comprising the HVR-H1, HVR-H2 and/or HVR-H3 sequence, and the HC-FR1, HC-FR2, HC-FR3 and/or HC-FR4 sequence depicted in FIGS. 1B, 2B, 4A, and 4B. In one embodiment, an antibody of the invention comprises a heavy chain variable domain comprising the HVR1-HC, HVR2-HC and/or HVR3-HC sequence depicted in FIGS. 1B, 2B, 4A and 4B, and a CH1 and/or Fc sequence.

In one aspect, the invention provides an antibody comprising a light chain variable domain comprising HVR1-LC, HVR2-LC and/or HVR3-LC sequence depicted in FIG. 1A or 2A. In one embodiment, the variable domain comprises a FR1-LC, FR2-LC, FR3-LC and/or FR4-LC sequence depicted in FIGS. 3A and 3B.

In one embodiment, an antibody of the invention comprises light and heavy chain variable domains as described in the preceding two paragraphs. In one embodiment, the antibody is monovalent and comprises an Fc region. In one embodiment, the Fc region comprises at least one protuberance (knob) and at least one cavity (hole), wherein presence of the protuberance and cavity enhances formation of a complex between an Fc polypeptide comprising the protuberance and an Fc polypeptide comprising the cavity, for example as described in WO 2005/063816. In one embodiment, the Fc region of an antibody of the invention comprises a first and a second Fc polypeptide, wherein the first and second polypeptide each comprises one or more mutations with respect to wild type human Fc. In one embodiment, a cavity mutation is T366S, L368A and/or Y407V. In one embodiment, a protuberance mutation is T366W. In one embodiment, the first polypeptide comprises the Fc sequence depicted in FIG. 13 and the second polypeptide comprises the Fc sequence depicted in FIG. 14.

In one embodiment, the invention provides methods of modulating one or more aspects of Robo4-associated effects (e.g., Robo4 activation, downstream molecular signaling (e.g., mitogen activated protein kinase (MAPK) phosphorylation), cell proliferation, cell migration, cell survival, cell morphogenesis and angiogenesis) by administering an anti-Robo4 antibody to a subject (e.g., a mammalian subject such as a human). In some embodiments, the anti-Robo4 antibody disrupts ligand binding to Robo4 (e.g., by binding to a sequence within the Robo4 extracellular domain, and thereby inhibiting interaction of said bound domain with its binding partner (such as a ligand molecule). In other embodiments, the Robo4 antibody binds to a sequence that is not within the Robo4 ligand binding site, wherein said binding results in disruption of the ability of the Robo4 to interact with its binding partner.

In one embodiment of the invention, binding of the antibody to Robo4 inhibits Robo4 associated endothelial cell proliferation. In another embodiment of a Robo4 antibody of the invention, binding of the antibody to Robo4 in a cell inhibits proliferation, survival, scattering, morphogenesis and/or motility of the cell. In another embodiment, the cell is an endothelial cell, such as, without limitation, a vascular endothelial cell.

In one embodiment, a Robo4 antibody of the invention specifically binds at least a portion of Robo4 shown in FIG. 5 (SEQ ID NO:138) or variant thereof. In one embodiment, an antibody of the invention specifically binds within the full length Robo4 amino acid sequence lacking the leader sequence (i.e., lacking the region indicated by dotted underlining in FIG. 5). In one embodiment, an antibody of the invention specifically binds within the extracellular domain sequence shown in FIG. 5 (indicated by solid underlining in FIG. 5). In one embodiment, an antibody of the invention specifically binds a conformational epitope formed by part or all of the Robo4 extracellular domain. In one embodiment, an antibody of the invention specifically binds an amino acid sequence having at least 50%, 60%, 70%, 80%, 90%, 95%, 98% sequence identity or similarity with the sequence shown in FIG. 5 (SEQ ID NO:138). In one embodiment, an antibody of the invention specifically binds an amino acid sequence having at least 50%, 60%, 70%, 80%, 90%, 95%, 98% sequence identity or similarity with the sequence of the Robo4 full length amino acid sequence lacking the leader sequence (i.e., lacking the region indicated by dotted underlining in FIG. 5). In one embodiment, an antibody of the invention specifically binds an amino acid sequence having at least 50%, 60%, 70%, 80%, 90%, 95%, 98% sequence identity or similarity with the sequence of the Robo4 extracellular domain (the region indicated by solid underlining in FIG. 5).

In one embodiment, an antibody of the invention specifically binds to Robo4 of a first animal species, and does not specifically bind to Robo4 of a second animal species. In one embodiment, the first animal species is human and/or primate (e.g., cynomolgus monkey), and the second animal species is ratus (e.g., rat), murine (e.g., mouse) and/or canine. In one embodiment, the first animal species is human. In one embodiment, the first animal species is primate, for example cynomolgus monkey. In one embodiment, the second animal species is murine, for example mouse. In one embodiment, the second animal species is canine. In one embodiment, an antibody of the invention specifically binds to Robo4 of at least two species. In one embodiment, the first animal species is human and/or primate (e.g., cynomolgus monkey), and the second animal species is murine (e.g., mouse). Antibodies of the invention that bind more than one species find use in animal modeling studies for therapeutic or diagnostic agents.

In one aspect, the invention provides a method of detecting Robo4 in serum of a mammal, where a concentration of Robo4 in the serum that is higher than normal levels of Robo4 indicate the presence of angiogenesis in the mammal. According to the method of the invention, a detectable or detectably labeled anti-Robo4 antibody of the invention is contacted with a serum sample from a test mammal, including but not limited to a human. The anti-Robo4 antibody is detected directly via the detectable label or indirectly by, for example, contact with a detectably labeled or detectable secondary antibody. A serum concentration (level) of anti-Robo4 in the test mammal that is higher than anti-Robo4 serum concentration from a normal mammal indicates angiogenesis in the test mammal. A normal mammal refers to a mammal known not to be experiencing angiogenesis or a population of mammals not experiencing angiogenesis. In one embodiment the test and normal mammal or population of mammals is the same species, including but not limited to humans. Serum levels of Robo4 protein have been detected in human patients with advanced non-small cell lung cancer (Gom et al., *Lung Cancer* 49:71-76 (2005)). Serum anti-Robo4 levels are useful for diagnosis and prognosis of angiogenesis associated with cancer.

In one aspect, the invention provides compositions comprising one or more antibodies of the invention and a carrier. In one embodiment, the carrier is pharmaceutically acceptable.

In one aspect, the invention provides nucleic acids encoding a Robo4 antibody of the invention, vectors comprising the nucleic acids, and host cells (e.g., *E. coli* or Chinese Hamster Ovary (CHO) cells), comprising the nucleic acids and/or vectors.cells comprising a nucleic acid or a vector of the invention. A vector can be of any type, for example a recombinant vector such as an expression vector. Any of a variety of host cells can be used. In one embodiment, a host cell is a prokaryotic cell, for example, *E. coli*. In one embodiment, a host cell is a eukaryotic cell, for example a mammalian cell such as Chinese Hamster Ovary (CHO) cell.

In one aspect, the invention provides methods for making an anti-Robo4. For example, the invention provides a method of making a Robo4 antibody, the method comprising expressing in a suitable host cell a recombinant vector of the invention encoding said antibody (or fragment thereof), and recovering said antibody.

In one aspect, the invention provides an article of manufacture comprising a container; and a composition contained within the container, wherein the composition comprises one or more anti-Robo4 antibodies of the invention. In one embodiment, the composition comprises a nucleic acid of the invention. In one embodiment, a composition comprising an antibody further comprises a carrier, which in some embodiments is pharmaceutically acceptable. In one embodiment, an article of manufacture of the invention further comprises instructions for administering the composition (e.g., the antibody) to a subject.

In one aspect, the invention provides a kit comprising a first container comprising a composition comprising one or more anti-Robo4 antibodies of the invention; and a second container comprising a buffer. In one embodiment, the buffer is pharmaceutically acceptable. In one embodiment, a composition comprising an antibody further comprises a carrier, which in some embodiments is pharmaceutically acceptable. In one embodiment, a kit further comprises instructions for administering the composition (e.g., the antibody) to a subject.

In one aspect, the invention provides use of a Robo4 antibody of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one aspect, the invention provides use of a nucleic acid of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one aspect, the invention provides use of an expression vector of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one aspect, the invention provides use of a host cell of the invention in the preparation of a medicament for the therapeutic and/or prophylactic treatment of a disease, such as a cancer, a tumor, a cell proliferative disorder, an immune disorder (e.g., an autoimmune disorder such as, for example rheumatoid arthritis) and/or an angiogenesis-related disorder.

In one aspect, the invention provides use of an article of manufacture of the invention in the preparation of a medicament for the therapeutic and/or prophylactic treatment of a disease, such as a cancer, a tumor, a cell proliferative disorder, an immune disorder (e.g., an autoimmune disorder such as, for example rheumatoid arthritis) and/or an angiogenesis-related disorder.

In one aspect, the invention provides use of a kit of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

The invention provides methods and compositions useful for modulating disease states associated with dysregulation of the Robo4 signaling axis. The Robo4 signaling pathway is involved in multiple biological and physiological functions, including, e.g., cell proliferation and angiogenesis. Thus, in one aspect, the invention provides a method comprising administering to a subject an antibody of the invention.

In one aspect, the invention provides a method of inhibiting Robo4 activated cell proliferation, said method comprising contacting a cell or tissue with an effective amount of a antibody of the invention, whereby cell proliferation associated with Robo4 activation is inhibited.

In one aspect, the invention provides a method of treating a pathological condition associated with dysregulation of Robo4 activation in a subject, said method comprising administering to the subject an effective amount of an antibody of the invention, whereby said condition is treated.

In one aspect, the invention provides a method of inhibiting the growth of a cell that expresses Robo4, said method comprising contacting said cell with an antibody of the invention or an antibody drug conjugate of the invention, thereby causing an inhibition of growth of said cell.

In one aspect, the invention provides a method of therapeutically treating a mammal having a cancerous tumor comprising a cell that expresses Robo4, said method comprising administering to said mammal an effective amount of an antibody of the invention or an antibody drug conjugate of the invention, thereby effectively treating said mammal.

In one aspect, the invention provides a method for treating or preventing a cell proliferative disorder associated with increased expression or activity of Robo4, said method comprising administering to a subject in need of such treatment an effective amount of an antibody of the invention or an antibody drug conjugate of the invention, thereby effectively treating or preventing said cell proliferative disorder. In one embodiment, said proliferative disorder is a pathological condition associated with abnormal or unwanted endothelial cell proliferation, such as abnormal or unwanted vascular cell proliferation in disorders including, but not limited to, cancer, angiogenesis and disorders associated with (e.g., augmented by endothelial cell proliferation within the tissue experiencing the disorder) solid tumors and metastasis, atherosclerosis, retrolental fibroplasia, hemangiomas, chronic inflammation, intraocular neovascular diseases such as proliferative retinopathies, e.g., diabetic retinopathy, age-related macular degeneration (AMD), neovascular glaucoma, immune rejection of transplanted corneal tissue and other tissues, rheumatoid arthritis, and psoriasis.

In another aspect, the invention provides a method of therapeutically treating a tumor in a mammal, wherein the growth of said tumor is at least in part dependent upon a growth potentiating effect of Robo4 expressed in endothelial cells, including without limitation vascular endothelial cells, the method comprising contacting said cell with an effective amount of an antibody of the invention or an antibody drug conjugate of the invention, thereby inhibiting the growth of endothelial cells in, for example, angiogenesis associated with the tumor, and thereby effectively treating said tumor.

Yet another embodiment of the invention provides methods of modulating angiogenesis, by contacting a cell or tissue with an effective amount of an anti-Robo4 antibody described herein. In some embodiments, the antibody further comprises a cytotoxic agent. In some embodiments, the angiogenesis is inhibited. In some embodiments, the angiogenesis is enhanced. In some embodiments, the angiogenesis is associated with a disorder selected from: cancer, atherosclerosis, retrolental fibroplasia, hemangiomas, chronic inflammation, intraocular neovascular diseases, proliferative retinopathies, diabetic retinopathy, age-related macular degeneration (AMD), neovascular glaucoma, immune rejection of transplanted corneal tissue and other tissues, rheumatoid arthritis, psoriasis, and combinations thereof. In some embodiments, the angiogenesis is associated with cancer. In some embodiments, the cancer is selected from the group consisting of: sarcomas including osteogenic sarcomas and angiosarcomas, squamous cell cancer, lung cancer, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain cancer, head and neck cancer, and associated metastases and combinations thereof. In some embodiments, the cell or tissue is in a mammal. In some embodiments, the mammal is a human. In some embodiments, the methods further comprise contacting the cell with an agent selected from: an anti-neoplastic agent, chemotherapeutic agent, a growth inhibitory agent, a cytotoxic agent, an anti-angiogenic agent, and combinations thereof. In some embodiments, the agent is an anti-VEGF antibody. In some embodiments, the methods further comprise contacting the cell with a second, third, or fourth agent selected from: an anti-neoplastic agent, chemotherapeutic agent, a growth inhibitory agent, a cytotoxic agent, an anti-angiogenic agent, and combinations thereof. In some embodiments, the second, third, or fourth agent is an anti-VEGF antibody.

Methods of the invention can be used to affect any suitable pathological state, for example, cells and/or tissues associated with upregulation of the Robo4 expression. In one embodiment, a cell that is targeted in a method of the invention is an endothelial cell or vascular endothelial cell proliferating within a tumor (including, e.g., a breast cancer, a colorectal cancer, a lung cancer, a papillary carcinoma (e.g., of the thyroid gland), a colon cancer, a pancreatic cancer, an ovarian cancer, a cervical cancer, a central nervous system cancer, an osteogenic sarcoma, a renal carcinoma, a hepatocellular carcinoma, a bladder cancer, a gastric carcinoma, a head and neck squamous carcinoma, a melanoma and a leukemia, or, a sarcomas (e.g., an osteogenic sarcoma or an angiosarcoma), or any cancer the growth of which is supported by endothelial cell proliferation in angiogenesis). In one embodiment, the pathological conditions are associated with abnormal or unwanted endothelial cell proliferation. In some embodiments, the target of an anti-Robo4 antibody or antibody drug conjugate of the invention, includes abnormal or unwanted vascular cell proliferation in disorders including, but not limited to, cancer, (including, e.g., solid tumors and metastasis), atherosclerosis, retrolental fibroplasia, hemangiomas, chronic inflammation, intraocular neovascular diseases such as proliferative retinopathies, e.g., diabetic retinopathy, age-related macular degeneration (AMD), neovascular glaucoma, immune rejection of transplanted corneal tissue and other tissues, rheumatoid arthritis, psoriasis, and disorders associated with angiogenesis (including, e.g., disorders augmented by endothelial cell proliferation within the tissue experiencing the disorder).

Methods of the invention can further comprise additional treatment steps. For example, in one embodiment, a method further comprises a step wherein a targeted cell and/or tissue (e.g., a cancer cell) is exposed to radiation treatment or a chemotherapeutic agent.

In one embodiment of methods of the invention, a cell that is targeted (e.g., an endothelial cell of a tumor tissue or a retina) is one in which Robo4 expression is increased as compared to an endothelial cell in normal tissue of the same tissue origin. In one embodiment, a method of the invention causes the death of a targeted cell. For example, contact with an anti-Robo4 antibody of the invention, including contact with an antibody drug conjugate of the invention, results in uptake of the cytotoxic moiety, which causes cell death. Alternatively, contact with an anti-Robo4 antibody of the invention conjugated to a cytotoxic compound may result in internalization of the cytotoxic compound, which results in cell death. In another alternative embodiment, contact with an anti-Robo4 antibody of the invention conjugated to a detectable moiety causes the endothelial cells of, for example, vasculature of a tissue (e.g. a tumor tissue or retina) to be detected, such as by imaging techniques well known in the relevant art.

Another embodiment of the invention provides methods of in vivo imaging, by administering an anti-Robo4 antibody described herein to a mammal. In some embodiments the mammal is a human. In some embodiments, the mammal is suspected of having a disease or disorder selected from: cancer, atherosclerosis, retrolental fibroplasia, hemangiomas, chronic inflammation, intraocular neovascular diseases, proliferative retinopathies, diabetic retinopathy, age-related macular degeneration (AMD), neovascular glaucoma, immune rejection of transplanted corneal tissue, rheumatoid arthritis, psoriasis, and combinations thereof.

Another embodiment of the invention provides methods of detecting a cell expressing Robo4, by contacting the cell with an anti-Robo4 antibody described herein. In some embodiments, the cell is a vascular endothelial cell. In some embodiments, the cell is in a mammal. In some embodiments, the mammal is suspected of having a disease or disorder selected from: cancer, atherosclerosis, retrolental fibroplasia, hemangiomas, chronic inflammation, intraocular neovascular diseases, proliferative retinopathies, diabetic retinopathy, age-related macular degeneration (AMD), neovascular glaucoma, immune rejection of transplanted corneal tissue, rheumatoid arthritis, psoriasis, and combinations thereof. In some embodiments, the mammal is suspected of having a cancer selected from: squamous cell cancer, lung cancer, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain cancer, head and neck cancer, and associated metastases and combinations thereof.

BRIEF DESCRIPTION OF THE DRAWINGS

FIGS. 1A and 1B depict alignment of amino acid sequences of the variable regions of the light and heavy chains for various anti-Robo4 clones of the invention (FIGS. 1A and 1B, respectively). The hypervariable regions (HVRs) of the light and heavy chains are indicated under the boxed complementary determining regions (CDRs). In FIG. 1A, the light chain HVRs-L1, L2, and L3 are Kabat positions 24-34, 50-56, and 89-102, respectively. In FIG. 1B, the heavy chain HVRs-H1, H2, and H3 are Kabat positions 26-35, 49-65, and 93-102, respectively. Clones were prepared by phage display as disclosed in the Examples and sequenced.

FIGS. 2A and 2B depict amino acid sequences of the variable regions of the light and heavy chains (FIGS. 2A and 2B, respectively) of selected affinity-matured antibodies from libraries with individually-randomized HVR. The HVRs in FIGS. 2A and 2B are the same positions as depicted in FIGS. 1A and 1B.

FIGS. 3A, 3B, 4A and 4B depict exemplary acceptor human consensus framework sequences for use in practicing the instant invention with sequence identifiers as follows:

Figure 8:
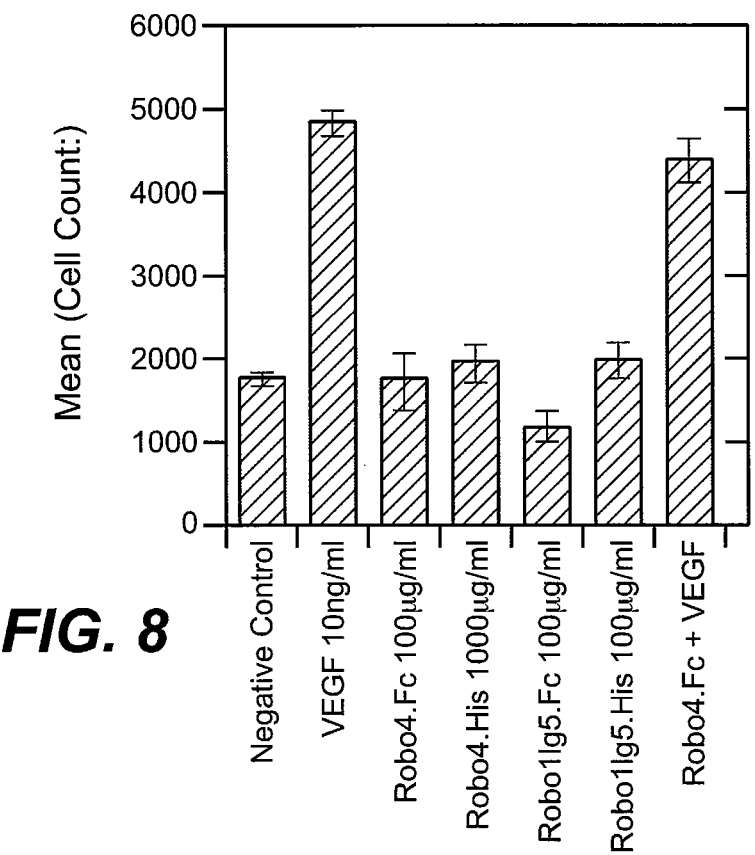

Variable light (VL) consensus framework regions minus Kabat HVRs (FIGS. 3A and 3B) human VL kappa subgroup I consensus frameworks 1-4 (SEQ ID NOS:9, 10, 99, 100) human VL kappa subgroup I' consensus frameworks 1-4 (SEQ ID NOS:9, 101, 99, 100) human VL kappa subgroup II consensus frameworks 1-4 (SEQ ID NOS:102, 103, 104, 100) human VL kappa subgroup III consensus frameworks 1-4 (SEQ ID NOS:105, 106, 107, 100) human VL kappa subgroup IV consensus frameworks 1-4 (SEQ ID NOS:108, 109, 110, 100) The locations of Kabat HVRs L1, L2, and L3 within the framework sequences are depicted as shaded boxes.

Variable heavy (VH) consensus framework regions minus Kabat HVRs (FIGS. 4A and B) human VH subgroup I consensus frameworks 1-4 minus Kabat HVRs (Subgroup IA, SEQ ID NOS:111, 112, 113, 16) and (subgroup IB, SEQ ID NOS:114, 115, 113, 16) human VH subgroup I consensus framework 1-4 minus extended HVRs, (subgroup IC, SEQ ID NOS:114, 115, 116, 16) and (subgroup ID, SEQ ID NOS:114, 115, 117, 16) human VH subgroup II consensus framework 1-4 minus Kabat HVRs (subgroup IIA, SEQ ID NOS:118, 119, 120, 16), (subgroup IB, SEQ ID NOS:121, 122, 120, 16) human VH subgroup II consensus framework 1-4 minus extended HVRs (subgroup IIC, SEQ ID NOS:121, 122, 123, 16), (subgroup IID, SEQ ID NOS:121, 122, 124, 16) human VH subgroup III consensus frameworks 1-4 minus Kabat HVRs (subgroup IIIA, SEQ ID NO:125, 126, 127, 16), (subgroup IIIB, SEQ ID NOS:128, 129, 127, 16) human VH subgroup III consensus frameworks 1-4 minus extended HVRs (subgroup IIIC, SEQ ID NOS:128, 129, 130, 16), (subgroup IIID, SEQ ID NOS:128, 129, 131, 16) human VH acceptor 1 frameworks 1-4 minus Kabat HVRs (subgroup Acceptor 1A, SEQ ID NOS:132, 126, 133, 16) and (subgroup Acceptor 1B, SEQ ID NOS:128, 129, 133, 16) human VH acceptor 1 frameworks 1-4 minus extended HVRs (subgroup Acceptor 1C, SEQ ID NOS:128, 129, 134, 16) human VH acceptor 2 frameworks 1-4 minus Kabat HVRs (subgroup Acceptor 2A, SEQ ID NOS:132, 126, 135, 16) and (subgroup Acceptor 2B, SEQ ID NOS:128, 129, 135, 16) human VH acceptor 2 frameworks 1-4 minus extended HVRs (subgroup Acceptor 2C, SEQ ID NOS:128, 129, 136, 16) and (subgroup Acceptor 2D, SEQ ID NOS:128, 129, 137, 16).

FIG. 5A depicts the full length amino acid sequence of the Robo4 polypeptide. A potential signal sequence is indicated by dotted underlining. A portion of the extracellular domain is indicated by solid underlining. FIG. 5B depicts the sequence of the His-tagged soluble Robo4 extracellular domain fragment (SEQ ID NO:171) used in, for example, anti-Robo4 Fab phage display experiments disclosed herein. The Robo4 extracellular domain was linked to a histidine tag for ease of recovery or detection.

FIG. 6A depicts the full length sequence of anti-Robo4 antibody YW71.22 heavy chain (SEQ ID NO:169). The alanine shown in bold text and underlined is the position at which a cysteine was substituted to generate the thioMAb. FIG. 6B depicts the full length sequence of anti-Robo4 antibody YW71.22 light chain (SEQ ID NO:170).

FIG. 7 depicts the amino acid sequence of murine Robo4 extracellular domain comprising a potential signal sequence and having the histidine tag RRA(H)$_5$ attached at position H232 (SEQ ID NO:172). A dotted underline indicates the potential signal sequence which is cleaved during expression in mammalian cells.

FIG. 8 is a bar graph of the results of a HUVEC migration assay using Robo4 constructs.

Figure 9:
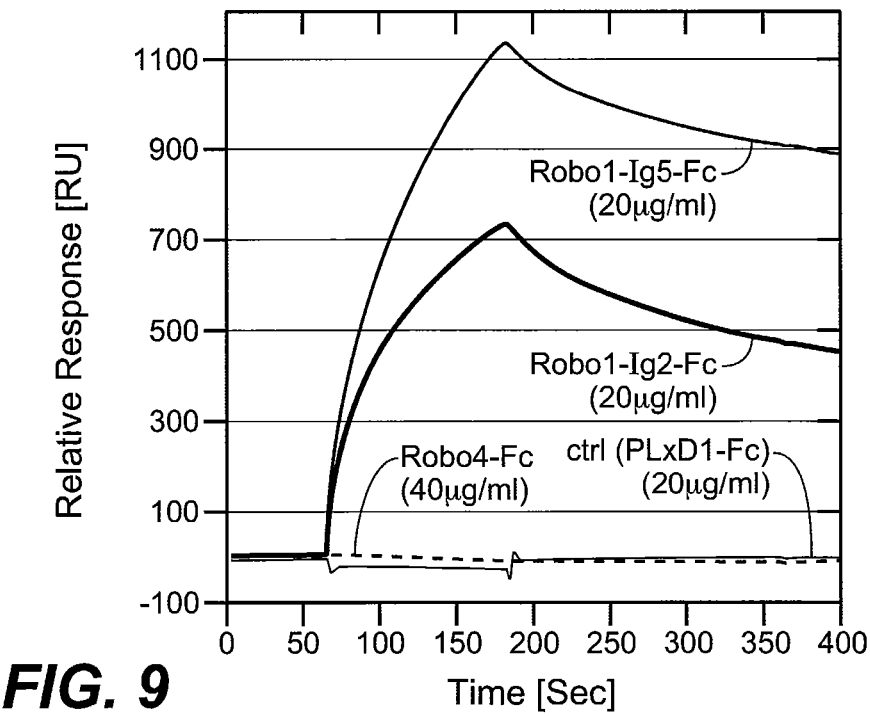

FIG. 9 shows the results of a BiaCore assay indicating that Robo4 does not bind Slit2.

Figure 10:
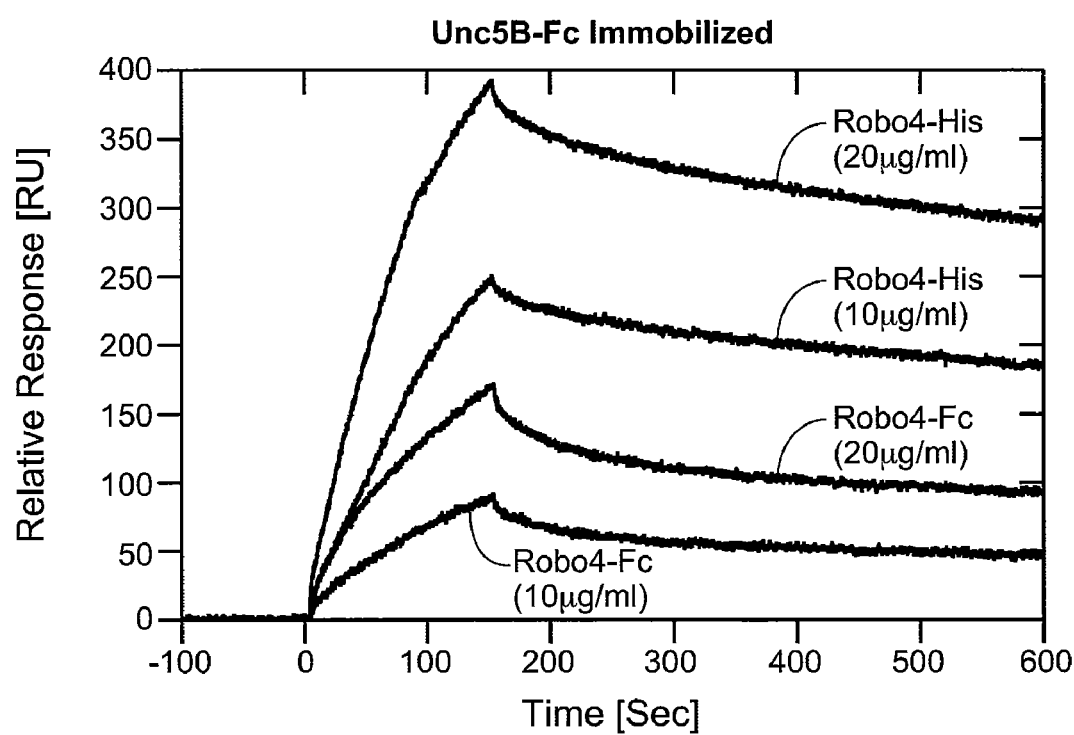

FIG. 10 shows the results of a BiaCore assay indicating that Robo4 interacts with UNC5B.

Figure 11:
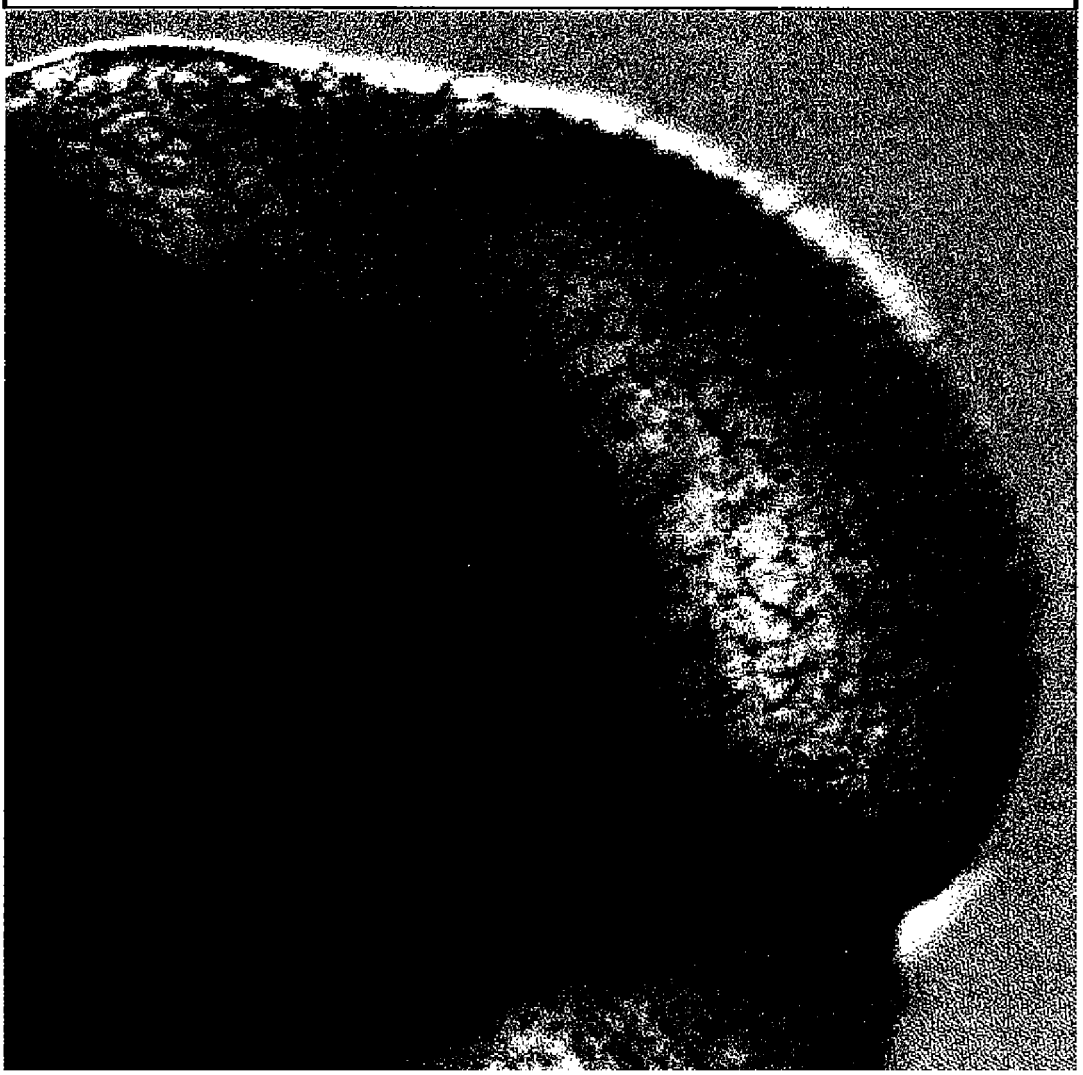

FIG. 11 is a photograph of an ISH assay showing that Robo4 is expressed in fetal mouse endothelium.

Figure 12A:
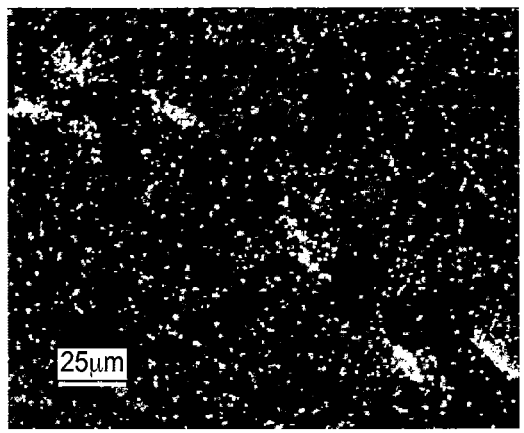
Figure 12B:
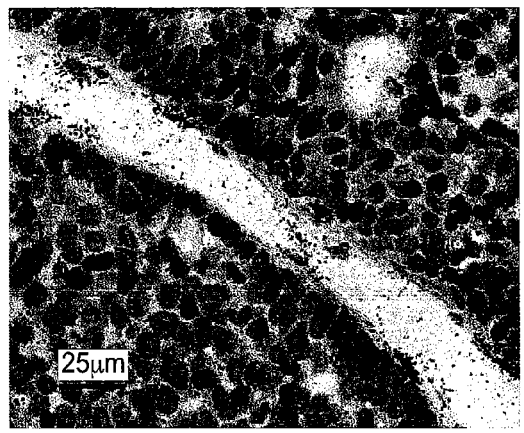
Figure 12C:
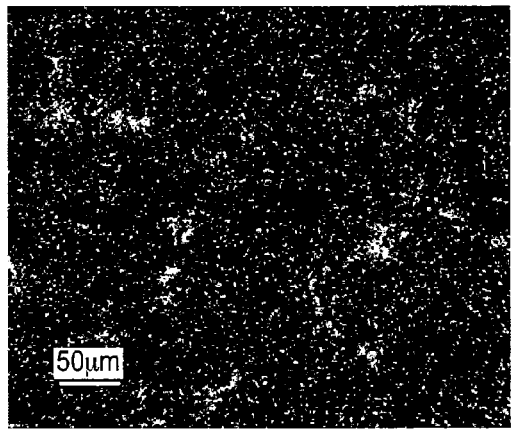
Figure 12D:
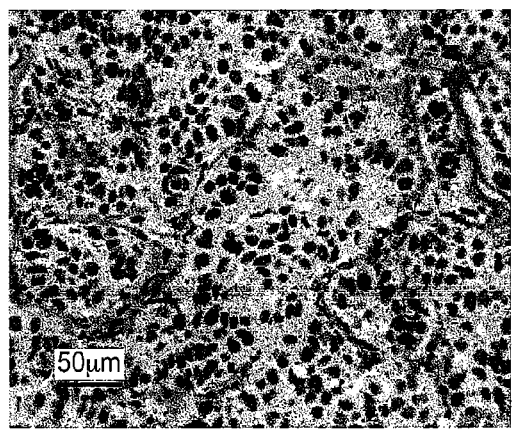

FIGS. 12A and 12B show expression of Robo4 in human HM-7 colon cancer mouse xenograft tumor model. FIGS. 12C and 12D show Robo4 expression in human MDA-MB-175 breast cancer tumor mouse xenograft model.

FIGS. 13A-D show expression of Robo4 in human malignant melanoma.

FIGS. 14A-D show expression of Robo4 in small cell lung cancer. FIGS. 14E-H show Robo4 expression in colon cancer.

Figure 15B:
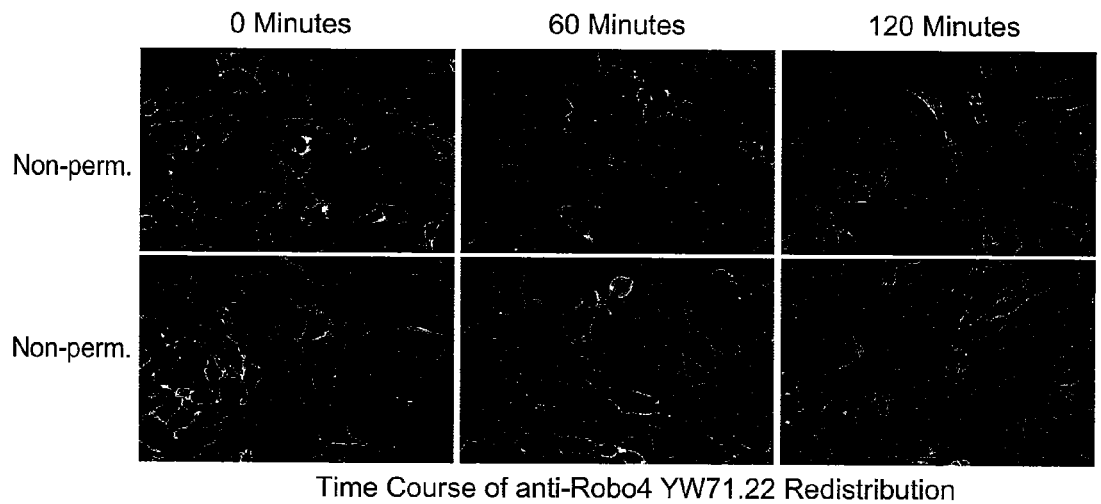
Figure 15C:
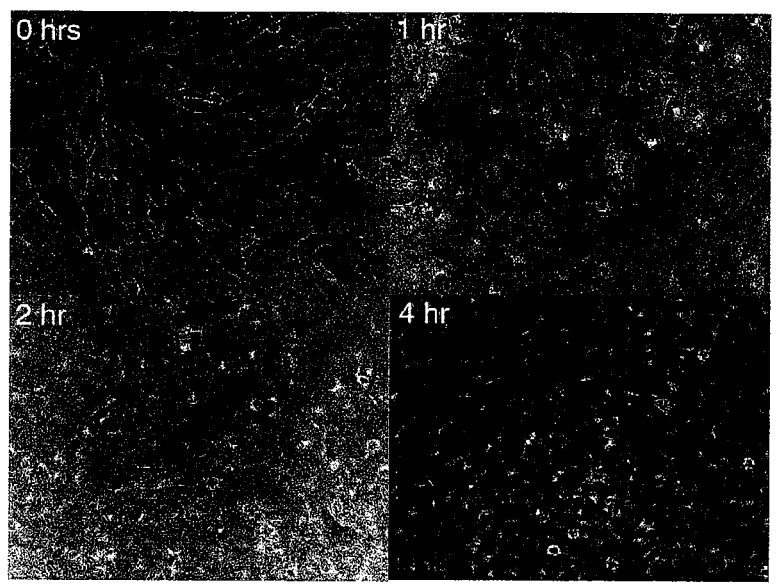

FIGS. 15A-15C depict internalization of anti-Robo4 antibody 71.22 by mouse MS1 cells (FIGS. 15A and 15B), and internalization of affinity matured anti-Robo4 antibody 71.22.S1.16 by mouse MS1 cells (FIG. 15C).

Figure 16:
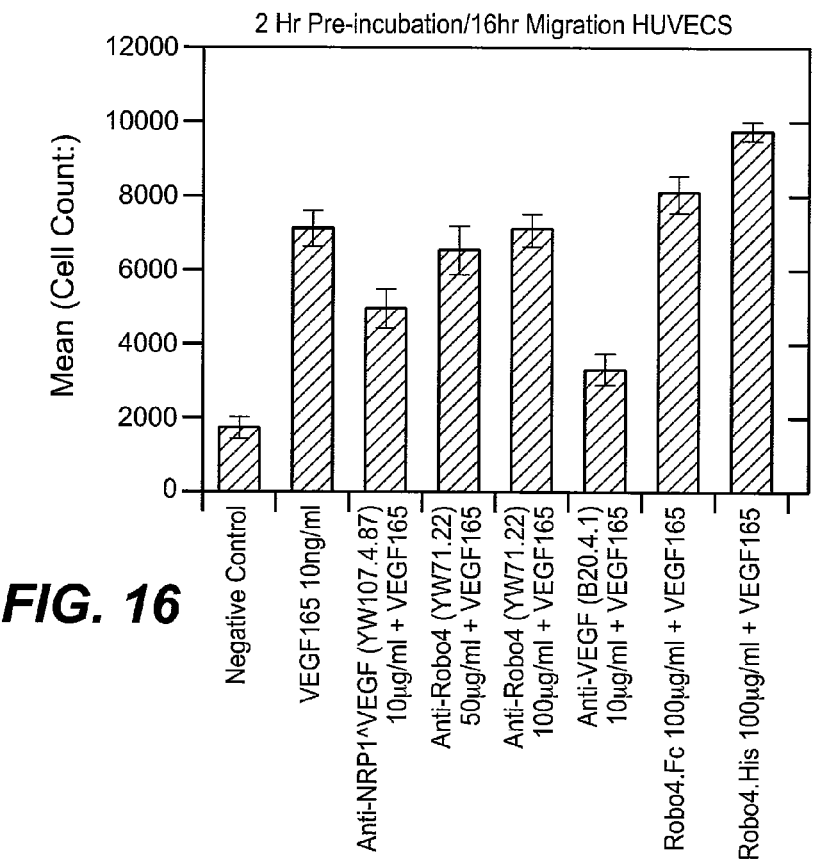

FIG. 16 is a bar graph showing the results of endothelial cell migration assay. Anti-Robo4 antibody did not block VEGF induced EC migration.

Figure 17:
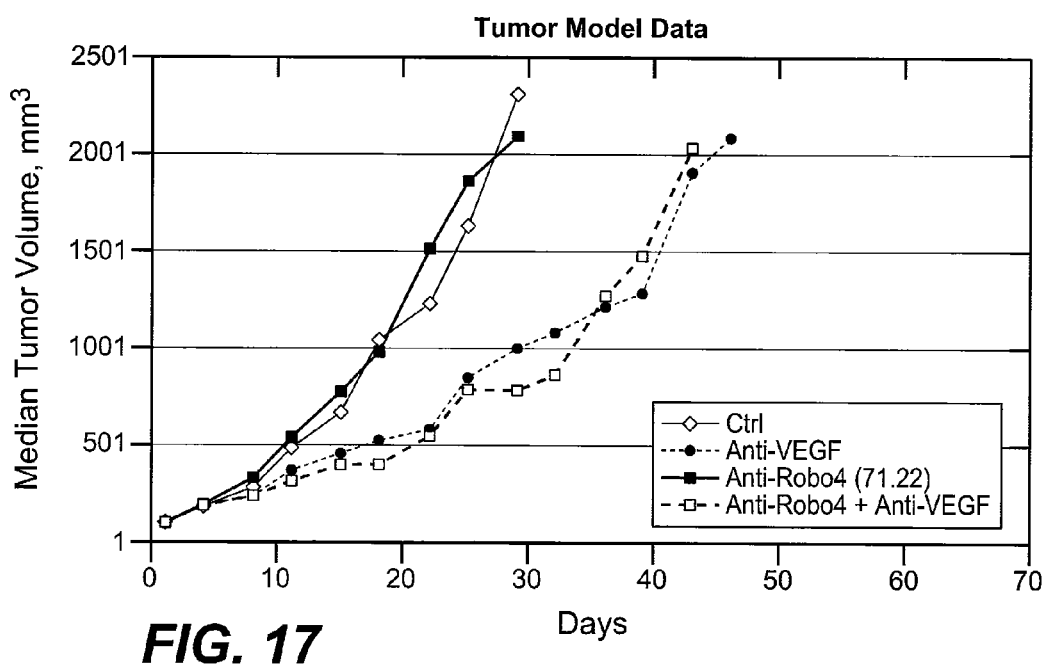

FIG. 17 is a graph of changes in median tumor volume as a function of time in xenograft mouse models dosed with control, anti-VEGF, anti-Robo4 (YW71.22), and anti-Robo4 plus anti-VEGF antibodies. Naked Robo4 antibody did not inhibit tumor growth in these experiments.

Figure 18A:
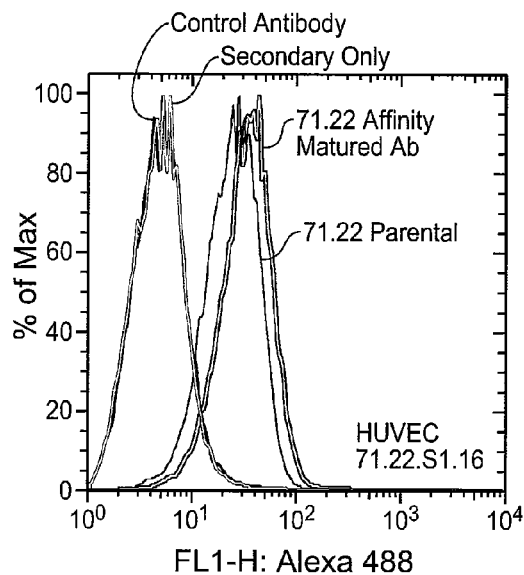
Figure 18B:
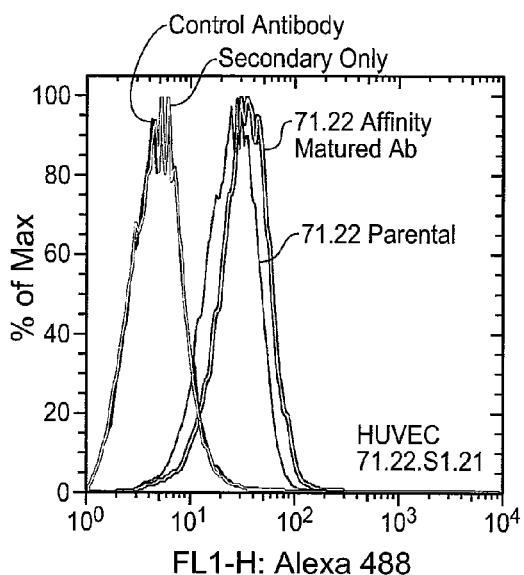
Figure 18C:
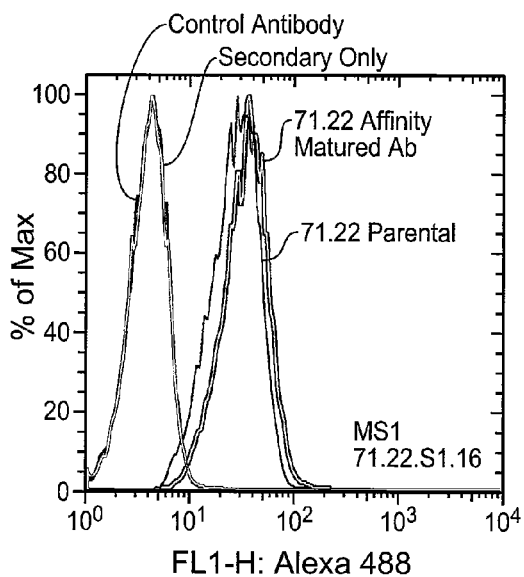
Figure 18D:
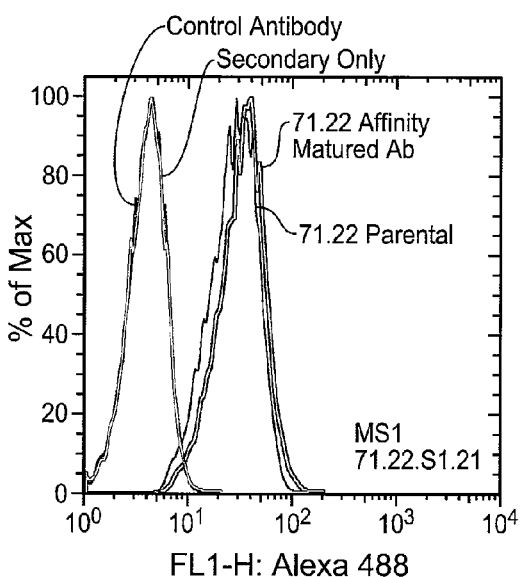

FIGS. 18A and 18B show the results of FACS plots indicating that affinity matured anti-Robo4 clones 71.22.S1.16 and 71.22.S1.21 bind Robo4 endogenously expressed on HUVEC cells. FIGS. 18C and 18D show the results of FACS plots indicating that the same affinity matured anti-Robo4 antibody clones bind murine Robo4 on the endogenously expressed on murine MS1 cells. These plots also show that the parent antibody, 71.22, also cross-reacts with human and murine Robo4.

Figure 19A:
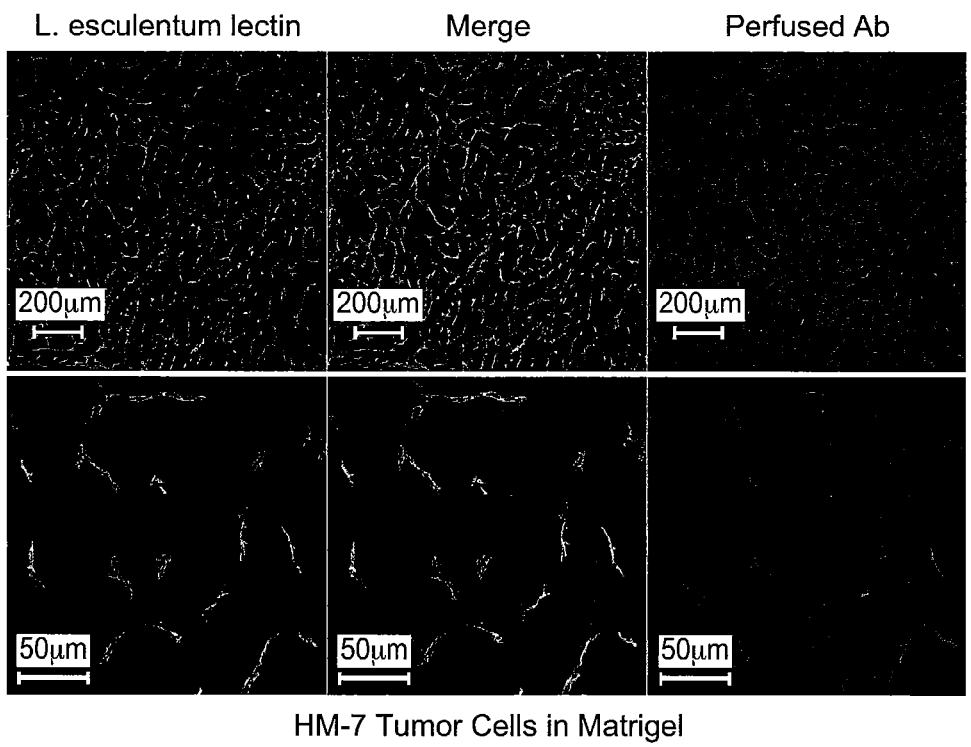
Figure 19B:
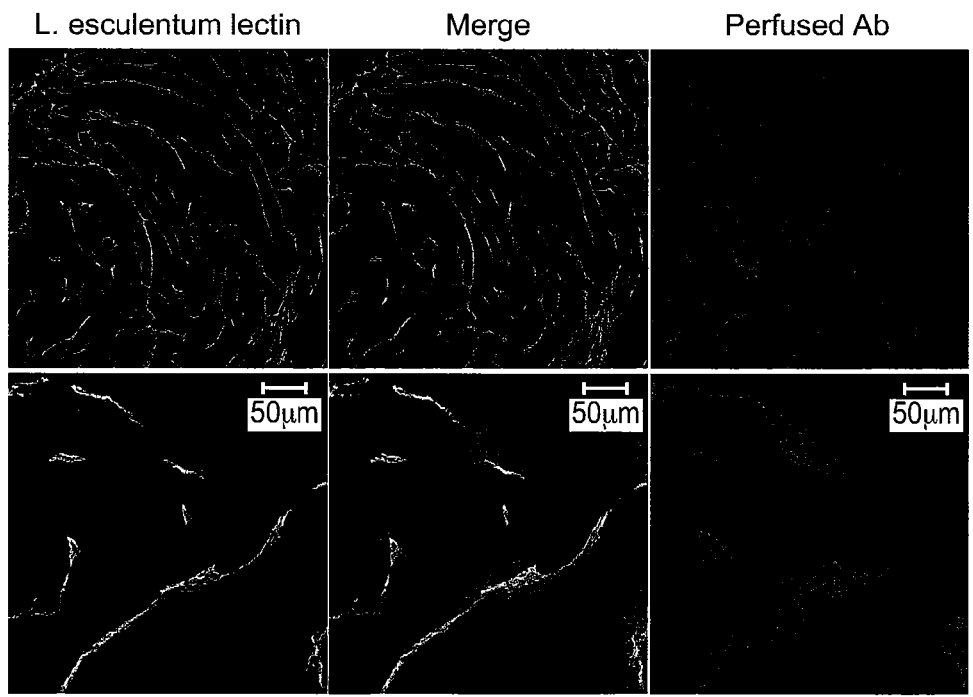

FIGS. 19A and 19B show that anti-Robo4 antibody 71.22 associates with vasculature following injection into mice as described in Example 12.

Figure 20A:
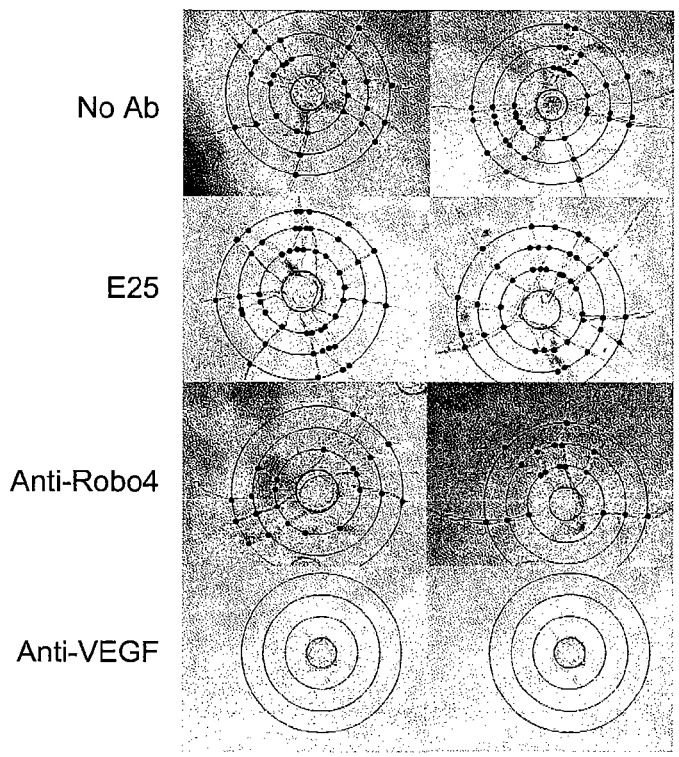
Figure 20B:
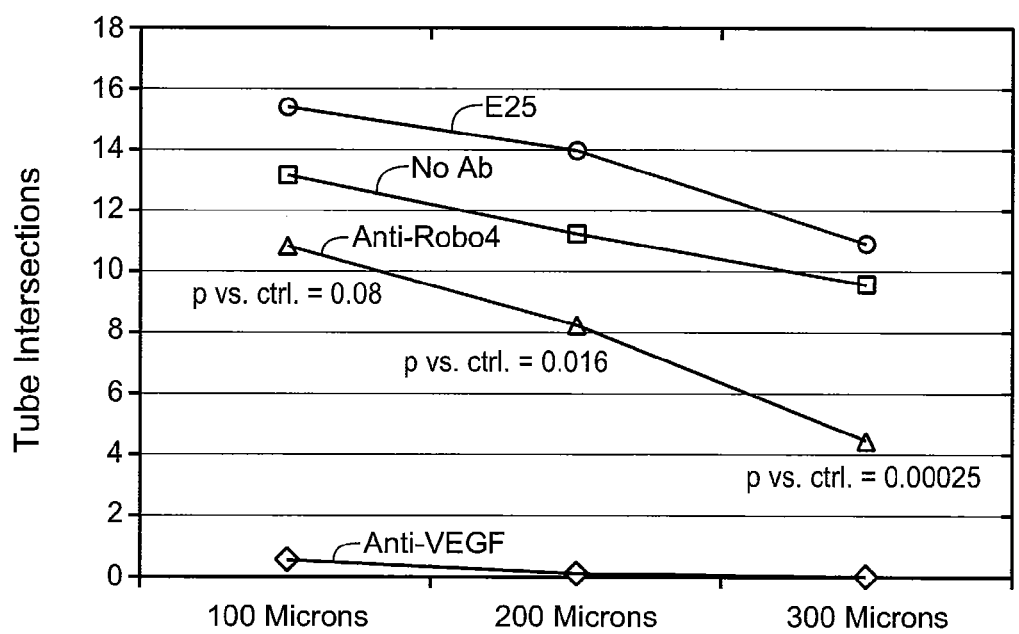

FIGS. 20A and 20B depict the results of a bead outgrowth assay indicating that anti-Robo4 antibody 71.22 inhibits HUVEC tube elongation. FIG. 20A shows that both total number and length of tubes are reduced upon treatment of HUVECs with 71.22 as compared to an irrelevant control antibody (anti-ragweed, E25). Anti-VEGF was used as positive control antibody. FIG. 20B shows representative examples with concentric circles drawn at 100, 200 and 300 µm.

DETAILED DESCRIPTION OF THE INVENTION

I. Introduction

The present invention provides compositions that bind Robo4 or a portion thereof, kits and articles of manufacture comprising such compositions, and methods of using such compositions, including, e.g., methods for modulating ligand binding to the Robo4 receptor and for modulating biological/physiological activities associated with ligand binding to the Robo4 receptor. The invention is based in part on the identification of a variety of anti-Robo4 antibodies that bind the Robo4 receptor, a receptor useful as a therapeutic and diagnostic (e.g., in vivo, in vitro, or ex vivo imaging) target. The anti-Robo4 antibodies of the invention can conveniently be used as therapeutic and diagnostic agents for use in targeting pathological conditions associated with abnormal or unwanted endothelial cell proliferation, such as abnormal or unwanted vascular cell proliferation in disorders including, but not limited to, cancer, dysregulated angiogenesis and disorders associated with (e.g., augmented by) endothelial cell proliferation within the tissue experiencing the disorder, solid tumors and metastasis, atherosclerosis, retrolental fibroplasia, hemangiomas, chronic inflammation, intraocular neovascular diseases such as proliferative retinopathies, e.g., diabetic retinopathy, age-related macular degeneration (AMD), neovascular glaucoma, immune rejection of transplanted corneal tissue and other tissues, rheumatoid arthritis, and psoriasis. The anti-Robo4 antibodies of the invention can be used alone or in combination with additional agents (including anti-neoplastic compositions, chemotherapeutic agents, cytotoxic agents, growth-inhibitory agents. In some embodiments, the invention provides methods for identifying and/or using Robo4-targeted antibodies to block Robo4 function, deliver cytotoxic agents to cells expressing Robo4 (e.g., on the cell surface), and/or deliver imaging agents to cells expressing Robo4 on the cell surface. For example, in some embodiments, detectably labeled anti-Robo4 antibodies can conveniently be used as an imaging agent for disease states in which increased vascularization is harmful (e.g. cancer and macular degeneration) or for physiological conditions in which endothelial cell proliferation, vascular cell proliferation, and/or angiogenesis is a desirable condition (such as in, for example, wound healing).

II. Definitions

As used herein, the following terms have the meanings ascribed to them below unless otherwise specified.

The term "Robo4" or "Magic Roundabout," "Endothelial Cell-Specific Molecule 4," or "ECSM4" as used herein refers to any native or variant (whether native or synthetic) Robo4 polypeptide comprising the amino acid sequence shown in FIG. 5, a variant or a subsequence thereof to which the antibody of the present invention specifically binds, including, e.g., the extracellular domain of Robo4 or any subsequence thereof. The term "wild type Robo4" generally refers to a polypeptide comprising the amino acid sequence of a naturally occurring Robo4 protein. The term "wild type Robo4 sequence" generally refers to an amino acid sequence found in a naturally occurring Robo4. The Robo4 polypeptide of the invention is a mammalian Robo4 polypeptide, such as, without limitation human, equine, bovine, porcine, canine, feline, rodent Robo4. "Robo4," "Magic Roundabout," "Endothelial Cell-Specific Molecule 4," or "ECSM4" also refer to nucleic acids and polypeptide polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to an amino acid sequence encoded by a Robo4 nucleic acid (for a human Robo4 polypeptide sequence, see, e.g., FIGS. 5 and 7 and SEQ ID NOS:138 and 171; for a murine Robo4 polypeptide sequence, see, e.g., SEQ ID NO:172); (2) bind to antibodies, e.g., polyclonal antibodies and/or monoclonal antibodies, raised against an immunogen comprising an amino acid sequence of a Robo4 protein, and conservatively modified variants thereof; (3) specifically hybridize under stringent hybridization conditions to an anti-sense strand corresponding to a nucleic acid sequence encoding a Robo4 protein, and conservatively modified variants thereof, (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to a Robo4 nucleic acid (e.g., a nucleic acid encoding the polypeptide set forth in FIGS. 5 and 7 and SEQ ID NOS: 138, 171, or 172. Preferably the Robo4 nucleic acid has greater than 80%, 85%, 90%, 95%, 96%, 97%, 98%, or 99% identity to the nucleic acid sequence encoding SEQ ID NOS: 138, 171, or 172, preferably over a region of at least about 25, 50, 100, 150, 200, 250, 300, 350, 400, 450, or 500, 600, 700, 800, 900, or 1000 or more nucleotides.

The term "anti-Robo4 antibody" or "an antibody that binds to Robo4" refers to an antibody that is capable of binding Robo4 with sufficient affinity such that the antibody is useful as a diagnostic and/or therapeutic agent in targeting Robo4. Preferably, the extent of binding of an anti-Robo4 antibody to an unrelated, non-Robo4 protein is less than about 10% of the binding of the antibody to Robo4 as measured, e.g., by a radioimmunoassay (RIA). In certain embodiments, an antibody that binds to Robo4 has a dissociation constant (Kd) of $\leq 1$ µM, $\leq 100$ nM, $\leq 10$ nM, $\leq 1$ nM, or $\leq 0.1$ nM. In certain embodiments, an anti-Robo4 antibody binds to an epitope of Robo4 that is conserved among Robo4 from different species. In other embodiments, an ant-Robo4 antibody binds to an epitope of Robo4 that is not conserved among Robo4 from different species.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. *Cellular and Mol. Immunology*, 4th ed. (W.B. Saunders, Co., 2000). An antibody may be part of a larger fusion molecule, formed by covalent or non-covalent association of the antibody with one or more other proteins or peptides.

The terms "full length antibody," "intact antibody" and "whole antibody" are used herein interchangeably to refer to an antibody in its substantially intact form, not antibody fragments as defined below. The terms particularly refer to an antibody with heavy chains that contain an Fc region.

A "naked antibody" for the purposes herein is an antibody that is not conjugated to a cytotoxic moiety or radiolabel.

"Antibody fragments" comprise a portion of an intact antibody, preferably comprising the antigen binding region thereof. Examples of antibody fragments include Fab, Fab', $F(ab')_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *PNAS USA*

90: 6444-6448 (1993). Triabodies and tetrabodies are also described in Hudson et al., *Nat. Med.* 9:129-134 (2003).

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein, *Nature,* 256:495-97 (1975); Hongo et al., *Hybridoma,* 14 (3): 253-260 (1995), Harlow et al., *Antibodies: A Laboratory Manual,* (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature,* 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *PNAS USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *PNAS USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al, *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *PNAS USA* 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.,* 227:381 (1991); Marks et al., *J. Mol. Biol.,* 222:581 (1991). Also available for the preparation of human monoclonal antibodies are methods described in Cole et al., Monoclonal Antibodies and Cancer Therapy, Alan R. Liss, p. 77 (1985); Boerner et al., *J. Immunol.,* 147 (1):86-95 (1991). See also van Dijk and van de Winkel, *Curr. Opin. Pharmacol.,* 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *PNAS USA,* 103:3557-3562 (2006) regarding human antibodies generated via a human B-cell hybridoma technology.

An "antigen" is a predetermined antigen (e.g. a Robo4 sequence) to which an antibody can selectively bind. The target antigen may be polypeptide, carbohydrate, nucleic acid, lipid, hapten or other naturally occurring or synthetic compound. Preferably, the target antigen is a polypeptide.

An "acceptor human framework" for the purposes herein is a framework comprising the amino acid sequence of a VL or VH framework derived from a human immunoglobulin framework, or from a human consensus framework. An acceptor human framework "derived from" a human immunoglobulin framework or human consensus framework may comprise the same amino acid sequence thereof, or may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less. Where pre-existing amino acid changes are present in a VH, preferably those changes occur at only three, two, or one of positions 71H, 73H and 78H; for instance, the amino acid residues at those positions may be 71A, 73T and/or 78A. In one embodiment, the VL acceptor human framework is identical in sequence to the VL human immunoglobulin framework sequence or human consensus framework sequence. Where pre-existing amino acid changes are present in a VH, preferably those changes are only at three, two or one of positions 71H, 73H and 78H; for instance, the amino acid residues at those positions may be 71A, 73T and/or 78A. In one embodiment, the VL acceptor human framework is identical in sequence to the VL human immunoglobulin framework sequence or human consensus framework sequence.

A "human consensus framework" is a framework which represents the most commonly occurring amino acid residue in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al. In one embodiment, for the VL, the subgroup is subgroup kappa I as in Kabat et al. In one embodiment, for the VH, the subgroup is subgroup III as in Kabat et al.

A "VH subgroup III consensus framework" comprises the consensus sequence obtained from the amino acid sequences in variable heavy subgroup III of Kabat et al. In one embodiment, the VH subgroup III consensus framework amino acid sequence comprises at least a portion or all of each of the following sequences: EVQLVESGGGLVQPGGSL-RLSCAAS (SEQ ID NO:128)-H1-WVRQAPGKGLEWV (SEQ ID NO:129)-H2-RFTISRDNSKNTLYLQMNSL-RAEDTAVYYC (SEQ ID NO:131)-H3-WGQGTLVTVSS (SEQ ID NO:16). In another embodiment, the VH subgroup III consensus framework amino acid sequence comprises at least a portion or all of each of the following sequences: EVQLVESGGGLVQPGGSLRLSCAAS (SEQ ID NO:128)-H1-WVRQAPGKGLEWV (SEQ ID NO:129)-H2-RFTI-SADTSKNTAYLQMNSLRLRAEDTAVYYC (SEQ ID NO:137)-H3-WGQGTLVTVSS (SEQ ID NO:16)

A "VL subgroup I consensus framework" comprises the consensus sequence obtained from the amino acid sequences in variable light kappa subgroup I of Kabat et al. In one embodiment, the VH subgroup I consensus framework amino acid sequence comprises at least a portion or all of each of the following sequences:

```
DIQMTQSPSSLSASVGDRVTITC           (SEQ ID NO:  9)
-L1-
WYQQKPGKAPKLLIY                   (SEQ ID NO: 10)
-L2-
GVPSRFSGSGSGTDFTLTISSLQPEDFATYYC  (SEQ ID NO: 99)
-L3-
FGQGTKVEIK.                       (SEQ ID NO: 100)
```

An "unmodified human framework" is a human framework which has the same amino acid sequence as the acceptor human framework, e.g. lacking human to non-human amino acid substitution(s) in the acceptor human framework.

The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are HVRs that are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

| Loop | Kabat | AbM | Chothia | Contact | |
|---|---|---|---|---|---|
| L1 | L24-L34 | L24-L34 | L26-L32 | L30-L36 | |
| L2 | L50-L56 | L50-L56 | L50-L52 | L46-L55 | |
| L3 | L89-L97 | L89-L97 | L91-L96 | L89-L96 | |
| H1 | H31-H35B | H26-H35B | H26-H32 | H30-H35B | (Kabat Numbering) |
| H1 | H31-H35 | H26-H35 | H26-H32 | H30-H35 | (Chothia Numbering) |
| H2 | H50-H65 | H50-H58 | H53-H55 | H47-H58 | |
| H3 | H95-H102 | H95-H102 | H96-H101 | H93-H101 | |

The amino acid position/boundary delineating a hypervariable region of an antibody can vary, depending on the context and the various definitions known in the art (as described below). Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. In one embodiment, these hybrid hypervariable positions include one or more of positions 26-30, 26-35 33-35B, 47-49, 49-65, 57-65, 95-102, 93, 94 and 102 in a heavy chain variable domain. In one embodiment, these hybrid hypervariable positions include one or more of positions 24-29, 24-34, 35-36, 46-49, 50-56, 89-97, 56 and 97 in a light chain variable domain.

As used herein, the HVRs of the light chain are referred to interchangeably as HVR-L1, -L2, or -L3, or HVR1-LC, HVR2-LC or HVR3-LC or other similar designation that indicates that a light chain HVR is referenced. As used herein, the HVRs of the heavy chain are referred to interchangeably as HVR-H1, -H2, or -H3, or HVR1-HC, HVR2-HC, or HVR3-HC, or other similar designation that indicates that a heavy chain HVR is referenced.

Hypervariable regions may comprise "extended hypervariable regions" as follows: 24-36 or 24-34 (L1), 46-56 or 50-56 (L2) and 89-97 (L3) in the VL and 26-35 (H1), 50-65 or 49-65 (H2) and 93-102, 94-102 or 95-102 (H3) in the VH. The variable domain residues are numbered according to Kabat et al., supra for each of these definitions.

An "altered hypervariable region" for the purposes herein is a hypervariable region comprising one or more (e.g. one to about 16) amino acid substitution(s) therein.

An "un-modified hypervariable region" for the purposes herein is a hypervariable region having the same amino acid sequence as a non-human antibody from which it was derived, i.e. one which lacks one or more amino acid substitutions therein.

"Framework" or "FR" residues are those variable domain residues other than the hypervariable region residues as herein defined. As used herein, LC-FR1-4 or FR1-4-LC or similar designation is used interchangeably and refers to framework regions of the light chain. As used herein, HC-FR1-4 or FR1-4-HC or similar designation is used interchangeably and refers to framework region of the heavy chain.

An "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al., *Bio/Technology* 10:779-783 (1992) describes affinity maturation by VH and VL domain shuffling. Random mutagenesis of CDR and/or framework residues is described by: Barbas et al., *PNAS USA* 91:3809-3813 (1994); Schier et al., *Gene* 169:147-155 (1995); Yelton et al., *J. Immunol.* 155:1994-2004 (1995); Jackson et al., *J. Immunol.* 154(7):3310-9 (1995); and Hawkins et al, *J. Mol. Biol.* 226:889-896 (1992).

A "blocking" antibody or an "antagonist" antibody is one which inhibits or reduces biological activity of the antigen it binds. For example blocking antibodies or antagonist anti-Robo4 antibodies substantially or completely inhibit the angiogenesis by binding Robo4.

The term "variable domain residue numbering as in Kabat" or "amino acid position numbering as in Kabat", and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

The phrase "substantially similar," or "substantially the same", as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristic measured by said values (e.g., Kd values). The difference between said two values is preferably less than about 50%, preferably less than about 40%, preferably less than about 30%, preferably less than about 20%, preferably less than about 10% as a function of the value for the reference/comparator antibody.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_d$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

In one embodiment, the "$K_d$," "$K_D$," or "$K_d$ value," is measured by a radiolabeled antigen binding assay (RIA) performed with the Fab version of an antibody of interest and its antigen as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) *J. Mol Biol* 293:865-881). To establish conditions for the assay, microtiter plates (Dynex) are coated overnight with 5 ug/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [$^{125}$I]-antigen are mixed with serial dilutions of a Fab of interest (e.g., Fab-12 as described in Presta et al., *Cancer Res.* 57:4593-4599 (1997)). The Fab of interest is then incubated overnight; however, the incubation may continue for a longer period (e.g., 65 hours) to insure that equilibrium is reached. Thereafter, the mixtures are transferred to the capture plate for incubation at room temperature (e.g., for one hour). The solution is then removed and the plate washed eight times with 0.1% Tween® 20 in PBS. When the plates have dried, 150 ul/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment the Kd or Kd value is measured by using surface plasmon resonance assays using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween® 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant ($K_d$) is calculated as the ratio $k_{off}/k_{on}$. See, e.g., Chen et al., *J. Mol. Biol* 293:865-881 (1999). If the on-rate exceeds $10^6 M^{-1} S^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco™ spectrophotometer (Thermo-Spectronic) with a stirred cuvette.

The phrase "substantially reduced," or "substantially different", as used herein, denotes a sufficiently high degree of difference between two numeric values (generally one associated with an antibody of the invention and the other associated with a reference/comparator antibody) such that one of skill in the art would consider the difference between the two values to be of statistical significance within the context of the biological characteristic measured by said values (e.g., $K_d$ values, HAMA response). The difference between said two values is preferably greater than about 10%, preferably greater than about 20%, preferably greater than about 30%, preferably greater than about 40%, preferably greater than about 50% as a function of the value for the reference/comparator antibody.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR™) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc. and the source code shown has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction X/Y}$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Unless specifically stated otherwise, all % amino acid sequence identity values used herein are obtained as described in the immediately preceding paragraph using the ALIGN-2 computer program.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C.) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

A "disorder" or "disease" is any condition that would benefit from treatment with a substance/molecule or method of the invention. This includes chronic and acute disorders or diseases including those pathological conditions which predispose the mammal to the disorder in question. Non-limiting examples of disorders to be treated herein include malignant and benign tumors; non-leukemias and lymphoid malignancies; neuronal, glial, astrocytal, hypothalamic and other glandular, macrophagal, epithelial, stromal and blastocoelic disorders; and inflammatory, immunologic and other angiogenesis-related disorders.

The terms "cell proliferative disorder" and "proliferative disorder" refer to disorders that are associated with some degree of abnormal cell proliferation. In one embodiment, the cell proliferative disorder is cancer. In one embodiment, the cell proliferative disorder is angiogenesis.

"Tumor", as used herein, refers to all neoplastic cell growth and proliferation, whether malignant or benign, and all pre-cancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell proliferation. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

The term "anti-neoplastic composition" or "anti-cancer composition" or "anti-cancer agent" refers to a composition useful in treating cancer comprising at least one active therapeutic agent, e.g., "anti-cancer agent." Examples of therapeutic agents (anti-cancer agents) include, but are limited to, e.g., chemotherapeutic agents, growth inhibitory agents, cytotoxic agents, agents used in radiation therapy, anti-angiogenesis agents, apoptotic agents, anti-tubulin agents, and other agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (Tarceva™), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA VEGF, or VEGF receptor(s), TRAIL/Apo2, and other bioactive and organic chemical agents, etc. Combinations thereof are also included in the invention.

An "angiogenic factor or agent" is a growth factor which stimulates the development of blood vessels, e.g., promote angiogenesis, endothelial cell growth, stability of blood vessels, and/or vasculogenesis, etc. For example, angiogenic factors, include, but are not limited to, e.g., VEGF and members of the VEGF family, PlGF, PDGF family, fibroblast growth factor family (FGFs), TIE ligands (Angiopoietins), ephrins, Del-1, fibroblast growth factors: acidic (aFGF) and basic (bFGF), Follistatin, Granulocyte colony-stimulating factor (G-CSF), Hepatocyte growth factor (HGF)/scatter factor (SF), Interleukin-8 (IL-8), Leptin, Midkine, Placental growth factor, Platelet-derived endothelial cell growth factor (PD-ECGF), Platelet-derived growth factor, especially PDGF-BB or PDGFR-beta, Pleiotrophin (PTN), Progranulin, Proliferin, Transforming growth factor-alpha (TGF-alpha), Transforming growth factor-beta (TGF-beta), Tumor necrosis factor-alpha (TNF-alpha), Vascular endothelial growth factor (VEGF)/vascular permeability factor (VPF), etc. It would also include factors that accelerate wound healing, such as growth hormone, insulin-like growth factor-I (IGF-I), VIGF, epidermal growth factor (EGF), CTGF and members of its family, and TGF-alpha and TGF-beta. See, e.g., Klagsbrun and D'Amore, *Annu. Rev. Physiol.,* 53:217-39 (1991); Streit and Detmar, *Oncogene,* 22:3172-3179 (2003); Ferrara & Alitalo, *Nature Medicine* 5(12):1359-1364 (1999); Tonini et al., *Oncogene,* 22:6549-6556 (2003) (e.g., Table 1 listing known angiogenic factors); and, Sato *Int. J. Clin. Oncol.,* 8:200-206 (2003).

The term "VEGF" as used herein refers to the 165-amino acid human vascular endothelial cell growth factor and related 121-, 189-, and 206-amino acid human vascular endothelial cell growth factors, as described by Leung et al. *Science,* 246:1306 (1989), and Houck et al. *Mol. Endocrin.,* 5:1806 (1991), together with the naturally occurring allelic and processed forms thereof. The term "VEGF" also refers to VEGFs from non-human species such as mouse, rat or primate. Sometimes the VEGF from a specific species are indicated by terms such as hVEGF for human VEGF, mVEGF for murine VEGF, and etc. The term "VEGF" is also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "VEGF (8-109)," "VEGF (1-109)" or "VEGF$_{165}$." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF. According to a preferred embodiment, the VEGF is a human VEGF.

A "VEGF antagonist" refers to a molecule capable of neutralizing, blocking, inhibiting, abrogating, reducing or interfering with VEGF activities including its binding to VEGF or one or more VEGF receptors or the nucleic acid encoding them. Preferrably, the VEGF antagonist binds VEGF or a VEGF receptor. VEGF antagonists include anti-VEGF antibodies and antigen-binding fragments thereof, polypeptides that bind VEGF and VEGF receptors and block ligand-receptor interaction (e.g., immunoadhesins, peptibodies), anti-VEGF receptor antibodies and VEGF receptor antagonists such as small molecule inhibitors of the VEGFR tyrosine kinases, aptamers that bind VEGF and nucleic acids that hybridize under stringent conditions to nucleic acid sequences that encode VEGF or VEGF receptor (e.g., RNAi). According to one preferred embodiment, the VEGF antagonist binds to VEGF and inhibits VEGF-induced endothelial cell proliferation in vitro. According to one preferred embodiment, the VEGF antagonist binds to VEGF or a VEGF receptor with greater affinity than a non-VEGF or non-VEGF receptor. According to one preferred embodiment, the VEG antagonist binds to VEGF or a VEGF receptor with a Kd of between 1 uM and 1 pM. According to another preferred embodiment, the VEGF antagonist binds to VEGF or a VEGF receptor between 500 nM and 1 pM.

According a preferred embodiment, the VEGF antagonist is selected from the group consisting of a polypeptide such as an antibody, a peptibody, an immunoadhesin, a small molecule or an aptamer. In a preferred embodiment, the antibody is an anti-VEGF antibody such as the AVASTIN® antibody or an anti-VEGF receptor antibody such as an anti-VEGFR2 or an anti-VEGFR3 antibody. Other examples of VEGF antagonists include: VEGF-Trap, Mucagen, PTK787, SU11248, AG-013736, Bay 439006 (sorafenib), ZD-6474, CP632, CP-547632, AZD-2171, CDP-171, SU-14813, CHIR-258, AEE-788, SB786034, BAY579352, CDP-791, EG-3306, GW-786034, RWJ-417975/CT6758 and KRN-633.

An "anti-VEGF antibody" is an antibody that binds to VEGF with sufficient affinity and specificity. Preferably, the anti-VEGF antibody of the invention can be used as a therapeutic agent in targeting and interfering with diseases or conditions wherein the VEGF activity is involved. An anti-VEGF antibody will usually not bind to other VEGF homologues such as VEGF-B or VEGF-C, nor other growth factors such as PlGF, PDGF or bFGF. A preferred anti-VEGF antibody is a monoclonal antibody that binds to the same epitope as the monoclonal anti-VEGF antibody A4.6.1 produced by hybridoma ATCC HB 10709. More preferably the anti-VEGF antibody is a recombinant humanized anti-VEGF monoclonal antibody generated according to Presta et al. (1997) Cancer Res. 57:4593-4599, including but not limited to the antibody known as bevacizumab (BV; Avastin®). According to another embodiment, anti-VEGF antibodies that can be used include, but are not limited to the antibodies disclosed in WO 2005/012359. According to one embodiment, the anti-VEGF antibody comprises the variable heavy and variable light region of any one of the antibodies disclosed in FIGS. 24, 25, 26, 27 and 29 of WO 2005/012359 (e.g., G6, G6-23, G6-31, G6-23.1, G6-23.2, B20, B20-4 and B20.4.1). In another preferred embodiment, the anti-VEGF antibody known as ranibizumab is the VEGF antagonist administered for ocular disease such as diabetic neuropathy and AMD.

The anti-VEGF antibody "Bevacizumab (BV)", also known as "rhuMAb VEGF" or "Avastin®", is a recombinant humanized anti-VEGF monoclonal antibody generated according to Presta et al. (1997) *Cancer Res.* 57:4593-4599. It comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of Bevacizumab, including most of the framework regions, is derived from human IgG1, and about 7% of the sequence is derived from the murine antibody A4.6.1. Bevacizumab has a molecular mass of about 149,000 daltons and is glycosylated. Other anti-VEGF antibodies include the antibodies described in U.S. Pat. No. 6,884,879 and WO 2005/044853.

The anti-VEGF antibody Ranibizumab or the LUCENTIS® antibody or rhuFab V2 is a humanized, affinity-matured anti-human VEGF Fab fragment. Ranibizumab is produced by standard recombinant technology methods in *Escherichia coli* expression vector and bacterial fermentation. Ranibizumab is not glycosylated and has a molecular mass of ~48, 000 daltons. See WO98/45331 and US20030190317.

Dysregulation of angiogenesis can lead to abnormal angiogenesis, i.e., when excessive or inappropriate growth of new blood vessels (e.g., the location, timing or onset of the angiogenesis being undesired from a medical standpoint) in a diseased state or such that it causes a diseased state. Excessive, inappropriate or uncontrolled angiogenesis occurs when there is new blood vessel growth that contributes to the worsening of the diseased state or causes a diseased state. The new blood vessels can feed the diseased tissues, destroy normal tissues, and in the case of cancer, the new vessels can allow tumor cells to escape into the circulation and lodge in other organs (tumor metastases). Disease states involving abnormal angiogenesis include both non-neoplastic and neoplastic conditions including, e.g., cancer, especially vascularized solid tumors and metastatic tumors (including colon cancer, breast cancer, lung cancer (especially small-cell lung cancer), or prostate cancer), undesired or aberrant hypertrophy, arthritis, rheumatoid arthritis (RA), inflammatory bowel disease or IBD (Crohn's disease and ulcerative colitis), psoriasis, psoriatic plaques, sarcoidosis, atherosclerosis, atherosclerotic plaques, diabetic and other proliferative retinopathies including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the anterior surface of the iris (rubeosis), ocular neovascular disease, vascular restenosis, arteriovenous malformations (AVM), meningioma, hemangioma, angiofibroma, thyroid hyperplasias (including Grave's disease), chronic inflammation, lung inflammation, acute lung injury/ARDS, sepsis, primary pulmonary hypertension, malignant pulmonary effusions, cerebral edema (e.g., associated with acute stroke/closed head injury/trauma), synovial inflammation, myositis ossificans, hypertropic bone formation, osteoarthritis (OA), refractory ascites, polycystic ovarian disease, endometriosis, 3rd spacing of fluid diseases (pancreatitis, compartment syndrome, burns, bowel disease), uterine fibroids, premature labor, chronic inflammation such as IBD, renal allograft rejection, inflammatory bowel disease, nephrotic syndrome, undesired or aberrant tissue mass growth (non-cancer), hemophilic joints, hypertrophic scars, inhibition of hair growth, Osler-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), and pleural effusion.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or disorder.

An "effective amount" refers to an amount effective, at dosages and for periods of time necessary, to achieve the desired therapeutic or prophylactic result.

A "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. The term "therapeutically effective amount" refers to an amount of an antibody, polypeptide or antagonist of this invention effective to "treat" a disease or disorder in a mammal (aka patient). In the case of cancer, the therapeutically effective amount of the drug can reduce the number of cancer cells; reduce the tumor size or weight; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug can prevent growth and/or kill existing cancer cells, it can be cytostatic and/or cytotoxic. In one embodiment, the therapeutically effective amount is a growth inhibitory amount. In another embodiment, the therapeutically effective amount is an amount that extends the survival of a patient. In another embodiment, the therapeutically effective amount is an amount that improves progression free survival of a patient.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount is less than the therapeutically effective amount.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxy-doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin. Additional chemotherapeutic agents include the cytotoxic agents useful as antibody drug conjugates, such as maytansinoids (DM1, for example) and the auristatins MMAE and MMAF, for example.

"Chemotherapeutic agents" also include "anti-hormonal agents" that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

A "growth inhibitory agent" when used herein refers to a compound or composition which inhibits growth and/or proliferation of a cell (e.g., a cell expressing Robo4) either in vitro or in vivo. Thus, the growth inhibitory agent may be one which significantly reduces the percentage of Robo4-expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3, 6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

III. Anti-Robo4 Antibodies

In one aspect, the invention provides antibodies that bind to Robo4. In one embodiment, an anti-Robo4 antibody is a monoclonal antibody. In one embodiment, an anti-Robo4 antibody is an antibody fragment, e.g., a Fab, Fab'-SH, Fv, scFv, or (Fab')₂ fragment. In one embodiment, an anti-Robo4 antibody is a chimeric, humanized, or human antibody. In one embodiment, an anti-Robo4 antibody is purified.

In another aspect of the invention, polynucleotides encoding anti-Robo4 antibodies are provided. In certain embodiments, vectors comprising polynucleotides encoding anti-Robo4 antibodies are provided. In certain embodiments, host cells comprising such vectors are provided. In another aspect of the invention, compositions comprising anti-Robo4 antibodies or polynucleotides encoding anti-Robo4 antibodies are provided. In certain embodiments, a composition is a pharmaceutical formulation for the treatment of diseases and disorders including, e.g., cancer, atherosclerosis, retrolental fibroplasia, hemangiomas, chronic inflammation, intraocular neovascular diseases, proliferative retinopathies, diabetic retinopathy, age-related macular degeneration (AMD), neovascular glaucoma, immune rejection of transplanted corneal tissue and other tissues, rheumatoid arthritis, psoriasis, and combinations thereof.

Figure 2B-2:
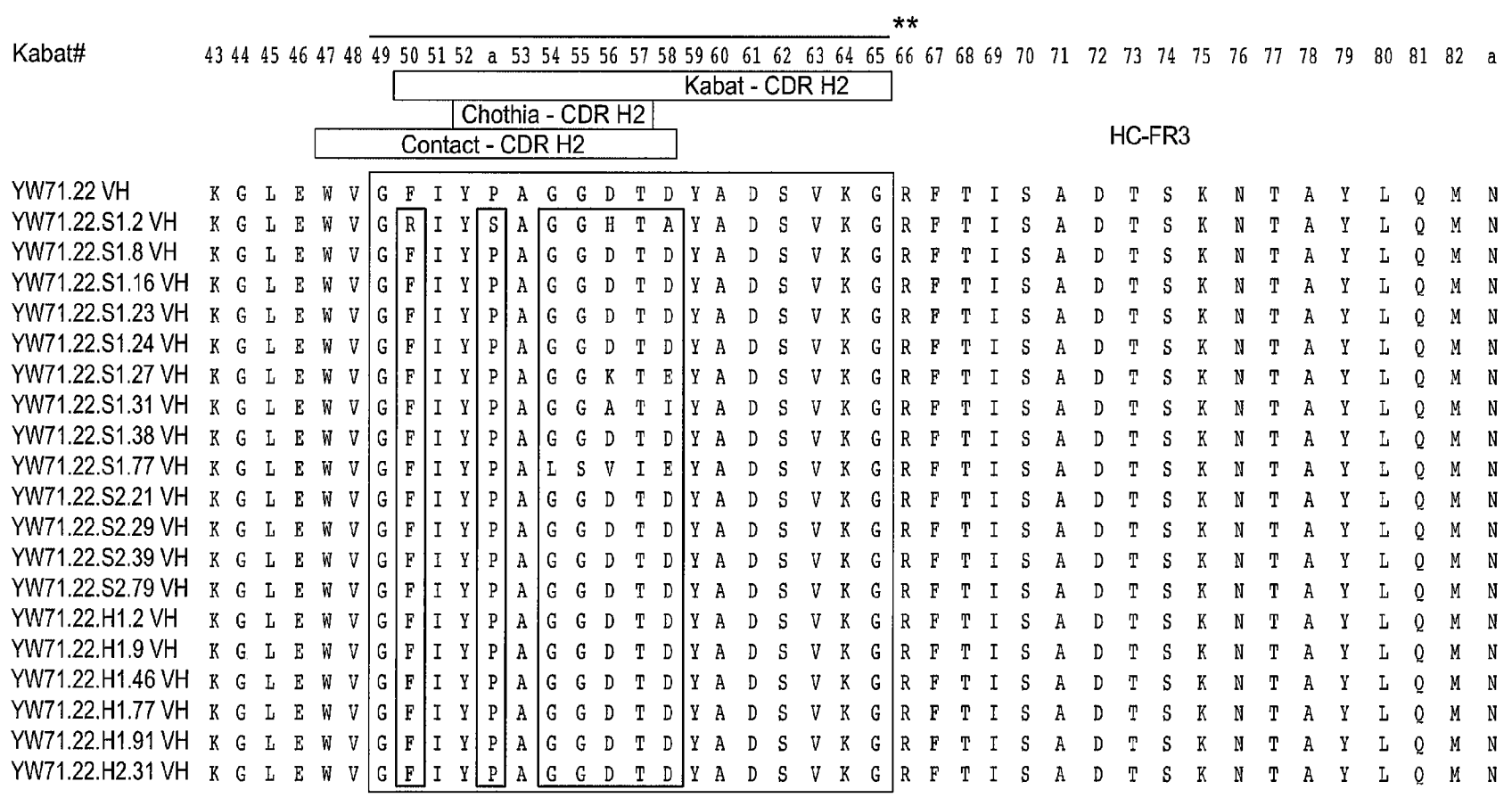

Exemplary monoclonal antibodies derived from a phage library are provided herein and described in the Examples below. Those antibodies are designated YW71.6, YW71.1, YW71.22, YW71.89, YW79.1, YW79.8, and YW79.11. Those antibodies were affinity matured to generate YW71.22.S1.2, YW71.22S1.8, YW71.22S1.16, YW71.22S1.23, YW71.22S1.24, YW71.22S1.27, YW71.22S1.31, YW71.22S1.38, YW71.22S1.77 YW71.22.S2.21, YW71.22.S2.79, YW71.22.H1.2, YW71.22.H1.9, YW71.22.H1.46, YW71.22.H1.77, YW71.22.H1.91, and YW71.22.H2.31. The sequences of the heavy and light chain variable domains of the antibodies are set forth in FIGS. 1 and 2.

An antibody of the invention can comprise any suitable human or human consensus light chain framework sequences, provided the antibody exhibits the desired biological characteristics (e.g., a desired binding affinity).

In one embodiment, human consensus frameworks herein are from, or derived from, VH subgroup III (see FIGS. 4A and 4B) and/or VL kappa subgroup I (see FIGS. 3A and 3B) consensus framework sequences.

Thus, the VH acceptor human framework may comprise one, two, three or all four of the following framework sequences:

```
FR1 comprising
EVQLVESGGGLVQPGGSLRLSCAAS,          (SEQ ID NO: 13)

FR2 comprising WVRQAPGKGLEWV,       (SEQ ID NO: 14)

FR3 comprising FR3 comprises
RFTISADTSKNTAYLQMNSLRAEDTAVYYC,     (SEQ ID NO: 15)

FR4 comprising
WGQGTLVTVSS.                        (SEQ ID NO: 16)
```

In other embodiments, the VH consensus frameworks include:

human VH subgroup I consensus frameworks 1-4 minus Kabat CDRs (SEQ ID NOS:111, 112, 113, 16);

human VH subgroup I consensus frameworks 1-4 minus extended hypervariable regions (SEQ ID NOS:114, 115, 113, 16 or SEQ ID NOS:114, 115, 116, 16 or SEQ ID NOS:114, 115, 117, 16);

human VH subgroup II consensus frameworks 1-4 minus Kabat CDRs (SEQ ID NOS: 118, 119, 120, 16);

human VH subgroup II consensus frameworks 1-4 minus extended hypervariable regions (SEQ ID NOS:121, 122, 120, 16 or SEQ ID NOS:121, 122, 123, 16 or SEQ ID NOS:121, 122, 124, 16);

human VH subgroup III consensus frameworks 1-4 minus Kabat CDRs (SEQ ID NO:125, 126, 127, 16);

human VH subgroup III consensus frameworks 1-4 minus extended hypervariable regions (SEQ ID NOS:128, 129, 127, 16 or SEQ ID NOS:128, 129, 130, 16 or SEQ ID NOS:128, 129, 131, 16);

human VH acceptor 1 frameworks 1-4 minus Kabat CDRs (SEQ ID NOS:132, 126, 133, 16);

human VH acceptor 1 frameworks 1-4 minus extended hypervariable regions (SEQ ID NOS:128, 129, 133, 16 or SEQ ID NOS:128, 129, 134, 16);

human VH acceptor 2 frameworks 1-4 minus Kabat CDRs (SEQ ID NO:132, 126, 135, 16); or human VH acceptor 2 frameworks 1-4 minus extended hypervariable regions (SEQ ID NOS:128, 126, 135, 16 or SEQ ID NOS:128, 126, 136, 16 or SEQ ID NOS:128, 126, 137, 16).

In one embodiment, the VH acceptor human framework region 4 (H-FR4) comprises WGQGTLVTVSS (SEQ ID NO:45).

The VL acceptor human framework may comprise one, two, three or four of the following framework sequences:

```
FR1 comprising
DIQMTQSPSSLSASVGDRVTITC,            (SEQ ID NO: 9)

FR2 comprising
WYQQKPGKAPKLLIY,                    (SEQ ID NO: 10)

FR3 comprising
GVPSRFSGSGSGTDFTLTISSLQPEDFATYYC,   (SEQ ID NO: 11)

FR4 comprising
FGQGTKVEIKR                         (SEQ ID NO: 173)
or

FGQGTKMEIKR.                        (SEQ ID NO: 139)
```

In other embodiment, the VL consensus frameworks include:

human VL kappa subgroup I consensus frameworks 1-4 (SEQ ID NOS:9, 10, 99, 100);

human VL kappa subgroup I consensus frameworks 1-4 (SEQ ID NOS:9, 101, 99, 100);

human VL kappa subgroup II consensus frameworks 1-4 (SEQ ID NOS:102, 103, 104, 100);

human VL kappa subgroup III consensus frameworks 1-4 (SEQ ID NOS:105, 106, 107, 100); or human VL kappa subgroup IV consensus frameworks 1-4 (SEQ ID NOS:108, 109, 110, 100)

While the acceptor may be identical in sequence to the human framework sequence selected, whether that be from a human immunoglobulin or a human consensus framework, the present invention contemplates that the acceptor sequence may comprise pre-existing amino acid substitutions relative to the human immunoglobulin sequence or human consensus framework sequence. These pre-existing substitutions are preferably minimal; usually four, three, two or one amino acid differences only relative to the human immunoglobulin sequence or consensus framework sequence.

Hypervariable region residues of the non-human antibody are incorporated into the VL and/or VH acceptor human frameworks. For example, one may incorporate residues corresponding to the Kabat CDR residues, the Chothia hypervariable loop residues, the Abm residues, and/or contact residues. Optionally, the extended hypervariable region residues as follows are incorporated: 24-34 (L1), 50-56 (L2) and 89-97 (L3), 26-35 (H1), 50-65 or 49-65 (H2) and 93-102, 94-102, or 95-102 (H3).

While "incorporation" of hypervariable region residues is discussed herein, it will be appreciated that this can be achieved in various ways, for example, nucleic acid encoding the desired amino acid sequence can be generated by mutating nucleic acid encoding the mouse variable domain sequence so that the framework residues thereof are changed to acceptor human framework residues, or by mutating nucleic acid encoding the human variable domain sequence so that the hypervariable domain residues are changed to non-human residues, or by synthesizing nucleic acid encoding the desired sequence, etc.

In the examples herein, hypervariable region-grafted variants were generated by Kunkel mutagenesis of nucleic acid encoding the human acceptor sequences, using a separate oligonucleotide for each hypervariable region. Kunkel et al., *Methods Enzymol.* 154:367-382 (1987). Appropriate changes can be introduced within the framework and/or hypervariable region, using routine techniques, to correct and re-establish proper hypervariable region-antigen interactions.

A. Antibody Fragments

The present invention encompasses antibody fragments. Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to solid tumors. For a review of certain antibody fragments, see Hudson et al. (2003) *Nat. Med.* 9:129-134.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science*, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10: 163-167 (1992)). According to another approach, F(ab')$_2$ fragments can be isolated directly from recombinant host cell culture. Fab and F(ab')$_2$ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See *Antibody Engineering*, ed. Borrebaeck, supra. The antibody fragment may also be a "linear antibody", e.g., as described in U.S. Pat. No. 5,641,870, for example. Such linear antibodies may be monospecific or bispecific.

B. Humanized Antibodies

The invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody. See, e.g., Sims et al. (1993) *J. Immunol.* 151:2296; Chothia et al. (1987) *J. Mol. Biol.* 196:901. Another method uses a particular framework derived from the consensus sequence of all human antibodies of a particular subgroup of light or heavy chains. The same framework may be used for several different humanized antibodies. See, e.g., Carter et al (1992) *PNAS USA*, 89:4285; Presta et al. (1993) *J. Immunol.*, 151:2623.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

In some embodiments, the invention provides antibodies that are humanized such that HAMA response is reduced or eliminated. Reduction or elimination of a HAMA response is a significant aspect of clinical development of suitable therapeutic agents. See, e.g., Khaxzaeli et al., *J. Natl. Cancer Inst.* (1988), 80:937; Jaffers et al., *Transplantation* (1986), 41:572; Shawler et al., *J. Immunol.* (1985), 135:1530; Sears et al., *J. Biol. Response Mod.* (1984), 3:138; Miller et al., *Blood*

(1983), 62:988; Hakimi et al., *J. Immunol.* (1991), 147:1352; Reichmann et al., *Nature* (1988), 332:323; Junghans et al., *Cancer Res.* (1990), 50:1495. Variants of these antibodies can further be obtained using routine methods known in the art, some of which are further described below.

For example, an amino acid sequence from an antibody as described herein can serve as a starting (parent) sequence for diversification of the framework and/or hypervariable sequence(s). A selected framework sequence to which a starting hypervariable sequence is linked is referred to herein as an acceptor human framework. While the acceptor human frameworks may be from, or derived from, a human immunoglobulin (the VL and/or VH regions thereof), preferably the acceptor human frameworks are from, or derived from, a human consensus framework sequence as such frameworks have been demonstrated to have minimal, or no, immunogenicity in human patients.

Where the acceptor is derived from a human immunoglobulin, one may optionally select a human framework sequence that is selected based on its homology to the donor framework sequence by aligning the donor framework sequence with various human framework sequences in a collection of human framework sequences, and select the most homologous framework sequence as the acceptor.

C. Human Antibodies

Human antibodies of the invention can be constructed by combining Fv clone variable domain sequence(s) selected from human-derived phage display libraries with known human constant domain sequences(s) as described above. Alternatively, human monoclonal antibodies of the invention can be made by the hybridoma method. Human myeloma and mouse-human heteromyeloma cell lines for the production of human monoclonal antibodies have been described, for example, by Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).

It is now possible to produce transgenic animals (e.g. mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *PNAS USA,* 90: 2551 (1993); Jakobovits et al., *Nature,* 362: 255 (1993); Bruggermann et al., *Year in Immunol.,* 7: 33 (1993).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

D. Antibody Variants

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) *Science,* 244: 1081-1085. Here, a residue or group of target residues are identified (e.g., charged residues such as arg, asp, his, lys, and glu) and replaced by a neutral or negatively charged amino acid (e.g., alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

In certain embodiments, an antibody of the invention is altered to increase or decrease the extent to which the antibody is glycosylated. Glycosylation of polypeptides is typically either N-linked or O-linked. N-linked refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition or deletion of glycosylation sites to the antibody is conveniently accomplished by altering the amino acid sequence such that one or more of the above-described tripeptide sequences (for N-linked glycosylation sites) is created or removed. The alteration may also be made by the addition, deletion, or substitution of one or more serine or threonine residues to the sequence of the original antibody (for O-linked glycosylation sites).

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. (1997) *TIBTECH* 15:26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

For example, antibody variants are provided having a carbohydrate structure that lacks fucose attached (directly or indirectly) to an Fc region. Such variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336: 1239-1249 (2004); Yamane-Ohnuki et al. *Biotech. Bioeng.* 87: 614 (2004). Examples of cell lines capable of producing defucosylated antibodies include Lec 13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

In certain embodiments, an antibody variant comprises an Fc region with one or more amino acid substitutions which further improve ADCC, for example, substitutions at positions 298, 333, and/or 334 of the Fc region (Eu numbering of residues). Such substitutions may occur in combination with any of the variations described above.

In certain embodiments, the invention contemplates an antibody variant that possesses some but not all effector functions, which make it a desirable candidate for many applications in which the half life of the antibody in vivo is important yet certain effector functions (such as complement and ADCC) are unnecessary or deleterious. In certain embodiments, the Fc activities of the antibody are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-92 (1991). Non-limiting examples of in vitro assays to assess ADCC activity of a molecule of interest is described in U.S. Pat. No. 5,500,362 (see, e.g. Hellstrom, I., et al. *PNAS USA* 83:7059-7063 (1986)) and Hellstrom, I et al., *PNAS USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS USA* 95:652-656 (1998). C1q binding assays may also be carried out to confirm that the antibody is unable to bind C1q and hence lacks CDC activity. To assess complement activation, a CDC assay may be performed (see, for example, Gazzano-Santoro et al., *J. Immunol. Methods* 202:163 (1996); Cragg, M. S. et al., *Blood* 101: 1045-1052 (2003); and Cragg, M. S. and M. J. Glennie, *Blood* 103:2738-2743 (2004)). FcRn binding and in vivo clearance/half life determinations can also be performed using methods known in the art (see, for example, Petkova, S. B. et al., *Int'l. Immunol.* 18(12):1759-1769 (2006)).

Other antibody variants having one or more amino acid substitutions are provided. Sites of interest for substitutional mutagenesis include the hypervariable regions, but FR alterations are also contemplated. Conservative substitutions are shown in Table 1 under the heading of "preferred substitutions." More substantial changes, denominated "exemplary substitutions" are provided in Table 1, or as further described below in reference to amino acid classes. Amino acid substitutions may be introduced into an antibody of interest and the products screened, e.g., for a desired activity, such as improved antigen binding, decreased immunogenicity, improved ADCC or CDC, etc.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |

TABLE 1-continued

| Original Residue | Exemplary Substitutions | Preferred Substitutions |
|---|---|---|
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Modifications in the biological properties of an antibody may be accomplished by selecting substitutions that affect (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):

```
(1) non-polar:
Ala (A), Val (V), Leu (L), Ile (I), Pro (P),
Phe (F), Trp (W), Met (M)

(2) uncharged polar:
Gly (G), Ser (S), Thr (T), Cys (C), Tyr (Y),
Asn (N), Gln (Q)

(3) acidic:
Asp (D), Glu (E)

(4) basic:
Lys (K), Arg (R), His(H)
```

Alternatively, naturally occurring residues may be divided into groups based on common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class. Such substituted residues also may be introduced into the conservative substitution sites or, into the remaining (non-conserved) sites.

One type of substitutional variant involves substituting one or more hypervariable region residues of a parent antibody (e.g. a humanized or human antibody). Generally, the resulting variant(s) selected for further development will have modified (e.g., improved) biological properties relative to the parent antibody from which they are generated. An exemplary substitutional variant is an affinity matured antibody, which may be conveniently generated using phage display-based affinity maturation techniques. Briefly, several hypervariable region sites (e.g. 6-7 sites) are mutated to generate all possible amino acid substitutions at each site. The antibodies thus generated are displayed from filamentous phage particles as fusions to at least part of a phage coat protein (e.g., the gene III product of M13) packaged within each particle. The phage-displayed variants are then screened for their biological activity (e.g. binding affinity). In order to identify candidate hypervariable region sites for modification, scanning mutagenesis (e.g., alanine scanning) can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to techniques known in the art, including those elaborated herein. Once such variants are generated, the panel of variants is subjected to screening using techniques known in the art, including those described herein, and variants with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of antibodies of the invention, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In accordance with this description and the teachings of the art, it is contemplated that in some embodiments, an antibody of the invention may comprise one or more alterations as compared to the wild type counterpart antibody, e.g. in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), e.g., as described in WO99/51642. See also Duncan & Winter, *Nature* 322:738-40 (1988); U.S. Pat. No. 5,648,260; U.S. Pat. No. 5,624,821; and WO94/29351 concerning other examples of Fc region variants. WO00/42072 (Presta) and WO 2004/056312 (Lowman) describe antibody variants with improved or diminished binding to FcRs. The content of these patent publications are specifically incorporated herein by reference. See, also, Shields et al. *J. Biol. Chem.* 9(2): 6591-6604 (2001). Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). These antibodies comprise an Fc region with one or more substitutions therein which improve binding of the Fc region to FcRn. Polypeptide variants with altered Fc region amino acid sequences and increased or decreased C1q binding capability are described in U.S. Pat. No. 6,194,551B1, WO99/51642. The contents of those patent publications are specifically incorporated herein by reference. See, also, Idusogie et al. *J. Immunol.* 164: 4178-4184 (2000).

In another aspect, the invention provides antibodies comprising modifications in the interface of Fc polypeptides comprising the Fc region, wherein the modifications facilitate and/or promote heterodimerization. These modifications comprise introduction of a protuberance into a first Fc polypeptide and a cavity into a second Fc polypeptide, wherein the protuberance is positionable in the cavity so as to promote complexing of the first and second Fc polypeptides. Methods of generating antibodies with these modifications are known in the art, e.g., as described in U.S. Pat. No. 5,731,168.

In yet another aspect, it may be desirable to create cysteine engineered antibodies, e.g., "thioMAbs," and "thioFabs" in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. In a preferred embodiment, A118 (EU numbering) of the heavy chain is substituted for cysteine. Cysteine engineered thioMabs and thioFabs are described in further detail herein below.

E. Antibody Derivatives

The antibodies of the present invention can be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly (n-vinyl pyrrolidone)polyethylene glycol, propropylene glycol homopolymers, polypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *PNAS USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

IV. Methods of Making Antibodies

A. Generating Phage-Derived Antibodies

Antibodies of the invention may be prepared by phage (mid) display techniques as disclosed in Lee et al., *J. Mol. Biol.* (2004), 340(5): 1073-93). Phage(mid) display allows the generation of large libraries of protein variants which can be rapidly sorted for those sequences that bind to a target molecule with high affinity. Nucleic acids encoding variant polypeptides are generally fused to a nucleic acid sequence encoding a viral coat protein, such as the gene III protein or the gene VIII protein. Monovalent phagemid display systems where the nucleic acid sequence encoding the protein or polypeptide is fused to a nucleic acid sequence encoding a portion of the gene III protein have been developed. (Bass, S., *Proteins,* 8:309 (1990); Lowman and Wells, *Methods: A Companion to Methods in Enzymology,* 3:205 (1991)). In a monovalent phagemid display system, the gene fusion is expressed at low levels and wild type gene III proteins are also expressed so that infectivity of the particles is retained. Methods of generating peptide libraries and screening those libraries have been disclosed in many patents (e.g. U.S. Pat. No. 5,723,286, U.S. Pat. No. 5,432,018, U.S. Pat. No. 5,580,717, U.S. Pat. No. 5,427,908 and U.S. Pat. No. 5,498,530).

Libraries of antibodies or antigen binding polypeptides have been prepared in a number of ways including by altering a single gene by inserting random DNA sequences or by cloning a family of related genes. Methods for displaying antibodies or antigen binding fragments using phage(mid) display have been described in U.S. Pat. Nos. 5,750,373, 5,733,743, 5,837,242, 5,969,108, 6,172,197, 5,580,717, and 5,658,727. The library is then screened for expression of antibodies or antigen binding proteins with the desired characteristics.

Methods of substituting an amino acid of choice into a template nucleic acid are well established in the art, some of which are described herein. For example, hypervariable region residues can be substituted using the Kunkel method. See, e.g., Kunkel et al., *Methods Enzymol.* 154:367-382 (1987).

The sequence of oligonucleotides includes one or more of the designed codon sets for the hypervariable region residues to be altered. A codon set is a set of different nucleotide triplet sequences used to encode desired variant amino acids. Codon sets can be represented using symbols to designate particular nucleotides or equimolar mixtures of nucleotides as shown in below according to the IUB code.

| IUB CODES | |
|---|---|
| G | Guanine |
| A | Adenine |
| T | Thymine |
| C | Cytosine |
| R | (A or G) |
| Y | (C or T) |
| M | (A or C) |
| K | (G or T) |
| S | (C or G) |
| W | (A or T) |
| H | (A or C or T) |
| B | (C or G or T) |
| V | (A or C or G) |

-continued

| IUB CODES | |
|---|---|
| D | (A or G or T) H |
| N | (A or C or G or T) |

For example, in the codon set DVK, D can be nucleotides A or G or T; V can be A or G or C; and K can be G or T. This codon set can present 18 different codons and can encode amino acids Ala, Trp, Tyr, Lys, Thr, Asn, Lys, Ser, Arg, Asp, Glu, Gly, and Cys.

Oligonucleotide or primer sets can be synthesized using standard methods. A set of oligonucleotides can be synthesized, for example, by solid phase synthesis, containing sequences that represent all possible combinations of nucleotide triplets provided by the codon set and that will encode the desired group of amino acids. Synthesis of oligonucleotides with selected nucleotide "degeneracy" at certain positions is well known in that art. Such sets of nucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can include restriction enzyme sites for cloning purposes.

In one method, nucleic acid sequences encoding variant amino acids can be created by oligonucleotide-mediated mutagenesis. This technique is well known in the art as described by Zoller et al., *Nucleic Acids Res.* 10:6487-6504 (1987). Briefly, nucleic acid sequences encoding variant amino acids are created by hybridizing an oligonucleotide set encoding the desired codon sets to a DNA template, where the template is the single-stranded form of the plasmid containing a variable region nucleic acid template sequence. After hybridization, DNA polymerase is used to synthesize an entire second complementary strand of the template that will thus incorporate the oligonucleotide primer, and will contain the codon sets as provided by the oligonucleotide set.

Generally, oligonucleotides of at least 25 nucleotides in length are used. An optimal oligonucleotide will have 12 to 15 nucleotides that are completely complementary to the template on either side of the nucleotide(s) coding for the mutation(s). This ensures that the oligonucleotide will hybridize properly to the single-stranded DNA template molecule. The oligonucleotides are readily synthesized using techniques known in the art such as that described by Crea et al., *PNAS USA,* 75:5765 (1978).

The DNA template is generated by those vectors that are either derived from bacteriophage M13 vectors (the commercially available M13 mp18 and M13 mp19 vectors are suitable), or those vectors that contain a single-stranded phage origin of replication as described by Viera et al., *Meth. Enzymol.,* 153:3 (1987). Thus, the DNA that is to be mutated can be inserted into one of these vectors in order to generate single-stranded template. Production of the single-stranded template is described in sections 4.21-4.41 of Sambrook et al., above.

To alter the native DNA sequence, the oligonucleotide is hybridized to the single stranded template under suitable hybridization conditions. A DNA polymerizing enzyme, usually T7 DNA polymerase or the Klenow fragment of DNA polymerase I, is then added to synthesize the complementary strand of the template using the oligonucleotide as a primer for synthesis. A heteroduplex molecule is thus formed such that one strand of DNA encodes the mutated form of gene 1, and the other strand (the original template) encodes the native, unaltered sequence of gene 1. This heteroduplex molecule is then transformed into a suitable host cell, usually a prokaryote such as *E. coli* JM101. After growing the cells, they are plated onto agarose plates and screened using the oligonucleotide primer radiolabeled with a 32-Phosphate to identify the bacterial colonies that contain the mutated DNA.

The method described immediately above may be modified such that a homoduplex molecule is created wherein both strands of the plasmid contain the mutation(s). The modifications are as follows: The single stranded oligonucleotide is annealed to the single-stranded template as described above. A mixture of three deoxyribonucleotides, deoxyriboadenosine (dATP), deoxyriboguanosine (dGTP), and deoxyribothymidine (dTT), is combined with a modified thiodeoxyribocytosine called dCTP-(aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell.

As indicated previously the sequence of the oligonucleotide set is of sufficient length to hybridize to the template nucleic acid and may also, but does not necessarily, contain restriction sites. The DNA template can be generated by those vectors that are either derived from bacteriophage M13 vectors or vectors that contain a single-stranded phage origin of replication as described by Viera et al., *Meth. Enzymol.,* 153:3 (1987). Thus, the DNA that is to be mutated must be inserted into one of these vectors in order to generate single-stranded template. Production of the single-stranded template is described in sections 4.21-4.41 of Sambrook et al., supra.

According to another method, a library can be generated by providing upstream and downstream oligonucleotide sets, each set having a plurality of oligonucleotides with different sequences, the different sequences established by the codon sets provided within the sequence of the oligonucleotides. The upstream and downstream oligonucleotide sets, along with a variable domain template nucleic acid sequence, can be used in a polymerase chain reaction to generate a "library" of PCR products. The PCR products can be referred to as "nucleic acid cassettes", as they can be fused with other related or unrelated nucleic acid sequences, for example, viral coat proteins and dimerization domains, using established molecular biology techniques.

The sequence of the PCR primers includes one or more of the designed codon sets for the solvent accessible and highly diverse positions in a hypervariable region. As described above, a codon set is a set of different nucleotide triplet sequences used to encode desired variant amino acids.

Antibody selectants that meet the desired criteria, as selected through appropriate screening/selection steps can be isolated and cloned using standard recombinant techniques.

In one aspect, the HVR-H1, HVR-H2, HVR-H3 sequences are varied by holding amino acids at particular positions constant and varying the amino acids at other positions.

In one aspect, the invention provides an antibody comprising at least one, at least two, or all three of the following:
(i) a HVR-L1 sequence comprising the sequence of SEQ ID NO:1;
(ii) a HVR-L2 sequence comprising the sequence of SEQ ID NO:2;
(iii) a HVR-L3 sequence comprising the sequence of SEQ ID NO:3.

The amino acid sequences of SEQ ID NOS:1, 2, and 3 are numbered with respect to individual HVR (i.e., L1, L2, or L3) as indicated in by in FIGS. 1A (positions 24-34, 50-56, and 89-97, respectively) and 2A (positions 24-34, 50-56, and 89-97, respectively), the numbering being consistent with the Kabat numbering system as described below.

In one aspect, the invention provides an antibody comprising at least one, at least two, or all three of the following:
(i) a HVR-H1 sequence comprising the sequence of SEQ ID NO: 4;
(ii) a HVR-H2 sequence comprising the sequence of SEQ ID NO:5;
(iii) a HVR-H3 sequence comprising the sequence of SEQ ID NO:6.

The amino acid sequences of SEQ ID NOS:4, 5, and 6 are numbered with respect to individual HVR (i.e., H1, H2 or H3) as indicated in by in FIGS. 1B (positions 26-35, 49-65, and 93-102, respectively) and 2B (positions 26-35, 49-65, and 93-102, respectively), the numbering being consistent with the Kabat numbering system as described below.

In one aspect, the invention provides antibodies comprising light chain HVR sequences as depicted in FIGS. 1A and 2A.

In one aspect, the invention provides antibodies comprising heavy chain HVR sequences as depicted in FIGS. 1B and 2B.

Some embodiments of antibodies of the invention comprise a light chain variable domain of humanized 4D5 antibody (huMAb4D5-8) (HERCEPTIN® anti-HER2 antibody, Genentech, Inc., South San Francisco, Calif., USA) (also referred to in U.S. Pat. No. 6,407,213 and Lee et al., J. Mol. Biol. (2004), 340(5):1073-93) as depicted in SEQ ID NO:98 below.

```
                                          (SEQ ID NO: 98)
1 Asp Ile Gln Met Thr Gln Ser Pro Ser Ser Leu Ser

Ala Ser Val Gly Asp Arg Val Thr Ile Thr Cys Arg

Ala Ser Gln Asp Val Asn Thr Ala Val Ala Trp Tyr

Gln Gln Lys Pro Gly Lys Ala Pro Lys Leu Leu Ile

Tyr Ser Ala Ser Phe Leu Tyr Ser Gly Val Pro Ser

Arg Phe Ser Gly Ser Arg Ser Gly Thr Asp Phe Thr

Leu Thr Ile Ser Ser Leu Gln Pro Glu Asp Phe Ala

Thr Tyr Tyr Cys Gln Gln His Tyr Thr Thr Pro Pro

Thr Phe Gly Gln Gly Thr Lys Val Glu Ile Lys 107
```

(HVR Residues are Underlined)

In one embodiment, the huMAb4D5-8 light chain variable domain sequence is modified at one or more of positions 30, 66 and 91 (Asn, Arg and His as indicated in bold/italics above, respectively). In one embodiment, the modified huMAb4D5-8 sequence comprises Ser in position 30, Gly in position 66 and/or Ser in position 91. Accordingly, in one embodiment, an antibody of the invention comprises a light chain variable domain comprising the sequence depicted in SEQ ID NO:167 below:

```
                                         (SEQ ID NO: 167)
1 Asp Ile Gln Met Thr Gln Ser Pro Ser Ser Leu Ser

Ala Ser Val Gly Asp Arg Val Thr Ile Thr Cys Arg

Ala Ser Gln Asp Val Ser Thr Ala Val Ala Trp Tyr

Gln Gln Lys Pro Gly Lys Ala Pro Lys Leu Leu Ile

Tyr Ser Ala Ser Phe Leu Tyr Ser Gly Val Pro Ser

Arg Phe Ser Gly Ser Gly Ser Gly Thr Asp Phe Thr

Leu Thr Ile Ser Ser Leu Gln Pro Glu Asp Phe Ala

Thr Tyr Tyr Cys Gln Gln Ser Tyr Thr Thr Pro Pro

Thr Phe Gly Gln Gly Thr Lys Val Glu Ile Lys 107
```

(HVR Residues are Underlined)

Substituted residues with respect to huMAb4D5-8 are indicated in bold/italics above.

Antibodies of the invention can comprise any suitable framework variable domain sequence, provided binding activity to Robo4 is substantially retained, such as at least 1%, at least 10%, at least 20%, at least 30%, at least 40%, at least 50%, at least 60%, at least 70%, at least 80%, at least 90%, at least 100% or greater binding activity relative to an antibody of the invention disclosed herein. For example, in some embodiments, antibodies of the invention comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiment, these antibodies comprise heavy chain variable domain framework sequences of huMAb4D5-8 (HERCEPTIN®, Genentech, Inc., South San Francisco, Calif., USA) (also referred to in U.S. Pat. Nos. 6,407,213 and 5,821,337, and Lee et al., *J. Mol. Biol.* 340(5): 1073-93 (2004)). In one embodiment, these antibodies further comprise a human κI light chain framework consensus sequence. In one embodiment, these antibodies comprise light chain HVR sequences of huMAb4D5-8 as described in U.S. Pat. Nos. 6,407,213 and 5,821,337.) In one embodiment, these antibodies comprise light chain variable domain sequences of huMAb4D5-8 (SEQ ID NOS: 98 or 167) (HERCEPTIN® anti-HER2 antibody, Genentech, Inc., South San Francisco, Calif., USA) (also referred to in U.S. Pat. Nos. 6,407,213 & 5,821,337, and Lee et al., *J. Mol. Biol.* 340(5): 1073-93 (2004)).

In one embodiment, antibodies of the invention may comprise framework region sequences of huMAb4D5-8 light and heavy chains as provided below (SEQ ID NOS:9, 10, 168, 12 (light chain) and SEQ ID NOS:13, 14, 15, 16 (heavy chain)). Numbers in superscript/bold indicate amino acid positions according to Kabat.

| Framework sequences of huMAb4D5-8 light chain |
| --- |
| LC-FR1 $^1$Asp Ile Gln Met Thr Gln Ser Pro Ser Ser Leu Ser Ala Ser Val Gly Asp Arg Val Thr Ile Thr Cys$^{23}$ (SEQ ID NO: 9) |
| LC-FR2 $^{35}$Trp Tyr Gln Gln Lys Pro Gly Lys Ala Pro Lys Leu Leu Ile Tyr$^{49}$ (SEQ ID NO: 10) |
| LC-FR3 $^{57}$Gly Val Pro Ser Arg Phe Ser Gly Ser Arg Ser Gly Thr Asp Phe Thr Leu Thr Ile Ser Ser Leu Gln Pro Glu Asp Phe Ala Thr Tyr Tyr Cys$^{88}$ (SEQ ID NO: 168) |
| LC-FR4 $^{98}$Phe Gly Gln Gly Thr Lys Val Glu Ile Lys$^{107}$ (SEQ ID NO: 12) |

| Framework sequences of huMAb4D5-8 heavy chain |
| --- |
| HC-FR1 $^1$Glu Val Gln Leu Val Glu Ser Gly Gly Gly Leu Val Gln Pro Gly Gly Ser Leu Arg Leu Ser Cys Ala Ala Ser$^{25}$ (SEQ ID NO: 13) |
| HC-FR2 $^{36}$Trp Val Arg Gln Ala Pro Gly Lys Gly Leu Glu Trp Val$^{48}$ (SEQ ID NO: 14) |
| HC-FR3 $^{66}$Arg Phe Thr Ile Ser Ala Asp Thr Ser Lys Asn Thr Ala Tyr Leu Gln Met Asn$^{82a}$ Ser$^{82b}$ Leu$^{82c}$ Arg$^{83}$ Ala Glu Asp Thr Ala Val Tyr Tyr Cys$^{92}$ (SEQ ID NO: 15) |
| HC-FR4 $^{103}$Trp Gly Gln Gly Thr Leu Val Thr Val Ser Ser$^{113}$ (SEQ ID NO: 16) |

In one embodiment, antibodies of the invention may comprise modified/variant_framework region sequences of huMAb4D5-8 light and heavy chains as provided below (SEQ ID NOS:9, 10, 11, 12 (light chain) and SEQ ID NOS: 13, 14, 15, 16 (heavy chain)). Numbers in superscript/bold indicate amino acid positions according to Kabat.

| Framework sequences of huMAb4D5-8 light chain modified at position 66 (underlined) |
| --- |
| LC-FR1 $^1$Asp Ile Gln Met Thr Gln Ser Pro Ser Ser Leu Ser Ala Ser Val Gly Asp Arg Val Thr Ile Thr Cys$^{23}$ (SEQ ID NO: 9) |
| LC-FR2 $^{35}$Trp Tyr Gln Gln Lys Pro Gly Lys Ala Pro Lys Leu Leu Ile Tyr$^{49}$ (SEQ ID NO: 10) |
| LC-FR3 $^{57}$Gly Val Pro Ser Arg Phe Ser Gly Ser <u>Gly</u> Ser Gly Thr Asp Phe Thr Leu Thr Ile Ser Ser Leu Gln Pro Glu Asp Phe Ala Thr Tyr Tyr Cys$^{88}$ (SEQ ID NO: 11) |
| LC-FR4 $^{98}$Phe Gly Gln Gly Thr Lys Val Glu Ile Lys$^{107}$ (SEQ ID NO: 12) |

| Framework sequences of huMAb4D5-8 heavy chain modified at positions 71, 73 and 78 (underlined) |
| --- |
| HC-FR1 $^1$Glu Val Gln Leu Val Glu Ser Gly Gly Gly Leu Val Gln Pro Gly Gly Ser Leu Arg Leu Ser Cys Ala Ala Ser$^{25}$ (SEQ ID NO: 13) |
| HC-FR2 $^{36}$Trp Val Arg Gln Ala Pro Gly Lys Gly Leu Glu Trp Val$^{48}$ (SEQ ID NO: 14) |
| HC-FR3 $^{66}$Arg Phe Thr Ile Ser <u>Arg</u> Asp <u>Asn</u> Ser Lys Asn Thr <u>Leu</u> Tyr Leu Gln Met Asn$^{82a}$ Ser$^{82b}$ Leu$^{82c}$ Arg$^{83}$ Ala Glu Asp Thr Ala Val Tyr Tyr Cys$^{92}$ (SEQ ID NO: 15) |
| HC-FR4 $^{103}$Trp Gly Gln Gly Thr Leu Val Thr Val Ser Ser$^{113}$ (SEQ ID NO: 16) |

In one embodiment, an antibody of the invention is affinity matured to obtain the target binding affinity desired. In one example, an affinity matured antibody of the invention comprises substitution at amino acid positions of the light chain as follows. In one embodiment, a variant HVR-L1 A1-A11 (Kabat positions 24-34) is RASQDVSTAVA (SEQ ID NO:1) having 1, 2, 3, 4, or 5 substitutions in any combination of the following positions: A6 (G), A7 (A), A8 (R or I), A9 (S or Y), and A10 (L). In one embodiment, a variant HVR-L2 B1-B7 (Kabat positions 50-56) is SASFLYS (SEQ ID NO:2) having 1, 2, 3, 4, or 5 substitutions in any combination of the following positions: B3 (T), B4 (L, N or T), B5 (E or A), B6 (A or S), and B7 (Y or a deletion). In one embodiment, a variant HVR-L3 C1-C9 (Kabat positions 89-97) is QQSYTTPPT (SEQ ID NO:3) having 1, 2, 3, 4, 5 or 6 substitutions in any combination of the following positions: C3 (P, T, F, or G), C4 (F, R, or N), C5 (A, S, D, F, H, N, V, or G), C6 (A, D, N, L, I, M, Y, or G), C7 (L, H, or T), and C8 (A, M, F, or S).

In one embodiment, an antibody of the affinity matured antibody of the invention comprises substitution at amino acid positions of the heavy chain as follows. In one embodiment, a variant HVR-H1 D1-D10 (Kabat positions 26-35) is GFTINGYYIH (SEQ ID NO:17) having 1, 2, 3, 4, or 5 substitutions in any combination of the following positions: D3 (S), D4 (L), D5 (Y, D, or K), D9 (F, L or N), and D10 (E or Q). In one embodiment, a variant HVR-H2 E1-E18 (Kabat positions 49-65) is GFIYPAGGDTDYADSVKG (SEQ ID NO:18) having 1, 2, 3, 4, or 5 substitutions in any combination of the following positions: E2 (R), E5 (S), E7 (L), E9 (H, K, A, or V), and E11 (A, E or I). In one embodiment, HVR-H3 F1-F18 (Kabat positions 93-102) is ARLIGNKFGWSSYG*MDY (SEQ ID NO:19), wherein "*" in the amino acid sequence indicates a deletion at position F15, Kabat position 100).

In one embodiment, the affinity matured antibody of the invention comprises one, two or three HVRs (L1, L2, and/or L3) depicted in FIG. 2A. In one embodiment, the affinity matured antibody of the invention comprises one, two, or three HVRs (H1, H2, and/or H3) depicted in FIG. 2B. In one embodiment, the affinity matured antibody of the invention comprises one, two, three, four, five, or all six HVRs selected from the HVRs depicted in FIGS. 2A and 2B.

In one embodiment, the affinity matured antibody of the invention comprises the light chain variable region sequence of any of the sequences depicted in FIG. 2A. In one embodiment, the affinity matured antibody of the invention comprises the heavy chain variable region sequence of any of the sequences depicted in FIG. 2B.

In one embodiment, the affinity matured antibody of the invention comprises a light chain variable region sequence (comprising framework sequences and HVR sequences) shown in FIG. 2A and the heavy chain variable region sequences (comprising framework sequences and HVR sequences) of the corresponding antibody shown in FIG. 2B.

In one aspect, the invention provides an antibody that competes with any of the above-mentioned antibodies for binding to Robo4. In one aspect, the invention provides an antibody that binds to the same epitope on Robo4 as any of the above-mentioned antibodies.

B. Hybridoma-Based Methods

Monoclonal antibodies of the invention can also be made using the hybridoma method first described by Kohler et al., *Nature*, 256:495 (1975), and further described, e.g., in Hongo et al., *Hybridoma*, 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981), and Ni, *Xiandai Mianyixue*, 26(4): 265-268 (2006) regarding human-human hybridomas. Additional methods include those described, for example, in U.S. Pat. No. 7,189,826 regarding production of monoclonal human natural IgM antibodies from hybridoma cell lines. Human hybridoma technology (Trioma technology) is described in Vollmers and Brandlein, *Histology and Histopathology*, 20(3):927-937 (2005) and Vollmers and Brandlein, *Methods and Findings in Experimental and Clinical Pharmacology*, 27(3): 185-91 (2005). Other hybridoma techniques, see, e.g., US 2006/258841; US 2006/183887 (fully human antibodies), US 2006/059575; US 2005/287149; US 2005/100546; US 2005/026229; and U.S. Pat. Nos. 7,078,492 and 7,153,507.

C. Vectors, Host Cells, and Recombinant Methods

Antibodies may also be produced using recombinant methods. For recombinant production of an anti-Robo4 antibody, nucleic acid encoding the antibody is isolated and inserted into a replicable vector for further cloning (amplification of the DNA) or for expression. DNA encoding the antibody may be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

1. Signal Sequence Component

An antibody of the invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process a native antibody signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, α factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

2. Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

3. Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up antibody-encoding nucleic acid, such as DHFR, glutamine synthetase (GS), thymidine kinase, metallothionein-I and -II, preferably primate metallothionein genes, adenosine deaminase, ornithine decarboxylase, etc.

For example, cells transformed with the DHFR gene are identified by culturing the transformants in a culture medium containing methotrexate (Mtx), a competitive antagonist of DHFR. Under these conditions, the DHFR gene is amplified along with any other co-transformed nucleic acid. A Chinese hamster ovary (CHO) cell line deficient in endogenous DHFR activity (e.g., ATCC CRL-9096) may be used.

Alternatively, cells transformed with the GS gene are identified by culturing the transformants in a culture medium containing L-methionine sulfoximine (Msx), an inhibitor of GS. Under these conditions, the GS gene is amplified along with any other co-transformed nucleic acid. The GS selection/amplification system may be used in combination with the DHFR selection/amplification system described above.

Alternatively, host cells (particularly wild-type hosts that contain endogenous DHFR) transformed or co-transformed with DNA sequences encoding an antibody of interest, wild-type DHFR gene, and another selectable marker such as aminoglycoside 3'-phosphotransferase (APH) can be selected by cell proliferation in medium containing a selection agent for the selectable marker such as an aminoglycosidic antibiotic, e.g., kanamycin, neomycin, or G418. See U.S. Pat. No. 4,965, 199.

A suitable selection gene for use in yeast is the trp1 gene present in the yeast plasmid YRp7 (Stinchcomb et al., *Nature*, 282:39 (1979)). The trp1 gene provides a selection marker for a mutant strain of yeast lacking the ability to grow in tryptophan, for example, ATCC No. 44076 or PEP4-1. Jones,

*Genetics*, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg, *Bio/Technology*, 8:135 (1990). Stable multi-copy expression vectors for secretion of mature recombinant human serum albumin by industrial strains of *Kluyveromyces* have also been disclosed. Fleer et al., *Bio/Technology*, 9:968-975 (1991).

4. Promoter Component

Expression and cloning vectors generally contain a promoter that is recognized by the host organism and is operably linked to nucleic acid encoding an antibody. Promoters suitable for use with prokaryotic hosts include the phoA promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding an antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), or from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

5. Enhancer Element Component

Transcription of a DNA encoding an antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the antibody-encoding sequence, but is preferably located at a site 5' from the promoter.

6. Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibody. One useful transcription termination component is the bovine growth hormone polyadenylation region. See WO94/11026 and the expression vector disclosed therein.

7. Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

Full length antibody, antibody fusion proteins, and antibody fragments can be produced in bacteria, in particular when glycosylation and Fc effector function are not needed, such as when the therapeutic antibody is conjugated to a cytotoxic agent (e.g., a toxin) that by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), U.S. Pat. No. 5,840,523 (Simmons et al.), which describes translation initiation region (TIR) and signal sequences for optimizing expression and secretion. See also Charlton, *Methods in Molecular Biology*, Vol. 248 (B.K.C. Lo, ed., Humana Press, Totowa, N.J., 2003), pp. 245-254, describing expression of antibody fragments in *E. coli*. After expression, the antibody may be isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*. For a review discussing the use of yeasts and filamentous fungi for the production of therapeutic proteins, see, e.g., Gerngross, *Nat. Biotech.* 22:1409-1414 (2004).

Certain fungi and yeast strains may be selected in which glycosylation pathways have been "humanized," resulting in the production of an antibody with a partially or fully human glycosylation pattern. See, e.g., Li et al., *Nat. Biotech.* 24:210-215 (2006) (describing humanization of the glycosylation pathway in *Pichia pastoris*); and Gerngross et al., supra.

Suitable host cells for the expression of glycosylated antibody are also derived from multicellular organisms (invertebrates and vertebrates). Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, duckweed (Lemnaceae), alfalfa (*M. truncatula*), and tobacco can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may be used as hosts, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR-CHO cells (Urlaub et al., *PNAS USA* 77:4216 (1980)); and myeloma cell lines such as NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J., 2003), pp. 255-268.

Host cells are transformed with the above-described expression or cloning vectors for antibody production and cultured in conventional nutrient media modified as appropriate for inducing promoters, selecting transformants, or amplifying the genes encoding the desired sequences.

8. Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

9. Purification of Antibodies

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10: 163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, hydrophobic interaction chromatography, gel electrophoresis, dialysis, and affinity chromatography, with affinity chromatography being among one of the typically preferred purification steps. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

In general, various methodologies for preparing antibodies for use in research, testing, and clinical are well-established in the art, consistent with the above-described methodologies and/or as deemed appropriate by one skilled in the art for a particular antibody of interest.

V. Immunoconjugates

The invention also provides immunoconjugates (interchangeably referred to as "antibody-drug conjugates," or "ADCs") comprising any of the anti-Robo4 antibodies of the invention conjugated to one or more cytotoxic agents, such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). Conjugates of an antibody and one or more small molecule toxins, such as a calicheamicin, maytansinoids, a trichothecene, and CC1065, and the derivatives of these toxins that have toxin activity, are also contemplated herein.

In certain embodiments, an immunoconjugate comprises an anti-Robo4 antibody and a chemotherapeutic agent or other toxin. Chemotherapeutic agents useful in the generation of immunoconjugates are described herein (e.g., above). Enzymatically active toxins and fragments thereof can also be used and are described herein.

In certain embodiments, an immunoconjugate comprises an anti-Robo4 antibody and one or more small molecule toxins, including, but not limited to, small molecule drugs such as a calicheamicin, maytansinoid, dolastatin, auristatin, trichothecene, and CC1065, and the derivatives of these drugs that have cytotoxic activity. Examples of such immunoconjugates are discussed in further detail below.

A. Exemplary Immunoconjugates

An immunoconjugate (or "antibody-drug conjugate" ("ADC")) of the invention may be of Formula I, below, wherein an anti-Robo4 antibody is conjugated (i.e., covalently attached) to one or more drug moieties (D) through an optional linker (L).

$$\text{Ab-(L-D)}_p \quad \quad \text{Formula I}$$

Accordingly, the anti-Robo4 antibody may be conjugated to the drug either directly or via a linker. In Formula I, p is the average number of drug moieties per antibody, which can range, e.g., from about 1 to about 20 drug moieties per antibody, and in certain embodiments, from 1 to about 8 drug moieties per antibody.

B. Exemplary Linkers

Exemplary linkers and drug moieties are disclosed herein and in U.S. Patent Publication Nos. 20050238649 A1; 20050276812 A1; and 20070092940 A1. A linker may comprise one or more linker components. Exemplary linker components include 6-maleimidocaproyl ("MC"), maleimidopropanoyl ("MP"), valine-citrulline ("val-cit" or "vc"), alanine-phenylalanine ("ala-phe"), p-aminobenzyloxycarbonyl (a "PAB"), N-Succinimidyl 4-(2-pyridylthio) pentanoate ("SPP"), N-succinimidyl 4-(N-maleimidomethyl)cyclohexane-1 carboxylate ("SMCC"), and N-Succinimidyl (4-iodoacetyl)aminobenzoate ("SIAB"), N-succinimidyl 3-(2-pyridyldithio) propionate (SPDP) (see, e.g., Carlsson et al., *Biochem. J.*, 173, 723-737 (1978)), N-succinimidyl 4-(2-pyridyldithio) butanoate (SPDB) (see, e.g., U.S. Pat. No. 4,563, 304), N-succinimidyl 4-methyl-4-[2-(5-nitro-pyridyl)-dithio]pentanoate (SMNP), and the polyethylene glycol derivative, methoxy-polyethylene oxide (mPEO). Various linker components are known in the art, some of which are described below.

A linker may be a "cleavable linker," facilitating release of a drug in the cell. For example, an acid-labile linker (e.g., hydrazone), protease-sensitive (e.g., peptidase-sensitive) linker, photolabile linker, dimethyl linker or disulfide-containing linker (Chari et al., Cancer Research 52:127-131 (1992); U.S. Pat. No. 5,208,020) may be used.

In some embodiments, a linker component may comprise a "stretcher unit" that links an antibody to another linker component or to a drug moiety. Exemplary stretcher units are shown below (wherein the wavy line indicates sites of covalent attachment to an antibody, another linker component or a drug moiety):

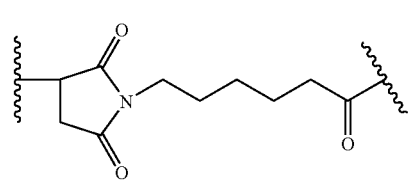

MC

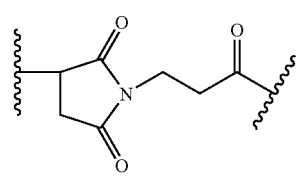

MP

-continued

MPEG

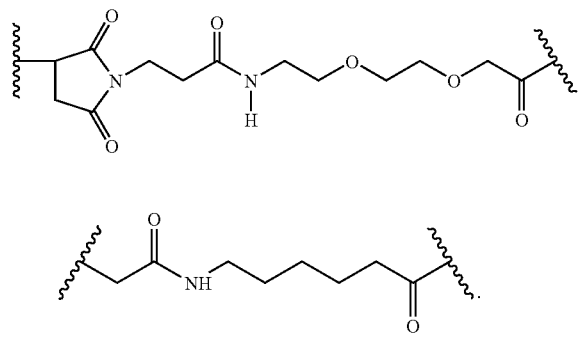

In some embodiments, a linker component may comprise an amino acid unit. In one such embodiment, the amino acid unit allows for cleavage of the linker by a protease, thereby facilitating release of the drug from the immunoconjugate upon exposure to intracellular proteases, such as lysosomal enzymes. See, e.g., Doronina et al. (2003). Nat. Biotechnol. 21:778-784. Exemplary amino acid units include, but are not limited to, a dipeptide, a tripeptide, a tetrapeptide, and a pentapeptide. Exemplary dipeptides include: valine-citrulline (vc or val-cit), alanine-phenylalanine (af or ala-phe); phenylalanine-lysine (fk or phe-lys); or N-methyl-valine-citrulline (Me-val-cit). Exemplary tripeptides include: glycine-valine-citrulline (gly-val-cit) and glycine-glycine-glycine (gly-gly-gly). An amino acid unit may comprise amino acid residues that occur naturally, as well as minor amino acids and non-naturally occurring amino acid analogs, such as citrulline. Amino acid units can be designed and optimized in their selectivity for enzymatic cleavage by a particular enzyme, for example, a tumor-associated protease, cathepsin B, C and D, or a plasmin protease.

In some embodiments, a linker component may comprise a "spacer" unit that links the antibody to a drug moiety, either directly or by way of a stretcher unit and/or an amino acid unit. A spacer unit may be "self-immolative" or a "non-self-immolative." A "non-self-immolative" spacer unit is one in which part or all of the spacer unit remains bound to the drug moiety upon enzymatic (e.g., proteolytic) cleavage of the ADC. Examples of non-self-immolative spacer units include, but are not limited to, a glycine spacer unit and a glycine-glycine spacer unit. Other combinations of peptidic spacers susceptible to sequence-specific enzymatic cleavage are also contemplated. For example, enzymatic cleavage of an ADC containing a glycine-glycine spacer unit by a tumor-cell associated protease would result in release of a glycine-glycine-drug moiety from the remainder of the ADC. In one such embodiment, the glycine-glycine-drug moiety is then subjected to a separate hydrolysis step in the tumor cell, thus cleaving the glycine-glycine spacer unit from the drug moiety.

A "self-immolative" spacer unit allows for release of the drug moiety without a separate hydrolysis step. In certain embodiments, a spacer unit of a linker comprises a p-aminobenzyl unit. In one such embodiment, a p-aminobenzyl alcohol is attached to an amino acid unit via an amide bond, and a carbamate, methylcarbamate, or carbonate is made between the benzyl alcohol and a cytotoxic agent. See, e.g., Hamann et al. (2005) Expert Opin. Ther. Patents (2005) 15:1087-1103. In one embodiment, the spacer unit is p-aminobenzyloxycarbonyl (PAB). In certain embodiments, the phenylene portion of a p-amino benzyl unit is substituted with Qm, wherein Q is —$C_1$-$C_8$ alkyl, —O—($C_1$-$C_8$ alkyl), -halogen, -nitro or -cyano; and m is an integer ranging from 0-4. Examples of self-immolative spacer units further include, but are not limited to, aromatic compounds that are electronically similar to p-aminobenzyl alcohol (see, e.g., US 2005/0256030 A1), such as 2-aminoimidazol-5-methanol derivatives (Hay et al. (1999) Bioorg. Med. Chem. Lett. 9:2237) and ortho- or para-aminobenzylacetals. Spacers can be used that undergo cyclization upon amide bond hydrolysis, such as substituted and unsubstituted 4-aminobutyric acid amides (Rodrigues et al., Chemistry Biology, 1995, 2, 223); appropriately substituted bicyclo[2.2.1] and bicyclo[2.2.2] ring systems (Storm, et al., J. Amer. Chem. Soc., 1972, 94, 5815); and 2-aminophenylpropionic acid amides (Amsberry, et al., J. Org. Chem., 1990, 55, 5867). Elimination of amine-containing drugs that are substituted at the a-position of glycine (Kingsbury, et al., J. Med. Chem., 1984, 27, 1447) are also examples of self-immolative spacers useful in ADCs.

In one embodiment, a spacer unit is a branched bis(hydroxymethyl)styrene (BHMS) unit as depicted below, which can be used to incorporate and release multiple drugs.

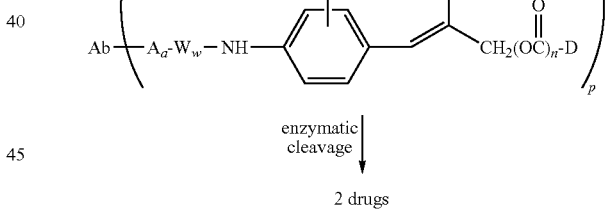

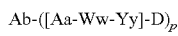

wherein Q is —$C_1$-$C_8$ alkyl, —O—($C_1$-$C_8$ alkyl), -halogen, -nitro or -cyano; m is an integer ranging from 0-4; n is 0 or 1; and p ranges raging from 1 to about 20.

A linker may comprise any one or more of the above linker components. In certain embodiments, a linker is as shown in brackets in the following ADC Formula II Ab-([Aa-Ww-Yy]-D)$_p$                                    Formula II wherein A is a stretcher unit, and a is an integer from 0 to 1; W is an amino acid unit, and w is an integer from 0 to 12; Y is a spacer unit, and y is 0, 1, or 2; and Ab, D, and p are defined as above for Formula I. Exemplary embodiments of such linkers are described in US 20050238649 A1, which is expressly incorporated herein by reference.

Exemplary linker components and combinations thereof are shown below in the context of ADCs of Formula II:

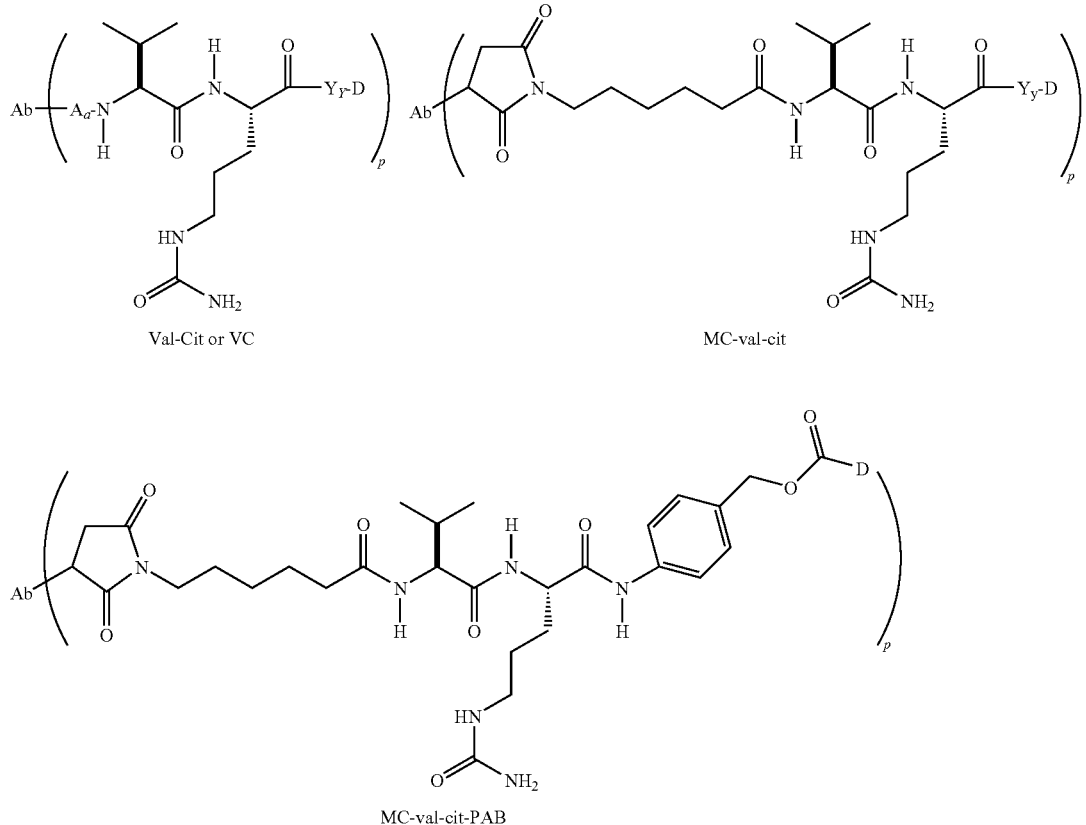

Linkers components, including stretcher, spacer, and amino acid units, may be synthesized by methods known in the art, such as those described in US 2005-0238649 A1.

C. Exemplary Drug Moieties

1. Maytansine and Maytansinoids

In some embodiments, an immunoconjugate comprises an antibody of the invention conjugated to one or more maytansinoid molecules. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansine compounds inhibit cell proliferation by inhibiting the formation of microtubules during mitosis through inhibition of polymerization of the microtubulin protein, tubulin (Remillard et al. (1975) Science 189:1002-1005; U.S. Pat. No. 5,208,020). Maytansine and maytansinoids are highly cytotoxic but their clinical use in cancer therapy has been greatly limited by their severe systemic side-effects primarily attributed to their poor selectivity for tumors. Clinical trials with maytansine had been discontinued due to serious adverse effects on the central nervous system and gastrointestinal system (Issel et al., (1978) Can. Treatment. Rev. 5:199-207).

Maytansinoid drug moieties are attractive drug moieties in antibody-drug conjugates because they are: (i) relatively accessible to prepare by fermentation or chemical modification or derivatization of fermentation products, (ii) amenable to derivatization with functional groups suitable for conjugation through non-disulfide linkers to antibodies, (iii) stable in plasma, and (iv) effective against a variety of tumor cell lines.

Maytansine compounds suitable for use as maytansinoid drug moieties are well known in the art and can be isolated from natural sources according to known methods or produced using genetic engineering techniques (see Yu et al. (2002) PNAS 99:7968-7973). Maytansinol and maytansinol analogues may also be prepared synthetically according to known methods. Exemplary embodiments of maytansinoid drug moieties include: DM1; DM3; and DM4, as disclosed herein below.

As with other drug moieties, all stereoisomers of the maytansinoid drug moiety are contemplated for the compounds of the invention, i.e. any combination of R and S configurations at the chiral carbons of D. In one embodiment, the maytansinoid drug moiety (D) will have the following stereochemistry:

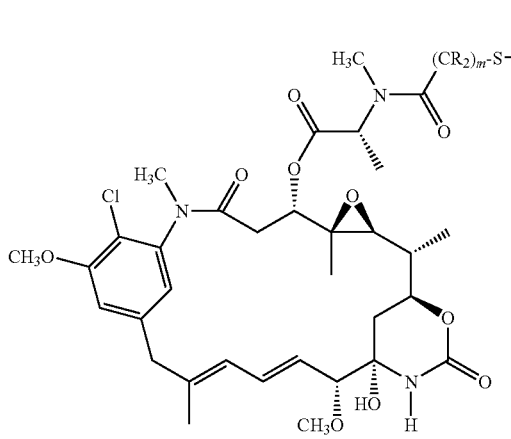

DM1

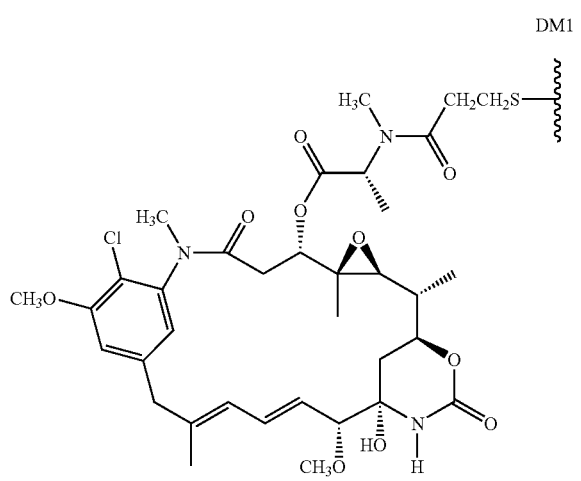

DM3

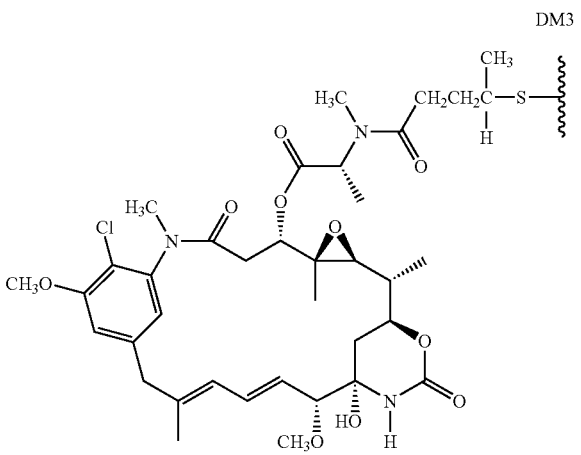

Exemplary embodiments of maytansinoid drug moieties include: DM1, $(CR_2)_m=CH_2CH_2$; DM3, $(CR_2)_m=CH_2CH_2CH(CH_3)$; and DM4, $(CR_2)_m=CH_2CH_2C(CH_3)_2$, having the structures:

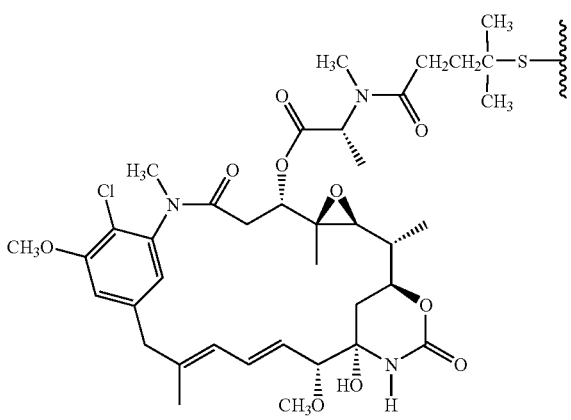

DM4

In an attempt to improve the therapeutic index of targeted antibodies, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *PNAS USA* 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., *Cancer Research* 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses $3\times10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates are prepared by chemically linking an antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al., *Cancer Research* 52:127-131

(1992). The linking groups include disulfide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate, iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al, *Biochem. J.* 173:723-737 [1978]) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

2. Auristatins, Dolastatins

In some embodiments, an immunoconjugate comprises an antibody of the invention conjugated to dolastatin or a dolastatin peptidic analog or derivative, e.g., an auristatin (U.S. Pat. Nos. 5,635,483; 5,780,588). Dolastatins and auristatins have been shown to interfere with microtubule dynamics, GTP hydrolysis, and nuclear and cellular division (Woyke et al. (2001) Antimicrob. Agents and Chemother. 45(12):3580-3584) and have anticancer (U.S. Pat. No. 5,663,149) and antifungal activity (Pettit et al. (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in Senter et al, Proceedings of the American Association for Cancer Research, Volume 45, Abstract Number 623, presented Mar. 28, 2004, the disclosure of which is expressly incorporated by reference in its entirety.

A peptidic drug moiety may be selected from Formulas $D_E$ and $D_F$ below:

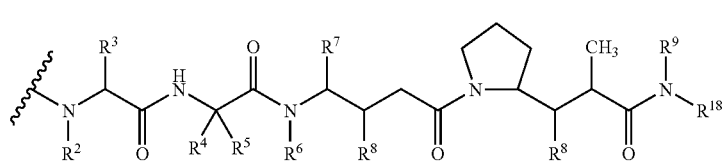

$D_E$

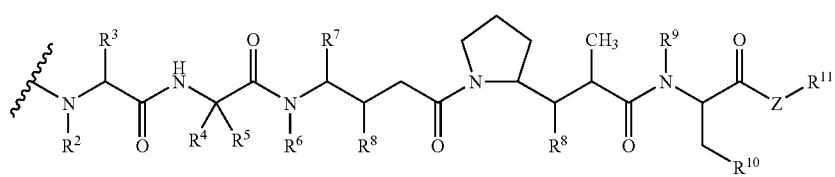

$D_F$ wherein the wavy line of $D_E$ and $D_F$ indicates the covalent attachment site to an antibody or antibody-linker component, and independently at each location:

$R^2$ is selected from H and $C_1$-$C_8$ alkyl;

$R^3$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or $R^4$ and $R^5$ jointly form a carbocyclic ring and have the formula —$(CR^aR^b)_n$— wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl;

$R^{10}$ is selected from aryl or $C_3$-$C_8$ heterocycle;

Z is O, S, NH, or NR, wherein $R^{12}$ is $C_1$-$C_8$ alkyl;

$R^{11}$ is selected from H, $C_1$-$C_{20}$ alkyl, aryl, $C_3$-$C_8$ heterocycle, —$(R^{13}O)_m$—$R^{14}$, or —$(R^{13}O)_m$—$CH(R^{15})_2$;

m is an integer ranging from 1-1000;

$R^{13}$ is $C_2$-$C_8$ alkyl;

$R^{14}$ is H or $C_1$-$C_8$ alkyl;

each occurrence of $R^{15}$ is independently H, COOH, —$(CH_2)_n$—$N(R^{16})_2$, —$(CH_2)_n$—$SO_3H$, or —$(CH_2)_n$—$SO_3$—$C_1$-$C_8$ alkyl;

each occurrence of $R^{16}$ is independently H, $C_1$-$C_8$ alkyl, or —$(CH_2)_n$—COOH;

$R^{18}$ is selected from —$C(R^8)_2$—$C(R^8)_2$-aryl, —$C(R^8)_2$—$C(R^8)_2$—($C_3$-$C_8$ heterocycle), and —$C(R^8)_2$—$C(R^8)_2$—($C_3$-$C_8$ carbocycle); and n is an integer ranging from 0 to 6.

In one embodiment, $R^3$, $R^4$ and $R^7$ are independently isopropyl or sec-butyl and $R^5$ is —H or methyl. In an exemplary embodiment, $R^3$ and $R^4$ are each isopropyl, $R^5$ is —H, and $R^7$ is sec-butyl.

In yet another embodiment, $R^2$ and $R^6$ are each methyl, and $R^9$ is —H.

In still another embodiment, each occurrence of $R^8$ is —OCH$_3$.

In an exemplary embodiment, $R^3$ and $R^4$ are each isopropyl, $R^2$ and $R^6$ are each methyl, $R^5$ is —H, $R^7$ is sec-butyl, each occurrence of $R^8$ is —OCH$_3$, and $R^9$ is —H.

In one embodiment, Z is —O— or —NH—.

In one embodiment, $R^{10}$ is aryl.

In an exemplary embodiment, $R^{10}$ is -phenyl.

In an exemplary embodiment, when Z is —O—, $R^{11}$ is —H, methyl or t-butyl.

In one embodiment, when Z is —NH, $R^{11}$ is —CH($R^{15}$)$_2$, wherein $R^{15}$ is —(CH$_2$)$_n$—N($R^{16}$)$_2$, and $R^{16}$ is —C$_1$-C$_8$ alkyl or —(CH$_2$)$_n$—COOH.

In another embodiment, when Z is —NH, $R^{11}$ is —CH($R^{15}$)$_2$, wherein $R^{15}$ is —(CH$_2$)$_n$—SO$_3$H.

An exemplary auristatin embodiment of formula $D_E$ is MMAE, wherein the wavy line indicates the covalent attachment to a linker (L) of an antibody-drug conjugate:

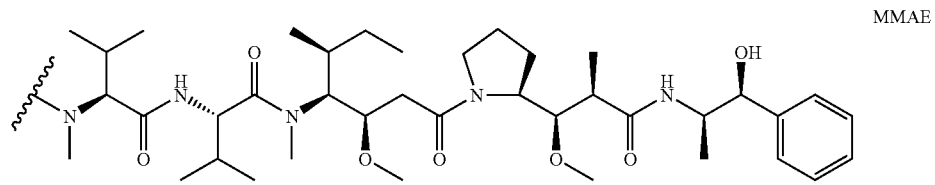

MMAE

An exemplary auristatin embodiment of formula $D_F$ is MMAF, wherein the wavy line indicates the covalent attachment to a linker (L) of an antibody-drug conjugate (see US 2005/0238649 and Doronina et al. (2006) *Bioconjugate Chem.* 17:114-124):

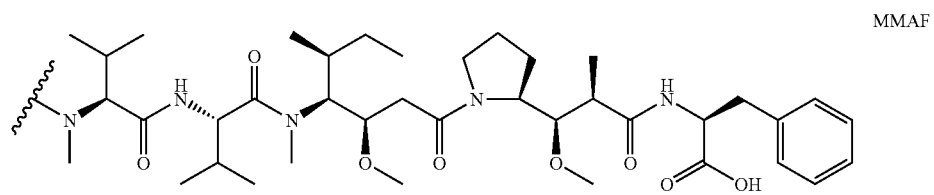

MMAF

Other drug moieties include the following MMAF derivatives, wherein the wavy line indicates the covalent attachment to a linker (L) of an antibody-drug conjugate:

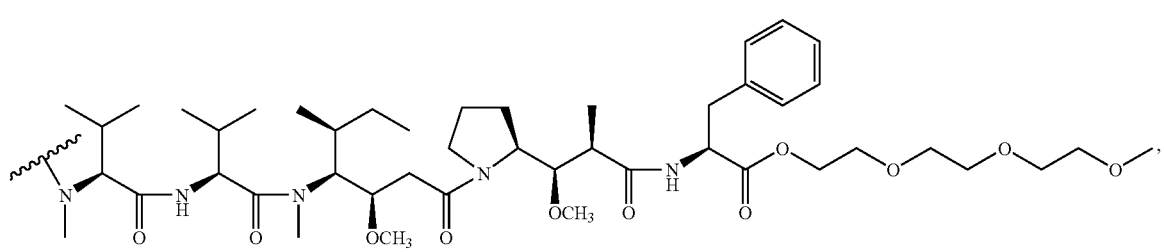

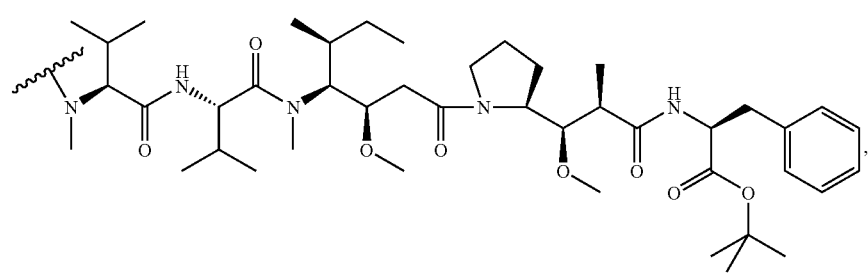

-continued
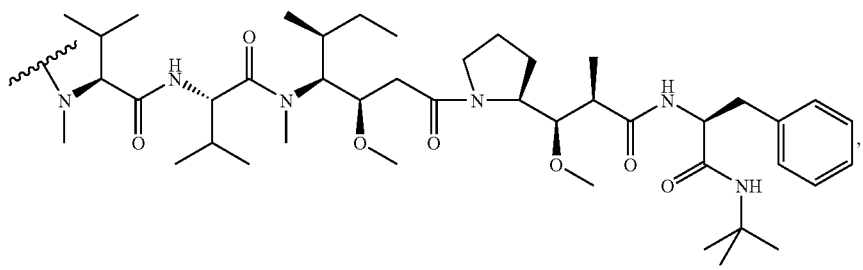
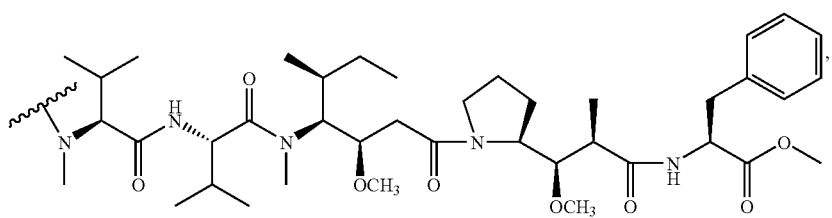
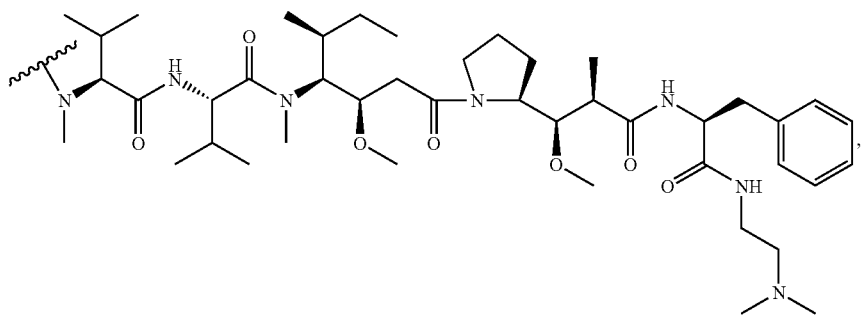
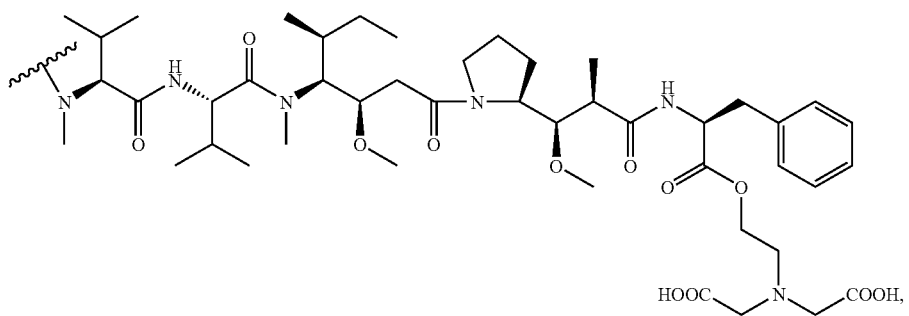
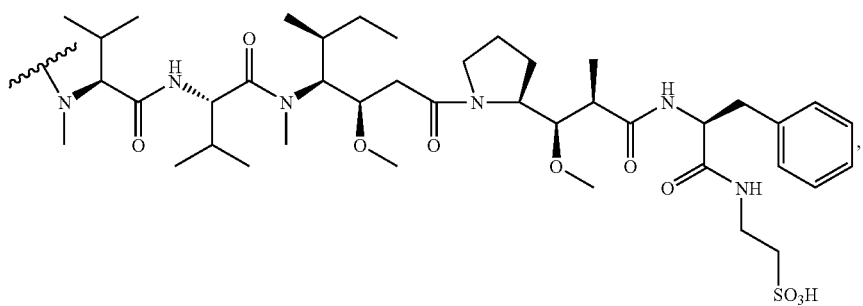

-continued

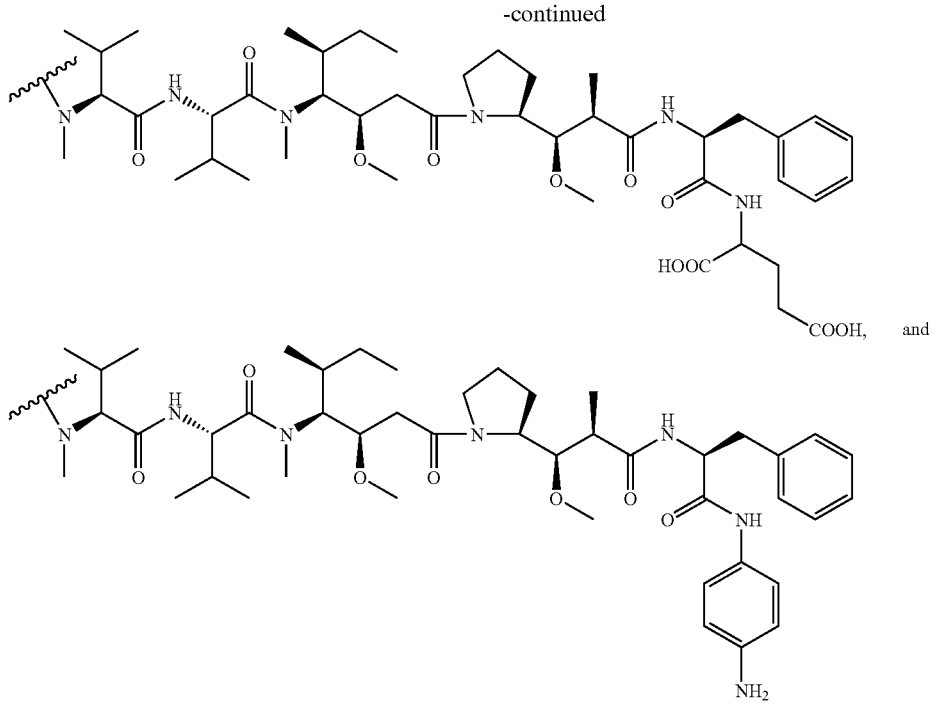

In one aspect, hydrophilic groups including but not limited to, triethylene glycol esters (TEG), as shown above, can be attached to the drug moiety at $R^{11}$. Without being bound by any particular theory, the hydrophilic groups assist in the internalization and non-agglomeration of the drug moiety.

Exemplary embodiments of ADCs of Formula I comprising an auristatin/dolastatin or derivative thereof are described in US 2005-0238649 A1 and Doronina et al. (2006) Bioconjugate Chem. 17:114-124, which is expressly incorporated herein by reference. Exemplary embodiments of ADCs of Formula I comprising MMAE or MMAF and various linker components have the following structures and abbreviations (wherein "Ab" is an antibody; p is 1 to about 8, "Val-Cit" is a valine-citrulline dipeptide; and "S" is a sulfur atom:

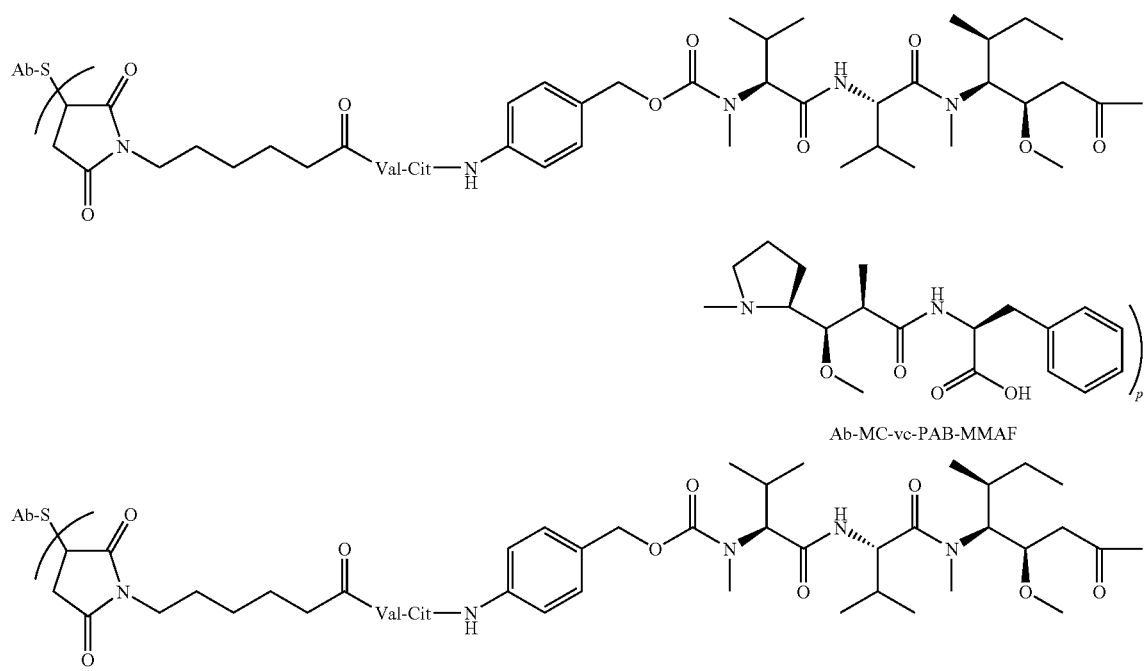

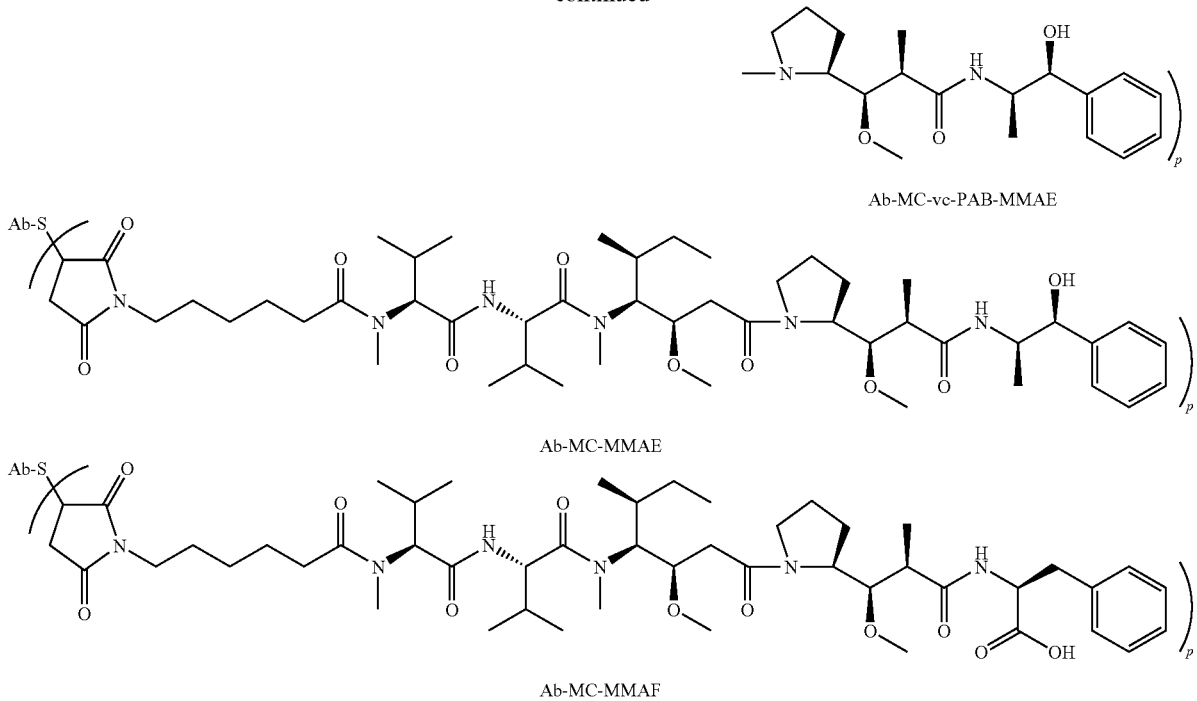

Exemplary embodiments of ADCs of Formula I comprising MMAF and various linker components further include Ab-MC-PAB-MMAF and Ab-PAB-MMAF. Interestingly, immunoconjugates comprising MMAF attached to an antibody by a linker that is not proteolytically cleavable have been shown to possess activity comparable to immunoconjugates comprising MMAF attached to an antibody by a proteolytically cleavable linker. See, Doronina et al. (2006) Bioconjugate Chem. 17:114-124. In such instances, drug release is believed to be effected by antibody degradation in the cell. Id.

Typically, peptide-based drug moieties can be prepared by forming a peptide bond between two or more amino acids and/or peptide fragments. Such peptide bonds can be prepared, for example, according to the liquid phase synthesis method (see E. Schroder and K. Lübke, "The Peptides", volume 1, pp 76-136, 1965, Academic Press) that is well known in the field of peptide chemistry. Auristatin/dolastatin drug moieties may be prepared according to the methods of: US 2005-0238649 A1; U.S. Pat. No. 5,635,483; U.S. Pat. No. 5,780,588; Pettit et al. (1989) J. Am. Chem. Soc. 111:5463-5465; Pettit et al. (1998) Anti-Cancer Drug Design 13:243-277; Pettit, G. R., et al. Synthesis, 1996, 719-725; Pettit et al. (1996) J. Chem. Soc. Perkin Trans. 15:859-863; and Doronina (2003) Nat. Biotechnol. 21(7):778-784.

In particular, auristatin/dolastatin drug moieties of formula $D_F$, such as MMAF and derivatives thereof, may be prepared using methods described in US 2005-0238649 A1 and Doronina et al. (2006) Bioconjugate Chem. 17:114-124. Auristatin/dolastatin drug moieties of formula $D_E$, such as MMAE and derivatives thereof, may be prepared using methods described in Doronina et al. (2003) Nat. Biotech. 21:778-784. Drug-linker moieties MC-MMAF, MC-MMAE, MC-vc-PAB-MMAF, and MC-vc-PAB-MMAE may be conveniently synthesized by routine methods, e.g., as described in Doronina et al. (2003) Nat. Biotech. 21:778-784, and U.S. Patent Publication No. 20050238649 A1, and then conjugated to an antibody of interest.

3. Calicheamicin

Another immunoconjugate of interest comprises an antibody conjugated to one or more calicheamicin molecules. The calicheamicin family of antibiotics is capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ (Hinman et al., Cancer Research 53:3336-3342 (1993), Lode et al., Cancer Research 58:2925-2928 (1998) and the aforementioned U.S. patents to American Cyanamid). Another antitumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

4. Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $Tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al. (1978) *Biochem. Biophys. Res. Commun.* 80: 49-57 can be used to incorporate iodine-123. "Monoclonal Antibodies in Immunoscintigraphy" (Chatal, CRC Press 1989) describes other methods in detail.

Anti-Robo4 antibodies of the invention may be conjugated to nanoparticulate agents which may in turn be conjugated to cytotoxic moieties. Suitable nanoparticular agents include, but are not limited to, microbubbles (see Ellegala et al., *Circulation* 108:336-341 (2003))), also referred to as acoustically active liposheres (AALs) (see Tartis et al., *Ultrasound Med. Biol.* 32(11):1771-80 (2006)), superparamagnetic agents, liposomes, perfluorocarbon nanoparticle emulsions (WO2005014051), and dendrimers (see Caruthers et al., *Methods in Molecular Medicine,* 124:387-400 (2006) and references cited therein, all of which references are hereby incorporated by reference in their entirety).

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate, iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., *Cancer Research* 52:127-131 (1992); U.S. Pat. No. 5,208, 020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

5. Drug Loading

Drug loading is represented by p and is the average number of drug moieties per antibody in a molecule of Formula I, Ia, Ia' or II. Drug loading may range from 1 to 20 drug moieties (D) per antibody. ADCs of Formula I include collections of antibodies conjugated with a range of drug moieties, from 1 to 20. The average number of drug moieties per antibody in preparations of ADC from conjugation reactions may be characterized by conventional means such as mass spectroscopy, ELISA assay, and HPLC. The quantitative distribution of ADC in terms of p may also be determined. In some instances, separation, purification, and characterization of homogeneous ADC where p is a certain value from ADC with other drug loadings may be achieved by means such as reverse phase HPLC or electrophoresis.

For some antibody-drug conjugates, p may be limited by the number of attachment sites on the antibody. For example, where the attachment is a cysteine thiol, as in the exemplary embodiments above, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the drug loading for an ADC of the invention ranges from 1 to about 8; from about 2 to about 6; from about 3 to about 5; from about 3 to about 4; from about 3.1 to about 3.9; from about 3.2 to about 3.8; from about 3.2 to about 3.7; from about 3.2 to about 3.6; from about 3.3 to about 3.8; or from about 3.3 to about 3.7. Indeed, it has been shown that for certain ADCs, the optimal ratio of drug moieties per antibody may be less than 8, and may be about 2 to about 5. See US 2005-0238649 A1 (herein incorporated by reference in its entirety).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, e.g., by: (i) limiting the molar excess of drug-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number and/or position of linker-drug attachements (such as thioMab or thioFab prepared as disclosed herein and in WO2006/034488 (herein incorporated by reference in its entirety)). In an embodiment of the invention, an amino acid residue of the antibody of the invention is substituted with a cysteine residue. In an embodiment, the amino acid at position 118 of the heavy chain Fc region of the antibody is a cysteine or is substituted with a cysteine residue (where 118 refers to the amino acid position in the Fc region of the antibody numbered according to EU numbering, see Kabat, E. A. et al., Sequences of Proteins of Immunological Interest (U.S. Dept. of Health and Hum. Serv., Bethesda (1991)). In an embodiment, the cysteine residue at position 118 of the heavy chain Fc region (EU numbering) is covalently attached to a drug moiety or a detectable label, such as the drug moieties or detectable labels disclosed herein. In FIG. 6A, the alanine of the heavy chain Fc region shown in bold text and underlined is the position at which a cysteine was substituted to generate the thioMAb.

It is to be understood that where more than one nucleophilic group reacts with a drug-linker intermediate or linker reagent followed by drug moiety reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography (see, e.g., Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous ADC with a single loading value may be isolated from the conjugation mixture by electrophoresis or chromatography.

D. Metabolites of the Antibody-Drug Conjugates

Also falling within the scope of this invention are the in vivo metabolic products of the ADC compounds described herein, to the extent such products are novel and unobvious over the prior art. Such products may result for example from the oxidation, reduction, hydrolysis, amidation, esterification, enzymatic cleavage, and the like, of the administered compound. Accordingly, the invention includes novel and unobvious compounds produced by a process comprising contacting a compound of this invention with a mammal for a period of time sufficient to yield a metabolic product thereof.

Metabolite products typically are identified by preparing a radiolabeled (e.g. $^{14}C$ or $^{3}H$) ADC, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS, LC/MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the ADC compounds of the invention.

VI. Methods of Preparing Immunconjugates

In the antibody drug conjugates (ADC) of the invention, an antibody (Ab) is conjugated to one or more drug moieties (D), e.g. about 1 to about 20 drug moieties per antibody, through a linker (L). An ADC of Formula I, Ia, Ia', or II may be prepared by several routes employing organic chemistry reactions, conditions, and reagents known to those skilled in the art, including: (1) reaction of a nucleophilic group of an antibody with a bivalent linker reagent to form Ab-L via a covalent bond, followed by reaction with a drug moiety D; and (2) reaction of a nucleophilic group of a drug moiety with a bivalent linker reagent, to form D-L, via a covalent bond, followed by reaction with a nucleophilic group of an antibody. Exemplary methods for preparing an ADC of Formula I via the latter route are described in U.S. Patent Publication No. 20050238649 A1, which is expressly incorporated herein by reference.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol) or tricarbonylethylphosphine (TCEP), such that the antibody is fully or partially reduced. Each cysteine bridge will thus form, theoretically, two reactive thiol nucleophiles. Additional nucleophilic groups can be introduced into antibodies through modification of lysine residues, e.g., by reacting lysine residues with 2-iminothiolane (Traut's reagent), resulting in conversion of an amine into a thiol. Reactive thiol groups may be introduced into an antibody by introducing one, two, three, four, or more cysteine residues (e.g., by preparing variant antibodies comprising one or more non-native cysteine amino acid residues).

Antibody-drug conjugates of the invention may also be produced by reaction between an electrophilic group on an antibody, such as an aldehyde or ketone carbonyl group, with a nucleophilic group on a linker reagent or drug. Useful nucleophilic groups on a linker reagent include, but are not limited to, hydrazide, oxime, amino, hydrazine, thiosemicarbazone, hydrazine carboxylate, and arylhydrazide. In one embodiment, an antibody is modified to introduce electrophilic moieties that are capable of reacting with nucleophilic substituents on the linker reagent or drug. In another embodiment, the sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the antibody that can react with appropriate groups on the drug (Hermanson, Bioconjugate Techniques). In another embodiment, antibodies containing N-terminal serine or threonine residues can react with sodium metaperiodate, resulting in production of an aldehyde in place of the first amino acid (Geoghegan & Stroh, (1992) Bioconjugate Chem. 3:138-146; U.S. Pat. No. 5,362,852). Such an aldehyde can be reacted with a drug moiety or linker nucleophile.

Nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

The compounds of the invention expressly contemplate, but are not limited to, ADC prepared with the following cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A; see pages 467-498, 2003-2004 Applications Handbook and Catalog.

Immunoconjugates comprising an antibody and a cytotoxic agent may also be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Alternatively, a fusion protein comprising an antibody and a cytotoxic agent may be made, e.g., by recombinant techniques or peptide synthesis. A recombinant DNA molecule may comprise regions encoding the antibody and cytotoxic portions of the conjugate either adjacent to one another or separated by a region encoding a linker peptide which does not destroy the desired properties of the conjugate.

The compounds of the invention include cysteine engineered antibodies where one or more amino acids of a parent antibody are replaced with a free cysteine amino acid. A cysteine engineered antibody comprises one or more free cysteine amino acids having a thiol reactivity value in the range of 0.6 to 1.0. A free cysteine amino acid is a cysteine residue which has been engineered into the parent antibody and is not part of a disulfide bridge.

In one aspect, the cysteine engineered antibody is prepared by a process comprising:

(a) replacing one or more amino acid residues of a parent antibody by cysteine; and (b) determining the thiol reactivity of the cysteine engineered antibody by reacting the cysteine engineered antibody with a thiol-reactive reagent.

The cysteine engineered antibody may be more reactive than the parent antibody with the thiol-reactive reagent.

The free cysteine amino acid residues may be located in the heavy or light chains, or in the constant or variable domains. Antibody fragments, e.g. Fab, may also be engineered with one or more cysteine amino acids replacing amino acids of the antibody fragment, to form cysteine engineered antibody fragments.

Another aspect of the invention provides a method of preparing (making) a cysteine engineered antibody, comprising:

(a) introducing one or more cysteine amino acids into a parent antibody in order to generate the cysteine engineered antibody; and (b) determining the thiol reactivity of the cysteine engineered antibody with a thiol-reactive reagent;

wherein the cysteine engineered antibody is more reactive than the parent antibody with the thiol-reactive reagent.

Step (a) of the method of preparing a cysteine engineered antibody may comprise:

(i) mutagenizing a nucleic acid sequence encoding the cysteine engineered antibody;

(ii) expressing the cysteine engineered antibody; and (iii) isolating and purifying the cysteine engineered antibody.

Step (b) of the method of preparing a cysteine engineered antibody may comprise expressing the cysteine engineered antibody on a viral particle selected from a phage or a phagemid particle.

Step (b) of the method of preparing a cysteine engineered antibody may also comprise:

(i) reacting the cysteine engineered antibody with a thiol-reactive affinity reagent to generate an affinity labeled, cysteine engineered antibody; and (ii) measuring the binding of the affinity labeled, cysteine engineered antibody to a capture media.

Another aspect of the invention is a method of screening cysteine engineered antibodies with highly reactive, unpaired cysteine amino acids for thiol reactivity comprising:

(a) introducing one or more cysteine amino acids into a parent antibody in order to generate a cysteine engineered antibody;

(b) reacting the cysteine engineered antibody with a thiol-reactive affinity reagent to generate an affinity labeled, cysteine engineered antibody; and (c) measuring the binding of the affinity labeled, cysteine engineered antibody to a capture media; and (d) determining the thiol reactivity of the cysteine engineered antibody with the thiol-reactive reagent.

Step (a) of the method of screening cysteine engineered antibodies may comprise:

(i) mutagenizing a nucleic acid sequence encoding the cysteine engineered antibody;

(ii) expressing the cysteine engineered antibody; and (iii) isolating and purifying the cysteine engineered antibody.

Step (b) of the method of screening cysteine engineered antibodies may comprise expressing the cysteine engineered antibody on a viral particle selected from a phage or a phagemid particle.

Step (b) of the method of screening cysteine engineered antibodies may also comprise:

(i) reacting the cysteine engineered antibody with a thiol-reactive affinity reagent to generate an affinity labeled, cysteine engineered antibody; and (ii) measuring the binding of the affinity labeled, cysteine engineered antibody to a capture media.

Cysteine engineered antibodies may be useful in the treatment of cancer and include antibodies specific for cell surface and transmembrane receptors, and tumor-associated antigens (TAA). Such antibodies may be used as naked antibodies (unconjugated to a drug or label moiety) or as Formula I, Ia, Ia' or II antibody-drug conjugates (ADC).

Embodiments of the methods for preparing and screening a cysteine engineered antibody include where the parent antibody is an antibody fragment, such as hu4D5Fabv8. The parent antibody may also be a fusion protein comprising an albumin-binding peptide sequence (ABP).

Cysteine engineered antibodies of the invention may be site-specifically and efficiently coupled with a thiol-reactive reagent. The thiol-reactive reagent may be a multifunctional linker reagent, a capture label reagent, a fluorophore reagent, or a drug-linker intermediate.

The cysteine engineered antibody may be labeled with a detectable label, immobilized on a solid phase support and/or conjugated with a drug moiety.

Another aspect of the invention is an antibody-drug conjugate compound comprising a cysteine engineered antibody (Ab), and a drug moiety (D) wherein the cysteine engineered antibody is attached through one or more free cysteine amino acids by a linker moiety (L) to D; the compound having Formula Ia:

$$Ab(LD)_p \qquad \text{Ia}$$

where p is 1, 2, 3, or 4; and wherein the cysteine engineered antibody is prepared by a process comprising replacing one or more amino acid residues of a parent antibody by one or more free cysteine amino acids. Drug moieties include, but are not limited to a maytansinoid, an auristatin, a dolastatin, a trichothecene, CC1065, a calicheamicin and other enediyne antibiotics, a taxane, an anthracycline, and stereoisomers, isosteres, analogs or derivatives thereof. Exemplary drug moieties include DM1, MMAE, and MMAF. Exemplary antibody-drug conjugates are set forth in U.S. Patent Publication No. 20070092940 A1.

The antibody-drug conjugate of Formula Ia may further comprise an albumin-binding peptide (ABP) sequence; the composition having Formula Ia':

$$ABPAb(LD)_p \qquad \text{Ia'}$$

Antibodies of the invention comprising fusion proteins with ABP sequences are taught by: (i) Dennis et al. (2002) J Biol. Chem. 277:35035-35043 at Tables III and IV, page 35038; (ii) US 20040001827 at [0076] SEQ ID NOS: 9-22; and (iii) WO 01/45746 at pages 12-13, SEQ ID NOS: z1-z14, and all of which are incorporated herein by reference.

VII. Cysteine Engineered Antibodies (ThioMAbs and ThioFabs)

The compounds of the invention include cysteine engineered antibodies where one or more amino acids of a wild-type or parent antibody are replaced with a cysteine amino acid. Any form of antibody may be so engineered, i.e. mutated. For example, a parent Fab antibody fragment may be engineered to form a cysteine engineered Fab, referred to herein as "ThioFab." Similarly, a parent monoclonal antibody may be engineered to form a "ThioMab." It should be noted that a single site mutation yields a single engineered cysteine residue in a ThioFab, while a single site mutation yields two engineered cysteine residues in a ThioMab, due to the dimeric nature of the IgG antibody. Mutants with replaced ("engineered") cysteine (Cys) residues are evaluated for the reactivity of the newly introduced, engineered cysteine thiol groups. The thiol reactivity value is a relative, numerical term in the range of 0 to 1.0 and can be measured for any cysteine engineered antibody. Thiol reactivity values of cysteine engineered antibodies of the invention are in the ranges of 0.6 to 1.0; 0.7 to 1.0; or 0.8 to 1.0.

The design, selection, and preparation methods of the invention enable cysteine engineered antibodies which are reactive with electrophilic functionality. These methods further enable antibody conjugate compounds such as antibody-drug conjugate (ADC) compounds with drug molecules at designated, designed, selective sites. Reactive cysteine residues on an antibody surface allow specifically conjugating a drug moiety through a thiol reactive group such as maleimide or haloacetyl. The nucleophilic reactivity of the thiol functionality of a Cys residue to a maleimide group is about 1000 times higher compared to any other amino acid functionality in a protein, such as amino group of lysine residues or the N-terminal amino group. Thiol specific functionality in iodoacetyl and maleimide reagents may react with amine groups, but higher pH (>9.0) and longer reaction times are required (Garman, 1997, Non-Radioactive Labelling: A Practical Approach, Academic Press, London).

Cysteine engineered antibodies of the invention preferably retain the antigen binding capability of their wild type, parent antibody counterparts. Thus, cysteine engineered antibodies are capable of binding, preferably specifically, to antigens. Such antigens include, for example, tumor-associated antigens (TAA), cell surface receptor proteins and other cell surface molecules, transmembrane proteins, signalling proteins, cell survival regulatory factors, cell proliferation regulatory factors, molecules associated with (for e.g., known or suspected to contribute functionally to) tissue development or differentiation, lymphokines, cytokines, molecules involved in cell cycle regulation, molecules involved in vasculogenesis and molecules associated with (for e.g., known or suspected to contribute functionally to) angiogenesis. The tumor-associated antigen may be a cluster differentiation factor (i.e., a CD protein). An antigen to which a cysteine engineered antibody is capable of binding may be a member of a subset of one of the above-mentioned categories, wherein the other subset(s) of said category comprise other molecules/antigens that have a distinct characteristic (with respect to the antigen of interest).

The parent antibody may also be a human or humanized anti-Robo4 antibody or Fab having any one, two, three, four, five or six of the HVR sequences disclosed herein. Cysteine engineered antibodies of the invention may be site-specifically and efficiently coupled with a thiol-reactive reagent. The thiol-reactive reagent may be a multifunctional linker reagent, a capture, i.e. affinity, label reagent (e.g. a biotin-linker reagent), a detection label (e.g. a fluorophore reagent), a solid phase immobilization reagent (e.g. SEPHAROSE™, polystyrene, or glass), or a drug-linker intermediate. One example of a thiol-reactive reagent is N-ethyl maleimide (NEM). In an exemplary embodiment, reaction of a ThioFab with a biotin-linker reagent provides a biotinylated ThioFab by which the presence and reactivity of the engineered cysteine residue may be detected and measured. Reaction of a ThioFab with a multifunctional linker reagent provides a ThioFab with a functionalized linker which may be further reacted with a drug moiety reagent or other label. Reaction of a ThioFab with a drug-linker intermediate provides a ThioFab drug conjugate.

Such an approach may be applied to the conjugation of other thiol-reactive agents in which the reactive group is, for example, a maleimide, an iodoacetamide, a pyridyl disulfide, or other thiol-reactive conjugation partner (Haugland, 2003, Molecular Probes Handbook of Fluorescent Probes and Research Chemicals, Molecular Probes, Inc.; Brinkley, 1992, Bioconjugate Chem. 3:2; Garman, 1997, Non-Radioactive Labelling: A Practical Approach, Academic Press, London; Means (1990) Bioconjugate Chem. 1:2; Hermanson, G. in Bioconjugate Techniques (1996) Academic Press, San Diego, pp. 40-55, 643-671). The partner may be a cytotoxic agent (e.g. a toxin such as doxorubicin or pertussis toxin), a fluorophore such as a fluorescent dye like fluorescein or rhodamine, a chelating agent for an imaging or radiotherapeutic metal, a peptidyl or non-peptidyl label or detection tag, or a clearance-modifying agent such as various isomers of polyethylene glycol, a peptide that binds to a third component, or another carbohydrate or lipophilic agent.

The sites identified on the exemplary antibody fragment are primarily in the constant domain of an antibody which is well conserved across all species of antibodies. These sites should be broadly applicable to other antibodies, without further need of structural design or knowledge of specific antibody structures, and without interference in the antigen binding properties inherent to the variable domains of the antibody.

The PHESELECTOR assay (Phage ELISA for Selection of Reactive Thiols, disclosed in WO2006/034488 (herein incorporated by reference in its entirety)) allows for detection of reactive cysteine groups in antibodies in an ELISA phage format. The process of coating the protein (e.g. antibody) of interest on well surfaces, followed incubation with phage particles and then HRP labeled secondary antibody with absorbance detection is detailed in WO2006/034488. Mutant proteins displayed on phage may be screened in a rapid, robust, and high-throughput manner. Libraries of cysteine engineered antibodies can be produced and subjected to binding selection using the same approach to identify appropriately reactive sites of free Cys incorporation from random protein-phage libraries of antibodies or other proteins. This technique includes reacting cysteine mutant proteins displayed on phage with an affinity reagent or reporter group which is also thiol-reactive.

Cysteine engineered antibodies which may be useful in the treatment of cancer include, but are not limited to, antibodies against cell surface receptors and tumor-associated antigens (TAA). Such antibodies may be used as naked antibodies (unconjugated to a drug or label moiety) or as Formula I, Ia, Ia', or II antibody-drug conjugates (ADC). Tumor-associated antigens are known in the art, and can prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s) or expressed on the surface of angiogenic cells (such as vascular endothelial cells) as compared to non-endothelial cells unassociated with cancer. Often, such tumor-associated polypeptides are more abundantly expressed on the surface of the cancer cells or angiogenic cells as compared to on the surface of the non-cancerous cells or non-angiogenic cells. The identification of such tumor-associated cell surface antigen polypeptides has given rise to the ability to specifically target cancer cells or angiogenic cells for destruction via antibody-based therapies.

In yet another embodiment, an antibody may be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

VIII. Methods of Treatment Using Anti-Robo4 Antibodies

It is contemplated that the anti-Robo4 antibodies (including, e.g., naked anti-Robo4 antibodies and ADC) of the present invention may be used to treat various diseases or disorders, e.g. characterized by the overexpression of a tumor or angiogenesis associated antigen such as Robo4. Exemplary conditions of hyperproliferative disorders include pathological conditions associated with abnormal or unwanted endothelial cell proliferation, such as abnormal or unwanted vascular cell proliferation in disorders including, but not limited to, cancer, angiogenesis and disorders associated with (e.g., augmented by endothelial cell proliferation within the tissue experiencing the disorder) solid tumors and metastasis, atherosclerosis, retrolental fibroplasia, hemangiomas, chronic inflammation, intraocular neovascular diseases such as proliferative retinopathies, e.g., diabetic retinopathy, age-related macular degeneration (AMD), neovascular glaucoma, immune rejection of transplanted corneal tissue and other tissues, rheumatoid arthritis, and psoriasis.

The anti-Robo4 antibodies and ADC compounds which are identified in animal models and cell-based assays can be further tested in tumor-bearing higher primates and human clinical trials. Human clinical trials can be designed to test the efficacy of the anti-Robo4 monoclonal antibody or immunoconjugate of the invention in patients experiencing a cell proliferative disorder including without limitation pathological conditions associated with abnormal or unwanted endothelial cell proliferation, such as abnormal or unwanted vascular cell proliferation in disorders including, but not limited to, cancer, angiogenesis and disorders associated with (e.g., augmented by endothelial cell proliferation within the tissue experiencing the disorder) solid tumors and metastasis, atherosclerosis, retrolental fibroplasia, hemangiomas, chronic inflammation, intraocular neovascular diseases such as proliferative retinopathies, e.g., diabetic retinopathy, age-related macular degeneration (AMD), neovascular glaucoma, immune rejection of transplanted corneal tissue and other tissues, rheumatoid arthritis, and psoriasis. The clinical trial may be designed to evaluate the efficacy of an anti-Robo4 antibody in combinations with known therapeutic regimens, such as radiation and/or chemotherapy involving known chemotherapeutic and/or cytotoxic agents.

The cancer may comprise Robo4-expressing cells, such that an anti-Robo4 antibody of the present invention is able to bind to the Robo4-expressing endothelial cells within the cancer tissue. To determine Robo4 expression in the cancer, various diagnostic/prognostic assays are available. In one embodiment, Robo4 overexpression may be analyzed by IHC. Paraffin-embedded tissue sections from a tumor biopsy may be subjected to the IHC assay and accorded a Robo4 protein staining intensity criteria with respect to the degree of staining and in what proportion of tumor cells examined. In one embodiment, Robo4 overexpression may be analyzed by detection in vivo or in vitro of anti-Robo4 antibody labeled with a detectable marker contacted with Robo4-expressing cells in vivo. Detectable markers include without limitation radioisotopes, fluorescent compounds, metallic and/or magnetic nanoparticles, microbubbles, chelating ligands, and other detectable markers as disclosed herein.

For the prevention or treatment of disease, the appropriate dosage of an anti-Robo4 antibody will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 µg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 µg/kg to 100 mg/kg or more, depending on the factors mentioned above. An exemplary dosage of ADC to be administered to a patient is in the range of about 0.1 to about 10 mg/kg of patient weight.

For repeated administrations over several days or longer, depending on the condition, the treatment is sustained until a desired suppression of disease symptoms occurs. An exemplary dosing regimen comprises administering an initial loading dose of about 4 mg/kg, followed by a weekly maintenance dose of about 2 mg/kg of an anti-Robo4 antibody. Other dosage regimens may be useful. In yet another embodiment, the dosage range is 275-375 mg/m2 The progress of this therapy is easily monitored by conventional techniques and assays.

A. Administration of Anti-Robo4 Antibodies

The anti-Robo4 antibodies (and adjunct therapeutic agent) of the invention may be administered by any route appropriate to the condition to be treated, including parenteral, subcutaneous, intraperitoneal, intrapulmonary, and intranasal, and, if desired for local treatment, intralesional administration. The anti-Robo4 antibodies will typically be administered parenterally, i.e. infusion, subcutaneous, intramuscular, intravenous, intradermal, intrathecal, epidural, intraarterial, and intraperitoneal. In addition, the antibody is suitably administered by pulse infusion, particularly with declining doses of the antibody. Dosing can be by any suitable route, e.g. by injections, such as intravenous or subcutaneous injections, depending in part on whether the administration is brief or chronic.

For treating cancers or any disease in which angiogenisis occurs, the anti-Robo4 antibody or antibody-drug conjugate is administered via intravenous infusion. The dosage administered via infusion is in the range of about 1 µg/m$^2$ to about 10,000 µg/m$^2$ per dose, generally one dose per week for a total of one, two, three or four doses. Alternatively, the dosage range is about 1 µg/m$^2$ to about 1000 µg/m$^2$, about 1 µg/m$^2$ to about 800 µg/m$^2$, about 1 µg/m$^2$ to about 600 µg/m$^2$, about 1 µg/m$^2$ to about 400 µg/m$^2$, about 10 µg/m$^2$ to about 500 µg/m$^2$, about 10 µg/m$^2$ to about 300 µg/m$^2$, about 10 µg/m$^2$ to about 200 µg/m$^2$, or about 1 µg/m$^2$ to about 200 µg/m$^2$. The dose may be administered once per day, once per week, multiple times per week, but less than once per day, multiple times per month but less than once per day, multiple times per month but less than once per week, once per month or intermittently to relieve or alleviate symptoms of the disease. Administration may continue at any of the disclosed intervals until the symptoms of the disease or disorder being treated are reduced, alleviated, or eliminated (e.g., as indicated by shrinkage of a tumor, reduction of elimination of symptoms of lymphoma, leukemia, inhibition of metastatic spread without shrinkage of the primary tumor (i.e., progression-free survival), inhibition of ocular neovascularization). Administration may continue after remission or relief of symptoms is achieved where such remission or relief is prolonged by such continued administration.

The invention also provides a method of treating a cancer, and/or a metastasis of a cancer and/or an ocular disorder characterized by proliferation of vascular endothelial cells, comprising administering to a patient suffering from such a disorder, a therapeutically effective amount of an anti-Robo4 antibody of any one of the preceding embodiments, which antibody is not conjugated to a cytotoxic molecule or a detectable molecule. The antibody will typically be administered in a dosage range of about 1 µg/m$^2$ to about 1000 mg/m$^2$. Alternatively, the dosage range is about 1 µg/m$^2$ to about 800 µg/m$^2$, about 1 µg/m$^2$ to about 600 µg/m$^2$, about 1 µg/m$^2$ to about 400 µg/m$^2$, about 10 µg/m$^2$ to about 500 µg/m$^2$, about 10 µg/m$^2$ to about 300 µg/m$^2$, about 10 µg/m$^2$ to about 200 µg/m$^2$, or about 1 µg/m$^2$ to about 200 µg/m$^2$.

The invention also provides a method of treating a cancer, and/or a metastasis of a cancer and/or an ocular disorder characterized by proliferation of vascular endothelial cells, comprising administering to a patient suffering from such a disorder, a therapeutically effective amount of an anti-Robo4 antibody of any one of the preceding embodiments, which antibody is conjugated to a cytotoxic molecule or a detectable molecule. The antibody will typically be administered in a dosage range of about 1 µg/m$^2$ to about 1000 mg/m$^2$. Alternatively, the dosage range is about 1 µg/m$^2$ to about 800 µg/m$^2$, about 1 µg/m$^2$ to about 600 µg/m$^2$, about 1 µg/m$^2$ to about 400 µg/m$^2$, about 10 µg/m$^2$ to about 500 µg/m$^2$, about 10 µg/m$^2$ to about 300 µg/m$^2$, about 10 µg/m$^2$ to about 200 µg/m$^2$, or about 1 µg/m$^2$ to about 200 µg/m$^2$.

B. Pharmaceutical Formulations

In one aspect, the invention further provides pharmaceutical formulations comprising at least one anti-Robo4 antibody of the invention and/or at least one immunoconjugate thereof and/or at least one anti-Robo4 antibody-drug conjugate of the invention. In some embodiments, a pharmaceutical formulation comprises 1) an anti-Robo4 antibody and/or an anti-Robo4 antibody-drug conjugate and/or an immunoconjugate thereof, and 2) a pharmaceutically acceptable carrier. In some embodiments, a pharmaceutical formulation comprises 1) an anti-Robo4 antibody and/or an immunoconjugate thereof, and optionally, 2) at least one additional therapeutic agent.

Pharmaceutical formulations comprising an antibody or immunoconjugate of the invention or the antibody-drug conjugate of the invention are prepared for storage by mixing the antibody or antibody-drug conjugate having the desired degree of purity with optional physiologically acceptable carriers, excipients or stabilizers (Remington's Pharmaceutical Sciences 16th edition, Osol, A. Ed. (1980)) in the form of aqueous solutions or lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride); phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Pharmaceutical formulations to be used for in vivo administration are generally sterile. This is readily accomplished by filtration through sterile filtration membranes.

Active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody or immunoconjugate of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies or immunoconjugates remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The formulation herein may also contain more than one active compound as necessary for the particular indication being treated, preferably those with complementary activities that do not adversely affect each other. Such molecules are suitably present in combination in amounts that are effective for the purpose intended.

C. Combination Therapy

An anti-Robo4 antibodies of the invention may be combined in a pharmaceutical combination formulation, or dosing regimen as combination therapy, with at least one additional compound having anti-cancer properties. The at least one additional compound of the pharmaceutical combination formulation or dosing regimen preferably has complementary activities to the anti-Robo4 antibody composition such that they do not adversely affect each other.

The at least one additional compound may be a chemotherapeutic agent, a cytotoxic agent, a cytokine, a growth inhibitory agent, an anti-hormonal agent, and combinations thereof. Such molecules are suitably present in combination in amounts that are effective for the purpose intended. A pharmaceutical composition containing an anti-Robo4 antibody of the invention may also comprise a therapeutically effective amount of a chemotherapeutic agent such as a tubulin-forming inhibitor, a topoisomerase inhibitor, or a DNA binder.

In one aspect, the first compound is an anti-Robo4 ADC of the invention and the at least one additional compound is a therapeutic antibody other than an anti-Robo4 (naked antibody or an ADC). In one embodiment, the at least one additional compound is an antibody that binds a cancer cell surface marker. In one embodiment the at least one additional compound is an anti-HER2 antibody, trastuzumab (e.g., Herceptin®, Genentech, Inc., South San Francisco, Calif.). In one embodiment the at least one additional compound is an anti-HER2 antibody, pertuzumab (Omnitarg™, Genentech, Inc., South San Francisco, Calif., see U.S. Pat. No. 6,949,245). In one embodiment, the at least one additional compound is an anti-VEGF antibody (e.g., AVASTIN®, Genentech, Inc.). In an embodiment, the at least one additional compound is an antibody (either a naked antibody or an ADC), and the additional antibody is a second, third, fourth, fifth, sixth antibody or more, such that a combination of such second, third, fourth, fifth, sixth, or more antibodies (either naked or as an ADC) is efficacious in treating a cell proliferative disease in a tissue expressing Robo4.

Other therapeutic regimens may be combined with the administration of an anticancer agent identified in accordance with this invention, including without limitation radiation therapy and/or bone marrow and peripheral blood transplants, and/or a cytotoxic agent, a chemotherapeutic agent, or a growth inhibitory agent. In one of such embodiments, a chemotherapeutic agent is an agent or a combination of agents such as, for example, cyclophosphamide, hydroxydaunorubicin, adriamycin, doxorubincin, vincristine (ONCOVIN™), prednisolone, CHOP, CVP, or COP, or immunotherapeutics such as anti-PSCA, anti-HER2 (e.g., HERCEPTIN®, OMNITARG™) or anti-VEGF (e.g., AVASTIN®). The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

In one embodiment, treatment with an anti-Robo4 antibody involves the combined administration of an anticancer agent identified herein, and one or more chemotherapeutic agents or growth inhibitory agents, including coadministration of cocktails of different chemotherapeutic agents. Chemotherapeutic agents include taxanes (such as paclitaxel and docetaxel) and/or anthracycline antibiotics. Preparation and dosing schedules for such chemotherapeutic agents may be used according to manufacturer's instructions or as determined empirically by the skilled practitioner. Preparation and dosing schedules for such chemotherapy are also described in "Chemotherapy Service", (1992) Ed., M. C. Perry, Williams & Wilkins, Baltimore, Md.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

For the prevention or treatment of disease, the appropriate dosage of an antibody of the invention (when used alone or in combination with other agents such as chemotherapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody is an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

IX. Labeled Antibodies and Uses Thereof

The invention also provides labeled anti-Robo4 antibodies. Labeled antibodies may be useful in diagnostic assays, e.g., in vitro, ex vivo, or in vivo assays for detecting expression of Robo4 in specific cells or tissues (e.g., to image angiogenesis, neovascularization, and/or tumor vasculature). In some embodiments, the labeled antibodies are used in in vivo imaging assays. The anti-Robo4 antibodies of the invention, may be conjugated with any label moiety which can be covalently attached to the antibody. In some embodiments, the anti-Robo4 antibodies of the invention (including, e.g., the cysteine engineered anti-Robo4 antibodies) are covalently attached to the antibody through a reactive group on the antibody, such as a reactive lysine or cysteine residue. Covalent attachment through a reactive cysteine thiol group is disclosed in Singh et al., *Anal. Biochem.* 304:147-15 (2002); Harlow E. and Lane, D. (1999) Using Antibodies: A Laboratory Manual, Cold Springs Harbor Laboratory Press, Cold Spring Harbor, N.Y.; Lundblad R. L. (1991) Chemical Reagents for Protein Modification, 2nd ed. CRC Press, Boca Raton, Fla.

The attached label may function to: (i) provide a detectable signal; (ii) interact with a second label to modify the detectable signal provided by the first or second label, e.g. to give FRET (fluorescence resonance energy transfer); (iii) stabilize interactions or increase affinity of binding, with antigen or ligand; (iv) affect mobility, e.g. electrophoretic mobility or cell-permeability, by charge, hydrophobicity, shape, or other physical parameters, or (v) provide a capture moiety, to modulate ligand affinity, antibody/antigen binding, or ionic complexation.

For diagnostic applications, the antibody will typically be labeled with a detectable moiety. Numerous labels are available which can be generally grouped into the following categories:

(a) In some embodiments, the anti-Robo4 antibodies are labeled with radioisotopes (radionuclides), such as $^3$H, $^{11}$C, $^{14}$C, $^{18}$F, $^{19}$F, $^{32}$P, $^{35}$S, $^{64}$Cu, $^{68}$Ga, $^{86}$Y, $^{99}$Tc, $^{111}$In, $^{123}$I, $^{124}$I, $^{125}$I, $^{131}$I, $^{133}$Xe, $^{177}$Lu, $^{211}$At, or $^{213}$Bi. Radioisotope labeled anti-Robo4 antibodies are useful in receptor targeted imaging of cells expressing Robo4, (e.g., for use in the diagnostic uses of the invention such as in vivo imaging of tumor endothelial cells, tumor vasculature, angiogenesis, and neovascularization).

(b) In some embodiments, the anti-Robo4 antibodies are labeled with ligand reagents that bind, chelate or otherwise complex a radioisotope metal where the reagent is reactive with the engineered cysteine thiol of the antibody, using the techniques described in *Current Protocols in Immunology*, Volumes 1 and 2, Coligen et al, Ed. Wiley-Interscience, New York, N.Y., Pubs. (1991). Chelating ligands which may complex a metal ion include DOTA, DOTP, DOTMA, DTPA and TETA (Macrocyclics, Dallas, Tex.). Chelating linker reagents such as DOTA-maleimide (4-maleimidobutyramidobenzyl-DOTA) can be prepared by the reaction of aminobenzyl-DOTA with 4-maleimidobutyric acid (Fluka) activated with isopropylchloroformate (Aldrich), following the procedure of Axworthy et al. (2000) *PNAS USA* 97(4):1802-1807). DOTA-maleimide reagents react with the free cysteine amino acids of the cysteine engineered antibodies and provide a metal complexing ligand on the antibody (Lewis et al., *Bioconj. Chem.* 9:72-86 (1998)). Chelating linker labelling reagents such as DOTA-NHS (1,4,7,10-tetraazacyclododecane-1,4,7,10-tetraacetic acid mono (N-hydroxysuccinimide ester) are commercially available (Macrocyclics, Dallas, Tex.). Radionuclides can be targeted via complexation with the antibody-drug conjugates of the invention (Wu et al. *Nature Biotech.* 23(9): 1137-1146 (2005)). Receptor target imaging with radionuclide labeled antibodies can provide a marker of increased target expression by detection and quantitation of progressive accumulation of antibodies in tumor tissue (Albert et al. *Bioorg. Med. Chem. Lett.* 8:1207-1210 (1998)). The conjugated radio-metals may remain intracellular following lysosomal degradation.

Metal-chelate complexes suitable as antibody labels for imaging experiments are disclosed: U.S. Pat. No. 5,342,606; U.S. Pat. No. 5,428,155; U.S. Pat. No. 5,316,757; U.S. Pat. No. 5,480,990; U.S. Pat. No. 5,462,725; U.S. Pat. No. 5,428,139; U.S. Pat. No. 5,385,893; U.S. Pat. No. 5,739,294; U.S. Pat. No. 5,750,660; U.S. Pat. No. 5,834,456; Hnatowich et al. (1983) *J. Immunol. Methods* 65:147-157; Meares et al., *Anal. Biochem.* 142:68-78 (1984); Mirzadeh et al., *Bioconjugate Chem.* 1:59-65 (1990); Meares et al., *J. Cancer*, Suppl. 10:21-26 (1990); Izard et al., *Bioconjugate Chem.* 3:346-350 (1992); Nikula et al., *Nucl. Med. Biol.* 22:387-90 (1995); Camera et al., *Nucl. Med. Biol.* 20:955-62 (1993); Kukis et al., *J. Nucl. Med.* 39:2105-2110 (1998); Verel et al., *J. Nucl. Med.* 44:1663-1670 (2003); Camera et al., *J. Nucl. Med.* 21:640-646 (1994); Ruegg et al., *Cancer Res.* 50:4221-4226 (1990); Verel et al., *J. Nucl. Med.* 44:1663-1670 (2003); Lee et al., *Cancer Res.* 61:4474-4482 (2001); Mitchell, et al., *J. Nucl. Med.* 44:1105-1112 (2003); Kobayashi et al., *Bioconjugate Chem.* 10:103-111 (1999); Miederer et al., *J. Nucl. Med.* 45:129-137 (2004); DeNardo et al., *Clinical Cancer Research* 4:2483-90 (1998); Blend et al., *Cancer Biotherapy & Radiopharmaceuticals* 18:355-363 (2003); Nikula et al., *J. Nucl. Med.* 40:166-76 (1999); Kobayashi et al., *J. Nucl. Med.* 39:829-36 (1998); Mardirossian et al., *Nucl. Med. Biol.* 20:65-74 (1993); Roselli et al., *Cancer Biotherapy & Radiopharmaceuticals*, 14:209-20 (1999).

(c) In some embodiments, the anti-Robo4 antibodies are labeled with fluorescent labels such as rare earth chelates (europium chelates), fluorescein types including FITC, 5-carboxyfluorescein, 6-carboxy fluorescein; rhodamine types including TAMRA; dansyl; Lissamine; cyanines; phycoerythrins; Texas Red; and analogs thereof. The fluorescent labels can be conjugated to antibodies using the techniques disclosed in *Current Protocols in Immunology*, supra, for example. Fluorescent dyes and fluorescent label reagents include those which are commercially available from Invitrogen/Molecular Probes (Eugene, Oreg.) and Pierce Biotechnology, Inc. (Rockford, Ill.).

(d) In some embodiments, the anti-Robo4 antibodies are labeled with various enzyme-substrate labels are available or disclosed (U.S. Pat. No. 4,275,149). The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), -galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al. (1981) "Methods for the Preparation of Enzyme-Antibody Conjugates for use in Enzyme Immunoassay", in *Methods in Enzym.* (ed J. Langone & H. Van Vunakis), Academic Press, New York, 73:147-166.

Examples of enzyme-substrate combinations include, for example:

(i) Horseradish peroxidase (HRP) with hydrogen peroxidase as a substrate, wherein the hydrogen peroxidase oxidizes a dye precursor (e.g., orthophenylene diamine (OPD) or 3,3', 5,5'-tetramethylbenzidine hydrochloride (TMB));

(ii) alkaline phosphatase (AP) with para-nitrophenyl phosphate as chromogenic substrate; and (iii) -D-galactosidase (-D-Gal) with a chromogenic substrate (e.g., p-nitrophenyl-D-galactosidase) or fluorogenic substrate 4-methylumbelliferyl-D-galactosidase.

Numerous other enzyme-substrate combinations are available to those skilled in the art. For a general review, see U.S. Pat. No. 4,275,149 and U.S. Pat. No. 4,318,980.

A label may be indirectly conjugated with an anti-Robo4 antibody (including, e.g., a cysteine engineered anti-Robo4 antibody). For example, the anti-Robo4 antibody can be conjugated with biotin and any of the three broad categories of labels mentioned above can be conjugated with avidin or streptavidin, or vice versa. Biotin binds selectively to streptavidin and thus, the label can be conjugated with the anti-Robo4 antibody in this indirect manner. Alternatively, to achieve indirect conjugation of the label with the anti-Robo4 antibody, the anti-Robo4 antibody is conjugated with a small hapten (e.g., digoxin) and one of the different types of labels mentioned above is conjugated with an anti-hapten polypeptide variant (e.g., anti-digoxin antibody). Thus, indirect conjugation of the label with the anti-Robo4 antibody can be achieved (Hermanson, G. (1996) in *Bioconjugate Techniques* Academic Press, San Diego).

The anti-Robo4 antibody of the present invention may be employed in any known assay method, such as ELISA, competitive binding assays, direct and indirect sandwich assays, and immunoprecipitation assays (Zola, (1987) *Monoclonal Antibodies: A Manual of Techniques*, pp. 147-158, CRC Press, Inc.).

The labeled anti-Robo4 antibodies of the invention can detect cell-surface receptors and are useful for localizing, visualizing, and quantitating endothelial cells (e.g., tumor endothelial cells), sites of angiogenesis, sites of neovascularization, and/or tumor vasculature. Another use for detectably labeled antibodies is a method of bead-based immunocapture comprising conjugating a bead with a fluorescent labeled antibody and detecting a fluorescence signal upon binding of a ligand. Similar binding detection methodologies utilize the surface plasmon resonance (SPR) effect to measure and detect antibody-antigen interactions. The detectably labeled anti-Robo4 antibody of the present invention may be employed in any known assay method, such as ELISA, competitive binding assays, direct and indirect sandwich assays, and immunoprecipitation assays (Zola, (1987) Monoclonal Antibodies: A Manual of Techniques, pp. 147-158, CRC Press, Inc.).

Detection labels such as fluorescent dyes and chemiluminescent dyes (Briggs et al, *J. Chem. Soc.*, Perkin-Trans. 1:1051-1058 (1997)) provide a detectable signal and are generally applicable for labelling antibodies, preferably with the following properties: (i) the labeled antibody should produce a very high signal with low background so that small quantities of antibodies can be sensitively detected in both cell-free and cell-based assays; and (ii) the labeled antibody should be photostable so that the fluorescent signal may be observed, monitored and recorded without significant photo bleaching. For applications involving cell surface binding of labeled antibody to membranes or cell surfaces, especially live cells, the labels preferably (iii) have good water-solubility to achieve effective conjugate concentration and detection sensitivity and (iv) are non-toxic to living cells so as not to disrupt the normal metabolic processes of the cells or cause premature cell death.

Direct quantification of cellular fluorescence intensity and enumeration of fluorescently labeled events, e.g. cell surface binding of peptide-dye conjugates may be conducted on an system (FMAT® 8100 HTS System, Applied Biosystems, Foster City, Calif.) that automates mix-and-read, non-radioactive assays with live cells or beads (Miraglia, "Homogeneous cell- and bead-based assays for high throughput screening using fluorometric microvolume assay technology", (1999) J. of Biomolecular Screening 4:193-204). Uses of labeled antibodies also include cell surface receptor binding assays, immunocapture assays, fluorescence linked immunosorbent assays (FLISA), caspase-cleavage (Zheng, "Caspase-3 controls both cytoplasmic and nuclear events associated with Fas-mediated apoptosis in vivo", (1998) PNAS USA 95:618-23; U.S. Pat. No. 6,372,907), apoptosis (Vermes, J. Immunol. Methods 184:39-51 (1995)) and cytotoxicity assays. Fluorometric microvolume assay technology can be used to identify the up or down regulation by a molecule that is targeted to the cell surface (Swartzman, Anal. Biochem. 271:143-51 (1999)).

Labeled cysteine engineered antibodies of the invention are useful as imaging biomarkers and probes by the various methods and techniques of biomedical and molecular imaging such as: (i) MRI (magnetic resonance imaging); (ii) X-ray computed tomography); (iii) SPECT (single photon emission computed tomography); (iv) PET (positron emission tomography) Chen et al. (2004) Bioconjugate Chem. 15:41-49; (v) bioluminescence; (vi) fluorescence; and (vii) ultrasound. Immunoscintigraphy is an imaging procedure in which antibodies labeled with radioactive substances are administered to an animal or human patient and a picture is taken of sites in the body (e.g., tumors including tumor vasculature, or metastases thereof) where the antibody localizes (U.S. Pat. No. 6,528,624). Imaging biomarkers may be objectively measured and evaluated as an indicator of normal biological processes, pathogenic processes, or pharmacological responses to a therapeutic intervention. Biomarkers may be of several types: Type 0 are natural history markers of a disease and correlate longitudinally with known clinical indices, e.g. MRI assessment of synovial inflammation in rheumatoid arthritis; Type I markers capture the effect of an intervention in accordance with a mechanism-of-action, even though the mechanism may not be associated with clinical outcome; Type II markers function as surrogate endpoints where the change in, or signal from, the biomarker predicts a clinical benefit to "validate" the targeted response, such as measured bone erosion in rheumatoid arthritis by planar X-ray, MRI or CT. Imaging biomarkers thus can provide pharmacodynamic (PD) therapeutic information about: (i) expression of a target protein, (ii) binding of a therapeutic to the target protein, i.e. selectivity, and (iii) clearance and half-life pharmacokinetic data. Advantages of in vivo imaging biomarkers relative to lab-based biomarkers include: non-invasive treatment, quantifiable, whole body assessment, repetitive dosing and assessment, i.e. multiple time points, and potentially transferable effects from preclinical (small animal) to clinical (human) results. For some applications, bioimaging supplants or minimizes the number of animal experiments in preclinical studies.

Peptide labelling methods are well known. See Haugland, 2003, Molecular Probes Handbook of Fluorescent Probes and Research Chemicals, Molecular Probes, Inc.; Brinkley, 1992, Bioconjugate Chem. 3:2; Garman, (1997) Non-Radioactive Labelling: A Practical Approach, Academic Press, London; Means (1990) Bioconjugate Chem. 1:2; Glazer et al. (1975) Chemical Modification of Proteins. Laboratory Techniques in Biochemistry and Molecular Biology (T. S. Work and E. Work, Eds.) American Elsevier Publishing Co., New York; Lundblad, R. L. and Noyes, C. M. (1984) Chemical Reagents for Protein Modification, Vols. I and II, CRC Press, New York; Pfleiderer, G. (1985) "Chemical Modification of Proteins", Modern Methods in Protein Chemistry, H. Tschesche, Ed., Walter DeGryter, Berlin and New York; and Wong (1991) Chemistry of Protein Conjugation and Crosslinking, CRC Press, Boca Raton, Fla.); De Leon-Rodriguez et al. (2004) Chem. Eur. J. 10:1149-1155; Lewis et al. (2001) Bioconjugate Chem. 12:320-324; Li et al. (2002) Bioconjugate Chem. 13:110-115; Mier et al. (2005) Bioconjugate Chem. 16:240-237.

Peptides and proteins labeled with two moieties, a fluorescent reporter and quencher in sufficient proximity undergo fluorescence resonance energy transfer (FRET). Reporter groups are typically fluorescent dyes that are excited by light at a certain wavelength and transfer energy to an acceptor, or quencher, group, with the appropriate Stokes shift for emission at maximal brightness. Fluorescent dyes include molecules with extended aromaticity, such as fluorescein and rhodamine, and their derivatives. The fluorescent reporter may be partially or significantly quenched by the quencher moiety in an intact peptide. Upon cleavage of the peptide by a peptidase or protease, a detectable increase in fluorescence may be measured (Knight, C. (1995) "Fluorimetric Assays of Proteolytic Enzymes", Methods in Enzymology, Academic Press, 248:18-34).

The anti-Robo4 labeled antibodies of the invention may also be used as an affinity purification agent. In this process, the labeled antibody is immobilized on a solid phase such a Sephadex resin or filter paper, using methods well known in the art. The immobilized antibody is contacted with a sample containing the antigen to be purified, and thereafter the support is washed with a suitable solvent that will remove substantially all the material in the sample except the antigen to be purified, which is bound to the immobilized antibody. Finally, the support is washed with another suitable solvent, such as glycine buffer, pH 5.0, that will release the antigen from the antibody.

Labelling reagents typically bear reactive functionality which may react (i) directly with a cysteine thiol of a cysteine engineered antibody to form the labeled antibody, (ii) with a linker reagent to form a linker-label intermediate, or (iii) with a linker antibody to form the labeled antibody. Reactive functionality of labelling reagents include: maleimide, haloacetyl, iodoacetamide succinimidyl ester (e.g. NHS, N-hydroxysuccinimide), isothiocyanate, sulfonyl chloride, 2,6-dichlorotriazinyl, pentafluorophenyl ester, and phosphoramidite, although other functional groups can also be used.

An exemplary reactive functional group is N-hydroxysuccinimidyl ester (NHS) of a carboxyl group substituent of a detectable label, e.g. biotin or a fluorescent dye. The NHS ester of the label may be preformed, isolated, purified, and/or characterized, or it may be formed in situ and reacted with a nucleophilic group of an antibody. Typically, the carboxyl form of the label is activated by reacting with some combination of a carbodiimide reagent, e.g. dicyclohexylcarbodiimide, diisopropylcarbodiimide, or a uronium reagent, e.g. TSTU (O—(N-Succinimidyl)-N,N,N',N'-tetramethyluronium tetrafluoroborate, HBTU (O-benzotriazol-1-yl)-N,N,N',N'-tetramethyluronium hexafluorophosphate), or HATU (O-(7-azabenzotriazol-1-yl)-N,N,N',N'-tetramethyluronium hexafluorophosphate), an activator, such as 1-hydroxybenzotriazole (HOBt), and N-hydroxysuccinimide to give the NHS ester of the label. In some cases, the label and the antibody may be coupled by in situ activation of the label and reaction with the antibody to form the label-antibody conjugate in one step. Other activating and coupling reagents include TBTU (2-(1H-benzotriazo-1-yl)-1-1,3,3-tetramethyluronium hexafluorophosphate), TFFH(N,N',N'',N'''-tetramethyluronium 2-fluoro-hexafluorophosphate), PyBOP (benzotriazole-1-yl-oxy-tris-pyrrolidino-phosphonium hexafluorophosphate, EEDQ (2-ethoxy-1-ethoxycarbonyl-1,2-dihydroquinoline), DCC (dicyclohexylcarbodiimide); DIPCDI (diisopropylcarbodiimide), MSNT (1-(mesitylene-2-sulfonyl)-3-nitro-1H-1,2,4-triazole, and aryl sulfonyl halides, e.g. triisopropylbenzenesulfonyl chloride.

A detectably labeled antibody of the invention may be detectable by being linked to (including covalently conjugated to) a magnetic particle or nanoparticle or metallic particle or nanoparticle. Metallic particles are detectable by such methods as magnetic resonance imaging (MRI), single-particle or single-molecule tracking, immunocytochemistry, plasmon frequency with dark-field illumination, differential interference contrast and video enhancement, total internal reflection, and photothermal interference contrast (PIC) technique (see, for example *PNAS USA* 100(20): 11350-11355 (2003); Sheetz et al. *Nature* 340:284-288 (1989); Baschong et al., *Histochemistry* 83:409-411 (1985); Slot and Geuze, *Eur. J. Cell Biol.* 38:87-93 (1935); Frey and Frey *J. Struct. Biol.* 127:94-100 (1999); Hainfeld and Powell, *J. Histochem. Cytochem.* 48:471-480 (2000); Schultz et al. *PNAS USA* 97:996-1001 (2000); Gelles et al., *Nature* 331:450-453 (1988); Sonnichsen et al., *Appl Phys. Lett.* 77:2949-2951 (2000); Boyer, D. et al., *Science* 297:1160-1163 (2002)). Anti-Robo4 antibodies of the invention may comprise nanoparticulate agents including, but not limited to, microbubbles (see Ellegala et al., *Circulation* 108:336-341 (2003))), also referred to as acoustically active lipospheres (AALs) (see Tartis et al., *Ultrasound Med. Biol.* 32(11):1771-80 (2006)), superparamagnetic agents, liposomes, perfluorocarbon nanoparticle emulsions (WO2005014051), and dendrimers (see Caruthers et al., *Methods in Molecular Medicine,* 124:387-400 (2006) and references cited therein, all of which references are hereby incorporated by reference in their entirety).

When the labeled anti-Robo4 antibodies are used for detection (e.g., in scintigraphic studies), the labels may comprise a radioactive atom (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu) or a spin label for nuclear magnetic resonance (NMR) imaging (also known as magnetic resonance imaging, mri), such as $Tc^{99m}$, $^{123}I$, $^{111}In$, $^{131}I$, $^{19}F$, $^{1}H$, $^{14}N$, $^{15}N$, $^{17}O$, $^{23}Na$, $^{31}P$, or $^{13}C$, gadolinium, manganese, iron, or iron oxides (e.g., super-paramagnetic iron oxide particles (SPIL) or ultra-small paramagnetic iron oxide particles (USPIL)), or other NMR observable agents.

X. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is by itself or when combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice, such as cancer. Moreover, the article of manufacture may comprise (a) a first container with a composition contained therein, wherein the composition comprises an antibody of the invention; and (b) a second container with a composition contained therein, wherein the composition comprises a further cytotoxic agent. The article of manufacture in this embodiment of the invention may further comprise a package insert indicating that the first and second antibody compositions can be used to treat a particular condition, e.g. cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following are examples of the methods and compositions of the invention. It is understood that various other embodiments may be practiced, given the general description provided above.

EXAMPLES

Amino acid residues within antibody amino acid sequences are numbered according to Kabat (Kabat et al., *Sequences of proteins of immunological interest,* 5th Ed., Public Health Service, National Institutes of Health, Bethesda, Md. (1991)). Single letter amino acid abbreviations are used. DNA degeneracies are represented using the IUB code (N=A/C/G/T, D=A/G/T, V=A/C/G, B=C/G/T, H=A/C/T, K=G/T, M=A/C, R=A/G, S=G/C, W=A/T, Y=C/T).

Example 1

Antibodies Derived from Phage Encoding Hypervariable Regions of a Starting Antibody The nucleic acid sequences of the VL and VH domains of the HERCEPTIN® anti-HER2 antibody rhuMAB 4D5-8 (Genentech, Inc.) was used as the starting sequence for mutagenesis of the HVRs and phage selection for binding to human Robo4 His-tagged antigen shown in FIG. 5B or human Rob4-Fc fusion protein. Antibody 4D5 is a humanized antibody specific for a cancer-associated antigen known as Her-2 (erbB2). The antibody includes variable domains having consensus framework regions; a few positions were reverted to mouse sequence during the process of increasing affinity of the humanized antibody. The sequence and crystal structure of humanized antibody 4D5 have been described in U.S. Pat. No. 6,054,297, Carter et al, *PNAS USA* 89:4285 (1992), the crystal structure is shown in *J. Mol. Biol.* 229:969 (1993) and online. The HERCEPTIN® VL and VH domains comprise the consensus human kappa I VL domain and a variant of the human subgroup III consensus VH domain, respectively. The variant VH domain has 3 changes from the human consensus: R71A, N73T and L78A.

The phagemid used for this work is a monovalent Fab-g3 display vector (pV0350-2B) having 2 open reading frames under control of the phoA promoter, essentially as described in Lee et al., J. Mol. Biol. (2004), 340(5): 1073-93. The first open reading frame consists of the stII signal sequence fused to the VL and CH1 domains acceptor light chain and the second consists of the stII signal sequence fused to the VH and CH1 domains of the acceptor heavy chain followed by a truncated minor phage coat protein P3. See Lee et al., J. Mol. Biol. (2004), 340(5):1073-93.

Example 2

Antibodies Generated by Mutagenesis of Heavy Chain HVRs

Fab clones YW71.6, YW71.1, YW71.22, and YW71.89 were generated by mutagenesis of HVR-H1, H2, and H3 of huMAb 4D5-8 (HERCEPTIN® anti-BER2 antibody, Genentech, Inc.) heavy chain and selection against human Robo4-His tagged antigen fusion protein. In HVR-H1, Kabat positions 26 (G), 27 (F), 28 (T), 29 (I), 34 (I), and 35 (H) were held constant, and the amino acids at positions 30-33 were varied. In HVR-H2, Kabat positions 51 (I), 52a (P), 55 (G), 57 (T), 59 (Y), 60 (A), 61 (D), 62 (S), 63 (V), 64 (K), and 65 (G) were held constant, and positions 49, 50, 52, 53, 54, 56, and 58 were varied. In HVR-H3, Kabat positions 93 (A) and 102 (Y) were held constant, and positions 94-100, 100a-h, and 101 were varied. The light chain of YW71.22 was the modified huMAb 4D5-8 sequence (modified at positions 30, 66 and 91 resulting in SEQ ID NO:168, comprising SEQ ID NOS:1, 2, and 3 as HVR-L1, L2, and L3, respectively), the HVRs of which were not varied during phage selection. Sequence diversity was introduced into each hypervariable region by mutagenesis of selected amino acid positions using standard mutagenesis techniques.

Generation of phage libraries—Randomized oligonucleotide pools designed for each hypervariable region were phoshorylated separately in six 20 µl reactions containing 660 ng of oligonucleotide, 50 mM Tris pH 7.5, 10 mM MgCl$_2$, 1 mM ATP, 20 mM DTT, and 5 U polynucleotide kinase for 1 h at 37° C. The six phosphorylated oligonucleotide pools were then combined with 20 µg of Kunkel template in 50 mM Tris pH 7.5, 10 mM MgCl$_2$ in a final volume of 500 µl resulting in an oligonucleotide to template ratio of 3. The mixture was annealed at 90° C. for 4 min, 50° C. for 5 min and then cooled on ice. Excess, unannealed oligonucleotide was removed with a QIAQUICK™ PCR purification kit (Qiagen kit 28106) using a modified protocol to prevent excessive denaturation of the annealed DNA. To the 500 µl of annealed mixture, 150 µl of PB was added, and the mixture was split between 2 silica columns. Following a wash of each column with 750 µl of PE and an extra spin to dry the columns, each column was eluted with 110 µl of 10 mM Tris, 1 mM EDTA, pH 8. The annealed and cleaned-up template (220 µl) was then filled in by adding 1 µl 100 mM ATP, 10 µl 25 mM dNTPs (25 mM each of dATP, dCTP, dGTP and dTTP), 15 µl 100 mM DTT, 25 µl 10×TM buffer (0.5 M Tris pH 7.5, 0.1 M MgCl$_2$), 2400 U T4 ligase, and 30 U T7 polymerase for 3 h at room temperature.

The filled in product was analyzed on Tris-Acetate-EDTA/ agarose gels (Sidhu et al., *Methods in Enzymology* 328:333-363 (2000)). Three bands were usually visible: the bottom band is a correctly filled and ligated product, the middle band is a filled but unligated product, and the top band is a strand displaced product. The top band is produced by an intrinsic side activity of T7 polymerase and is difficult to avoid (Lechner et al., *J. Biol. Chem.* 258:11174-11184 (1983)); however, this band transforms 30-fold less efficiently than the bottom band and usually contributes little to the library. The middle band is due to the absence of a 5' phosphate for the final ligation reaction; this band transforms efficiently and gives mainly wild type sequence.

The filled in product was then purified and electroporated into SS320 cells and propagated in the presence of M13/KO7 helper phage as described by Sidhu et al., *Methods in Enzymology* 328:333-363 (2000). Library sizes ranged from 1-2× $10^9$ independent clones. Random clones from the initial libraries were sequenced to assess library quality.

Phage Selection—The human Robo4-Fc and Robo4-His-tagged proteins were used as the selection antigens. Human Robo4-Fc and Robo4-His was coated on MaxiSorp microtiter plates (Nunc) at 10 µg/mil in PBS and incubated overnight at 4 degrees. For the first round of selection 12 wells of target were used. Wells were blocked for 1 hour at room temperature using Phage Blocking Buffer (1% BSA, 0.05% Tween® 20, PBS). Phage libraries were PEG precipitates from frozen glycerol stocks, resuspended in Phage Blocking Buffer and incubated for 1 hour at room temperature. Phage libraries were then added to the blocked antigen plates incubated overnight at room temperature. After overnight binding, unbound or non-specifically bound phage were removed from the antigen plates by washing with Wash Buffer (PBS, 05% Tween®20). Bound phage were eluted by incubating the wells with 50 mM HCl, 0.5 M KCl for 30 min. Phage were amplified using XL-1 Blue cells and M13/KO7 helper phage and grown for 36 hours at 30° C. in 2YT, 50 µg/mil carbanecillin, 50 ug/ml kanamycin, 10 µg/ml tetracycline. Amplified phage were then recovered using a modified PEG precipitation protocol (Clackson & Lowman 2004). The titers of phage eluted from a target coated well were compared to titers of phage recovered from a non-target coated well to assess enrichment. Four rounds of phage selection were completed with the number of target wells decreasing to 4 (round 2) and 2 (round 3 and 4). Casein Blocking Buffer (Pierce) was used as the blocking reagent for antigen plates and phage for rounds 2 and 4. Selection rounds 2-4 used a 3-4 hour phage-antigen binding period and increased washing stringency. Four phage clones were selected: YW71.6, YW7.1, YW71.22, and YW71.89. The sequences of the light and heavy chain domains were determined and are shown in FIGS. 1A and 1B. The Robo4 binding characteristics were determined as disclosed herein below.

Example 3

Antibodies Generated by Variation of HVRs H1, H2, H3 and L3

Clones YW79.1, YW79.8, and YW79.11 were generated by mutagenesis of HVR-H1, H2, H3 and L3 of huMAb 4D5-8 (HERCEPTIN® anti-HER2 antibody, Genentech, Inc.) heavy chain variable domain and huMAb 4D5-8 modified light chain variable domain, SEQ ID NO:168. In HVR-H1, Kabat positions 26 (G), 28 (T), 29 (F), 30 (S), 31 (S), and 35 (S) were held constant, and the amino acids at positions 27, 32-34 were varied. In HVR-H2, Kabat positions 49 (S), 51 (I), 55 (G), 57 (T), 59 (Y), 60 (A), 61 (D), 62 (S), 63 (V), 64 (K), and 65 (G) were held constant, and positions 50, 52, 52a, 53, 54, 56, and 58 were varied. In HVR-H3, Kabat positions 93 (A), 94 (R), 100f-g (deletion) were held constant, and positions 95-100, 100a-e, 100h, and 102 were varied. In HVR-L3, Kabat positions 89 (Q), 90 (Q), 95 (P) and 97 (T) were held constant, and positions 91-94 and 96 were varied. The sequence of HVR-L1 was held constant as RASQSISSYLA (SEQ ID NO:7) and the sequence of HVR-L2 was held constant as GASSRAS (SEQ ID NO:8). Sequence diversity was introduced into each hypervariable region by mutagenesis of selected amino acid positions using standard mutagenesis techniques. Anti-Robo4 antibody clones YW79.1, YW79.8, and YW79.11 were selected and sequenced. The sequences of the light chain and heavy chain variable regions are shown in FIGS. 1A and 1B.

Example 4

Purification of Soluble Robo4 and Anti-Robo4 Antibodies

This example describes methods useful in the purification of the Robo4 antigen and the anti-Robo4 antibodies of the invention. Robo4 antigen was purified as a soluble Robo4 extracellular domain fused to a histidine tag as shown in FIG. 5B.

Robo4 Antigen Purification

Human Robo4 constructs (amino acid M1 to amino acid L461 and amino acid M1 to amino acid Y231) were cloned into the eukaryotic expression vector pRK5 either as fusions to the Fc portion of human IgG1 or to a C-terminal Histidine tag. Murine Robo4 (M1 to H232) was cloned into pRK5 as fusion to a C-terminal Histidine tag only. All proteins were produced by transient transfection of CHO cells. Proteins were purified to >90% purity by affinity chromatography using either protein-A Sepharose™ (GE Healthcare) for Fc fusion proteins or NiNTA Superflow™ (Qiagen) for Histidine tag fusions. If necessary an ion exchange chromatography step (Q- or SP-Sepharose™, GE Healthcare) was added and/or a size exclusion chromatography step (Superdex™ 75, GE Healthcare). Protein identities were confirmed by N-terminal sequencing using the Edman degradation method, concentrations were determined by the BCA assay and by OD 280 absorption measurements, and purity was assessed by size exclusion chromatography and SDS-PAGE.

Antibody Purification

Full length Robo4 antibodies were transiently expressed in CHO cells and purified to >95% purity by affinity chromatography using protein-A Sepharose™ (GE Healthcare), followed by ion exchange chromatography using SP-Sepharose™ (GE Healthcare). If necessary, an additional size exclusion chromatography step (Superdex™ 200, GE Healthcare) was added. Antibody concentrations were determined by the BCA assay according to manufacturer's instructions (Pierce Chemical Co.) and by OD 280 absorption measurements, and purity was assessed by size exclusion chromatography and SDS-PAGE. For all antibody purifications, aggregate levels as determined by laser light scattering were below 5%, protein A levels as determined by protein A ELISA were below 50 ppm, and endotoxin levels as determined by the LAL (Limulus Amoebocyte Lysate) chromogenic endotoxin assay were below 0.5 EU/mg.

Example 5

Affinity Maturation of YW71.22

To improve the affinity of anti-Robo4 antibody YW71.22, three phage display libraries were generated in the background of YW71.22, each targeting multiple HVRs for soft randomization mutagenesis as described in Lee et al., J. Mol. Biol. 340(5):1073-93 (2004). To avoid re-selecting YW71.22 from a potential high background of template, stop codons were introduced into the HVR to be mutated prior to generating each library. A solution sorting method was used to enhance the efficiency of the affinity-based phage selection process. By manipulating the biotinylated target concentration, reducing the phage capture time to lower backgrounds and the addition of unbiotinylated target to eliminate clones with faster off rates, high affinity clones can be proficiently selected. Lee et al., J. Mol. Biol. (2004), 340(5): 1073-93. From the first round of selection, enrichment (target dependent phage capture) was observed suggesting a large number of clones were present in each library with reasonably high affinity for human Robo4. Selection stringency was increased in subsequent rounds. After 5 rounds of selection, clones from each library were analyzed. New sequences were observed in libraries targeting each of the six HVRs (FIGS. 2A and 2B). Selected clones were screened by phage ELISA and then expressed as IgG protein and their affinity characterized using Biacore™ binding analysis.

Phage libraries of affinity matured clones were sorted using a solid/solution sorting method. Human Robo4-His was biotinylated by mixing 500 μl of 3.6 mg/ml human Robo4-His in PBS, and 10 μl of 1 M potassium phosphate, pH 8 with 20 μl 4 mM Sulfo-NHS-LC-biotin (Pierce). For the first round of selection, biotinylated Robo4-His was coated on MaxiSorp microtiter plates (Nunc) at 10 μg/ml in PBS and incubated overnight at 4° C. For the first round of selection 16 wells of target were used. Wells were blocked for 1 hour at room temperature using SuperBlock (Pierce). Maturation phage libries were diluted in SuperBlock buffer and incubated 1 hour at room temperature. Phage libraries were then added to the blocked antigen plates incubated 2 hours at room temperature. After binding, unbound and non-specifically bound phage were removed from the antigen plates by washing with Wash Buffer (PBS, 05% Tween®20). Bound phage were eluted by incubating the wells with 50 mM HCl, 0.5 M KCl for 30 min. Phage were amplified using XL-1 Blue cells and M13/KO7 helper phage and grown for 36 hours at 30° C. in 2YT, 50 μg/ml carbanecillin, 50 ug/ml kanamycin, 10 μg/ml tetracycline. Amplified phage were then recovered using a modified PEG precipitation protocol (Clackson & Lowman 2004). The titers of phage eluted from a target coated well were compared to titers of phage recovered from a non-target coated well to assess enrichment. For selection rounds 2-5 a solution sorting protocol was implemented. Microtiter wells were coated with 10 μg/ml neutravidin in PBS overnight at 4° C. and then blocked for 1 hour using SuperBlock (Pierce). Recovered phage libraries were suspended in SuperBlock and were mixed with 50 nM biotinylated Robo4-His for 1 hour. Phage bound to biotinylated Robo4-His were captured on neutravidin coated wells for 30 min and unbound phage were washed away with Wash Buffer. Phage were eluted using 50 mM HCl, 500 mM KCl for 30 min, neutralized, and propagated in XL1 blue cells (Stratagene) in the presence of KO7 helper phage (New England Biolabs). Subsequent rounds of sorting were performed similarly with the following exceptions: in round 2 the final biotinylated Robo4-His concentration was 50 nM, in round 3 the final biotinylated Robo4-His concentration was 25 nM, in round 4 the final biotinylated Robo4-His concentration was 5 nM and in round 5 the final biotinylated Robo4-His concentration was 0.5 nM with 50 nM unbiotinylated Robo4-His added to the mixture for 1 hour prior to capture on neutravidin.

Several affinity matured clones were selected for binding to human Robo4-His and sequenced. The variable region sequences of the antibody clones derived by affinity maturation of clone YW71.22 are shown in FIG. 2A (light chain variable regions) and FIG. 2B (heavy chain variable region).

Example 6

Characterization of Selected Anti-Robo4 Antibody Clones

Phage ELISA—Phage competition binding assays were performed to determine the approximate binding affinity (determined as phage $IC_{50}$) of phage-displayed Fabs for Robo4. The assays were performed as follows. Briefly, purified phage supernatants from each clone were produced using a modified PEG precipitation protocol as described above. Purified phage supernatants were serially diluted in Phage Blocking buffer, then incubated on plates coated with Robo4-His (1 µg/ml) for 15 minutes. The plates were washed with Wash Buffer and were incubated for 30 minutes with horseradish peroxidase/anti-M13 antibody conjugate (diluted 1:5000 in PBS buffer) (Amersham Pharmacia Biotech). The plates were washed, developed with tetramethylbenzidine (TMB) substrate (Kirkegaard and Perry Laboratories) and quenched with $0.1NH_2SO_4$. Absorbance was measured spectrophotometrically at 450 nm to determine the phage concentration giving about 50% of the signal at saturation. A fixed, subsaturating concentration of phage was diluted in Phage Blocking buffer containing two-fold serial dilutions of Robo4-His protein from 350 nM Robo4 to 5 nM Robo4. The mixtures were incubated for one hour with gentle shaking at room temperature, transferred to plates coated with Robo4-His (1 µg/ml) and the plates were incubated for 20 minutes. The plates were washed and treated as above. The binding affinities were estimated as $IC_{50}$ values (defined as the concentration of antigen that blocked 50% of the phage binding to the immobilized antigen). The $IC_{50}$ results for the seven clones are shown in Table 2.

TABLE 2

Anti-Robo4 Phage Competition Summary

| Clone | Phage $IC_{50}$ versus human Robo4 |
|---|---|
| YW71.6 | 15 nM |
| YW71.22 | 5 nM |
| YW71.1 | 15 nM |
| YW71.89 | 20 nM |
| YW79.1 | 15 nM |
| YW79.11 | <5 nM |
| YW79.8 | <5 nM |

Fab Production and Affinity Determination—To express Fab protein for affinity measurements, a stop codon was introduced between the heavy chain and g3 in the phage display vector. Clones were transformed into *E. coli* 34B8 cells and grown in AP5 media at 30 C (Presta et al. *Cancer Res.* 57: 4593-4599 (1997)). Cells were harvested by centrifugation, suspended in 10 mM Tris, 1 mM EDTA pH 8 and broken open using a microfluidizer. Fab was purified with Protein G affinity chromatography.

Affinity determinations were performed by surface plasmon resonance using a BIAcore™ 2000 system (BIAcore, Piscataway, N.J.). Robo4-His was immobilized (~1000 response units (RU)) on a CM5 chip and varied concentrations of Fab (4 to 500 nM) in PBST were injected. After each injection the chip was regenerated using 100 mM HCl.

The binding affinity of three phage-derived anti-Robo4 antibodies for soluble Robo4 extracellular domain (ECD) was determined by surface plasmon resonance measurement using a BIACORE® 3000 system (Biacore, Inc., Piscataway, N.J.). The antibodies tested included YW71.6, YW71.22, and YW79.8. Briefly, carboxymethylated dextran biosensor chips (CM5, Biacore Inc.) were activated with N-ethyl-N'-(3-dimethylaminopropyl)-carbodiimide hydrochloride (EDC) and N-hydroxysuccinimide (NHS) according to the supplier's instructions. These activated chips were coated with anti-Robo Fab by dilution to 5 ug/ml with 10 mM sodium acetate, pH 4.8, before injection at a flow rate of 5 µl/minute to achieve approximately 500 response units (RU) of coupled antibody. Next, 1M ethanolamine was injected to block unreacted groups. For kinetics measurements, two-fold serial dilutions of human or mouse-ECD-His tagged soluble antigen (approximately 500 nM to approximately 7.8 nM) were injected in PBS with 0.05% Tween® 20 at 25° C. at a flow rate of 25 µl/min. Binding response was corrected by subtracting the RU from a blank flow cell. Association rates ($k_{on}$) and dissociation rates ($k_{off}$) were calculated using a simple one-to-one Langmuir binding model (BIAevaluation Software version 3.2). The equilibrium dissociation constant ($K_D$) was calculated as the ratio $k_{dissociation}/k_{association}$. The results of this experiment are shown in Table 3 below. Antibody YW71.22 cross-reacts with human and mouse Robo4.

TABLE 3

Anti-Robo4 BIAcore™ Binding Analysis Summary

| Clone | ka | kd | $K_D$ |
|---|---|---|---|
| | Human Robo4 | | |
| YW71.22 | 2.90E+05 | 3.70E−03 | 1.30E−08 |
| | Murine Robo4 | | |
| YW71.22 | 4.50E+05 | 2.80E−03 | 6.20E−09 |

An affinity matured anti-Robo4 antibody clone derived from YW71.22 were tested for binding to human Robo4 expressed endogenously in HUVEC cells and to murine Robo4 expressed endogenously in MS1 cells. A FACS analysis revealed that clones YW71.22.S1.16 and YW71.22.S1.21 bound to both human and murine Robo4 and that binding was comparable to the YW71.22 antibody (FIG. 18).

Example 7

Binding Analysis of Affinity Matured Robo4 Antibodies

Affinity matured YW71.22.S1.16 was used to generate a full-length IgG1 and a Fab fragment both with a Cys substitution at position 118 of the heavy chain Fc region according to EU numbering. The Cys is used for site specific conjugation of the antibody to a label or drug of interest.

Binding affinities to human and mouse Robo4 were determined by in vitro binding measurements and by radiolabeled cell binding for full-length YW71.22.S1.16 (Mab), full-length YW71.22.S1.16 with engineered Cys (thioMab), and a Fab fragment of YW71.22.S1.16 with engineered Cys (Thio-Fab).

The in vitro binding experiments were performed by SPR measurements on a ProteOn XPR36 instrument (Bio-Rad Laboratories, Inc.) at 25° C. Affinity matured Robo4 antibodies (Mab, ThioMab and ThioFab) were immobilized at surface densities of 500-1000 RUs on an activated ProteOn GLC sensor chip (Bio-Rad Laboratories, Inc.) using standard amine coupling procedures as described by the manufacturer. Briefly, antibodies were injected at a concentration of 10 µg/ml in 20 mM sodium acetate, pH 4.5 and at a flow rate of 30 µl/min for 5 min. Unreacted groups were blocked by injecting 1 M ethanolamine. To perform binding assays, samples were injected at a flow rate of 30 µl/min. For kinetics measurements serial dilutions of either purified human or mouse Robo4-His (approximately 25 nM to 0.8 nM) were injected in PBS with 0.01% Tween-20 and sensorgrams for association and dissociation phases were recorded. Blank surfaces were used for background corrections. There was no need to regenerate surfaces since the ProteOn protein interaction array system allows to run up to six binding experiments on an identical surface in parallel. Association rates ($k_a$) and dissociation rates ($k_d$) were calculated using a simple one-to-one Longmuir binding model (ProteOn Manager Software V2.0, Bio-Rad Laboratories, Inc.) and the equilibrium dissociation constant ($K_D$) was calculated as the ration $k_d/k_a$. The results are summarized in Table 4 below.

TABLE 4

Anti-Robo4 Antibody Affinities ($K_D$) Summary

| Antibody format | In vitro (SPR) | | Radiolabeled Cell Binding | |
|---|---|---|---|---|
| (YW71.22.S1.16) | hRobo4 | mRobo4 | HUVEC | MS1 |
| thioMAb | 1.2E–09 | 1.1E–09 | 1.2E–09 | 1.0E–09 |
| MAb | 1.1E–09 | 0.9E–09 | ND | ND |
| thioFab | 8.0E–09 | 1.5E–09 | ND | 3.2E–09 |

HUVECs and MS1 cells, which endogenously express Robo4 protein were used in radioligand cell binding experiments.

For the cell binding experiments anti-Robo4 thioMab and thioFab antibodies were iodinated using the Iodogen method. Each radiolabeled antibody was purified from free $^{125}$I—Na by gel filtration using a NAP-5 column; the purified thioMab antibody had a specific activity of 6.96 µCi/µg and the purified thioFab antibody had a specific activity of 16.05 µCi/µg. 50 µL competition mixtures containing a fixed concentration of iodinated antibody and decreasing concentrations of the unlabeled antibody were placed into 96-well plates. MS1 and HUVEC cells were cultured in growth media at 37° C. in 5% $CO_2$ and then were detached from tissue culture plates using a non-enzymatic cell dissociating solution (Sigma #C5914) for subsequent binding studies. Cells were washed with binding buffer (50:50 DMEM/F12 media containing 2% FBS, 2 mM sodium azide and 50 mM HEPES, pH 7.2) and were placed into the 96-well plates containing the competition mixtures at approximately 200,000 cells in 0.2 mL of binding buffer. The final concentration of the iodinated Mab antibody in each incubation with cells was ~150 pM (~70,000 cpms per 0.25 ml) and the final concentration of the unlabeled antibody in the incubations with cells started at 400 nM and was serially diluted by 2 fold for 10 concentrations. The final concentration of the iodinated Fab antibody in each incubation with cells was ~400 pM (~150,000 cpms per 0.25 ml) and the final concentration of the unlabeled antibody in the incubations with cells started at 1.0 uM and was serially diluted by 2 fold for 10 concentrations. Competition reactions were assayed in triplicate. The competition reactions were incubated for 2 hours at room temperature. Then they were transferred to a Millipore Multiscreen filter plate and washed three times with binding buffer to separate the free from bound iodinated antibody. The filters were counted on a Wallac Wizard 1470 gamma counter (PerkinElmer Life and Analytical Sciences Inc. Wellesley, Mass.). The binding data was evaluated using NewLigand software (Genentech), which uses the fitting algorithm of Munson and Robard, *Anal. Biochem.* 107: 220-39 (1980), to determine the binding affinity of the antibody and the concentration of binding sites per well. The number of binding sites per cell was determined by dividing the total binding sites by the number of cells per well.

Example 8

Anti-Robo4 Antibody Inhibits HUVEC Tube Elongation

Anti-Robo4 antibody (YW71.22) significantly inhibits HUVEC tube elongation in a bead outgrowth assay. Both total number and length of the tubes are reduced as compared to the control antibody E25 (FIG. 20). For example the number of tubes with a length of 300 µm or more is reduced by 60%.

For the bead outgrowth assay, dextran-coated Cytodex 3 microcarrier beads (Amersham) were incubated with HUVECs (400 cells per bead) in EGM-2, overnight at 37° C. and 5% $CO_2$. To induce clotting, 0.5 ml cell-coated beads in PBS with 2.5 µg/ml fibrinogen (200 beads/ml) was added into one well of a 24-well tissue culture plate containing 0.625 units thrombin and incubated for 5 min at room temperature and then for 20 min at 37° C. The clot was equilibrated in EGM-2 for 30 min at 37° C. The medium was then replaced with EGM-2 containing skin fibroblast cells (Detroit 551, 20,000 cells/ml). Antibodies (50 µg/ml) were added to each well, and the assay was monitored for 8 days with change in medium every alternate day. Images of the beads were captured by an inverted microscope, and concentric circles spaced at 100, 200, and 300 µm were drawn around the bead in each image. The number of vessels crossing each circle was counted 10-12 beads were used per condition for quantification (Nakatsu et al., *Microvascular Research* 66: 102-112 (2003)).

Example 9

Anti-Robo4 Antibody and Anti-Robo4 Antibody Drug Conjugates as Therapeutics

Anti-Robo4 ADCs were produced by conjugating anti-Robo4 antibodies to the drug-linker moieties MCC-DM1, SPDB-DM4, and mPEO-DM1. Prior to conjugation, the antibodies were partially reduced with TCEP using standard methods in accordance with the methodology described in WO 2004/010957. The partially reduced antibodies were conjugated to the above drug-linker moieties using standard methods in accordance with the methodology described in Doronina et al., *Nat. Biotechnol.* 21:778-784 (2003) and U.S. Patent Application No. 2005/0238649. Briefly, the partially reduced antibodies were combined with the drug linker moieties to allow conjugation of the moieties to cysteine residues (including without limitation, cysteine engineered residues of thioMAbs as disclosed herein). The conjugation reactions were quenched, and the ADCs were purified. The drug load (average number of drug moieties per antibody) for each ADC was determined by HPLC. Additional anti-Robo4 ADCs are made using e.g., drug linker moieties including spp-DM1, smcc-DM1, MC-vc-PAB-MMAE; MC-vc-PAB-MMAF; MC-MMAE and MC-MMAF (see, e.g., WO 2004/010957, and WO2006/034488 (each of which is herein incorporated by reference in its entirety).

Example 10

In Vivo Tumor Volume Reduction Assay

Naked anti-Robo4 antibody: Tumor growth was not inhibited by naked anti-Robo4 antibody YW71.22 (antibody not conjugated to a cytotoxic agent or other agent) in mouse xenograft models of human non-small cell lung carcinoma SK-MES-1. For this study, each HRLN female nude mouse received a 1 mm$^3$ tumor fragment s.c. implant in the flank. Tumor growth was monitored twice weekly by caliper measurements. When tumors reached an average size of 80-120 mm$^3$, mice were sorted to give nearly identical group mean tumor sizes, and treatment was started (Day 1). Animals were dosed twice weekly i.p. with 10 mg/kg anti-Robo4 and/or 5 mg/kg anti-VEGF or control antibody for 5 weeks. All treatments were body weight-adjusted at 0.2 mg/20 g. The results are shown in FIG. 17. In addition, no reduction of tumor growth in Fo5 mouse model with MDA-MB-231 breast cancer xenograft was observed.

An anti-Robo4 antibody comprising an Fc region having enhanced ADCC activity may be used to inhibit tumor growth. The ADCC-enhanced anti-Robo4 antibody may be a naked antibody or an antibody drug conjugate as disclosed herein. ADCC enhancement is achieved, for example, by enhancing IgG1-FcgammaRIII interactions, which are dependent on the carbohydrate moieties linked to the antibody Fc region. Non-limiting exemplary methods for ADCC enhancement include reducing antibody fucosylation by expressing anti-Robo4 in a host cell overexpressing GnTIII, which encodes N-acetylglucosaminyltransferase (Narishimhan, *J. Biol. Chem.* 257:10235-10242 (1982) and Umana et al., *Nature Biotech.* 17:176-180 (1999)); a host cell underexpressing or lacking expression of FUT8, which encodes alpha-1,6-fucosyltransferase (Shinkawa et al., *J. Biol. Chem.* 278:3466-3473 (2003)); or a host cell lacking or underexpressing UDP-N-acetylglucosamine 2-epinerase (such as Lec3 CHO cells) (Hong and Stanley, *J. Biol. Chem.* 278: 53045-53054 (2003)). In addition, ADCC is enhanced by amino acid changes in the Fc region (see for example WO2000042072 and WO2004029207). Thus, anti-Robo4 antibodies of the invention are useful as cytotoxic agents include anti-Robo4 antibodies exhibiting enhanced ADCC function relative to an anti-Robo4 antibody exhibiting wild type Fc ADCC activity.

Anti-Robo4 antibody drug conjugate (Anti-Robo4 ADC): To test the efficacy of toxin-conjugated anti-Robo4 ADCs for the ability to reduce tumor volume in vivo, the following protocol is employed.

SCID mice are each inoculated subcutaneously in the flank with cells of a human cancer cell line. The human cancer cell lines include, as non-limiting examples, SK-MES-1 human non-small lung cancer cells and MDA-MB-231 breast cancer cells. When the tumors reach a mean tumor volume of between approximately 80-200 mm$^3$, the mice are divided into groups, and treated by intravenous injection with toxin-conjugated antibody or unconjugated antibody.

Use of a Anti-Robo4 Maytansine Drug Conjugates to Reduce Solid Tumor Volume

SCID mice are injected with human tumor cells subcutaneously in a volume of 0.2 ml/20 g mouse body weight in the flank. Cells are suspended in HBSS. When the mean tumor size reaches approximately 80-200 mm$^3$, mice are randomly grouped into groups and given a single or multiple I.V. treatments (via the tail vein) of either a anti-Robo4 ADC conjugated to maytansine or a control antibody.

Mean tumor volume is monitored in each treatment group for approximately 30 days post-antibody injection. Tumor may be detected by, for example, fluorescence detection of remaining luciferase where the tumor cells are engineered to express luciferase. Efficacy of the toxin-conjugated anti-CD22 antibodies is determined by comparison to control and unconjugated antibodies.

The same experiment is performed using anti-Robo4 ADC wherein the drug conjugated to the antibody is an auristatin.

The same experiment is repeated using an anti-Robo4 ADC comprising an Fc region having enhanced ADCC activity.

Example 11

Anti-Robo4 Antibodies Conjugated to Detectable Markers sDOTA-labeled anti-Robo4 antibodies are prepared as follows. The DOTA-NHS-ester was dissolved in dimethylacetamide (DMA, Fluka Chemika, Switzerland) and prepared to concentrations of 60-100 mg/mL. Typical procedures involved buffer exchanging the MAb into PBS with 2 mM EDTA at pH 7.2. Reactions were performed at a ratio of 1 molecule MAb to 4 DOTA molecules (1:4) and carried out at 25° C. while gently stirring on a Thermomixer plate (Eppendorf, Westbury, N.Y.). The DOTA-labeled anti-Robo4 antibody is useful as a detectable marker in vitro or in vivo when associated with, as non-limiting examples, yttrium $^{90}$Y, $^{111}$In, $^{177}$Lu and the like. The mAb conjugates are labeled with, for example, $^{111}$In by incubating the conjugate with $^{111}$InCl$_3$ in 0.25 M ammonium acetate for 45 min at 43° C. EDTA is added to a final concentration of 1 mM, and the mixture is incubated at 37° C. for 15 minutes. Labeling with $^{90}$Y, for example, is performed using a one-hour incubation at 43° C., after which DTPA is added to a final concentration of 1 mM, and the mixture is incubated for an additional 15 min at 37° C. The radiometal-labeled mAb conjugates are purified by size exclusion HPLC, using a TosoHaas TSKgel G2000 SW column and a mobile phase of normal saline.

Example 12

Additional Characterization of Robo4 and Anti-Robo4 Antibodies

Robo4 does not block endothelial cell (EC) migration. Robo4-Fc and Robo4-His were contacted with vascular ECs using a HUVEC migration assay and in the presence or absence of VEGF. FIG. 8 shows the results of the assay. Robo4-Fc or Robo4-His alone did not induce EC migration and VEGF-induced EC migration was not enhanced by Robo4.

Robo4 does not bind to Slit2. Robo4-Fc contacted with Slit2 did not show binding by Biocore™ analysis, whereas Robo1 and Slit 2 did show binding in the same assay (FIG. 9). Slit2-His (histidine-tagged full-length Slit2) was immobilized on a CM5 Biacore™ chip at high density. A 5 µl aliquot of each analyte (Robo4-Fc or Robo1-Fc fusion proteins) was injected and allowed to interact with the immobilized ligand in buffer (HEPES/EDTA/NaCl, pH7.5).

Robo4 interacts in vitro with UNC5B, a cell surface receptor involved in vascular guidance. It has been shown that netrin binding to members of the uncoordinated-5 (UNC5) family of receptors (UNC5A, B, C, and D) results in neural axon repression (Klagsbrun, M. and Eichmann, A., Cytokine & Growth Factor Reviews 16(4-5):535-548 (2005)). Netrin-UNC5B interaction has been implicated in angiogenesis (Klagsbrun, M. and Eichmann, A., supra (2005) and Lu, X. et al., Nature 432:179-186 (2004)). The interaction of Robo4 with UNC5B in vitro was determined by SPR binding measurements in which UNC5B-Fc fusion protein (extracellular domain of UNC5B fused to an Fc region) was immobilized on a chip and soluble Robo4-Fc or Robo4-His was allowed to interact with it at different concentrations. SPR measurements were performed as described in Example 7 and the interaction results are shown in FIG. 10.

Figure 13A:
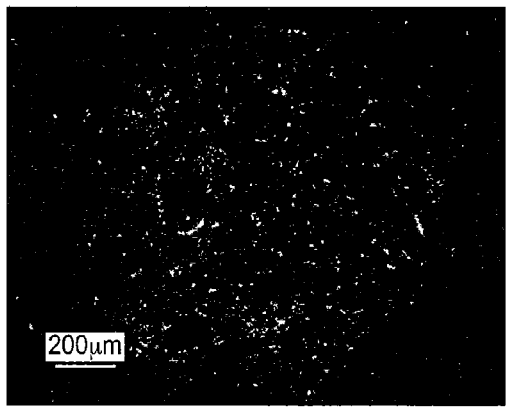
Figure 13B:
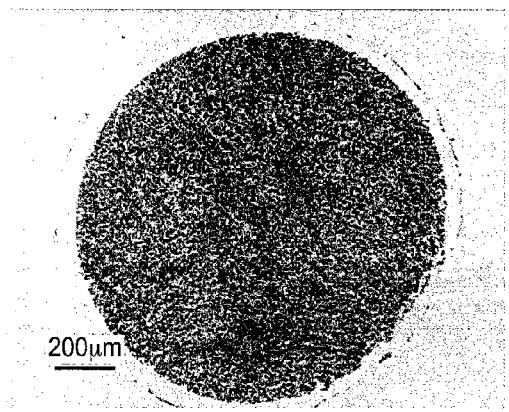
Figure 13C:
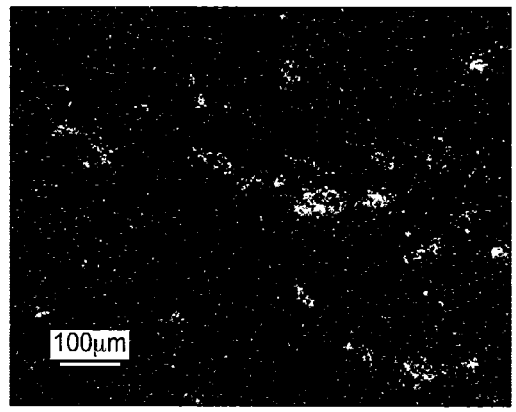
Figure 13D:
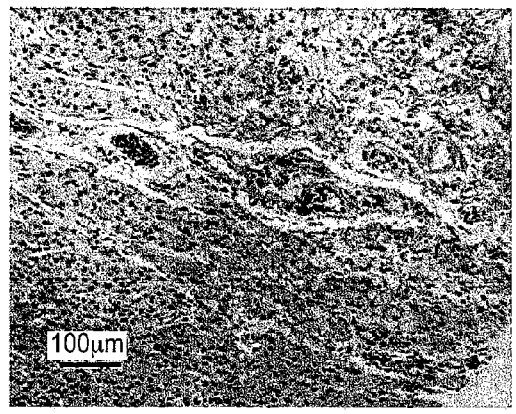
Figure 14A:
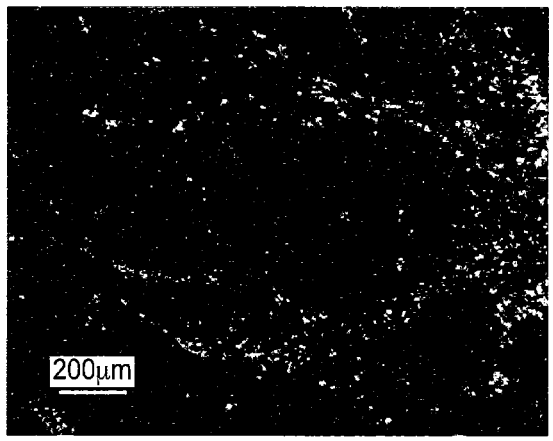
Figure 14C:
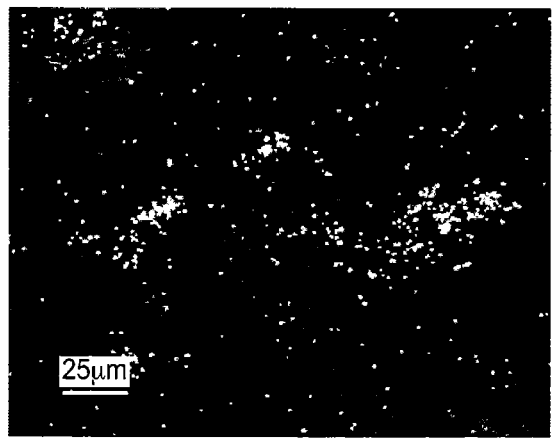
Figure 14B:
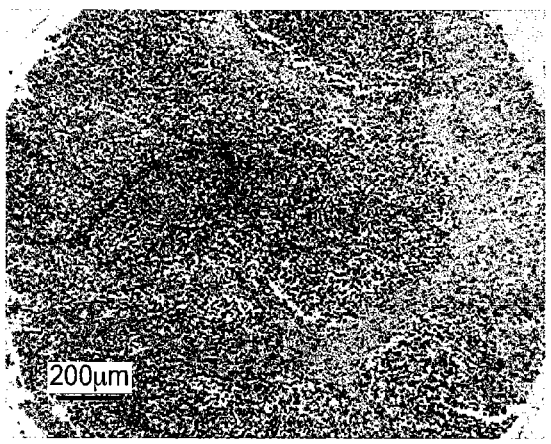
Figure 14D:
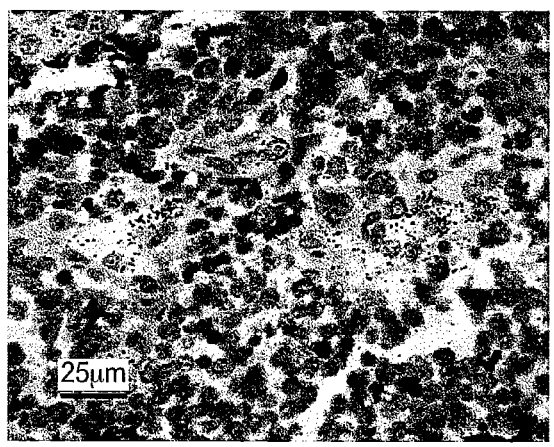

Robo4 is expressed in fetal mouse endothelium as shown by an ISH assay using Robo4 specific RNA probes (FIG. 11). Robo4 is also expressed in mouse tumor models of colon tumor (human HM-7 colon tumor xenograft, FIGS. 12A and 12B) and in mammary tumor (human MDA-MB-175 breast cancer tumor xenograft, FIGS. 12C and 12D). Robo4 shows increased expression in human tumor tissue relative to normal human tissue as evidenced in FIGS. 13A and 13C (increased expression in malignant melanoma) relative to normal tissue (FIGS. 13B and 13D). Robo4 expression is also seen in human small cell lung cancer (FIGS. 14A-D), human colon cancer (FIGS. 14G-H), human prostate tumor, and mouse angiosarcoma. Robo4 is expressed in tumor endothelial cells in colon, non-small cell lung cancer, renal cell carcinoma (RCC), transitional cell carcinoma (TCC, a common form of bladder cancer), breast cancer, glioma, and sarcoma.

Anti-Robo4 antibody YW71.22 was internalized by Robo4-expressing mouse microvascular endothelial MS1 cells over a period of 2 hours. The YW71.22 antibody was allowed to bind Robo4 on mouse microvasculature endothelial MS1 cells at 0° C. for 30 minutes, incubated at 37° C. for 0-2 hours. At intervals, cells were fixed and permeabilized or not permeabilized. Anti-Robo4 antibodies on the cell surface or internalized by the cell were interacted with a fluorescently labeled (Alexa-labeled) anti-human IgG secondary antibody. The results are shown in FIGS. 15A and 15B. The YW71.22.S1.16 anti-Robo4 antibody was internalized by the same protocol except that anti-Robo4 was incubated on MS1 cells at 37° C. was for 0-4 hours. Cells were permeabilized and stained as above. The results are shown in FIG. 15C.

Endothelial cell migration was not blocked by anti-Robo4 antibody in an in vitro assay using human umbilical vascular endothelial cells (HUVEC) cellular migration assay. HUVECs endogenously express human Robo4. The assay was performed as follows. HUVECs were pre-incubated for 2 hours with VEGF. Cellular migration was allowed to continue for 16 hours in the presence of anti-Robo4 antibody YW71.22, anti-VEGF antibody, or Robo4-Fc or Robo4-His. Neither anti-Robo4 nor the soluble Robo4 extracellular domain fusion proteins (Robo4-Fc and Robo4-His) blocked EC migration under these conditions (FIG. 16).

Anti-Robo4 antibody associates with vasculature in vivo. Fifty micrograms of anti-Robo4 antibody 71.22 (FIG. 19A) or control antibody (anti-HER2, FIG. 19B) were injected via tail vein and allowed to circulate for 10 minutes. One hundred micrograms of FITC-Lycopersicum esculentum was injected and allowed to circulate for 5 minutes. Mice were perfused with 1% PFA in PBS, tissues were collected into 30% sucrose and frozen in OCT. Antibodies were detected with Cy3 goat anti-human IgG. FIG. 19A shows that the location of FITC-Lycopersicum esculentum staining in vasculature overlaps with the location of anti-Robo4 Cy3 staining, unlike the control antibody which migrated into surrounding tissue.

Although the foregoing invention has been described in some detail by way of illustration and example for purposes of clarity of understanding, the descriptions and examples should not be construed as limiting the scope of the invention. The disclosures of all patents, patent applications, scientific references, and Genbank Accession Nos. cited herein are expressly incorporated by reference in their entirety for all purposes as if each patent, patent application, scientific reference, and Genbank Accession No. were specifically and individually incorporated by reference.

We claim:

1. An isolated anti-Robo4 antibody comprising:
   (i) an HVR-L1 comprising sequence A1-A11, wherein A1-A11 is RASQDVSTAVA (SEQ ID NO:1)
   (ii) an HVR-L2 comprising sequence B1-B7, wherein B1-B7 is SASFLYS (SEQ ID NO:2)
   (iii) an HVR-L3 comprising sequence C1-C9, wherein C1-C9 is QQSYTTPPT (SEQ ID NO:3)
   (iv) an HVR-H1 comprising sequence D1-D10, wherein D1-D10 is GFTINGYYIH (SEQ ID NO:17)
   (v) an HVR-H2 comprising sequence E1-E18, wherein E1-E18 is GFIYPAGGDTDYADSVKG (SEQ ID NO:18); and
   (vi) an HVR-H3 comprising sequence F1-F17 wherein F1-F17 is ARLIGNKFGWSSYGMDY (SEQ ID NO:19).

2. An isolated anti-Robo4 antibody comprising a light chain variable domain comprising an amino acid sequence selected from the group consisting of: SEQ ID NOS:72-97 as shown in FIGS. 1A and 2A.

3. An isolated anti-Robo4 antibody comprising a heavy chain variable domain comprising an amino acid sequence selected from the group consisting of: SEQ ID NOS:140-165 as shown in FIGS. 1B and 2B.

4. An isolated anti-Robo4 antibody comprising
   (i) a light chain variable domain comprising
   an HVR-L1 comprising SEQ ID NO:1,
   an HVR-L2 comprising SEQ ID NO:2, and
   an HVR-L3 comprising QQSRSDHPT (SEQ ID NO:20); and
   (ii) a heavy chain variable domain comprising
   an HVR-H1 comprising SEQ ID NO:17,
   an HVR-H2 comprising SEQ ID NO:18, and
   an HVR-H3 comprising SEQ ID NO:19.

5. The antibody of any one of claims 1-3 and 4, wherein the antibody is humanized.

6. The antibody of any one of claims 1-3 and 4, wherein the antibody is selected from the group consisting of a Fab, a Fab', and a (Fab')$_2$.

7. The antibody of any one of claims 1-3 and 4, further comprising a cytotoxic agent.

8. The antibody of claim 7, wherein the cytotoxic agent is selected from the group consisting of: $N^{2'}$-deacetyl-$N$-$^{2'}$(3-mercapto-1-oxopropyl)-maytansine (DM1), monomethyl auristatin E (MMAE), monomethyl auristatin F (MMAF), and combinations thereof.

9. The antibody of claim 8, further comprising a detectable label.

10. The antibody of claim 9, wherein the detectable label is selected from the group consisting of: biotin, a fluorescent dye, a radionuclide, chelating agent 1, 4, 7, 10-tetraazacyclododecane-N, N', N", N'''-tetraacetic acid (DOTA), a microbubble, a perfluorocarbon nanoparticle emulsion, a metallic particle, and combinations thereof.

11. The antibody of claim 9, wherein the detectable label is covalently attached to the antibody at a cysteine residue.

12. The antibody of claim 11, wherein the cysteine residue is at position 118 of the heavy chain Fc region according to EU numbering.

* * * * *